(12) United States Patent
Funahashi et al.

(10) Patent No.: US 7,001,728 B1
(45) Date of Patent: Feb. 21, 2006

(54) PROTEIN HAVING PDZ DOMAIN SEQUENCE

(75) Inventors: Shin-Ichi Funahashi, Niihari-mura (JP); Shoji Miyata, Niihari-mura (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/502,698

(22) Filed: Feb. 11, 2000

Related U.S. Application Data

(63) Continuation-in-part of application No. PCT/JP98/03603, filed on Aug. 12, 1998.

(30) Foreign Application Priority Data

Aug. 12, 1997 (JP) .................................. 9/230356
Jun. 19, 1998 (JP) .................................. 10/189944

(51) Int. Cl.
*G01N 33/53* (2006.01)
*C07K 14/705* (2006.01)

(52) U.S. Cl. ...................... 435/7.1; 530/350; 435/69.1; 435/471

(58) Field of Classification Search ................ 530/350; 536/23.1, 23.5, 24.3, 24.31; 435/69.1, 471, 435/71.2, 71.1, 325, 252.3, 254.11, 320.1
See application file for complete search history.

(56) References Cited

OTHER PUBLICATIONS

Doerks et al. TIG, vol. 14, No. 6, pp. 248-250, Jun. 1998.*
Mikayama et al. Proc. Natl. Acad. Sci. USA vol. 90, pp. 10056-10060, 1993.*
Voet et al. Biochemistry, John Wiley & Sons, Inc., pp. 126-128 & 228-234, 1990.*
Skolnick et al. Nature Biotechnology, Mar. 2000, vol. 8, pp. 283-287.*
Ullmer et al., "Cloning and characterization of MUPP1 . . . ," FEBS Letters, 424:63-68, 1998.
Seměnov et al., "Human Dishevelled Genes . . . ," Genomics, 42:302-310, 1997.
Morais Cabral et al., "Crystal structure of a PDZ domain," Letters to Nature, 382:649-652, 1996.
Lee et al., "Binding of human virus . . . ," Proc. Natl. Acad. Sci. USA, 94:6670-6675, 1997.
Simpson et al., "Identification, Sequence, and Mapping . . . ," Genomics, 59:102-104, 1999.
Huang et al., "PDZ domains: Structural modules for protein complex assembly," *Journal of Biological Chemistry*, vol. 277, No. 8, Feb. 22, 2002, pp. 5699-5702.
Ponting et al., "DHR domains in syntrophins, neuronal NO synthases and other intracellular proteins", *TIBS Trends in Biochemical Sciences*, Elsevier Publication, vol. 20, No. 3, Mar. 1995, pp. 102-103.
Saras et al., "PDZ domains bind carboxy-terminal sequences of target proteins," *TIBS Trends in Biochemical Sciences*, Elsevier Publication, vol. 21, No. 12, Dec. 1, 1996, pp. 455-458.
EMBL Accession No. AJ001319 (Mar. 26, 1998).
EMBL Accession No. AJ001320 (Mar. 26, 1998).
EMBL Accession No. AF000168 (May 23, 1997) Lee et al.
Lee et al., "Multi-PDZ Domain Protein MUPP1 Is a Cellular Target for both Adenovirus E4-ORF1 and High-Risk Papillomavirus Type 18 E6 Oncoproteins" *J. Virol.* 74(20):9680-9693 (2000).
Mancini et al., "The direct association of the multiple PDZ domain containing proteins (MUPP-1) with the human c-Kit C-terminus is regulated by tyrosine kinase activity" *FEBS Letters* 482:54-58 (2000).

\* cited by examiner

*Primary Examiner*—Prema Mertz
(74) *Attorney, Agent, or Firm*—Fish & Richardson P.C.

(57) ABSTRACT

While analyzing changes in gene expression by TNFα in umbilical vascular endothelial cells, a gene showing enhanced expression due to stimulation with TNFα was isolated. After screening with this gene as a probe, a gene encoding a protein was isolated. Analysis of the protein encoded by this isolated gene revealed that this novel protein has never been reported and has a PDZ domain in its molecule that plays an important role in protein—protein interactions.

8 Claims, 22 Drawing Sheets

```
848  FISLLKTAKMTVKLTIHAENPDSQAVPSAAGAASGEKKNSSQSLMVPQSG 897
     |||||||||| ||||  : ||||    ||||.|    |||:|..||.  ||
  2  FISLLKTAKATVKLIVRAENPACPAVPSSAVTVSGERKDNSQTPAVP... 48

898  SPEPESIRNTSRSSTPAIFASDPATCPIIPGCETTIEISKGRTGLGLSIV 947
      .|:  | |  .|||||||||:|||||||||||||||||| :|||.||||||||
 49  APDLEPIPSTSRSSTPAVFASDPATCPIIPGCETTIGVSKGQTGLGLSIV 98

948  GGSDTLLGAFIIHEVYEEGAACKDGRLWAGDQILEVNGIDLRKATHDEAI 997
     ||||||||  |||||||||||||||||||||||||||||||||||||||
 99  GGSDTLLGAIIIHEVYEEGAACKDGRLWAGDQILEVNGIDLRKATHDEAI 148

998  NVLRQTPQRVRLTLYRDEAPYKEEEVCDTLTIE..LQKKPGKGLGLSIVG 1045
     |||||||||||.|||||||||||||:|||| |||   |||:||||||||||||
149  NVLRQTPQRVRVTLYRDEAPYKEEDVCDTFTIELQLQKRPGKGLGLSIVG 198

1046 KRNDTGVFVSDIVKGGIADPDGRLIQGDQILLVNGEDVRNASQEAVAALL 1095
     ||||||||||||||||||| ||||.|||||||:||||||||.|.||||||||
199  KRNDTGVFVSDIVKGGIADADGRLMQGDQILMVNGEDVRHATQEAVAALL 248

1096 KCSLGTVTLEVGRIKAGPFHSERRPSQTSQVSEGSLSSFTFPLSGSSTSE 1145
     |||||  |||||||:||  ||||||||||.|||||  ||||||  ||||  .|||
249  KCSLGAVTLEVGRVKAAPFHSERRPSQSSQVSESSLSSFTPPLSGINTSE 298

1146 SLESSSKKNALASEIQGLRTVEMKKGPTDSLGISIAGGVGSPLGDVPIFI 1195
     ||||.|||||||||||  |||||.|||| |||||:|||||||||||||||||||||
299  SLESNSKKNALASEIQRLRTVEIKKGPADSLGLSIAGGVGSPLGDVPIFI 348

1196 AMMHPTGVAAQTQKLRVGDRIVTICGTSTEGMTHTQAVNLLKNASGSIEM 1245
     |||||  |||||||||||||||||||||||:||||||||||:|||||||.
349  AMMHPNGVAAQTQKLRVGDRIVTICGTSTDGMTHTQAVNLMKNASGSIEV 398

1246 QVVAGGDVSVVTGHHQEPASSSLSFTGLTSTSIFQDDLGPPQCKSITLER 1295
     ||||||||||||| || |.    |.||||||.||| |||||||  |.|||:|
399  QVVAGGDVSVVTGHQQELANPCLAFTGLTSSSIFPDDLGPPQSKTITLDR 448

1296 GPDGLGFSIVGGYGSPHGDLPIYVKTVFAKGAASEDGRLKRGDQIIAVNG 1345
     |||||||||||||||||||||||||||||||||.||||||||||||||||||
449  GPDGLGFSIVGGYGSPHGDLPIYVKTVFAKGAAAEDGRLKRGDQIIAVNG 498

1346 QSLEGVTHEEAVAILKRTKGTVTLMVLS 1373
     ||||||||||||||||||||||||||||
499  QSLEGVTHEEAVAILKRTKGTVTLMVLS 526
```

FIG. 1

```
 921 ATCPIIPGCETTIEISKGRTGLGLSIVGGSDTLLGAFIIHEVYEEGAACK  970
     |||||||||||||||||||||||||||||||||| |||||||||||||||
   1 ATCPIIPGCETTIEISKGRTGLGLSIVGGSDTLLGAIIIHEVYEEGAACK   50

971 DGRLWAGDQILEVNGIDLRKATHDEAINVLRQTPQRVRLTLYRDEAPYKE 1020
     |||||||||||||||||||||||||||||||||||||||||||||||||
  51 DGRLWAGDQILEVNGIDLRKATHDEAINVLRQTPQRVRLTLYRDEAPYKE  100

1021 EEVCDTLTIELQKKPGKGLGLSIVGKRNDTGVFVSDIVKGGIADPDGRLI 1070
     ||||||||||||||||||||||||||||||||||||||||||||| ||||
 101 EEVCDTLTIELQKKPGKGLGLSIVGKRNDTGVFVSDIVKGGIADADGRLM  150

1071 QGDQILLVNGEDVRNASQEAVAALLKCSLGTVTLEVGRIKAGPFHSERRP 1120
     ||||||:|||||||||.|||||||||||||||||||||||||||||||||
 151 QGDQILMVNGEDVRNATQEAVAALLKCSLGTVTLEVGRIKAGPFHSERRP  200

1121 SQTSQVSEGSLSSFTFPLSGSSTSESLESSSKKNALASEIQGLRTVEMKK 1170
     ||.|||||||||||||||||||||||||||||||||||||||||||||||
 201 SQSSQVSEGSLSSFTFPLSGSSTSESLESSSKKNALASEIQGLRTVEMKK  250

1171 GPTDSLGISIAGGVGSPLGDVPIFIAMMHPTGVAAQTQKLRVGDRIVTIC 1220
     |||||||||||||||||||||||||||||||||||||||||||||||||
 251 GPTDSLGISIAGGVGSPLGDVPIFIAMMHPTGVAAQTQKLRVGDRIVTIC  300

1221 GTSTEGMTHTQAVNLLKNASGSIEMQVVAGGDVSVVTGHHQEPASSSLSF 1270
     ||||||||||||||||||||||||||||||||||||||| |||||||||
 301 GTSTEGMTHTQAVNLLKNASGSIEMQVVAGGDVSVVTGHQQEPASSSLSF  350

1271 TGLTSTSIFQDDLGPPQCKSITLERGPDGLGFSIVGGYGSPHGDLPIYVK 1320
     |||||.|||||||||||||||||||||||||||||||||||||||||||
 351 TGLTSSSIFQDDLGPPQCKSITLERGPDGLGFSIVGGYGSPHGDLPIYVK  400

1321 TVFAKGAASEDGRLKRGDQIIAVNGQSLEGVTHEEAVAILKRTKGTVTLM 1370
     |||||||||||||||||||||||||||||||||||||||||||||||||
 401 TVFAKGAASEDGRLKRGDQIIAVNGQSLEGVTHEEAVAILKRTKGTVTLM  450

1371 VLS 1373
     |||
 451 VLS  453
```

FIG. 2

```
  1 MVCCRRTVPPTTQSELDSLDLCDIELTEKPHVDLGEFIGSSETEDPVLAM  50    401 GLGMIVRSIIHGGAISRDGRIAIGDCILSINEESTISVTNAQARAMLRRH 450
    ||||||||| || |||| |:|||:|  |:|:||||||||||||||||||        |||:|||||||||||||||||||||||||||||||:|||||||||||||
620 MVCCRRTVPPTALSEVDSLDIHDLELTEKPHIDLGEFIGSSETEDPMLAM 669   1015 GLGVIVRSIIHGGAISRDGRIAVGDCILSINEESTISLTNAQARAMLRRH 1064

51 TDACGSTEEVQAPLAMWEAGIQHIELEKGSKGLGFSILDYQDPIDPASTV 100    451 SLIGPDIKITYVPAEHLEEFKISLGQQSGRVMALDIFSSYTGRDIPELPE 500
    |||||||||||||||||||| |||||||||||||||||||||||||||         ||||||||||||||||||||| :: |||.| :|||||||||||||||||
 51 TDACGSTEEVQAPLAMWEAGIQHIELEKGSKGLGFSILDYQDPIDPASTV 100   1065 SLIGPDIKITYVPAEHLEEFRVSFGQQAGGIMALDIFSSYTGRDIPELPE 1114
    .| |.  |:|  |||||||| |||||||| ||||:||||||| ||||||
670 SDVDQNAEEIQIPLAMWEAGIQATELEKGSRGLGFSILDYQDPIOPANTV 719    501 REEGEGEESELQNTAYSWWNQPRRVELWREPSKSLGISIVGGRGMGSRLS 550
                                                                |||||||||| ||| .|. |.|||||||||||||||||||||||||||
101 IIIRSLVPGGIAEKDGRLLPGDRLMFVNDVNLENSSLEEAVEALKGAPSG 150   1115 REEGEGEESELQNAAYSSWSQPRRVELWREPSKSLGISIVGGRGMGSRLS 1164
    |:|||||||||||||||||||||||||||||||||||||||||||||||
720 IVIRSLVPGGIAEKDGRLFPGDRLMFVNDINLENSTLEEAVEALKGAPSG 769    551 NGEVMRGIFIKHVLEDSPAGKNGTLKPGDRIVE...............  583
                                                                |||||||||||||||||||||||||||
151 TVRIGVAKPLPLSPEEGYVSAKEDSFLYPPHSCEEAGLADKPLFRADLAL 200   1165 NGEVMRGIFIKHVLEDSPAGKNGTLKPGDRIVEVDGHDLRQASHEQAVEA 1214
    |||||||||||||||||||||||| :| ||.:|| ||: ||| |||||
770 MVRIGVAKPLPLSPEEGYVSAKEDTFLCSPHITCKEMGLSDKALFRADLAL 819   584 ...APSQSESEPEKAPLCSVPPPPSAFAEMGSDHTQSSASKISQDVDKE  630
                                                                   ||| ||| |||||  || ||| |:.:|| |:. :::.|| |||
201 VGTNDADLVDESTFESPSPSPENDSTYSTQASILSLHGSSCGDGLNYGSSL 250   1265 SDKAPSQSESESEKATLCSVPSSSPSVFSEMSSDYAQPSATTVAEDEDKE 1314
    : | |||| |  ||| ||:.|||||||::|||| |||                
820 IDTPDAESVAESRFESQFSPDNDSVYSTQASVLSLHDGACSDGMNYGPSL 869   631 DEFGYSWKNIRERYGTLTGELHMIELEKGHSGLGLSLAGNKDRSMSVFI 680
                                                                ||||||||||||||||||||| ||||||||||||:|||||||||||||
251 PSSPPKDVIENSCDPVLDLHMSLEELYTQNLLERDENTPSVDISMGPAS 300   1315 DEFGYSWKNIQERYGTLTGQLHMIELEKGHSGLGLSLAGNKDRTRMSVFI 1364
    |||||||| |||.|||||||||||||||||||||||| :|.||
870 PSSPPKDV.TNSSDLVLGLHLSLEELYTQNLLQRQHAGSPPTDMSPAATS 918   681 VGIDPNGAAGKDGRLQIADELLEINGQILYGRSHQMASSIIKCAPSKVKI 730
                                                                ||||||||||| | |.|||||||||| : |||| :|||:|||||||||
301 GFTINDYTPANAIECQYECENTIVMTESHLPSEVISSAELPSVLPDSAGK 350   1365 VGIDPTGAAGRDGRLQIADELLEINGQILYGRSHQNASSIIKCAPSKVKI 1414
    |||:.||||||| :|:|:||: || |||. :|: :  |: ::|
919 GFTVSDYTPANAVEQKYECANTVAWTPSQLPSG.LSTTELAPALPAVAPK 967   731 IFIRNKDAVNQMAVCPGNAVEPLPSNSENLQNKETEPTVTSDAAVDLSS 780
                                                                |:||||||||:||:|||||||| | ||||| ||| ||::. |||. ||
351 GSEHILEQSSLACMAECVMLQNVSKESFERTINIAKGNSSLGMTVSANKD 400   1415 IFIRNADAVNQMAVCPGSAADPLPSTSESPQNKEVEPSITTSASAVDLSS 1464
    . | |||||: |||||..|.|.|||| ||:|||:|| ||||||
968 ...YLTEQSSLVSDAESVTLQSMSQEAFERTVTIAKGSSSLGMTVSANKD 1014
```

FIG. 3

```
 781 FKNVQHLELPKDQGLGIAISEEDTLSGVIIKSLTENGVAATDGRLKVGD  830       1181 AGGVGSPLGDVPIFIAMMHPTGVAAQTQKLRVGDRIVTICGTSTEGMTHT 1230
     ||  ||||||||||||||||||   |||||  ||  |||||  ||                ||||||||||||||||||||||     |||||||||||||||||:||||
1465 LTNVYHLELPKDQGLGIAICEEDTLNGVTIKSLTERGGAAKDGRLKPGD 1514      1862 AGGVGSPLGDVPIFIAMMHPNGVAAQTQKLRVGDRIVTICGTSTDGMTHT 1911

831 QILAVDDEIVVGYPIEKFISLLKTAKMTVKLTIIHAENPDSQAVPSAAGAA  880      1231 QAVNLLKNASGSIEHQVVAGGDVSVVTGHHQEPASSSLSFTGLTSTSIFQ 1280
     |||||||:|  ||||||||||||||| ||||||  |||   ||   |  |               ||||:|||||||||||  |||||||||||| ||  |  |  ||||||..||
1515 RILAVDDELVAGCPIEKFISLLKTAKTTVKLTVGAENPGCQAVPSAAVTA 1564      1912 QAVNLMKNASGSIEVQVVAGGDVSVVTGHQQELANPCLAFIGLTSSTIFP 1961

881 SGEKKNSSQSLMVPQSGSPEPESIRNTSRSSTPAIFASDPATCPIIPGCE  930      1281 DDLGPPQCKSITLERGPDGLGFSIVGGYGSPHGDLPIYVKTVFAKGAASE 1330
     |||:|.|||.    :|   | |  |||||||||||||||||||||||||             |||| |.|||.:|||||||||||||||||||||||||||||||||||||||..|
1565 SGERKQSSQIPAVP...APDLEPIPSTSRSSTPAIFASDPATCPIIPGCE 1611      1962 DDLGPPQSKTITLDRGPDGLGFSIVGGYGSPHGDLPIYVKTVFAKGAAAE 2011

931 TTIEISKGRTGLGLSIVGGSDTLLGAFIIHEVYEEGAACKDGRLWAGDQI  980      1331 DGRLKRGDQIIAVNGQSLEGVTHEEAVAILKRTKGTVTLMVLS 1373
     |||||||| |.||||||||||||||| |||||||||||||||||||||||             ||||||||||||||||||||||||||||||||||||||||||
1612 TTIEISKGQTGLGLSIVGGSDTLLGAIIHEVYEEGAACKDGRLWAGDQI 1661      2012 DGRLKRGDQIIAVNGQSLEGVTHEEAVAILKRTKGTVTLMVLS 2054

981 LEVNGIDLRKATHDEAINVLRQTPQRVRLTLYRDEAPYKEEVCDTLTIE 1030
     |||||||||||||||||||||||||||||||||||||||||||| |:|
1662 LEVNGIDLRKATHDEAINVLRQTPQRVRLTLYRDEAPYKEEDVCDTFTVE 1711

1031 LQKKPGKGLGLSIVGKRNDTGVFVSDIVKGGIADPDGRLIQGDQILLVNG 1080
     ||||||||||||||||||||||||||||||| ||| |:|||||||||||
1712 LQKRPGKGLGLSIVGKRNDTGVFVSDIVKGGIADADGRLMQGDQILHVNG 1761

1081 EDVRNASQEAVAALLKCSLGTVTLEVGRIKAGPFHSERRPSQTSQVSEGS 1130
     |||||:||||||||||||||||||||||||||| ||||||||| |||:|
1762 EDVRNATQEAVAALLKCSLGTVTLEVGRIKAAPFHSERRPSQSSQVSESS 1811

1131 LSSFTFPLSGSSTSESLESSSKKNMALASEIQGLRTVEMKKGPTDSLGISI 1180
     ||||.| ||||||||.:|||||.|||||||||||||||:||| .|:||||
1812 LSSFSLPRSGINTSESSESSAKKNMALASEIQGLRTVEIKKGPADALGLSI 1861
```

FIG. 4

```
              1                                                    50
PDZ-E  AGIQHIELE. KGSKGLGFSI LDYQD..... PIDPASTVII IRSLVPGGIA
PDZ-F  QNVSKESFER TINIAKGNSS LGMTV..... SANKDGLGMI VRSIIHGGAI
PDZ-G  NQPRRVELWR EPSKSLGISI VGGRGMGSRL SNGEVMRGIF IKHVLEDSPA
PDZ-H  GELHMIELEK GHS.GLGLSL AGNKD..... RSR.M..SVF IVGIDPNGAA
PDZ-I  KNVQHLELPK DQG.GLGIAI .......... SEEDTLSGVI IKSLTEHGVA
PDZ-J  GCETTIEISK GRT.GLGLSI VGGSD..... TLL.G..AFI IHEVYEEGAA
PDZ-K  CDTLTIELQK KPGKGLGLSI VGKRN..... .....DTGVF VSDIVKGGIA
PDZ-L  QGLRTVEMKK GPTDSLGISI AGGVG..... SPL.GDVPIF IAMMHPTGVA
PDZ-M  PQCKSITLER GP.DGLGFSI VGGYG..... SPH.GDLPIY VKTVFAKGAA 51                                                   96
PDZ-E  EKDGRLLPGD RLMFVNDVNL ENSSLEEAVE ALKGAPSGTV RIGVAK
PDZ-F  SRDGRIAIGD CILSINEEST ISVTNAQARA MLRRHSLIGP DIKITY
PDZ-G  GKNGTLKPGD RIVEAPSQSE SEPEKAPLCS VPPPPPSAFA EMGSDH
PDZ-H  GKDGRLQIAD ELLEINGQIL YGRSHQNASS IIKCAP.SKV KIIFIR
PDZ-I  ATDGRLKVGD QILAVDDEIV VGYPIEKFIS LLKTAKM.TV KLTIHA
PDZ-J  CKDGRLWAGD QILEVNGIDL RKATHDEAIN VLRQTP.QRV RLTLYR
PDZ-K  DPDGRLIQGD QILLVNGEDV RNAS.QEAVA ALLKCSLGTV TLEVGR
PDZ-L  AQTQKLRVGD RIVTICGTST EGMTHTQAVN LLKNAS.GSI EMQVVA
PDZ-M  SEDGRLKRGD QIIAVNGQSL EGVTHEEAVA ILKRTK.GTV TLMVLS
```

FIG. 8

|  |  |  |  |  |  |  |  |
|---|---|---|---|---|---|---|---|
| 1 | | | | | 50 | | |
| FH750 | TTCCTTCTGT | GCTACCCGAT | TCAGCTGGAA | AGGGCTCTGA | GTACCTGCTT | | |
| FH850 | TTCCTTCTGT | GCTACCCGAT | TCAGCTGGAA | AGGGCTCTGA | GTACCTGCTT | | |
| FH950 | TTCCTTCTGT | GCTACCCGAT | TCAGCTGGAA | AGGGCTCTGA | GTACCTGCTT | | |
| 51 | | | | | 100 | | |
| FH750 | GAACAGAGCT | CCCTGGCCTG | TAATGCTGAG | TGTGTCATGC | TTCAAAATGT | | |
| FH850 | GAACAGAGCT | CCCTGGCCTG | TAATGCTGAG | TGTGTCATGC | TTCAAAATGT | | |
| FH950 | GAACAGAGCT | CCCTGGCCTG | TAATGCTGAG | TGTGTCATGC | TTCAAAATGT | | |
| 101 | | | | | 150 | | |
| FH750 | ATCTAAAGAA | TCTTTTGAAA | GGACTATTAA | TATAGCAAAA | GGCAATTCTA | | |
| FH850 | ATCTAAAGAA | TCTTTTGAAA | GGACTATTAA | TATAGCAAAA | GGCAATTCTA | | |
| FH950 | ATCTAAAGAA | TCTTTTGAAA | GGACTATTAA | TATAGCAAAA | GGCAATTCTA | | |
| 151 | | | | | 200 | | |
| FH750 | CCCTAGGAAT | GACAGTTAGT | GCTAATAAAG | ATGGCTTGG | GATGATCGTT | | |
| FH850 | CCCTAGGAAT | GACAGTTAGT | GCTAATAAAG | ATGGCTTGG | GATGATCGTT | | |
| FH950 | CCCTAGGAAT | GACAGTTAGT | GCTAATAAAG | ATGGCTTGG | GATGATCGTT | | |
| 201 | | | | | 250 | | |
| FH750 | CGAAGCATTA | TTCATGGAGG | ATCTTGTCCA | TTAATGAAGA | GTCTACCATC | | |
| FH850 | CGAAGCATTA | TTCATGGAGG | ATCTTGTCCA | TTAATGAAGA | GTCTACCATC | | |
| FH950 | CGAAGCATTA | TTCATGGAGG | ATCTTGTCCA | TTAATGAAGA | GTCTACCATC | | |
| 251 | | | | | 300 | | |
| FH750 | TGGGGACTGC | ATCTTGTCCA | TTAATGAAGA | GTCTACCATC | AGTGTAACCA | | |
| FH850 | TGGGGACTGC | ATCTTGTCCA | TTAATGAAGA | GTCTACCATC | AGTGTAACCA | | |
| FH950 | TGGGGACTGC | ATCTTGTCCA | TTAATGAAGA | GTCTACCATC | AGTGTAACCA | | |
| 301 | | | | | 350 | | |
| FH750 | ATCCCCAGGC | ACAGCTATG | TTGAGAAGAC | ATTCTCTCAT | TGCCCCTGAC | | |
| FH850 | ATCCCCAGGC | ACAGCTATG | TTGAGAAGAC | ATTCTCTCAT | TGCCCCTGAC | | |
| FH950 | ATCCCCAGGC | ACAGCTATG | TTGAGAAGAC | ATTCTCTCAT | TGCCCCTGAC | | |
| 351 | | | | | 400 | | |
| FH750 | ATAAAAATTA | CTTATGTGCC | TGCAGAACAT | TTGGAAGAGT | TCAAAATAAG | | |
| FH850 | ATAAAAATTA | CTTATGTGCC | TGCAGAACAT | TTGGAAGAGT | TCAAAATAAG | | |
| FH950 | ATAAAAATTA | CTTATGTGCC | TGCAGAACAT | TTGGAAGAGT | TCAAAATAAG | | |
| 401 | | | | | 450 | | |
| FH750 | CTTGGGACAA | CAATCTGGAA | GAGTAATGCC | ACTGGATATT | TTTTCTTCAT | | |
| FH850 | CTTGGGACAA | CAATCTGGAA | GAGTAATGCC | ACTGGATATT | TTTTCTTCAT | | |
| FH950 | CTTGGGACAA | CAATCTGGAA | GAGTAATGCC | ACTGGATATT | TTTTCTTCAT | | |
| 451 | | | | | 500 | | |
| FH750 | ACACTGGCAG | AGACATTCCA | GAATTACCAG | AGCAGAGAA | GGGAGAGGGT | | |
| FH850 | ACACTGGCAG | AGACATTCCA | GAATTACCAG | AGCAGAGAA | GGGAGAGGGT | | |
| FH950 | ACACTGGCAG | AGACATTCCA | GAATTACCAG | AGCAGAGAA | GGGAGAGGGT | | |
| 501 | | | | | 550 | | |
| FH750 | GAAGAAACG | AACTTCAAA | CACAGCATAT | AGCAATTGGA | ATCAGCCCAG | | |
| FH850 | GAAGAAACG | AACTTCAAA | CACAGCATAT | AGCAATTGGA | ATCAGCCCAG | | |
| FH950 | GAAGAAACG | AACTTCAAA | CACAGCATAT | AGCAATTGGA | ATCAGCCCAG | | |
| 551 | | | | | 600 | | |
| FH750 | CCGGGTGGAA | CTCTGGAGAG | AACCAAGCAA | ATCCTTAGCC | ATCAGCATTG | | |
| FH850 | CCGGGTGGAA | CTCTGGAGAG | AACCAAGCAA | ATCCTTAGCC | ATCAGCATTG | | |
| FH950 | CCGGGTGGAA | CTCTGGAGAG | AACCAAGCAA | ATCCTTAGCC | ATCAGCATTG | | |
| 601 | | | | | 650 | | |
| FH750 | TTGGTGGACG | AGGGATGGGG | AGTCGGCTAA | GCAATGGAGA | AGTGATGAGG | | |
| FH850 | TTGGTGGACG | AGGGATGGGG | AGTCGGCTAA | GCAATGGAGA | AGTGATGAGG | | |
| FH950 | TTGGTGGACG | AGGGATGGGG | AGTCGGCTAA | GCAATGGAGA | AGTGATGAGG | | |
| 651 | | | | | 700 | | |
| FH750 | GGCATTTTCA | TCAAACATGT | TCTGGAAGAT | AGTCCAGCTG | GCAAAATGG | | |
| FH850 | GGCATTTTCA | TCAAACATGT | TCTGGAAGAT | AGTCCAGCTG | GCAAAATGG | | |
| FH950 | GGCATTTTCA | TCAAACATGT | TCTGGAAGAT | AGTCCAGCTG | GCAAAATGG | | |

FIG. 17

```
       701                                              750
FH750  AACCTTGAAA CCTGGAGATA GAATCGTAGA G
FH850  AACCTTGAAA CCTGGAGATA GAATCGTAGA GGTGGATGGA ATGGACCTCA
FH950  AACCTTGAAA CCTGGAGATA GAATCGTAGA GGTGGATGGA ATGGACCTCA 751                                              800
FH750
FH850  GAGATGCAAG CCATGAACAA GCTGTGGAAG CCATTCGGAA AGCAGGCAAC
FH950  GAGATGCAAG CCATGAACAA GCTGTGGAAG CCATTCGGAA AGCAGGCAAC 801                                              850
FH750
FH850  CCTGTAGTCT TTATGGTATA GAGCTTTATT ACAGACCAAG G
FH950  CCTGTAGTCT TTATGGTACA GAGCATTATA AACAGACCAA GGAAATCCCC 851                                              900
FH750
FH850
FH950  TTTGCCTTCC TTGCTGCACA ACCTTTACCC TAAGTACAAC TTCAGCAGCA 901                                              950
FH750                                              GCACCCAGT
FH850                                              GCACCCAGT
FH950  CTAACCCATT TGCTGACTCT CTACAAATCA ACGCCGACAA GGCACCCAGT 951        965
FH750  CAGTCAGAGT CAGAG
FH850  CAGTCAGAGT CAGAG           FIG. 18
FH950  CAGTCAGAGT CAGAG
```

```
  1 MLEAIDKNRALJHAAERLQTKLRERGDVANEDKLSLLKSVLQSPLFSQILS 50
    |||  ||||||| ||||||:|||||| ||||||:|| .||||||||||||
  1 MLETIDKNRALQAAERLQSKLKERGDVANEDKLSLLKSVLQSPLFSQILS 50

51 LQTSVQQLKDQVNIATSATSNIEYAIRYHLSPAVIPTLQNESFLLSPNNG 100
    ||||  |||:|||    ||||||  || ||.|| :|| ||.|| ||||
 51 LQTSLQQLKQQVNVATLATANADIAHTPQFSSAIISNLQSESLLLSPSNG 100

101 NLEALTGPCI.PHINGKPACIDEFDQLIKNMAQGRIVEVFELLKPPSCGLG 149
    |||||||| |  :||||| ||||||||||  |||||||||||||||||
101 NLEAISGPCAPPANDGKPACEELDQLIKSMAQGRIVELFELLKPPCCGLG 150

150 FSVVGLRSENRGELGIFVQEIQEGSVAIRDGRLKETDQILAINQAlDQT 199
    ||||||||||||||||||||||||||||||||||||||||||||||||
151 FSVVGLRSENRGELGIFVQEIQEGSVAIRDGRLKETDQILAINQVLDQT 200

200 ITIKQAISILQKAKDTVQLVIARGSLPQLVSPIVSRSPSAASTISAISNP 249
    ||||||||||||||||||||||||||||||| :: :||||||||||:|||||
201 ITIKQAAISILQKAKDTIQLVIARGSLPHILSSPRISRSPSAASTVSAHSNP 250

250 VINIQMETIELVNDCSGLGFGIIGCKATCGVIVKTILPCGVADQHGRLCSG 299
    |||| |||||||||||||||||||||||||||||||||||||||||||||
251 TIHQAVETIELVNDCSGLGFGIIGCKATCGVIVKTILPCGVADQHGRLCSG 300

300 DHIIKIGDTDLACMSSEEQVAQVLRQCGNRVKLMIARSAIEERTAPTALGI 349
    ||||||||||||||||||||||||||||||||||||:|||  ||:  |||
301 DHIIKIGDTDLACMSSEEQVAQVLRQCGNRVKLMIARGAVEETPAPSSLGI 350

350 TLSSSPTSPELRVDASTQKGEESETFDVELTKNVQGLGITTIAGYICDKK 399
    ||||   | ||||||||| ::|||||||||||||||||||||||||||
351 TLSSS.TSTSEMRVDASTQKNEESETFDVELTKNVQGLGITTIAGYICDKK 399

400 LEPSGIFVKSITKSSAVEHDGRIQIGDQIIAVDGTNLQGFTNQQAVEVLR 449
    |||||||||||||||||||||||||||||||||||||||||||||||||
400 LEPSGIFVKSITKSSAVELDGRIQIGDQIVAVDGTNLQGFTNQQAVEVLR 449

450 HTGQTYLTLMRRGMKQEAELMSREDVTKDADLSPVNASIIKENYEKDED 499
    ||||| ||||||:| ||||  :|| ||| ||     :||||||:
450 HTGQTVRLTLMRKQASQEAEITSREDTAKDVDLP........AENYEKDEE 492

500 FLSSTRNTNILPTEEEGYPLLSAEIEEDAQKQEAALLTKMQRIMGINY 549
    ||  |.|||| ||||||||||||::||  |: |||||||||||||||||
493 SLSLKRSTSILPIEEEGYPLLSTELBETEDVQ.QEAALLTKMQRIMGINY 541

550 EIYVAINVSKPSENSGLGISLEATVGHFIRSVLPEGPVGHSGKLFSGDEL 599
    |||||||||||||||||||||||||||||||||||||||||||||||||
542 EIYVAINVSKPSENSGLGISLEATVGHFIRSVLPEGPVGHSGKLFSGDEL 591

600 LEVNGITLLGENHQDVVNILKELPIEVTMVCCKRTVPPTTQSELDSLDLC 649
    |||||:||||||:|||||||||||||||||||||||||||    |:::|
592 LEVNGINLLGENAQDVVNILKELPIDVTMVCCRRTVPPTALSEVDSLDIH 641

650 DIELTEKPHVDLGEFICGSSEPEDPVLAMTDACQGSTEEVQAPLAMTEAGIQ 699
    ||:||||||:||||||||||||||||||| |:| :||     |:||||||:
642 DLELTEKPHIDLGEFICGSSETEDPVLAMSDVDQNAEETQTPLAMTEAGIQ 691

700 HHMLEKCGSKGLGFSILDYQOPIDPASTVIIRSLVPGGIAEKDGRLLPGD 749
    | |||||:|||||||||||:|||||||||||||||||||||||||||||
692 AIELEKGSRGLGFSILDYQOPIDPANTVIVIRSLVPGGIAEKDGRLLPGD 741

750 RLMFVNDVMNLENSSLEEAVEALKGAPSGTVRIGVAKPLPLSPEEGYVSAK 799
    ||||||:|:|||||||||||||||||||||| ||||||||||||||||||
742 RLMFVNDINLENSTLEEAVEALKGAPSGCVRIGVAKPLPLSPEEGYVSAK 791

800 EDSFLVPHSCEEAGLADKPLFRADLALVGTNDADLVDESTPESPYSPEN 849
    ||:|| ||:|  ||:|| ||||:||||:|||   ||| |::|| ||:|
792 EDTFLCSPITCKEMCGLSDKALFRADLALLDTPDAESVAESRPESQFSPDN 841
```

FIG. 23

```
1750 FVSDIVKGGIADPDGRLIQGDQILLVNGEDVRNASQEAVAALLKCSLGTV 1799
     |||||||||||| ||||.||||||:|||||||||.||||||||||||||
1734 FVSDIVKGGIADADGRLMQGDQILMVNGEDVRNATQEAVAALLKCSLGTV 1783

1800 TLEVGRIKAGPFHSERRPSQTSQVSEGSLSSFTFPLSGSSTSESLESSSK 1849
     |||||||||  |||||||||.|||||  |||||. |  ||||  ||.|
1784 TLEVGRIKAAPFHSERRPSQSSQVSESSLSSFSLPRSGIHTSESSESSAK 1833

1850 KNALASEIQGLRTVEMKKGPTDSLGISIAGGVGSPLGDVPIFIAMMHPTG 1899
     ||||||||||||||.||||.||||  |.||:|||||||||||||||| |
1834 KNALASEIQGLRTVEIKKGPADALGLSIAGGVGSPLGDVPIFIAMMHPNG 1883

1900 VAAQTQKLRVGDRIVTICGTSTEGMTHTQAVNLLKNASGSIEMQVVAGGD 1949
     ||||||||||||||||||||||:|||||||||:|||||||||.|||||||
1884 VAAQTQKLRVGDRIVTICGTSTDGMTHTQAVNLMKNASGSIEVQVVAGGD 1933

1950 VSVVTGIHQEPASSSLSFTGLTSTSIFQDDLGPPQCKSITLERGPDGLGF 1999
     ||||||| || |.  |.||||||..|| ||||||| |.|||:|||||||
1934 VSVVTGHQQELANPCLAFTGLTSSTIFPDDLGPPQSKTITLDRGPDGLGF 1983

2000 SIVGGYGSPHGDLPIYVKTVFAKGAASEDGRLKRGDQIIAVNGQSLEGVT 2049
     |||||||||||||||||||||||||||.|||||||||||||||||||||
1984 SIVGGYGSPHGDLPIYVKTVFAKGAAAEDGRLKRGDQIIAVNGQSLEGVT 2033

2050 HEEAVAILKRTKGTVTLMVLS 2070
     |||||||||||||||||||||
2034 HEEAVAILKRTKGTVTLMVLS 2054
```

FIG. 24

```
        1                                                          50
PDZ-A  RHVEVFELLK .PPSGGLGFS VVGLRS.... .ENRGEL.GI FVQEIQEGSV
PDZ-B  QHMETIEL.V .NDGSGLGFG IIGGK..... ......ATGV IVKTILPGGV
PDZ-C  SETFDVELTK .N.VQGLGIT IAGYIG.... .DKKLEPSGI FVKSITKSSA
PDZ-D  YEIVVAHVSK FSENSGLGIS LEATVGHH.. .......... FIRSVLPEGP
PDZ-E  AGIQHIMLEK .G.SKGLGFS ILDYQD.... .PIDPASTVI IIRSLVPGGI
PDZ-F  SFERTINIAK .G.NSSLGMT VSANKDGL.. ........GM IVRSIIHGGA
PDZ-G  NQPRRVELWR .EPSKSLGIS IVGGRGMGSR LSNGEVMRGI FIKHVLEDRP
PDZ-H  GELHMIELEK .G.HSGLGLS LAG....... .NKDRSRMSV FIVGIDPNGA
PDZ-I  KNVQHLELPK .D.QGGLGIA IS........ ..EEDTLSGV IIKSLTEHGV
PDZ-J  GCETTIEISK .G.RTGLGLS IVG....... GSDTLLGAF IIHEVYEEGA
PDZ-K  CDTLTIELQK .KPGKGLGLS IVGKRN.... ......DTGV FVSDIVKGGI
PDZ-L  QGLRTVEMKK .GPTDSLGIS IAGGVG.... .SPLGDV.PI FIAMMHPTGV
PDZ-M  PQCKSITLER .GP.DGLGFS IVGGYG.... .SPHGDL.PI YVKTVFAKGA 51                                                          97
PDZ-A  AHRDGRLKET DQILAINGQA LDQTITHQQA ISILQKAKDT VQLVIAR
PDZ-B  ADQHGRLCSG DHILKIGDTD LA.GMSSEQV AQVLRQCGNR VKLMIAR
PDZ-C  VEHDGRIQIG DQIIAVDGTN L.QGFTNQQA VEVLRHTGQT VLLTLMR
PDZ-D  VGHSGKLFSG DELLEVNGIT LL.GENHQDV VNILKELPIE VTMVCCR
PDZ-E  AEKDGRLLPG DRLMFVNDVN L.ENSSLEEA VEALKGAPSG TVRIGVA
PDZ-F  ISRDGRIAIG DCILSINEES TI.SVTNAQA RAMLRRHSLI GPDIKIT
PDZ-G  AGKNGTLKPG DRIVEVDGMD LRD.ASHEQA VEAIRKAGNP VVFMVQS
PDZ-H  AGKDGRLQIA DELLEINGQI L.YGRSHQNA SSIIKCAPSK VKIIFIR
PDZ-I  AATDGRLKVG DQILAVDDEI V.VGYPIEKF ISLLKTAKMT VKLTIHA
PDZ-J  ACKDGRLWAG DQILEVNGID L.RKATHDEA INVLRQTPQR VRLTLYR
PDZ-K  ADPDGRLIQG DQILLVNGED VR.NASQEAV AALLKCSLGT VTLEVGR
PDZ-L  AAQTQKLRVG DRIVTICGTS T.EGMTHTQA VNLLKNASGS IEMQVVA
PDZ-M  ASEDGRLKRG DQIIAVNGQS L.EGVTHEEA VAILKRTKGT VTLMVLS
```

FIG. 25

SEQUENCE LISTING

<160> NUMBER OF SEQ ID NOS: 93

<210> SEQ ID NO 1
<211> LENGTH: 1373
<212> TYPE: PRT
<213> ORGANISM: Homo sapiens

<400> SEQUENCE: 1

```
Met Val Cys Cys Arg Arg Thr Val Pro Pro Thr Thr Gln Ser Glu Leu
 1               5                  10                  15

Asp Ser Leu Asp Leu Cys Asp Ile Glu Leu Thr Glu Lys Pro His Val
            20                  25                  30

Asp Leu Gly Glu Phe Ile Gly Ser Ser Glu Thr Glu Asp Pro Val Leu
        35                  40                  45

Ala Met Thr Asp Ala Gly Gln Ser Thr Glu Glu Val Gln Ala Pro Leu
    50                  55                  60

Ala Met Trp Glu Ala Gly Ile Gln His Ile Glu Leu Glu Lys Gly Ser
65                  70                  75                  80

Lys Gly Leu Gly Phe Ser Ile Leu Asp Tyr Gln Asp Pro Ile Asp Pro
                85                  90                  95

Ala Ser Thr Val Ile Ile Ile Arg Ser Leu Val Pro Gly Gly Ile Ala
               100                 105                 110

Glu Lys Asp Gly Arg Leu Leu Pro Gly Asp Arg Leu Met Phe Val Asn
            115                 120                 125

Asp Val Asn Leu Glu Asn Ser Ser Leu Glu Glu Ala Val Glu Ala Leu
        130                 135                 140

Lys Gly Ala Pro Ser Gly Thr Val Arg Ile Gly Val Ala Lys Pro Leu
145                 150                 155                 160

Pro Leu Ser Pro Glu Glu Gly Tyr Val Ser Ala Lys Glu Asp Ser Phe
                165                 170                 175

Leu Tyr Pro Pro His Ser Cys Glu Glu Ala Gly Leu Ala Asp Lys Pro
            180                 185                 190

Leu Phe Arg Ala Asp Leu Ala Leu Val Gly Thr Asn Asp Ala Asp Leu
        195                 200                 205

Val Asp Glu Ser Thr Phe Glu Ser Pro Tyr Ser Pro Glu Asn Asp Ser
    210                 215                 220

Ile Tyr Ser Thr Gln Ala Ser Ile Leu Ser Leu His Gly Ser Ser Cys
225                 230                 235                 240

Gly Asp Gly Leu Asn Tyr Gly Ser Ser Leu Pro Ser Ser Pro Pro Lys
                245                 250                 255

Asp Val Ile Glu Asn Ser Cys Asp Pro Val Leu Asp Leu His Met Ser
            260                 265                 270

Leu Glu Glu Leu Tyr Thr Gln Asn Leu Leu Glu Arg Gln Asp Glu Asn
        275                 280                 285
```

-continued

```
Thr Pro Ser Val Asp Ile Ser Met Gly Pro Ala Ser Gly Phe Thr Ile
    290                 295                 300
Asn Asp Tyr Thr Pro Ala Asn Ala Ile Glu Gln Gln Tyr Glu Cys Glu
305                 310                 315                 320
Asn Thr Ile Val Trp Thr Glu Ser His Leu Pro Ser Glu Val Ile Ser
                325                 330                 335
Ser Ala Glu Leu Pro Ser Val Leu Pro Asp Ser Ala Gly Lys Gly Ser
            340                 345                 350
Glu His Leu Leu Glu Gln Ser Ser Leu Ala Cys Asn Ala Glu Cys Val
            355                 360                 365
Met Leu Gln Asn Val Ser Lys Glu Ser Phe Glu Arg Thr Ile Asn Ile
    370                 375                 380
Ala Lys Gly Asn Ser Ser Leu Gly Met Thr Val Ser Ala Asn Lys Asp
385                 390                 395                 400
Gly Leu Gly Met Ile Val Arg Ser Ile Ile His Gly Gly Ala Ile Ser
                405                 410                 415
Arg Asp Gly Arg Ile Ala Ile Gly Asp Cys Ile Leu Ser Ile Asn Glu
            420                 425                 430
Glu Ser Thr Ile Ser Val Thr Asn Ala Gln Ala Arg Ala Met Leu Arg
            435                 440                 445
Arg His Ser Leu Ile Gly Pro Asp Ile Lys Ile Thr Tyr Val Pro Ala
    450                 455                 460
Glu His Leu Glu Glu Phe Lys Ile Ser Leu Gly Gln Gln Ser Gly Arg
465                 470                 475                 480
Val Met Ala Leu Asp Ile Phe Ser Ser Tyr Thr Gly Arg Asp Ile Pro
                485                 490                 495
Glu Leu Pro Glu Arg Glu Glu Gly Glu Glu Ser Glu Leu Gln
            500                 505                 510
Asn Thr Ala Tyr Ser Asn Trp Asn Gln Pro Arg Arg Val Glu Leu Trp
            515                 520                 525
Arg Glu Pro Ser Lys Ser Leu Gly Ile Ser Ile Val Gly Gly Arg Gly
    530                 535                 540
Met Gly Ser Arg Leu Ser Asn Gly Glu Val Met Arg Gly Ile Phe Ile
545                 550                 555                 560
Lys His Val Leu Glu Asp Ser Pro Ala Gly Lys Asn Gly Thr Leu Lys
                565                 570                 575
Pro Gly Asp Arg Ile Val Glu Ala Pro Ser Gln Ser Glu Ser Glu Pro
            580                 585                 590
Glu Lys Ala Pro Leu Cys Ser Val Pro Pro Pro Ser Ala Phe
            595                 600                 605
Ala Glu Met Gly Ser Asp His Thr Gln Ser Ser Ala Ser Lys Ile Ser
    610                 615                 620
Gln Asp Val Asp Lys Glu Asp Glu Phe Gly Tyr Ser Trp Lys Asn Ile
625                 630                 635                 640
Arg Glu Arg Tyr Gly Thr Leu Thr Gly Glu Leu His Met Ile Glu Leu
                645                 650                 655
Glu Lys Gly His Ser Gly Leu Gly Leu Ser Leu Ala Gly Asn Lys Asp
            660                 665                 670
Arg Ser Arg Met Ser Val Phe Ile Val Gly Ile Asp Pro Asn Gly Ala
            675                 680                 685
Ala Gly Lys Asp Gly Arg Leu Gln Ile Ala Asp Glu Leu Leu Glu Ile
    690                 695                 700
```

-continued

```
Asn Gly Gln Ile Leu Tyr Gly Arg Ser His Gln Asn Ala Ser Ser Ile
705                 710                 715                 720

Ile Lys Cys Ala Pro Ser Lys Val Lys Ile Phe Ile Arg Asn Lys
                725                 730                 735

Asp Ala Val Asn Gln Met Ala Val Cys Pro Gly Asn Ala Val Glu Pro
            740                 745                 750

Leu Pro Ser Asn Ser Glu Asn Leu Gln Asn Lys Glu Thr Glu Pro Thr
        755                 760                 765

Val Thr Thr Ser Asp Ala Ala Val Asp Leu Ser Ser Phe Lys Asn Val
    770                 775                 780

Gln His Leu Glu Leu Pro Lys Asp Gln Gly Gly Leu Gly Ile Ala Ile
785                 790                 795                 800

Ser Glu Glu Asp Thr Leu Ser Gly Val Ile Ile Lys Ser Leu Thr Glu
                805                 810                 815

His Gly Val Ala Ala Thr Asp Gly Arg Leu Lys Val Gly Asp Gln Ile
            820                 825                 830

Leu Ala Val Asp Asp Glu Ile Val Val Gly Tyr Pro Ile Glu Lys Phe
        835                 840                 845

Ile Ser Leu Leu Lys Thr Ala Lys Met Thr Val Lys Leu Thr Ile His
850                 855                 860

Ala Glu Asn Pro Asp Ser Gln Ala Val Pro Ser Ala Ala Gly Ala Ala
865                 870                 875                 880

Ser Gly Glu Lys Lys Asn Ser Ser Gln Ser Leu Met Val Pro Gln Ser
                885                 890                 895

Gly Ser Pro Glu Pro Glu Ser Ile Arg Asn Thr Ser Arg Ser Ser Thr
            900                 905                 910

Pro Ala Ile Phe Ala Ser Asp Pro Ala Thr Cys Pro Ile Ile Pro Gly
        915                 920                 925

Cys Glu Thr Thr Ile Glu Ile Ser Lys Gly Arg Thr Gly Leu Gly Leu
    930                 935                 940

Ser Ile Val Gly Gly Ser Asp Thr Leu Leu Gly Ala Phe Ile Ile His
945                 950                 955                 960

Glu Val Tyr Glu Glu Gly Ala Ala Cys Lys Asp Gly Arg Leu Trp Ala
                965                 970                 975

Gly Asp Gln Ile Leu Glu Val Asn Gly Ile Asp Leu Arg Lys Ala Thr
            980                 985                 990

His Asp Glu Ala Ile Asn Val Leu Arg Gln Thr Pro Gln Arg Val Arg
        995                 1000                1005

Leu Thr Leu Tyr Arg Asp Glu Ala Pro Tyr Lys Glu Glu Val Cys
    1010                1015                1020

Asp Thr Leu Thr Ile Glu Leu Gln Lys Lys Pro Gly Lys Gly Leu Gly
1025                1030                1035                1040

Leu Ser Ile Val Gly Lys Arg Asn Asp Thr Gly Val Phe Val Ser Asp
            1045                1050                1055

Ile Val Lys Gly Gly Ile Ala Asp Pro Asp Gly Arg Leu Ile Gln Gly
        1060                1065                1070

Asp Gln Ile Leu Leu Val Asn Gly Glu Asp Val Arg Asn Ala Ser Gln
    1075                1080                1085

Glu Ala Val Ala Ala Leu Leu Lys Cys Ser Leu Gly Thr Val Thr Leu
    1090                1095                1100

Glu Val Gly Arg Ile Lys Ala Gly Pro Phe His Ser Glu Arg Arg Pro
1105                1110                1115                1120

Ser Gln Thr Ser Gln Val Ser Glu Gly Ser Leu Ser Ser Phe Thr Phe
```

```
                    1125                1130                1135
Pro Leu Ser Gly Ser Ser Thr Ser Glu Ser Leu Glu Ser Ser Lys
            1140                1145                1150

Lys Asn Ala Leu Ala Ser Glu Ile Gln Gly Leu Arg Thr Val Glu Met
            1155                1160                1165

Lys Lys Gly Pro Thr Asp Ser Leu Gly Ile Ser Ile Ala Gly Gly Val
            1170                1175                1180

Gly Ser Pro Leu Gly Asp Val Pro Ile Phe Ile Ala Met Met His Pro
1185                1190                1195                1200

Thr Gly Val Ala Ala Gln Thr Gln Lys Leu Arg Val Gly Asp Arg Ile
            1205                1210                1215

Val Thr Ile Cys Gly Thr Ser Thr Glu Gly Met Thr His Thr Gln Ala
            1220                1225                1230

Val Asn Leu Leu Lys Asn Ala Ser Gly Ser Ile Glu Met Gln Val Val
            1235                1240                1245

Ala Gly Gly Asp Val Ser Val Val Thr Gly His His Gln Glu Pro Ala
            1250                1255                1260

Ser Ser Ser Leu Ser Phe Thr Gly Leu Thr Ser Thr Ser Ile Phe Gln
1265                1270                1275                1280

Asp Asp Leu Gly Pro Pro Gln Cys Lys Ser Ile Thr Leu Glu Arg Gly
            1285                1290                1295

Pro Asp Gly Leu Gly Phe Ser Ile Val Gly Gly Tyr Gly Ser Pro His
            1300                1305                1310

Gly Asp Leu Pro Ile Tyr Val Lys Thr Val Phe Ala Lys Gly Ala Ala
            1315                1320                1325

Ser Glu Asp Gly Arg Leu Lys Arg Gly Asp Gln Ile Ile Ala Val Asn
            1330                1335                1340

Gly Gln Ser Leu Glu Gly Val Thr His Glu Glu Ala Val Ala Ile Leu
1345                1350                1355                1360

Lys Arg Thr Lys Gly Thr Val Thr Leu Met Val Leu Ser
            1365                1370

<210> SEQ ID NO 2
<211> LENGTH: 1005
<212> TYPE: PRT
<213> ORGANISM: Homo sapiens

<400> SEQUENCE: 2

Met Leu Gln Asn Val Ser Lys Glu Ser Phe Glu Arg Thr Ile Asn Ile
  1               5                  10                  15

Ala Lys Gly Asn Ser Ser Leu Gly Met Thr Val Ser Ala Asn Lys Asp
                 20                  25                  30

Gly Leu Gly Met Ile Val Arg Ser Ile Ile His Gly Gly Ala Ile Ser
             35                  40                  45

Arg Asp Gly Arg Ile Ala Ile Gly Asp Cys Ile Leu Ser Ile Asn Glu
         50                  55                  60

Glu Ser Thr Ile Ser Val Thr Asn Ala Gln Ala Arg Ala Met Leu Arg
 65                  70                  75                  80

Arg His Ser Leu Ile Gly Pro Asp Ile Lys Ile Thr Tyr Val Pro Ala
                 85                  90                  95

Glu His Leu Glu Glu Phe Lys Ile Ser Leu Gly Gln Gln Ser Gly Arg
                100                 105                 110

Val Met Ala Leu Asp Ile Phe Ser Ser Tyr Thr Gly Arg Asp Ile Pro
            115                 120                 125
```

-continued

```
Glu Leu Pro Glu Arg Glu Gly Glu Gly Glu Ser Glu Leu Gln
    130                 135             140

Asn Thr Ala Tyr Ser Asn Trp Asn Gln Pro Arg Arg Val Glu Leu Trp
145                 150                 155                 160

Arg Glu Pro Ser Lys Ser Leu Gly Ile Ser Ile Val Gly Gly Arg Gly
                165                 170                 175

Met Gly Ser Arg Leu Ser Asn Gly Glu Val Met Arg Gly Ile Phe Ile
            180                 185                 190

Lys His Val Leu Glu Asp Ser Pro Ala Gly Lys Asn Gly Thr Leu Lys
        195                 200                 205

Pro Gly Asp Arg Ile Val Glu Ala Pro Ser Gln Ser Glu Ser Glu Pro
    210                 215                 220

Glu Lys Ala Pro Leu Cys Ser Val Pro Pro Pro Ser Ala Phe
225                 230                 235             240

Ala Glu Met Gly Ser Asp His Thr Gln Ser Ser Ala Ser Lys Ile Ser
                245                 250                 255

Gln Asp Val Asp Lys Glu Asp Glu Phe Gly Tyr Ser Trp Lys Asn Ile
            260                 265                 270

Arg Glu Arg Tyr Gly Thr Leu Thr Gly Glu Leu His Met Ile Glu Leu
        275                 280                 285

Glu Lys Gly His Ser Gly Leu Gly Leu Ser Leu Ala Gly Asn Lys Asp
    290                 295                 300

Arg Ser Arg Met Ser Val Phe Ile Val Gly Ile Asp Pro Asn Gly Ala
305                 310                 315                 320

Ala Gly Lys Asp Gly Arg Leu Gln Ile Ala Asp Glu Leu Leu Glu Ile
                325                 330                 335

Asn Gly Gln Ile Leu Tyr Gly Arg Ser His Gln Asn Ala Ser Ser Ile
            340                 345                 350

Ile Lys Cys Ala Pro Ser Lys Val Lys Ile Ile Phe Ile Arg Asn Lys
        355                 360                 365

Asp Ala Val Asn Gln Met Ala Val Cys Pro Gly Asn Ala Val Glu Pro
    370                 375                 380

Leu Pro Ser Asn Ser Glu Asn Leu Gln Asn Lys Glu Thr Glu Pro Thr
385                 390                 395                 400

Val Thr Thr Ser Asp Ala Ala Val Asp Leu Ser Ser Phe Lys Asn Val
                405                 410                 415

Gln His Leu Glu Leu Pro Lys Asp Gln Gly Leu Gly Ile Ala Ile
            420                 425                 430

Ser Glu Glu Asp Thr Leu Ser Gly Val Ile Ile Lys Ser Leu Thr Glu
        435                 440                 445

His Gly Val Ala Ala Thr Asp Gly Arg Leu Lys Val Gly Asp Gln Ile
    450                 455                 460

Leu Ala Val Asp Asp Glu Ile Val Val Gly Tyr Pro Ile Glu Lys Phe
465                 470                 475                 480

Ile Ser Leu Leu Lys Thr Ala Lys Met Thr Val Lys Leu Thr Ile His
                485                 490                 495

Ala Glu Asn Pro Asp Ser Gln Ala Val Pro Ser Ala Ala Gly Ala Ala
            500                 505                 510

Ser Gly Glu Lys Lys Asn Ser Ser Gln Ser Leu Met Val Pro Gln Ser
        515                 520                 525

Gly Ser Pro Glu Pro Glu Ser Ile Arg Asn Thr Ser Arg Ser Ser Thr
    530                 535                 540

Pro Ala Ile Phe Ala Ser Asp Pro Ala Thr Cys Pro Ile Ile Pro Gly
```

-continued

```
            545                 550                 555                 560
       Cys Glu Thr Thr Ile Glu Ile Ser Lys Gly Arg Thr Gly Leu Gly Leu
                       565                 570                 575
       Ser Ile Val Gly Gly Ser Asp Thr Leu Leu Gly Ala Phe Ile Ile His
                       580                 585                 590
       Glu Val Tyr Glu Glu Gly Ala Ala Cys Lys Asp Gly Arg Leu Trp Ala
                       595                 600                 605
       Gly Asp Gln Ile Leu Glu Val Asn Gly Ile Asp Leu Arg Lys Ala Thr
                       610                 615                 620
       His Asp Glu Ala Ile Asn Val Leu Arg Gln Thr Pro Gln Arg Val Arg
       625                 630                 635                 640
       Leu Thr Leu Tyr Arg Asp Glu Ala Pro Tyr Lys Glu Glu Val Cys
                       645                 650                 655
       Asp Thr Leu Thr Ile Glu Leu Gln Lys Lys Pro Gly Lys Gly Leu Gly
                       660                 665                 670
       Leu Ser Ile Val Gly Lys Arg Asn Asp Thr Gly Val Phe Val Ser Asp
                       675                 680                 685
       Ile Val Lys Gly Gly Ile Ala Asp Pro Asp Gly Arg Leu Ile Gln Gly
                       690                 695                 700
       Asp Gln Ile Leu Leu Val Asn Gly Glu Asp Val Arg Asn Ala Ser Gln
       705                 710                 715                 720
       Glu Ala Val Ala Ala Leu Leu Lys Cys Ser Leu Gly Thr Val Thr Leu
                       725                 730                 735
       Glu Val Gly Arg Ile Lys Ala Gly Pro Phe His Ser Glu Arg Arg Pro
                       740                 745                 750
       Ser Gln Thr Ser Gln Val Ser Glu Gly Ser Leu Ser Ser Phe Thr Phe
                       755                 760                 765
       Pro Leu Ser Gly Ser Ser Thr Ser Glu Ser Leu Glu Ser Ser Ser Lys
                       770                 775                 780
       Lys Asn Ala Leu Ala Ser Glu Ile Gln Gly Leu Arg Thr Val Glu Met
       785                 790                 795                 800
       Lys Lys Gly Pro Thr Asp Ser Leu Gly Ile Ser Ile Ala Gly Gly Val
                       805                 810                 815
       Gly Ser Pro Leu Gly Asp Val Pro Ile Phe Ile Ala Met Met His Pro
                       820                 825                 830
       Thr Gly Val Ala Ala Gln Thr Gln Lys Leu Arg Val Gly Asp Arg Ile
                       835                 840                 845
       Val Thr Ile Cys Gly Thr Ser Thr Glu Gly Met Thr His Thr Gln Ala
                       850                 855                 860
       Val Asn Leu Leu Lys Asn Ala Ser Gly Ser Ile Glu Met Gln Val Val
       865                 870                 875                 880
       Ala Gly Gly Asp Val Ser Val Val Thr Gly His His Gln Glu Pro Ala
                       885                 890                 895
       Ser Ser Ser Leu Ser Phe Thr Gly Leu Thr Ser Thr Ser Ile Phe Gln
                       900                 905                 910
       Asp Asp Leu Gly Pro Pro Gln Cys Lys Ser Ile Thr Leu Glu Arg Gly
                       915                 920                 925
       Pro Asp Gly Leu Gly Phe Ser Ile Val Gly Gly Tyr Gly Ser Pro His
                       930                 935                 940
       Gly Asp Leu Pro Ile Tyr Val Lys Thr Val Phe Ala Lys Gly Ala Ala
       945                 950                 955                 960
       Ser Glu Asp Gly Arg Leu Lys Arg Gly Asp Gln Ile Ile Ala Val Asn
                       965                 970                 975
```

-continued

```
Gly Gln Ser Leu Glu Gly Val Thr His Glu Ala Val Ala Ile Leu
            980                 985                 990
Lys Arg Thr Lys Gly Thr Val Thr Leu Met Val Leu Ser
            995                1000                1005

<210> SEQ ID NO 3
<211> LENGTH: 4880
<212> TYPE: DNA
<213> ORGANISM: Homo sapiens
<220> FEATURE:
<221> NAME/KEY: CDS
<222> LOCATION: (292)...(4410)

<400> SEQUENCE: 3
cccgggcccg ggcgacagtg ggacatcatt ttatccgatc tgttctacca gagggtcctg      60
ttggacacag cgggaagctc ttcagtggag acgagctatt ggaaaataag taacgcattc    120
agatgtttaa atcacagag aatacaaaga taaagaatgg aaaagggtct ccttcctgtc     180
ccaattcatc cagttctcat caccccttcat taggtaaatg cataactttt acttggggaa    240
aatcaccaag atgtggtgaa tatcttaaaa gaactgccta tagaagtgac a atg gtg      297
                                                         Met Val
                                                           1 tgc tgt cgt cga act gtg cca ccc acc acc caa tca gaa ttg gat agc      345
Cys Cys Arg Arg Thr Val Pro Pro Thr Thr Gln Ser Glu Leu Asp Ser
         5                  10                  15 ctg gac tta tgt gat att gag cta aca gaa aag cct cac gta gat cta      393
Leu Asp Leu Cys Asp Ile Glu Leu Thr Glu Lys Pro His Val Asp Leu
     20                  25                  30 ggt gag ttc atc ggg tca tca gag aca gag gat cca gtg ctg gcg atg      441
Gly Glu Phe Ile Gly Ser Ser Glu Thr Glu Asp Pro Val Leu Ala Met
 35                  40                  45                  50 act gat gcg ggt cag agt aca gaa gag gtt caa gca cct ttg gcc atg      489
Thr Asp Ala Gly Gln Ser Thr Glu Glu Val Gln Ala Pro Leu Ala Met
             55                  60                  65 tgg gag gct ggc att cag cac ata gag ctg gag aaa ggg agc aaa gga      537
Trp Glu Ala Gly Ile Gln His Ile Glu Leu Glu Lys Gly Ser Lys Gly
         70                  75                  80 ctt ggt ttt agc att tta gat tat cag gat cca att gat cca gca agc      585
Leu Gly Phe Ser Ile Leu Asp Tyr Gln Asp Pro Ile Asp Pro Ala Ser
     85                  90                  95 act gtg att ata att cgt tct ttg gtg cct ggc ggc att gct gaa aag      633
Thr Val Ile Ile Ile Arg Ser Leu Val Pro Gly Gly Ile Ala Glu Lys
100                 105                 110 gat gga cga ctt ctt cct ggt gac cga ctc atg ttt gta aac gat gtt      681
Asp Gly Arg Leu Leu Pro Gly Asp Arg Leu Met Phe Val Asn Asp Val
115                 120                 125                 130 aac ttg gaa aac agc agt ctt gag gaa gct gta gaa gca ctg aag gga      729
Asn Leu Glu Asn Ser Ser Leu Glu Glu Ala Val Glu Ala Leu Lys Gly
             135                 140                 145 gca ccg tca ggg act gtg aga ata gga gtt gct aag cct tta ccc ctt      777
Ala Pro Ser Gly Thr Val Arg Ile Gly Val Ala Lys Pro Leu Pro Leu
         150                 155                 160 tca cca gaa gaa ggt tat gtt tct gct aag gag gat tcc ttt ctc tac      825
Ser Pro Glu Glu Gly Tyr Val Ser Ala Lys Glu Asp Ser Phe Leu Tyr
     165                 170                 175 cca cca cac tcc tgt gag gaa gca ggg ctg gct gac aaa ccc ctc ttc      873
Pro Pro His Ser Cys Glu Glu Ala Gly Leu Ala Asp Lys Pro Leu Phe
180                 185                 190 agg gct gac ttg gct ctg gtg ggc aca aat gat gct gac tta gta gat      921
```

```
                                                          -continued

Arg Ala Asp Leu Ala Leu Val Gly Thr Asn Asp Ala Asp Leu Val Asp
195                 200                 205                 210 gaa tcc aca ttt gag tct cca tac tct cct gaa aat gac agc atc tac    969
Glu Ser Thr Phe Glu Ser Pro Tyr Ser Pro Glu Asn Asp Ser Ile Tyr
                215                 220                 225 tct act caa gcc tct att tta tct ctt cat ggc agt tct tgt ggt gat    1017
Ser Thr Gln Ala Ser Ile Leu Ser Leu His Gly Ser Ser Cys Gly Asp
                230                 235                 240 ggc ctg aac tat ggt tct tcc ctt cca tca tct cct cct aag gat gtt    1065
Gly Leu Asn Tyr Gly Ser Ser Leu Pro Ser Ser Pro Pro Lys Asp Val
                245                 250                 255 att gaa aat tct tgt gat cca gta ctt gat ctg cat atg tct ctg gag    1113
Ile Glu Asn Ser Cys Asp Pro Val Leu Asp Leu His Met Ser Leu Glu
260                 265                 270 gaa cta tat acc cag aat ctc ctg gaa aga cag gat gag aat aca cct    1161
Glu Leu Tyr Thr Gln Asn Leu Leu Glu Arg Gln Asp Glu Asn Thr Pro
275                 280                 285                 290 tcg gtg gac ata agt atg ggg cct gct tct ggc ttt act ata aat gac    1209
Ser Val Asp Ile Ser Met Gly Pro Ala Ser Gly Phe Thr Ile Asn Asp
                295                 300                 305 tac aca cct gca aat gct att gaa caa caa tat gaa tgt gaa aac aca    1257
Tyr Thr Pro Ala Asn Ala Ile Glu Gln Gln Tyr Glu Cys Glu Asn Thr
                310                 315                 320 ata gtg tgg act gaa tct cat tta cca agt gaa gtt ata tca agt gca    1305
Ile Val Trp Thr Glu Ser His Leu Pro Ser Glu Val Ile Ser Ser Ala
                325                 330                 335 gaa ctt cct tct gtg cta ccc gat tca gct gga aag ggc tct gag cac    1353
Glu Leu Pro Ser Val Leu Pro Asp Ser Ala Gly Lys Gly Ser Glu His
340                 345                 350 ctt ctt gaa cag agc tcc ctg gcc tgt aat gct gag tgt gtc atg ctt    1401
Leu Leu Glu Gln Ser Ser Leu Ala Cys Asn Ala Glu Cys Val Met Leu
355                 360                 365                 370 caa aat gta tct aaa gaa tct ttt gaa agg act att aat ata gca aaa    1449
Gln Asn Val Ser Lys Glu Ser Phe Glu Arg Thr Ile Asn Ile Ala Lys
                375                 380                 385 ggc aat tct agc cta gga atg aca gtt agt gct aat aaa gat ggc ttg    1497
Gly Asn Ser Ser Leu Gly Met Thr Val Ser Ala Asn Lys Asp Gly Leu
                390                 395                 400 ggg atg atc gtt cga agc att att cat gga ggt gcc att agt cga gat    1545
Gly Met Ile Val Arg Ser Ile Ile His Gly Gly Ala Ile Ser Arg Asp
                405                 410                 415 ggc cgg att gcc att ggg gac tgc atc ttg tcc att aat gaa gag tct    1593
Gly Arg Ile Ala Ile Gly Asp Cys Ile Leu Ser Ile Asn Glu Glu Ser
                420                 425                 430 acc atc agt gta acc aat gcc cag gca cga gct atg ttg aga aga cat    1641
Thr Ile Ser Val Thr Asn Ala Gln Ala Arg Ala Met Leu Arg Arg His
435                 440                 445                 450 tct ctc att ggc cct gac ata aaa att act tat gtg cct gca gaa cat    1689
Ser Leu Ile Gly Pro Asp Ile Lys Ile Thr Tyr Val Pro Ala Glu His
                455                 460                 465 ttg gaa gag ttc aaa ata agc ttg gga caa caa tct gga aga gta atg    1737
Leu Glu Glu Phe Lys Ile Ser Leu Gly Gln Gln Ser Gly Arg Val Met
                470                 475                 480 gca ctg gat att ttt tct tca tac act ggc aga gac att cca gaa tta    1785
Ala Leu Asp Ile Phe Ser Ser Tyr Thr Gly Arg Asp Ile Pro Glu Leu
                485                 490                 495 cca gag cga gaa gag gga gag ggt gaa gaa agc gaa ctt caa aac aca    1833
Pro Glu Arg Glu Glu Gly Glu Gly Glu Glu Ser Glu Leu Gln Asn Thr
500                 505                 510
```

-continued

| | | |
|---|---|---|
| gca tat agc aat tgg aat cag ccc agg cgg gtg gaa ctc tgg aga gaa<br>Ala Tyr Ser Asn Trp Asn Gln Pro Arg Arg Val Glu Leu Trp Arg Glu<br>515                   520                   525                530 | 1881 |
| cca agc aaa tcc tta ggc atc agc att gtt ggt gga cga ggg atg ggg<br>Pro Ser Lys Ser Leu Gly Ile Ser Ile Val Gly Gly Arg Gly Met Gly<br>                     535                   540                   545 | 1929 |
| agt cgg cta agc aat gga gaa gtg atg agg ggc att ttc atc aaa cat<br>Ser Arg Leu Ser Asn Gly Glu Val Met Arg Gly Ile Phe Ile Lys His<br>550                   555                   560 | 1977 |
| gtt ctg gaa gat agt cca gct ggc aaa aat gga acc ttg aaa cct gga<br>Val Leu Glu Asp Ser Pro Ala Gly Lys Asn Gly Thr Leu Lys Pro Gly<br>                  565                   570                   575 | 2025 |
| gat aga atc gta gag gca ccc agt cag tca gag tca gag cca gag aag<br>Asp Arg Ile Val Glu Ala Pro Ser Gln Ser Glu Ser Glu Pro Glu Lys<br>580                   585                   590 | 2073 |
| gct cca ttg tgc agt gtg ccc cca ccc cct cct tca gcc ttt gcc gaa<br>Ala Pro Leu Cys Ser Val Pro Pro Pro Pro Pro Ser Ala Phe Ala Glu<br>595                   600                   605                610 | 2121 |
| atg ggt agt gat cac aca cag tca tct gca agc aaa atc tca caa gat<br>Met Gly Ser Asp His Thr Gln Ser Ser Ala Ser Lys Ile Ser Gln Asp<br>                  615                   620                   625 | 2169 |
| gtg gac aaa gag gat gag ttt ggt tac agc tgg aaa aat atc aga gag<br>Val Asp Lys Glu Asp Glu Phe Gly Tyr Ser Trp Lys Asn Ile Arg Glu<br>630                   635                   640 | 2217 |
| cgt tat gga acc cta aca ggc gag ctg cat atg att gaa ctg gag aaa<br>Arg Tyr Gly Thr Leu Thr Gly Glu Leu His Met Ile Glu Leu Glu Lys<br>                  645                   650                   655 | 2265 |
| ggt cat agt ggt ttg ggc cta agt ctt gct ggg aac aaa gac cga tcc<br>Gly His Ser Gly Leu Gly Leu Ser Leu Ala Gly Asn Lys Asp Arg Ser<br>660                   665                   670 | 2313 |
| agg atg agt gtc ttc ata gtg ggg att gat cca aat gga gct gca gga<br>Arg Met Ser Val Phe Ile Val Gly Ile Asp Pro Asn Gly Ala Ala Gly<br>675                   680                   685                690 | 2361 |
| aaa gat ggt cga ttg caa att gca gat gag ctt cta gag atc aat ggt<br>Lys Asp Gly Arg Leu Gln Ile Ala Asp Glu Leu Leu Glu Ile Asn Gly<br>                  695                   700                   705 | 2409 |
| cag att tta tat gga aga agt cat cag aat gcc tca tca atc att aaa<br>Gln Ile Leu Tyr Gly Arg Ser His Gln Asn Ala Ser Ser Ile Ile Lys<br>710                   715                   720 | 2457 |
| tgt gcc cct tct aaa gtg aaa ata att ttt atc aga aat aaa gat gca<br>Cys Ala Pro Ser Lys Val Lys Ile Ile Phe Ile Arg Asn Lys Asp Ala<br>                  725                   730                   735 | 2505 |
| gtg aat cag atg gcc gta tgt cct gga aat gca gta gaa cct ttg cct<br>Val Asn Gln Met Ala Val Cys Pro Gly Asn Ala Val Glu Pro Leu Pro<br>740                   745                   750 | 2553 |
| tct aac tca gaa aat ctt caa aat aag gag aca gag cca act gtt act<br>Ser Asn Ser Glu Asn Leu Gln Asn Lys Glu Thr Glu Pro Thr Val Thr<br>755                   760                   765                770 | 2601 |
| act tct gat gca gct gtg gac ctc agt tca ttt aaa aat gtg caa cat<br>Thr Ser Asp Ala Ala Val Asp Leu Ser Ser Phe Lys Asn Val Gln His<br>                  775                   780                   785 | 2649 |
| ctg gag ctt ccc aag gat cag ggg ggt ttg ggt att gct atc agc gaa<br>Leu Glu Leu Pro Lys Asp Gln Gly Gly Leu Gly Ile Ala Ile Ser Glu<br>790                   795                   800 | 2697 |
| gaa gat aca ctc agt gga gtc atc ata aag agc tta aca gag cat ggg<br>Glu Asp Thr Leu Ser Gly Val Ile Ile Lys Ser Leu Thr Glu His Gly<br>                  805                   810                   815 | 2745 |
| gta gca gcc acg gat gga cga ctc aaa gtc gga gat cag ata ctg gct<br>Val Ala Ala Thr Asp Gly Arg Leu Lys Val Gly Asp Gln Ile Leu Ala<br>820                   825                   830 | 2793 |

```
gta gat gat gaa att gtt gtt ggt tac cct att gaa aag ttt att agc     2841
Val Asp Asp Glu Ile Val Val Gly Tyr Pro Ile Glu Lys Phe Ile Ser
835                 840                 845                 850 ctt ctg aag aca gca aag atg aca gta aaa ctt acc atc cat gct gag     2889
Leu Leu Lys Thr Ala Lys Met Thr Val Lys Leu Thr Ile His Ala Glu
                855                 860                 865 aat cca gat tcc cag gct gtt cct tca gca gct ggt gca gcc agt gga     2937
Asn Pro Asp Ser Gln Ala Val Pro Ser Ala Ala Gly Ala Ala Ser Gly
        870                 875                 880 gaa aaa aag aac agc tcc cag tct ctg atg gtc cca cag tct ggc tcc     2985
Glu Lys Lys Asn Ser Ser Gln Ser Leu Met Val Pro Gln Ser Gly Ser
885                 890                 895 cca gaa ccg gag tcc atc cga aat aca agc aga tca tca aca cca gca     3033
Pro Glu Pro Glu Ser Ile Arg Asn Thr Ser Arg Ser Ser Thr Pro Ala
        900                 905                 910 att ttt gct tct gat cct gca acc tgc ccc att atc cct ggc tgc gaa     3081
Ile Phe Ala Ser Asp Pro Ala Thr Cys Pro Ile Ile Pro Gly Cys Glu
915                 920                 925                 930 aca acc atc gag att tcc aaa ggg cga aca ggg ctg ggc ctg agc atc     3129
Thr Thr Ile Glu Ile Ser Lys Gly Arg Thr Gly Leu Gly Leu Ser Ile
                935                 940                 945 gtt ggg ggt tca gac acg ctg ctg ggt gcc ttt att atc cat gaa gtt     3177
Val Gly Gly Ser Asp Thr Leu Leu Gly Ala Phe Ile Ile His Glu Val
        950                 955                 960 tat gaa gaa gga gca gca tgt aaa gat gga aga ctc tgg gct gga gat     3225
Tyr Glu Glu Gly Ala Ala Cys Lys Asp Gly Arg Leu Trp Ala Gly Asp
965                 970                 975 cag atc tta gag gtg aat gga att gac ttg agg aag gcc aca cat gat     3273
Gln Ile Leu Glu Val Asn Gly Ile Asp Leu Arg Lys Ala Thr His Asp
                980                 985                 990 gaa gca atc aat gtc ctg aga cag acg cca cag aga gtg cgc ctg aca     3321
Glu Ala Ile Asn Val Leu Arg Gln Thr Pro Gln Arg Val Arg Leu Thr
        995                 1000                1005                1010 ctc tac aga gat gag gcc cca tac aaa gag gag gaa gtg tgt gac acc     3369
Leu Tyr Arg Asp Glu Ala Pro Tyr Lys Glu Glu Glu Val Cys Asp Thr
                    1015                1020                1025 ctc act att gag ctg cag aag aag ccg gga aaa ggc cta gga tta agt     3417
Leu Thr Ile Glu Leu Gln Lys Lys Pro Gly Lys Gly Leu Gly Leu Ser
            1030                1035                1040 att gtt ggt aaa aga aac gat act gga gta ttt gtg tca gac att gtc     3465
Ile Val Gly Lys Arg Asn Asp Thr Gly Val Phe Val Ser Asp Ile Val
        1045                1050                1055 aaa gga gga att gca gat ccc gat gga aga ctg atc cag gga gac cag     3513
Lys Gly Gly Ile Ala Asp Pro Asp Gly Arg Leu Ile Gln Gly Asp Gln
                1060                1065                1070 ata tta ttg gtg aat ggg gaa gac gtt cgt aat gcc tcc caa gaa gcg     3561
Ile Leu Leu Val Asn Gly Glu Asp Val Arg Asn Ala Ser Gln Glu Ala
1075                1080                1085                1090 gtt gcc gct ttg cta aag tgt tcc cta ggc aca gta acc ttg gaa gtt     3609
Val Ala Ala Leu Leu Lys Cys Ser Leu Gly Thr Val Thr Leu Glu Val
                1095                1100                1105 gga aga atc aaa gct ggt cca ttc cat tca gag agg agg cca tct caa     3657
Gly Arg Ile Lys Ala Gly Pro Phe His Ser Glu Arg Arg Pro Ser Gln
        1110                1115                1120 acc agc cag gtg agt gaa ggc agc ctg tct tct ttc act ttt cca ctc     3705
Thr Ser Gln Val Ser Glu Gly Ser Leu Ser Ser Phe Thr Phe Pro Leu
                1125                1130                1135 tct gga tcc agt aca tct gag tca ctg gaa agt agc tca aag aag aat     3753
Ser Gly Ser Ser Thr Ser Glu Ser Leu Glu Ser Ser Ser Lys Lys Asn
```

```
                1140                1145                1150
gca ttg gca tct gaa ata cag gga tta aga aca gtc gaa atg aaa aag    3801
Ala Leu Ala Ser Glu Ile Gln Gly Leu Arg Thr Val Glu Met Lys Lys
1155                1160                1165                1170 ggc cct act gac tca ctg gga atc agc atc gct gga gga gta ggc agc    3849
Gly Pro Thr Asp Ser Leu Gly Ile Ser Ile Ala Gly Gly Val Gly Ser
                1175                1180                1185 cca ctt ggt gat gtg cct ata ttt att gca atg atg cac cca act gga    3897
Pro Leu Gly Asp Val Pro Ile Phe Ile Ala Met Met His Pro Thr Gly
            1190                1195                1200 gtt gca gca cag acc caa aaa ctc aga gtt ggg gat agg att gtc acc    3945
Val Ala Ala Gln Thr Gln Lys Leu Arg Val Gly Asp Arg Ile Val Thr
        1205                1210                1215 atc tgt ggc aca tcc act gag ggc atg act cac acc caa gca gtt aac    3993
Ile Cys Gly Thr Ser Thr Glu Gly Met Thr His Thr Gln Ala Val Asn
    1220                1225                1230 cta ctg aaa aat gca tct ggc tcc att gaa atg cag gtg gtt gct gga    4041
Leu Leu Lys Asn Ala Ser Gly Ser Ile Glu Met Gln Val Val Ala Gly
1235                1240                1245                1250 gga gac gtg agt gtg gtc aca ggt cat cat cag gag cct gca agt tcc    4089
Gly Asp Val Ser Val Val Thr Gly His His Gln Glu Pro Ala Ser Ser
                1255                1260                1265 agt ctt tct ttc act ggg ctg acg tca acc agt ata ttt cag gat gat    4137
Ser Leu Ser Phe Thr Gly Leu Thr Ser Thr Ser Ile Phe Gln Asp Asp
            1270                1275                1280 tta gga cct cct caa tgt aag tct att aca cta gag cga gga cca gat    4185
Leu Gly Pro Pro Gln Cys Lys Ser Ile Thr Leu Glu Arg Gly Pro Asp
        1285                1290                1295 ggc tta ggc ttc agt ata gtt gga gga tat ggc agc cct cat gga gac    4233
Gly Leu Gly Phe Ser Ile Val Gly Gly Tyr Gly Ser Pro His Gly Asp
    1300                1305                1310 tta ccc att tat gtt aaa aca gtg ttt gca aag gga gca gcc tct gaa    4281
Leu Pro Ile Tyr Val Lys Thr Val Phe Ala Lys Gly Ala Ala Ser Glu
1315                1320                1325                1330 gac gga cgt ctg aaa agg ggc gat cag atc att gct gtc aat ggg cag    4329
Asp Gly Arg Leu Lys Arg Gly Asp Gln Ile Ile Ala Val Asn Gly Gln
                1335                1340                1345 agt cta gaa gga gtc acc cat gaa gaa gct gtt gcc atc ctt aaa cgg    4377
Ser Leu Glu Gly Val Thr His Glu Glu Ala Val Ala Ile Leu Lys Arg
            1350                1355                1360 aca aaa ggc act gtc act ttg atg gtt ctc tct tgaattggct gccagaattg   4430
Thr Lys Gly Thr Val Thr Leu Met Val Leu Ser
        1365                1370 aaccaaccca accctagct cacctcctac tgtaaagaga atgcactggt cctgacaatt    4490
tttatgctgt gttcagccgg gtcttcaaaa ctgtagggg gaaataacac ttaagttct     4550 ttttctcatc tagaaatgct ttccttactg acaacctaac atcattttc ttttcttctt    4610 gcatttgtg aacttaaaga gaaggaatat ttgtgtaggt gaatctcgtt tttatttgtg    4670
gagatatcta atgttttgta gtcacatggg caagaattat tacatgctaa gctggttagt   4730
ataaagaaag ataattctaa agctaaccaa agaaaatggc ttcagtaagt taggatgaaa   4790
aatgaaaata taaataaag aagaaaatct cggggagttt aaaaaaaatg cctcaatttg    4850
gcaatctacc tcctctcccc accccaaact                                    4880

<210> SEQ ID NO 4
<211> LENGTH: 90
<212> TYPE: PRT
<213> ORGANISM: Homo sapiens
```

```
<400> SEQUENCE: 4

Ala Gly Ile Gln His Ile Glu Leu Glu Lys Gly Ser Lys Gly Leu Gly
 1               5                  10                  15

Phe Ser Ile Leu Asp Tyr Gln Asp Pro Ile Asp Pro Ala Ser Thr Val
             20                  25                  30

Ile Ile Ile Arg Ser Leu Val Pro Gly Gly Ile Ala Glu Lys Asp Gly
             35                  40                  45

Arg Leu Leu Pro Gly Asp Arg Leu Met Phe Val Asn Asp Val Asn Leu
         50                  55                  60

Glu Asn Ser Ser Leu Glu Gly Ala Val Glu Ala Leu Lys Gly Ala Pro
 65                  70                  75                  80

Ser Gly Thr Val Arg Ile Gly Val Ala Lys
                 85                  90

<210> SEQ ID NO 5
<211> LENGTH: 91
<212> TYPE: PRT
<213> ORGANISM: Homo sapiens

<400> SEQUENCE: 5

Gln Asn Val Ser Lys Glu Ser Phe Glu Arg Thr Ile Asn Ile Ala Lys
 1               5                  10                  15

Gly Asn Ser Ser Leu Gly Met Thr Val Ser Ala Asn Lys Asp Gly Leu
             20                  25                  30

Gly Met Ile Val Arg Ser Ile Ile His Gly Gly Ala Ile Ser Arg Asp
             35                  40                  45

Gly Arg Ile Ala Ile Gly Asp Cys Ile Leu Ser Ile Asn Glu Glu Ser
         50                  55                  60

Thr Ile Ser Val Thr Asn Ala Gln Ala Arg Ala Met Leu Arg Arg His
 65                  70                  75                  80

Ser Leu Ile Gly Pro Asp Ile Lys Ile Thr Tyr
                 85                  90

<210> SEQ ID NO 6
<211> LENGTH: 96
<212> TYPE: PRT
<213> ORGANISM: Homo sapiens

<400> SEQUENCE: 6

Asn Gln Pro Arg Arg Val Glu Leu Trp Arg Glu Pro Ser Lys Ser Leu
 1               5                  10                  15

Gly Ile Ser Ile Val Gly Gly Arg Gly Met Gly Ser Arg Leu Ser Asn
             20                  25                  30

Gly Glu Val Met Arg Gly Ile Phe Ile Lys His Val Leu Glu Asp Ser
             35                  40                  45

Pro Ala Gly Lys Asn Gly Thr Leu Lys Pro Gly Asp Arg Ile Val Glu
         50                  55                  60

Ala Pro Ser Gln Ser Glu Ser Glu Pro Glu Lys Ala Pro Leu Cys Ser
 65                  70                  75                  80

Val Pro Pro Pro Pro Ser Ala Phe Ala Glu Met Gly Ser Asp His
                 85                  90                  95

<210> SEQ ID NO 7
<211> LENGTH: 86
<212> TYPE: PRT
<213> ORGANISM: Homo sapiens
```

```
<400> SEQUENCE: 7

Gly Glu Leu His Met Ile Glu Leu Glu Lys Gly His Ser Gly Leu Gly
 1               5                  10                  15

Leu Ser Leu Ala Gly Asn Lys Asp Arg Ser Arg Met Ser Val Phe Ile
            20                  25                  30

Val Gly Ile Asp Pro Asn Gly Ala Ala Gly Lys Asp Gly Arg Leu Gln
        35                  40                  45

Ile Ala Asp Glu Leu Leu Glu Ile Asn Gly Gln Ile Leu Tyr Gly Arg
50                  55                  60

Ser His Gln Asn Ala Ser Ser Ile Ile Lys Cys Ala Pro Ser Lys Val
65                  70                  75                  80

Lys Ile Ile Phe Ile Arg
                85

<210> SEQ ID NO 8
<211> LENGTH: 84
<212> TYPE: PRT
<213> ORGANISM: Homo sapiens

<400> SEQUENCE: 8

Lys Asn Val Gln His Leu Glu Leu Pro Lys Asp Gln Gly Gly Leu Gly
 1               5                  10                  15

Ile Ala Ile Ser Glu Glu Asp Thr Leu Ser Gly Val Ile Ile Lys Ser
            20                  25                  30

Leu Thr Glu His Gly Val Ala Ala Thr Asp Gly Arg Leu Lys Val Gly
        35                  40                  45

Asp Gln Ile Leu Ala Val Asp Asp Glu Ile Val Val Gly Tyr Pro Ile
50                  55                  60

Glu Lys Phe Ile Ser Leu Leu Lys Thr Ala Lys Met Thr Val Lys Leu
65                  70                  75                  80

Thr Ile His Ala

<210> SEQ ID NO 9
<211> LENGTH: 86
<212> TYPE: PRT
<213> ORGANISM: Homo sapiens

<400> SEQUENCE: 9

Gly Cys Glu Thr Thr Ile Glu Ile Ser Lys Gly Arg Thr Gly Leu Gly
 1               5                  10                  15

Leu Ser Ile Val Gly Gly Ser Asp Thr Leu Leu Gly Ala Phe Ile Ile
            20                  25                  30

His Glu Val Tyr Glu Glu Gly Ala Ala Cys Lys Asp Gly Arg Leu Trp
        35                  40                  45

Ala Gly Asp Gln Ile Leu Glu Val Asn Gly Ile Asp Leu Arg Lys Ala
50                  55                  60

Thr His Asp Glu Ala Ile Asn Val Leu Arg Gln Thr Pro Gln Arg Val
65                  70                  75                  80

Arg Leu Thr Leu Tyr Arg
                85

<210> SEQ ID NO 10
<211> LENGTH: 85
<212> TYPE: PRT
<213> ORGANISM: Homo sapiens

<400> SEQUENCE: 10
```

```
Cys Asp Thr Leu Thr Ile Glu Leu Gln Lys Lys Pro Gly Lys Gly Leu
  1               5                  10                  15
Gly Leu Ser Ile Val Gly Lys Arg Asn Asp Thr Gly Val Phe Val Ser
             20                  25                  30
Asp Ile Val Lys Gly Gly Ile Ala Asp Pro Asp Gly Arg Leu Ile Gln
         35                  40                  45
Gly Asp Gln Ile Leu Leu Val Asn Gly Glu Asp Val Arg Asn Ala Ser
     50                  55                  60
Gln Glu Ala Val Ala Ala Leu Leu Lys Cys Ser Leu Gly Thr Val Thr
 65                  70                  75                  80
Leu Glu Val Gly Arg
                 85

<210> SEQ ID NO 11
<211> LENGTH: 89
<212> TYPE: PRT
<213> ORGANISM: Homo sapiens

<400> SEQUENCE: 11

Gln Gly Leu Arg Thr Val Glu Met Lys Lys Gly Pro Thr Asp Ser Leu
  1               5                  10                  15
Gly Ile Ser Ile Ala Gly Gly Val Gly Ser Pro Leu Gly Asp Val Pro
             20                  25                  30
Ile Phe Ile Ala Met Met His Pro Thr Gly Val Ala Ala Gln Thr Gln
         35                  40                  45
Lys Leu Arg Val Gly Asp Arg Ile Val Thr Ile Cys Gly Thr Ser Thr
     50                  55                  60
Gln Gly Met Thr His Thr Gln Ala Val Asn Leu Leu Lys Asn Ala Ser
 65                  70                  75                  80
Gly Ser Ile Glu Met Gln Val Val Ala
                 85

<210> SEQ ID NO 12
<211> LENGTH: 88
<212> TYPE: PRT
<213> ORGANISM: Homo sapiens

<400> SEQUENCE: 12

Pro Gln Cys Lys Ser Ile Thr Leu Glu Arg Gly Pro Asp Gly Leu Gly
  1               5                  10                  15
Phe Ser Ile Val Gly Gly Tyr Gly Ser Pro His Gly Asp Leu Pro Ile
             20                  25                  30
Tyr Val Lys Thr Val Phe Ala Lys Gly Ala Ala Ser Glu Asp Gly Arg
         35                  40                  45
Leu Lys Arg Gly Asp Gln Ile Ile Ala Val Asn Gly Gln Ser Leu Glu
     50                  55                  60
Gly Val Thr His Glu Glu Ala Val Ala Ile Leu Lys Arg Thr Lys Gly
 65                  70                  75                  80
Thr Val Thr Leu Met Val Leu Ser
                 85

<210> SEQ ID NO 13
<211> LENGTH: 184
<212> TYPE: DNA
<213> ORGANISM: Homo sapiens
<220> FEATURE:
<221> NAME/KEY: misc_feature
<222> LOCATION: (1)...(184)
<223> OTHER INFORMATION: n = A,T,C or G
```

<400> SEQUENCE: 13

```
gctattttga aaatatattt atatctacga aaagaattgg gaaaacaaat atttaatcag    60
agaattattc cttaaagatt taaaatgtat ttagttgtac attttatatg ggttcacccc   120
agcacatgaa gtataatggt cagatttatt tngtatttat ttactattat aaccactttt   180
tagg                                                                184
```

<210> SEQ ID NO 14
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 14

```
ctccccatcc ctcgtccacc                                                20
```

<210> SEQ ID NO 15
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 15

```
ctctgactct gactgactgg                                                20
```

<210> SEQ ID NO 16
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 16

```
atgagtttgg ttacagctgg                                                20
```

<210> SEQ ID NO 17
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 17

```
tcagagagcg ttatggaacc                                                20
```

<210> SEQ ID NO 18
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 18

```
agtcttgctg ggaacaaaga                                                20
```

<210> SEQ ID NO 19
<211> LENGTH: 20
<212> TYPE: DNA
<213> ORGANISM: Artificial Sequence
<220> FEATURE:
<223> OTHER INFORMATION: Artificially synthesized primer sequence

```
<400> SEQUENCE: 19
actgttacta cttctgatgc                                              20

<210> SEQ ID NO 20
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 20
tctgatggtc ccacagtctg                                              20

<210> SEQ ID NO 21
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 21
gttgtttcgc agccagggat                                              20

<210> SEQ ID NO 22
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 22
ctgagcatcg ttggggttc                                               20

<210> SEQ ID NO 23
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 23
cctcatctct gtagagtgtc                                              20

<210> SEQ ID NO 24
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 24
tgttagcccc ctcactaagg                                              20

<210> SEQ ID NO 25
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 25
gctatgtgct aggaaatacg                                              20

<210> SEQ ID NO 26
<211> LENGTH: 20
```

```
<212> TYPE: DNA
<213> ORGANISM: Artificial Sequence
<220> FEATURE:
<223> OTHER INFORMATION: Artificially synthesized primer sequence

<400> SEQUENCE: 26
tagggagaag gatcagagcg                                                    20

<210> SEQ ID NO 27
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 27
acagatttct gactcactgg                                                    20

<210> SEQ ID NO 28
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 28
tggaaatagg cattcttcag                                                    20

<210> SEQ ID NO 29
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 29
atacaaagac ggtctaatcc                                                    20

<210> SEQ ID NO 30
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 30
ccgctttccc atctttagaa ac                                                 22

<210> SEQ ID NO 31
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 31
tatctcgtgt ggaagatgtg                                                    20

<210> SEQ ID NO 32
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 32
```

```
acataaatgt tgctatcacc                                              20

<210> SEQ ID NO 33
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 33
tgccacttag tagccgagtg                                              20

<210> SEQ ID NO 34
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 34
gcattgcatt acagttgagc                                              20

<210> SEQ ID NO 35
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 35
tcctcctttg acaatgtctg                                              20

<210> SEQ ID NO 36
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 36
catttcgact gttcttaatc                                              20

<210> SEQ ID NO 37
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 37
tcagtggatg tgccacagat                                              20

<210> SEQ ID NO 38
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 38
cagtaggtta actgcttcgg                                              20

<210> SEQ ID NO 39
<211> LENGTH: 20
<212> TYPE: DNA
<213> ORGANISM: Artificial Sequence
```

```
<220> FEATURE:
<223> OTHER INFORMATION: Artificially synthesized primer sequence

<400> SEQUENCE: 39
agttccagtc tttctttcgg                                              20

<210> SEQ ID NO 40
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 40
tttctttcac tgggctgaag tc                                           22

<210> SEQ ID NO 41
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 41
cctctgaaga cggacgtctg                                              20

<210> SEQ ID NO 42
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 42
ccatcctaat acgactcact atagggc                                      27

<210> SEQ ID NO 43
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 43
ttggggtggg gagaggaggt agattgc                                      27

<210> SEQ ID NO 44
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 44
actcactata gggctcgagc ggc                                          23

<210> SEQ ID NO 45
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 45
gcacatcacc aagtgggctg cctactc                                      27
```

<210> SEQ ID NO 46
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 46
atgagtttgg ttacagctgg                                              20

<210> SEQ ID NO 47
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 47
aatctaatgc agctcgcctg                                              20

<210> SEQ ID NO 48
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 48
agtcttgctg ggaacaaaga                                              20

<210> SEQ ID NO 49
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 49
tcactttaga agggcacat                                               20

<210> SEQ ID NO 50
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 50
actgttacta cttctgatgc                                              20

<210> SEQ ID NO 51
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 51
tctgatggtc ccacagtctg                                              20

<210> SEQ ID NO 52
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 52
gttgtttcgc agccagggat                                               20

<210> SEQ ID NO 53
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 53
ctgagcatcg ttgggggttc                                               20

<210> SEQ ID NO 54
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 54
cctcatctct gtagagtgtc                                               20

<210> SEQ ID NO 55
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 55
tagggagaag gatcagagcg                                               20

<210> SEQ ID NO 56
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 56
tcctcctttg acaatgtctg                                               20

<210> SEQ ID NO 57
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 57
tttcatcatc tacagccagt                                               20

<210> SEQ ID NO 58
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 58
tgacaccctc actattgagc                                               20

<210> SEQ ID NO 59

```
<211> LENGTH: 2819
<212> TYPE: DNA
<213> ORGANISM: Homo sapiens
<220> FEATURE:
<221> NAME/KEY: CDS
<222> LOCATION: (43)...(2331)

<400> SEQUENCE: 59
accaccgcct ccgcggcacc ccctccttca gcctttgccg aa atg ggt agt aat         54
                                              Met Gly Ser Asn
                                              1 cac aca cag tca tct gca agc aaa atc tca caa gat gtg gac aaa gag       102
His Thr Gln Ser Ser Ala Ser Lys Ile Ser Gln Asp Val Asp Lys Glu
  5              10                  15                  20 gat gag ttt ggt tac agc tgg aaa aat atc aga gag cgt tat gga acc       150
Asp Glu Phe Gly Tyr Ser Trp Lys Asn Ile Arg Glu Arg Tyr Gly Thr
             25                  30                  35 cta aca ggc gag ctg cat atg att gaa ctg gag aaa ggt cat agt ggt       198
Leu Thr Gly Glu Leu His Met Ile Glu Leu Glu Lys Gly His Ser Gly
         40                  45                  50 ttg ggc cta agt ctt gct ggg aac aaa gac cga tcc agg atg agt gtc       246
Leu Gly Leu Ser Leu Ala Gly Asn Lys Asp Arg Ser Arg Met Ser Val
     55                  60                  65 ttc ata gtg ggg att gat cca aat gga gct gca gga aaa gat ggt cga       294
Phe Ile Val Gly Ile Asp Pro Asn Gly Ala Ala Gly Lys Asp Gly Arg
 70                  75                  80 ttg caa att gca gat gag ctt cta gag atc aat ggt cag att tta tat       342
Leu Gln Ile Ala Asp Glu Leu Leu Glu Ile Asn Gly Gln Ile Leu Tyr
 85                  90                  95                 100 gga aga agt cat cag aat gcc tca tca atc att aaa tgt gcc cct tct       390
Gly Arg Ser His Gln Asn Ala Ser Ser Ile Ile Lys Cys Ala Pro Ser
                105                 110                 115 aaa gtg aaa ata att ttt atc aga aat aaa gat gca gtg aat cag atg       438
Lys Val Lys Ile Ile Phe Ile Arg Asn Lys Asp Ala Val Asn Gln Met
            120                 125                 130 gcc gta tgt cct gga aat gca gta gaa cct ttg cct tct aac tca gaa       486
Ala Val Cys Pro Gly Asn Ala Val Glu Pro Leu Pro Ser Asn Ser Glu
        135                 140                 145 aat ctt caa aat aag gag cca gag cca act gtt act act tct gat gca       534
Asn Leu Gln Asn Lys Glu Pro Glu Pro Thr Val Thr Thr Ser Asp Ala
    150                 155                 160 gct gtg gac ctc agt tca ttt aaa aat gtg caa cat ctg gag ctt ccc       582
Ala Val Asp Leu Ser Ser Phe Lys Asn Val Gln His Leu Glu Leu Pro
165                 170                 175                 180 aag gat cag ggg ggt ttg ggt att gct atc agc gaa gaa gat aca ctc       630
Lys Asp Gln Gly Gly Leu Gly Ile Ala Ile Ser Glu Glu Asp Thr Leu
                185                 190                 195 agt gga gtc atc ata aag agc tta aca gag cat ggg gta gca gcc acg       678
Ser Gly Val Ile Ile Lys Ser Leu Thr Glu His Gly Val Ala Ala Thr
            200                 205                 210 gat gga cga ctc aaa gtc gga gat cag ata ctg gct gta gat gat gaa       726
Asp Gly Arg Leu Lys Val Gly Asp Gln Ile Leu Ala Val Asp Asp Glu
        215                 220                 225 att gtt gtt ggt tac cct att gaa aag ttt att agc ctt ctg aag aca       774
Ile Val Val Gly Tyr Pro Ile Glu Lys Phe Ile Ser Leu Leu Lys Thr
    230                 235                 240 gca aag atg aca gta aaa ctt acc atc cat gct gag aat cca gat tcc       822
Ala Lys Met Thr Val Lys Leu Thr Ile His Ala Glu Asn Pro Asp Ser
245                 250                 255                 260 cag gct gtt cct tca gca gct ggt gca gcc agt gga gaa aaa aag aac       870
Gln Ala Val Pro Ser Ala Ala Gly Ala Ala Ser Gly Glu Lys Lys Asn
```

```
                    265                 270                 275
agc tcc cag tct ctg atg gtc cca cag tct ggc tcc cca gaa ccg gag      918
Ser Ser Gln Ser Leu Met Val Pro Gln Ser Gly Ser Pro Glu Pro Glu
            280                 285                 290 tcc atc cga aat aca agc aga tca tca aca cca gca att ttt gct tct      966
Ser Ile Arg Asn Thr Ser Arg Ser Ser Thr Pro Ala Ile Phe Ala Ser
            295                 300                 305 gat cct gca acc tgc ccc att atc cct ggc tgc gaa aca acc atc gag     1014
Asp Pro Ala Thr Cys Pro Ile Ile Pro Gly Cys Glu Thr Thr Ile Glu
    310                 315                 320 att tcc aaa ggg cga aca ggg ctg ggc ctg agc atc gtt ggg ggt tca     1062
Ile Ser Lys Gly Arg Thr Gly Leu Gly Leu Ser Ile Val Gly Gly Ser
325                 330                 335                 340 gac acg ctg ctg ggt gcc ttt att atc cat gaa gtt tat gaa gaa gga     1110
Asp Thr Leu Leu Gly Ala Phe Ile Ile His Glu Val Tyr Glu Glu Gly
                345                 350                 355 gca gca tgt aaa gat gga aga ctc tgg gct gga gat cag atc tta gag     1158
Ala Ala Cys Lys Asp Gly Arg Leu Trp Ala Gly Asp Gln Ile Leu Glu
            360                 365                 370 gtg aat gga att gac ttg agg aag gcc aca cat gat gaa gca atc aat     1206
Val Asn Gly Ile Asp Leu Arg Lys Ala Thr His Asp Glu Ala Ile Asn
            375                 380                 385 gtc ctg aga cag acg cca cag aga gtg cgc ctg aca ctc tac aga gat     1254
Val Leu Arg Gln Thr Pro Gln Arg Val Arg Leu Thr Leu Tyr Arg Asp
    390                 395                 400 gag gcc cca tac aaa gag gag gaa gtg tgt gac acc ctc act att gag     1302
Glu Ala Pro Tyr Lys Glu Glu Glu Val Cys Asp Thr Leu Thr Ile Glu
405                 410                 415                 420 ctg cag aag aag ccg gga aaa ggc cta gga tta agt att gtt ggt aaa     1350
Leu Gln Lys Lys Pro Gly Lys Gly Leu Gly Leu Ser Ile Val Gly Lys
                425                 430                 435 aga aac gat act gga gta ttt gtg tca gac att gtc aaa gga gga att     1398
Arg Asn Asp Thr Gly Val Phe Val Ser Asp Ile Val Lys Gly Gly Ile
            440                 445                 450 gca gat ccc gat gga aga ctg atc cag gga gac cag ata tta ttg gtg     1446
Ala Asp Pro Asp Gly Arg Leu Ile Gln Gly Asp Gln Ile Leu Leu Val
            455                 460                 465 aat ggg gaa gac gtt cgt aat gcc tcc caa gaa gcg gtt gcc gct ttg     1494
Asn Gly Glu Asp Val Arg Asn Ala Ser Gln Glu Ala Val Ala Ala Leu
    470                 475                 480 cta aag tgt tcc cta ggc aca gta acc ttg gaa gtt gga aga atc aaa     1542
Leu Lys Cys Ser Leu Gly Thr Val Thr Leu Glu Val Gly Arg Ile Lys
485                 490                 495                 500 gct ggt cca ttc cat tca gag agg agg cca tct caa acc agc cag gtg     1590
Ala Gly Pro Phe His Ser Glu Arg Arg Pro Ser Gln Thr Ser Gln Val
                505                 510                 515 agt gaa ggc agc ctg tct tct ttc act ttt cca ctc tct gga tcc agt     1638
Ser Glu Gly Ser Leu Ser Ser Phe Thr Phe Pro Leu Ser Gly Ser Ser
            520                 525                 530 aca tct gag tca ctg gaa agt agc tca aag aag aat gca ttg gca tct     1686
Thr Ser Glu Ser Leu Glu Ser Ser Ser Lys Lys Asn Ala Leu Ala Ser
            535                 540                 545 gaa ata cag gga tta aga aca gtc gaa atg aaa aag ggc cct act gac     1734
Glu Ile Gln Gly Leu Arg Thr Val Glu Met Lys Lys Gly Pro Thr Asp
    550                 555                 560 tca ctg gga atc agc atc gct gga gga gta ggc agc cca ctt ggt gat     1782
Ser Leu Gly Ile Ser Ile Ala Gly Gly Val Gly Ser Pro Leu Gly Asp
565                 570                 575                 580 gtg cct ata ttt att gca atg atg cac cca act gga gtt gca gca cag     1830
```

```
                        Val Pro Ile Phe Ile Ala Met Met His Pro Thr Gly Val Ala Ala Gln
                                        585                 590                 595 acc caa aaa ctc aga gtt ggg gat agg att gtc acc atc tgt ggc aca           1878
Thr Gln Lys Leu Arg Val Gly Asp Arg Ile Val Thr Ile Cys Gly Thr
                600                 605                 610 tcc act gag ggc atg act cac acc caa gca gtt aac cta ctg aaa aat           1926
Ser Thr Glu Gly Met Thr His Thr Gln Ala Val Asn Leu Leu Lys Asn
                615                 620                 625 gca tct ggc tcc att gaa atg cag gtg gtt gct gga gga gac gtg agt           1974
Ala Ser Gly Ser Ile Glu Met Gln Val Val Ala Gly Gly Asp Val Ser
            630                 635                 640 gtg gtc aca ggt cat cat cag gag cct gca agt tcc agt ctt tct ttc           2022
Val Val Thr Gly His His Gln Glu Pro Ala Ser Ser Ser Leu Ser Phe
645                 650                 655                 660 act ggg ctg acg tca acc agt ata ttt cag gat gat tta gga cct cct           2070
Thr Gly Leu Thr Ser Thr Ser Ile Phe Gln Asp Asp Leu Gly Pro Pro
                665                 670                 675 caa tgt aag tct att aca cta gag cga gga cca gat ggc tta ggc ttc           2118
Gln Cys Lys Ser Ile Thr Leu Glu Arg Gly Pro Asp Gly Leu Gly Phe
                680                 685                 690 agt ata gtt gga gga tat ggc agc cct cat gga gac tta ccc att tat           2166
Ser Ile Val Gly Gly Tyr Gly Ser Pro His Gly Asp Leu Pro Ile Tyr
            695                 700                 705 gtt aaa aca gtg ttt gca aag gga gca gcc tct gaa gac gga cgt ctg           2214
Val Lys Thr Val Phe Ala Lys Gly Ala Ala Ser Glu Asp Gly Arg Leu
            710                 715                 720 aaa agg ggc gat cag atc att gct gtc aat ggg cag agt cta gaa gga           2262
Lys Arg Gly Asp Gln Ile Ile Ala Val Asn Gly Gln Ser Leu Glu Gly
725                 730                 735                 740 gtc acc cat gaa gaa gct gtt gcc atc ctt aaa cgg aca aaa ggc act           2310
Val Thr His Glu Glu Ala Val Ala Ile Leu Lys Arg Thr Lys Gly Thr
                745                 750                 755 gtc act ttg atg gtt ctc tct tgaattggct gccagaattg aaccaaccca              2361
Val Thr Leu Met Val Leu Ser
                760 accctagct cacctcctac tgtaaagaga atgcactggt cctgacaatt tttatgctgt          2421
gttcagccgg gtcttcaaaa ctgtaggggg gaaataacac ttaagtttct ttttctcatc         2481
tagaaatgct ttccttactg acaacctaac atcattttc ttttcttctt gcattttgtg          2541
aacttaaaga gaaggaatat ttgtgtaggt gaatctcgtt tttatttgtg gagatatcta         2601
atgttttgta gtcacatggg caagaattat tacatgctaa gctggttagt ataaagaaag         2661
ataattctaa agctaaccaa agaaaatggc ttcagtaagt taggatgaaa aatgaaaata         2721
taaaataaag aagaaaatct cggggagttt aaaaaaaatg cctcaatttg gcaatctacc         2781
tcctctcccc accccaaact aaaaaaaaaa aaaaaaa                                  2819

<210> SEQ ID NO 60
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 60
gcccttagga cgcgtaatac gactc                                               25

<210> SEQ ID NO 61
<211> LENGTH: 25
<212> TYPE: DNA
```

```
<213> ORGANISM: Artificial Sequence
<220> FEATURE:
<223> OTHER INFORMATION: Artificially synthesized primer sequence

<400> SEQUENCE: 61
agccagtatc tgatctccga ctttg                                    25

<210> SEQ ID NO 62
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 62
attttcactt tagaaggggc acat                                     24

<210> SEQ ID NO 63
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 63
ggcataactt tacttacttg                                          20

<210> SEQ ID NO 64
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 64
atctactaag tcagcatcat                                          20

<210> SEQ ID NO 65
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 65
atttgcaggt gtgtagtcat                                          20

<210> SEQ ID NO 66
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 66
ttccttctgt gctacccgat                                          20

<210> SEQ ID NO 67
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 67
ggactatctt ccagaacatg                                          20
```

<210> SEQ ID NO 68
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 68
atcgggtcca ttccattcag agagg 25

<210> SEQ ID NO 69
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 69
aattgtcaag agagaaccat caaagtgg 28

<210> SEQ ID NO 70
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 70
atcgatgggt agtaatcaca cacag 25

<210> SEQ ID NO 71
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 71
aattgctata ctggatccag agagtgg 27

<210> SEQ ID NO 72
<211> LENGTH: 21
<212> TYPE: PRT
<213> ORGANISM: Artificial Sequence
<220> FEATURE:
<223> OTHER INFORMATION: Artificially synthesized peptide sequence

<400> SEQUENCE: 72

Val Asp Lys Glu Asp Glu Phe Gly Tyr Ser Trp Lys Asn Ile Arg Glu
 1               5                  10                  15
Arg Tyr Gly Cys Gly
            20

<210> SEQ ID NO 73
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 73
tttgtgccca ccagagccaa gtcag 25

<210> SEQ ID NO 74

-continued

```
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 74
gtgaaagggg taaaggctta gcaac                                              25

<210> SEQ ID NO 75
<211> LENGTH: 1776
<212> TYPE: DNA
<213> ORGANISM: Homo sapiens
<220> FEATURE:
<221> NAME/KEY: CDS
<222> LOCATION: (3)...(1772)

<400> SEQUENCE: 75 ca att aca cat cag cag gct atc agc atc ctg cag aaa gcc aaa gat          47
   Ile Thr His Gln Gln Ala Ile Ser Ile Leu Gln Lys Ala Lys Asp
    1               5                  10                  15 acc gtc cag cta gtt att gcc aga ggc tca ttg cct cag ctt gtc agc         95
Thr Val Gln Leu Val Ile Ala Arg Gly Ser Leu Pro Gln Leu Val Ser
                20                  25                  30 ccc ata gtt tcc cgt tct cca tct gca gcc agc aca att tca gct cac        143
Pro Ile Val Ser Arg Ser Pro Ser Ala Ala Ser Thr Ile Ser Ala His
            35                  40                  45 tct aat ccg gtt cac tgg caa cac atg gaa acg att gaa ttg gtg aat        191
Ser Asn Pro Val His Trp Gln His Met Glu Thr Ile Glu Leu Val Asn
        50                  55                  60 gat gga tct ggt ttg gga ttt ggc atc ata gga gga aaa gca act ggt        239
Asp Gly Ser Gly Leu Gly Phe Gly Ile Ile Gly Gly Lys Ala Thr Gly
    65                  70                  75 gtg ata gta aaa acc att ctg cct gga gga gta gct gat cag cat ggg        287
Val Ile Val Lys Thr Ile Leu Pro Gly Gly Val Ala Asp Gln His Gly
 80                  85                  90                  95 cgt tta tgc agt gga gac cac att cta aag att ggt gac aca gat cta        335
Arg Leu Cys Ser Gly Asp His Ile Leu Lys Ile Gly Asp Thr Asp Leu
                100                 105                 110 gca gga atg agc agt gag caa gta gca caa gtc ctt agg caa tgt gga        383
Ala Gly Met Ser Ser Glu Gln Val Ala Gln Val Leu Arg Gln Cys Gly
            115                 120                 125 aat aga gtt aag ttg atg att gca aga agt gcc ata gaa gaa cgt aca        431
Asn Arg Val Lys Leu Met Ile Ala Arg Ser Ala Ile Glu Glu Arg Thr
        130                 135                 140 gca ccc act gct ttg ggc atc acc ctc tcc tca tcc cca act tca acg        479
Ala Pro Thr Ala Leu Gly Ile Thr Leu Ser Ser Ser Pro Thr Ser Thr
    145                 150                 155 cca gag ttg cgg gtt gat gct tct act cag aaa ggt gaa gaa agt gag        527
Pro Glu Leu Arg Val Asp Ala Ser Thr Gln Lys Gly Glu Glu Ser Glu
160                 165                 170                 175 aca ttt gat gta gaa ctc act aaa aat gtc caa gga tta gga att acc        575
Thr Phe Asp Val Glu Leu Thr Lys Asn Val Gln Gly Leu Gly Ile Thr
                180                 185                 190 att gct ggc tac att gga gat aaa aaa ttg gaa cct tca gga atc ttt        623
Ile Ala Gly Tyr Ile Gly Asp Lys Lys Leu Glu Pro Ser Gly Ile Phe
            195                 200                 205 gta aag agc att aca aaa agc agt gcc gtt gag cat gat gga aga atc        671
Val Lys Ser Ile Thr Lys Ser Ser Ala Val Glu His Asp Gly Arg Ile
        210                 215                 220 caa att gga gac caa att ata gca gta gat ggc aca aac ctt cag ggt        719
Gln Ile Gly Asp Gln Ile Ile Ala Val Asp Gly Thr Asn Leu Gln Gly
```

```
                  225                 230                 235
ttt act aat cag caa gca gta gag gta ttg cga cat aca gga caa act    767
Phe Thr Asn Gln Gln Ala Val Glu Val Leu Arg His Thr Gly Gln Thr
240                 245                 250                 255 gtg ctc ctg aca cta atg agg aga gga atg aag cag gaa gcc gag ctc    815
Val Leu Leu Thr Leu Met Arg Arg Gly Met Lys Gln Glu Ala Glu Leu
                260                 265                 270 atg tca agg gaa gac gtc aca aaa gat gca gat ttg tct cct gtt aat    863
Met Ser Arg Glu Asp Val Thr Lys Asp Ala Asp Leu Ser Pro Val Asn
            275                 280                 285 gcc agc ata atc aaa gaa aat tat gaa aaa gat gaa gat ttt tta tct    911
Ala Ser Ile Ile Lys Glu Asn Tyr Glu Lys Asp Glu Asp Phe Leu Ser
        290                 295                 300 tcg acg aga aac acc aac ata tta cca act gaa gaa gaa ggg tat cca    959
Ser Thr Arg Asn Thr Asn Ile Leu Pro Thr Glu Glu Glu Gly Tyr Pro
    305                 310                 315 tta ctg tca gct gag ata gaa gaa ata gaa gat gca caa aaa caa gaa   1007
Leu Leu Ser Ala Glu Ile Glu Glu Ile Glu Asp Ala Gln Lys Gln Glu
320                 325                 330                 335 gct gct ctg ctg aca aaa tgg caa agg att atg gga att aac tat gaa   1055
Ala Ala Leu Leu Thr Lys Trp Gln Arg Ile Met Gly Ile Asn Tyr Glu
                340                 345                 350 ata gtg gtg gcc cat gtg agc aag ttt agt gag aac agt gga ttg ggg   1103
Ile Val Val Ala His Val Ser Lys Phe Ser Glu Asn Ser Gly Leu Gly
            355                 360                 365 ata agc ctg gaa gcg aca gtg gga cat cat ttt atc cga tct gtt cta   1151
Ile Ser Leu Glu Ala Thr Val Gly His His Phe Ile Arg Ser Val Leu
        370                 375                 380 cca gag ggt cct gtt gga cac agc ggg aag ctc ttc agt gga gac gag   1199
Pro Glu Gly Pro Val Gly His Ser Gly Lys Leu Phe Ser Gly Asp Glu
    385                 390                 395 cta ttg gaa gta aat ggc ata act tta ctt ggg gaa aat cac caa gat   1247
Leu Leu Glu Val Asn Gly Ile Thr Leu Leu Gly Glu Asn His Gln Asp
400                 405                 410                 415 gtg gtg aat atc tta aaa gaa ctg cct ata gaa gtg aca atg gtg tgc   1295
Val Val Asn Ile Leu Lys Glu Leu Pro Ile Glu Val Thr Met Val Cys
                420                 425                 430 tgt cgt cga act gtg cca ccc acc acc caa tca gaa ttg gat agc ctg   1343
Cys Arg Arg Thr Val Pro Pro Thr Thr Gln Ser Glu Leu Asp Ser Leu
            435                 440                 445 gac tta tgt gat att gag cta aca gaa aag cct cac gta gat cta ggt   1391
Asp Leu Cys Asp Ile Glu Leu Thr Glu Lys Pro His Val Asp Leu Gly
        450                 455                 460 gag ttc atc ggg tca tca gag cca gag gat cca gtg ctg gcg atg act   1439
Glu Phe Ile Gly Ser Ser Glu Pro Glu Asp Pro Val Leu Ala Met Thr
    465                 470                 475 gat gcg ggt cag agt aca gaa gag gtt caa gca cct ttg gcc atg tgg   1487
Asp Ala Gly Gln Ser Thr Glu Glu Val Gln Ala Pro Leu Ala Met Trp
480                 485                 490                 495 gag gct ggc att cag cac ata atg ctg gag aaa ggg agc aaa gga ctt   1535
Glu Ala Gly Ile Gln His Ile Met Leu Glu Lys Gly Ser Lys Gly Leu
                500                 505                 510 ggt ttt agc att tta gat tat cag gat cca att gat cca gca agc act   1583
Gly Phe Ser Ile Leu Asp Tyr Gln Asp Pro Ile Asp Pro Ala Ser Thr
            515                 520                 525 gtg att ata att cgt tct ttg gtg cct ggc ggc att gct gaa aag gat   1631
Val Ile Ile Ile Arg Ser Leu Val Pro Gly Gly Ile Ala Glu Lys Asp
        530                 535                 540 gga cga ctt ctt cct ggt gac cga ctc atg ttt gta aac gat gtt aac   1679
```

-continued

| | |
|---|---|
| Gly Arg Leu Leu Pro Gly Asp Arg Leu Met Phe Val Asn Asp Val Asn<br>545 550 555 | |
| ttg gaa aac agc agt ctt gag gaa gct gta gaa gca ctg aag gga gca<br>Leu Glu Asn Ser Ser Leu Glu Glu Ala Val Glu Ala Leu Lys Gly Ala<br>560 565 570 575 | 1727 |
| ccg tca ggg act gtg aga ata gga gtt gct aag cct tta ccc ctt<br>Pro Ser Gly Thr Val Arg Ile Gly Val Ala Lys Pro Leu Pro Leu<br>580 585 590 | 1772 |
| tcac | 1776 |

<210> SEQ ID NO 76
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 76
gcagatggag aacgggaaac tatgg                25

<210> SEQ ID NO 77
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 77
gaacgggaaa ctatggggct gacaa                25

<210> SEQ ID NO 78
<211> LENGTH: 777
<212> TYPE: DNA
<213> ORGANISM: Homo sapiens
<220> FEATURE:
<221> NAME/KEY: CDS
<222> LOCATION: (71)...(775)

<400> SEQUENCE: 78

| | |
|---|---|
| ttctcagtca cgcagttcca ttttaattgc tgttaatcat ttcagagaag aacactgaac | 60 |
| tttgaaaaaa atg ttg gaa gcc att gac aaa aat cgg gcc ctg cat gca<br>Met Leu Glu Ala Ile Asp Lys Asn Arg Ala Leu His Ala<br>1 5 10 | 109 |
| gca gag cgc ttg caa acc aag ctg cga gaa cgt ggg gat gta gca aat<br>Ala Glu Arg Leu Gln Thr Lys Leu Arg Glu Arg Gly Asp Val Ala Asn<br>15 20 25 | 157 |
| gaa gac aaa ctg agc ctt ctg aag tca gtc ctg cag agc cct ctc ttc<br>Glu Asp Lys Leu Ser Leu Leu Lys Ser Val Leu Gln Ser Pro Leu Phe<br>30 35 40 45 | 205 |
| agt cag att ctg agc ctt cag act tct gta cag cag ctg aaa gac cag<br>Ser Gln Ile Leu Ser Leu Gln Thr Ser Val Gln Gln Leu Lys Asp Gln<br>50 55 60 | 253 |
| gta aat att gca act tca gca act tca aat att gaa tat gcc cac gtt<br>Val Asn Ile Ala Thr Ser Ala Thr Ser Asn Ile Glu Tyr Ala His Val<br>65 70 75 | 301 |
| cct cat ctc agc cca gct gtg att cct act ctg caa aat gaa tcg ttt<br>Pro His Leu Ser Pro Ala Val Ile Pro Thr Leu Gln Asn Glu Ser Phe<br>80 85 90 | 349 |
| tta tta tcc cca aac aat ggg aat ctg gaa gca ctt aca gga cct ggt<br>Leu Leu Ser Pro Asn Asn Gly Asn Leu Glu Ala Leu Thr Gly Pro Gly<br>95 100 105 | 397 |
| att cca cac att aat ggg aaa cct gct tgt gat gaa ttt gat cag ctt | 445 |

```
Ile Pro His Ile Asn Gly Lys Pro Ala Cys Asp Glu Phe Asp Gln Leu
110             115                 120                 125 atc aaa aat atg gcc cag ggt cgc cat gta gaa gtt ttt gag ctc ctc        493
Ile Lys Asn Met Ala Gln Gly Arg His Val Glu Val Phe Glu Leu Leu
            130                 135                 140 aaa cct cca tct gga ggc ctt ggg ttt agt gtt gtg gga cta aga agt        541
Lys Pro Pro Ser Gly Gly Leu Gly Phe Ser Val Val Gly Leu Arg Ser
                145                 150                 155 gaa aac aga gga gag ctg gga ata ttt gtt caa gag ata caa gag ggc        589
Glu Asn Arg Gly Glu Leu Gly Ile Phe Val Gln Glu Ile Gln Glu Gly
            160                 165                 170 agt gtg gcc cat aga gat gga aga ttg aaa gaa act gat caa att ctt        637
Ser Val Ala His Arg Asp Gly Arg Leu Lys Glu Thr Asp Gln Ile Leu
        175                 180                 185 gct atc aat gga cag gct ctt gat cag aca att aca cat cag cag gct        685
Ala Ile Asn Gly Gln Ala Leu Asp Gln Thr Ile Thr His Gln Gln Ala
190                 195                 200                 205 atc agc atc ctg cag aaa gcc aaa gat act gtc cag cta gtt att gcc        733
Ile Ser Ile Leu Gln Lys Ala Lys Asp Thr Val Gln Leu Val Ile Ala
                210                 215                 220 aga ggc tca ttg cct cag ctt gtc agc ccc ata gtt tcc cgt tc             777
Arg Gly Ser Leu Pro Gln Leu Val Ser Pro Ile Val Ser Arg
            225                 230                 235

<210> SEQ ID NO 79
<211> LENGTH: 755
<212> TYPE: DNA
<213> ORGANISM: Homo sapiens
<220> FEATURE:
<221> NAME/KEY: CDS
<222> LOCATION: (3)...(755)

<400> SEQUENCE: 79 tt cct tct gtg cta ccc gat tca gct gga aag ggc tct gag tac ctg         47
   Pro Ser Val Leu Pro Asp Ser Ala Gly Lys Gly Ser Glu Tyr Leu
   1               5                   10                  15 ctt gaa cag agc tcc ctg gcc tgt aat gct gag tgt gtc atg ctt caa        95
Leu Glu Gln Ser Ser Leu Ala Cys Asn Ala Glu Cys Val Met Leu Gln
                20                  25                  30 aat gta tct aaa gaa tct ttt gaa agg act att aat ata gca aaa ggc        143
Asn Val Ser Lys Glu Ser Phe Glu Arg Thr Ile Asn Ile Ala Lys Gly
            35                  40                  45 aat tct agc cta gga atg aca gtt agt gct aat aaa gat ggc ttg ggg        191
Asn Ser Ser Leu Gly Met Thr Val Ser Ala Asn Lys Asp Gly Leu Gly
        50                  55                  60 atg atc gtt cga agc att att cat gga ggt gcc att agt cga gat ggc        239
Met Ile Val Arg Ser Ile Ile His Gly Gly Ala Ile Ser Arg Asp Gly
65                  70                  75 cgg att gcc att ggg gac tgc atc ttg tcc att aat gaa gag tct acc        287
Arg Ile Ala Ile Gly Asp Cys Ile Leu Ser Ile Asn Glu Glu Ser Thr
80                  85                  90                  95 atc agt gta acc aat gcc cag gca cga gct atg ttg aga aga cat tct        335
Ile Ser Val Thr Asn Ala Gln Ala Arg Ala Met Leu Arg Arg His Ser
                100                 105                 110 ctc att ggc cct gac ata aaa att act tat gtg cct gca gaa cat ttg        383
Leu Ile Gly Pro Asp Ile Lys Ile Thr Tyr Val Pro Ala Glu His Leu
            115                 120                 125 gaa gag ttc aaa ata agc ttg gga caa caa tct gga aga gta atg gca        431
Glu Glu Phe Lys Ile Ser Leu Gly Gln Gln Ser Gly Arg Val Met Ala
        130                 135                 140 ctg gat att ttt tct tca tac act ggc aga gac att cca gaa tta cca        479
Leu Asp Ile Phe Ser Ser Tyr Thr Gly Arg Asp Ile Pro Glu Leu Pro
```

```
Leu Asp Ile Phe Ser Ser Tyr Thr Gly Arg Asp Ile Pro Glu Leu Pro
    145                 150                 155 gag cga gaa gag gga gag ggt gaa gaa agc gaa ctt caa aac aca gca      527
Glu Arg Glu Glu Gly Glu Gly Glu Glu Ser Glu Leu Gln Asn Thr Ala
160                 165                 170                 175 tat agc aat tgg aat cag ccc agg cgg gtg gaa ctc tgg aga gaa cca      575
Tyr Ser Asn Trp Asn Gln Pro Arg Arg Val Glu Leu Trp Arg Glu Pro
                180                 185                 190 agc aaa tcc tta ggc atc agc att gtt ggt gga cga ggg atg ggg agt      623
Ser Lys Ser Leu Gly Ile Ser Ile Val Gly Gly Arg Gly Met Gly Ser
            195                 200                 205 cgg cta agc aat gga gaa gtg atg agg ggc att ttc atc aaa cat gtt      671
Arg Leu Ser Asn Gly Glu Val Met Arg Gly Ile Phe Ile Lys His Val
        210                 215                 220 ctg gaa gat agt cca gct ggc aaa aat gga acc ttg aaa cct gga gat      719
Leu Glu Asp Ser Pro Ala Gly Lys Asn Gly Thr Leu Lys Pro Gly Asp
    225                 230                 235 aga atc gta gag gca ccc agt cag tca gag tca gag                      755
Arg Ile Val Glu Ala Pro Ser Gln Ser Glu Ser Glu
240                 245                 250

<210> SEQ ID NO 80
<211> LENGTH: 865
<212> TYPE: DNA
<213> ORGANISM: Homo sapiens
<220> FEATURE:
<221> NAME/KEY: CDS
<222> LOCATION: (3)...(818)

<400> SEQUENCE: 80 tt cct tct gtg cta ccc gat tca gct gga aag ggc tct gag tac ctg       47
   Pro Ser Val Leu Pro Asp Ser Ala Gly Lys Gly Ser Glu Tyr Leu
   1               5                   10                  15 ctt gaa cag agc tcc ctg gcc tgt aat gct gag tgt gtc atg ctt caa      95
Leu Glu Gln Ser Ser Leu Ala Cys Asn Ala Glu Cys Val Met Leu Gln
                20                  25                  30 aat gta tct aaa gaa tct ttt gaa agg act att aat ata gca aaa ggc     143
Asn Val Ser Lys Glu Ser Phe Glu Arg Thr Ile Asn Ile Ala Lys Gly
            35                  40                  45 aat tct agc cta gga atg aca gtt agt gct aat aaa gat ggc ttg ggg     191
Asn Ser Ser Leu Gly Met Thr Val Ser Ala Asn Lys Asp Gly Leu Gly
        50                  55                  60 atg atc gtt cga agc att att cat gga ggt gcc att agt cga gat ggc     239
Met Ile Val Arg Ser Ile Ile His Gly Gly Ala Ile Ser Arg Asp Gly
    65                  70                  75 cgg att gcc att ggg gac tgc atc ttg tcc att aat gaa gag tct acc     287
Arg Ile Ala Ile Gly Asp Cys Ile Leu Ser Ile Asn Glu Glu Ser Thr
80                  85                  90                  95 atc agt gta acc aat gcc cag gca cga gct atg ttg aga aga cat tct     335
Ile Ser Val Thr Asn Ala Gln Ala Arg Ala Met Leu Arg Arg His Ser
                100                 105                 110 ctc att ggc cct gac ata aaa att act tat gtg cct gca gaa cat ttg     383
Leu Ile Gly Pro Asp Ile Lys Ile Thr Tyr Val Pro Ala Glu His Leu
            115                 120                 125 gaa gag ttc aaa ata agc ttg gga caa caa tct gga aga gta atg gca     431
Glu Glu Phe Lys Ile Ser Leu Gly Gln Gln Ser Gly Arg Val Met Ala
        130                 135                 140 ctg gat att ttt tct tca tac act ggc aga gac att cca gaa tta cca     479
Leu Asp Ile Phe Ser Ser Tyr Thr Gly Arg Asp Ile Pro Glu Leu Pro
    145                 150                 155 gag cga gaa gag gga gag ggt gaa gaa agc gaa ctt caa aac aca gca     527
```

-continued

```
Glu Arg Glu Glu Gly Glu Gly Glu Ser Glu Leu Gln Asn Thr Ala
160             165                 170                 175 tat agc aat tgg aat cag ccc agg cgg gtg gaa ctc tgg aga gaa cca       575
Tyr Ser Asn Trp Asn Gln Pro Arg Arg Val Glu Leu Trp Arg Glu Pro
                180                 185                 190 agc aaa tcc tta ggc atc agc att gtt ggt gga cga ggg atg ggg agt       623
Ser Lys Ser Leu Gly Ile Ser Ile Val Gly Gly Arg Gly Met Gly Ser
            195                 200                 205 cgg cta agc aat gga gaa gtg atg agg ggc att ttc atc aaa cat gtt       671
Arg Leu Ser Asn Gly Glu Val Met Arg Gly Ile Phe Ile Lys His Val
        210                 215                 220 ctg gaa gat agt cca gct ggc aaa aat gga acc ttg aaa cct gga gat       719
Leu Glu Asp Ser Pro Ala Gly Lys Asn Gly Thr Leu Lys Pro Gly Asp
    225                 230                 235 aga atc gta gag gtg gat gga atg gac ctc aga gat gca agc cat gaa       767
Arg Ile Val Glu Val Asp Gly Met Asp Leu Arg Asp Ala Ser His Glu
240                 245                 250                 255 caa gct gtg gaa gcc att cgg aaa gca ggc aac cct gta gtc ttt atg       815
Gln Ala Val Glu Ala Ile Arg Lys Ala Gly Asn Pro Val Val Phe Met
                260                 265                 270 gta tagagcttta ttacagacca agggcaccca gtcagtcaga gtcagag                865
Val

<210> SEQ ID NO 81
<211> LENGTH: 965
<212> TYPE: DNA
<213> ORGANISM: Homo sapiens
<220> FEATURE:
<221> NAME/KEY: CDS
<222> LOCATION: (3)...(965)

<400> SEQUENCE: 81 tt cct tct gtg cta ccc gat tca gct gga aag ggc tct gag tac ctg         47
   Pro Ser Val Leu Pro Asp Ser Ala Gly Lys Gly Ser Glu Tyr Leu
   1               5                  10                  15 ctt gaa cag agc tcc ctg gcc tgt aat gct gag tgt gtc atg ctt caa        95
Leu Glu Gln Ser Ser Leu Ala Cys Asn Ala Glu Cys Val Met Leu Gln
                20                  25                  30 aat gta tct aaa gaa tct ttt gaa agg act att aat ata gca aaa ggc       143
Asn Val Ser Lys Glu Ser Phe Glu Arg Thr Ile Asn Ile Ala Lys Gly
            35                  40                  45 aat tct agc cta gga atg aca gtt agt gct aat aaa gat ggc ttg ggg       191
Asn Ser Ser Leu Gly Met Thr Val Ser Ala Asn Lys Asp Gly Leu Gly
        50                  55                  60 atg atc gtt cga agc att att cat gga ggt gcc att agt cga gat ggc       239
Met Ile Val Arg Ser Ile Ile His Gly Gly Ala Ile Ser Arg Asp Gly
    65                  70                  75 cgg att gcc att ggg gac tgc atc ttg tcc att aat gaa gag tct acc       287
Arg Ile Ala Ile Gly Asp Cys Ile Leu Ser Ile Asn Glu Glu Ser Thr
80                  85                  90                  95 atc agt gta acc aat gcc cag gca cga gct atg tta aga aga cat tct       335
Ile Ser Val Thr Asn Ala Gln Ala Arg Ala Met Leu Arg Arg His Ser
                100                 105                 110 ctc att ggc cct gac ata aaa att act tat gtg cct gca gaa cat ttg       383
Leu Ile Gly Pro Asp Ile Lys Ile Thr Tyr Val Pro Ala Glu His Leu
            115                 120                 125 gaa gag ttc aaa ata agc ttg gga caa caa tct gga aga gta atg gca       431
Glu Glu Phe Lys Ile Ser Leu Gly Gln Gln Ser Gly Arg Val Met Ala
        130                 135                 140 ctg gat att ttt tct tca tac act ggc aga gac att cca gaa tta cca       479
Leu Asp Ile Phe Ser Ser Tyr Thr Gly Arg Asp Ile Pro Glu Leu Pro
```

```
        145                 150                 155
gag cga gaa gag gga gag ggt gaa gaa agc gaa ctt caa aac aca gca       527
Glu Arg Glu Glu Gly Glu Gly Glu Glu Ser Glu Leu Gln Asn Thr Ala
160                 165                 170                 175 tat agc aat tgg aat cag ccc agg cgg gtg gaa ctc tgg aga gaa cca       575
Tyr Ser Asn Trp Asn Gln Pro Arg Arg Val Glu Leu Trp Arg Glu Pro
                180                 185                 190 agc aaa tcc tta ggc atc agc att gtt ggt gga cga ggg atg ggg agt       623
Ser Lys Ser Leu Gly Ile Ser Ile Val Gly Gly Arg Gly Met Gly Ser
            195                 200                 205 cgg cta agc aat gga gaa gtg atg agg ggc att ttc atc aaa cat gtt       671
Arg Leu Ser Asn Gly Glu Val Met Arg Gly Ile Phe Ile Lys His Val
        210                 215                 220 ctg gaa gat agt cca gct ggc aaa aat gga acc ttg aaa cct gga gat       719
Leu Glu Asp Ser Pro Ala Gly Lys Asn Gly Thr Leu Lys Pro Gly Asp
    225                 230                 235 aga atc gta gag gtg gat gga atg gac ctc aga gat gca agc cat gaa       767
Arg Ile Val Glu Val Asp Gly Met Asp Leu Arg Asp Ala Ser His Glu
240                 245                 250                 255 caa gct gtg gaa gcc att cgg aaa gca ggc aac cct gta gtc ttt atg       815
Gln Ala Val Glu Ala Ile Arg Lys Ala Gly Asn Pro Val Val Phe Met
                260                 265                 270 gta cag agc att ata aac aga cca agg aaa tcc cct ttg cct tcc ttg       863
Val Gln Ser Ile Ile Asn Arg Pro Arg Lys Ser Pro Leu Pro Ser Leu
            275                 280                 285 ctg cac aac ctt tac cct aag tac aac ttc agc agc act aac cca ttt       911
Leu His Asn Leu Tyr Pro Lys Tyr Asn Phe Ser Ser Thr Asn Pro Phe
        290                 295                 300 gct gac tct cta caa atc aac gcc gac aag gca ccc agt cag tca gag       959
Ala Asp Ser Leu Gln Ile Asn Ala Asp Lys Ala Pro Ser Gln Ser Glu
    305                 310                 315 tca gag                                                               965
Ser Glu
320

<210> SEQ ID NO 82
<211> LENGTH: 2000
<212> TYPE: PRT
<213> ORGANISM: Homo sapiens

<400> SEQUENCE: 82

Met Leu Glu Ala Ile Asp Lys Asn Arg Ala Leu His Ala Ala Glu Arg
1               5                   10                  15

Leu Gln Thr Lys Leu Arg Glu Arg Gly Asp Val Ala Asn Glu Asp Lys
            20                  25                  30

Leu Ser Leu Leu Lys Ser Val Leu Gln Ser Pro Leu Phe Ser Gln Ile
        35                  40                  45

Leu Ser Leu Gln Thr Ser Val Gln Gln Leu Lys Asp Gln Val Asn Ile
    50                  55                  60

Ala Thr Ser Ala Thr Ser Asn Ile Glu Tyr Ala His Val Pro His Leu
65                  70                  75                  80

Ser Pro Ala Val Ile Pro Thr Leu Gln Asn Glu Ser Phe Leu Leu Ser
                85                  90                  95

Pro Asn Asn Gly Asn Leu Glu Ala Leu Thr Gly Pro Gly Ile Pro His
            100                 105                 110

Ile Asn Gly Lys Pro Ala Cys Asp Glu Phe Asp Gln Leu Ile Lys Asn
        115                 120                 125

Met Ala Gln Gly Arg His Val Glu Val Phe Glu Leu Leu Lys Pro Pro
```

```
            130                 135                 140
Ser Gly Gly Leu Gly Phe Ser Val Val Gly Leu Arg Ser Glu Asn Arg
145                 150                 155                 160

Gly Glu Leu Gly Ile Phe Val Gln Glu Ile Gln Glu Gly Ser Val Ala
                165                 170                 175

His Arg Asp Gly Arg Leu Lys Glu Thr Asp Gln Ile Leu Ala Ile Asn
                180                 185                 190

Gly Gln Ala Leu Asp Gln Thr Ile Thr His Gln Gln Ala Ile Ser Ile
            195                 200                 205

Leu Gln Lys Ala Lys Asp Thr Val Gln Leu Val Ile Ala Arg Gly Ser
210                 215                 220

Leu Pro Gln Leu Val Ser Pro Ile Val Ser Arg Ser Pro Ser Ala Ala
225                 230                 235                 240

Ser Thr Ile Ser Ala His Ser Asn Pro Val His Trp Gln His Met Glu
                245                 250                 255

Thr Ile Glu Leu Val Asn Asp Gly Ser Gly Leu Gly Phe Gly Ile Ile
                260                 265                 270

Gly Gly Lys Ala Thr Gly Val Ile Val Lys Thr Ile Leu Pro Gly Gly
            275                 280                 285

Val Ala Asp Gln His Gly Arg Leu Cys Ser Gly Asp His Ile Leu Lys
290                 295                 300

Ile Gly Asp Thr Asp Leu Ala Gly Met Ser Ser Glu Gln Val Ala Gln
305                 310                 315                 320

Val Leu Arg Gln Cys Gly Asn Arg Val Lys Leu Met Ile Ala Arg Ser
                325                 330                 335

Ala Ile Glu Glu Arg Thr Ala Pro Thr Ala Leu Gly Ile Thr Leu Ser
                340                 345                 350

Ser Ser Pro Thr Ser Thr Pro Glu Leu Arg Val Asp Ala Ser Thr Gln
            355                 360                 365

Lys Gly Glu Glu Ser Glu Thr Phe Asp Val Glu Leu Thr Lys Asn Val
                370                 375                 380

Gln Gly Leu Gly Ile Thr Ile Ala Gly Tyr Ile Gly Asp Lys Lys Leu
385                 390                 395                 400

Glu Pro Ser Gly Ile Phe Val Lys Ser Ile Thr Lys Ser Ser Ala Val
                405                 410                 415

Glu His Asp Gly Arg Ile Gln Ile Gly Asp Gln Ile Ile Ala Val Asp
                420                 425                 430

Gly Thr Asn Leu Gln Gly Phe Thr Asn Gln Gln Ala Val Glu Val Leu
            435                 440                 445

Arg His Thr Gly Gln Thr Val Leu Leu Thr Leu Met Arg Arg Gly Met
450                 455                 460

Lys Gln Glu Ala Glu Leu Met Ser Arg Glu Asp Val Thr Lys Asp Ala
465                 470                 475                 480

Asp Leu Ser Pro Val Asn Ala Ser Ile Ile Lys Glu Asn Tyr Glu Lys
                485                 490                 495

Asp Glu Asp Phe Leu Ser Ser Thr Arg Asn Thr Asn Ile Leu Pro Thr
                500                 505                 510

Glu Glu Glu Gly Tyr Pro Leu Leu Ser Ala Glu Ile Glu Glu Ile Glu
            515                 520                 525

Asp Ala Gln Lys Gln Glu Ala Leu Leu Thr Lys Trp Gln Arg Ile
530                 535                 540

Met Gly Ile Asn Tyr Glu Ile Val Val Ala His Val Ser Lys Phe Ser
545                 550                 555                 560
```

```
Glu Asn Ser Gly Leu Gly Ile Ser Leu Glu Ala Thr Val Gly His His
            565                 570                 575
Phe Ile Arg Ser Val Leu Pro Glu Gly Pro Val Gly His Ser Gly Lys
            580                 585                 590
Leu Phe Ser Gly Asp Glu Leu Leu Glu Val Asn Gly Ile Thr Leu Leu
            595                 600                 605
Gly Glu Asn His Gln Asp Val Val Asn Ile Leu Lys Glu Leu Pro Ile
        610                 615                 620
Glu Val Thr Met Val Cys Cys Arg Arg Thr Val Pro Pro Thr Thr Gln
625                 630                 635                 640
Ser Glu Leu Asp Ser Leu Asp Leu Cys Asp Ile Glu Leu Thr Glu Lys
            645                 650                 655
Pro His Val Asp Leu Gly Glu Phe Ile Gly Ser Ser Glu Pro Glu Asp
            660                 665                 670
Pro Val Leu Ala Met Thr Asp Ala Gly Gln Ser Thr Glu Glu Val Gln
            675                 680                 685
Ala Pro Leu Ala Met Trp Glu Ala Gly Ile Gln His Ile Met Leu Glu
        690                 695                 700
Lys Gly Ser Lys Gly Leu Gly Phe Ser Ile Leu Asp Tyr Gln Asp Pro
705                 710                 715                 720
Ile Asp Pro Ala Ser Thr Val Ile Ile Ile Arg Ser Leu Val Pro Gly
            725                 730                 735
Gly Ile Ala Glu Lys Asp Gly Arg Leu Leu Pro Gly Asp Arg Leu Met
            740                 745                 750
Phe Val Asn Asp Val Asn Leu Glu Asn Ser Ser Leu Glu Glu Ala Val
            755                 760                 765
Glu Ala Leu Lys Gly Ala Pro Ser Gly Thr Val Arg Ile Gly Val Ala
        770                 775                 780
Lys Pro Leu Pro Leu Ser Pro Glu Glu Gly Tyr Val Ser Ala Lys Glu
785                 790                 795                 800
Asp Ser Phe Leu Tyr Pro Pro His Ser Cys Glu Glu Ala Gly Leu Ala
            805                 810                 815
Asp Lys Pro Leu Phe Arg Ala Asp Leu Ala Leu Val Gly Thr Asn Asp
            820                 825                 830
Ala Asp Leu Val Asp Glu Ser Thr Phe Glu Ser Pro Tyr Ser Pro Glu
            835                 840                 845
Asn Asp Ser Ile Tyr Ser Thr Gln Ala Ser Ile Leu Ser Leu His Gly
            850                 855                 860
Ser Ser Cys Gly Asp Gly Leu Asn Tyr Gly Ser Ser Leu Pro Ser Ser
865                 870                 875                 880
Pro Pro Lys Asp Val Ile Glu Asn Ser Cys Asp Pro Val Leu Asp Leu
            885                 890                 895
His Met Ser Leu Glu Glu Leu Tyr Thr Gln Asn Leu Leu Glu Arg Gln
            900                 905                 910
Asp Glu Asn Thr Pro Ser Val Asp Ile Ser Met Gly Pro Ala Ser Gly
            915                 920                 925
Phe Thr Ile Asn Asp Tyr Thr Pro Ala Asn Ala Ile Glu Gln Gln Tyr
            930                 935                 940
Glu Cys Glu Asn Thr Ile Val Trp Thr Glu His Leu Pro Ser Glu
945                 950                 955                 960
Val Ile Ser Ser Ala Glu Leu Pro Ser Val Leu Pro Asp Ser Ala Gly
            965                 970                 975
```

-continued

```
Lys Gly Ser Glu His Leu Leu Glu Gln Ser Ser Leu Ala Cys Asn Ala
            980                 985                 990

Glu Cys Val Met Leu Gln Asn Val Ser Lys Glu Ser Phe Glu Arg Thr
            995                 1000                1005

Ile Asn Ile Ala Lys Gly Asn Ser Ser Leu Gly Met Thr Val Ser Ala
            1010                1015                1020

Asn Lys Asp Gly Leu Gly Met Ile Val Arg Ser Ile Ile His Gly Gly
1025                1030                1035                1040

Ala Ile Ser Arg Asp Gly Arg Ile Ala Ile Gly Asp Cys Ile Leu Ser
            1045                1050                1055

Ile Asn Glu Glu Ser Thr Ile Ser Val Thr Asn Ala Gln Ala Arg Ala
            1060                1065                1070

Met Leu Arg Arg His Ser Leu Ile Gly Pro Asp Ile Lys Ile Thr Tyr
            1075                1080                1085

Val Pro Ala Glu His Leu Glu Glu Phe Lys Ile Ser Leu Gly Gln Gln
            1090                1095                1100

Ser Gly Arg Val Met Ala Leu Asp Ile Phe Ser Ser Tyr Thr Gly Arg
1105                1110                1115                1120

Asp Ile Pro Glu Leu Pro Glu Arg Glu Glu Gly Glu Gly Glu Glu Ser
            1125                1130                1135

Glu Leu Gln Asn Thr Ala Tyr Ser Asn Trp Asn Gln Pro Arg Arg Val
            1140                1145                1150

Glu Leu Trp Arg Glu Pro Ser Lys Ser Leu Gly Ile Ser Ile Val Gly
            1155                1160                1165

Gly Arg Gly Met Gly Ser Arg Leu Ser Asn Gly Glu Val Met Arg Gly
            1170                1175                1180

Ile Phe Ile Lys His Val Leu Glu Asp Ser Pro Ala Gly Lys Asn Gly
1185                1190                1195                1200

Thr Leu Lys Pro Gly Asp Arg Ile Val Glu Ala Pro Ser Gln Ser Glu
            1205                1210                1215

Ser Glu Pro Glu Lys Ala Pro Leu Cys Ser Val Pro Pro Pro Pro Pro
            1220                1225                1230

Ser Ala Phe Ala Glu Met Gly Ser Asp His Thr Gln Ser Ser Ala Ser
            1235                1240                1245

Lys Ile Ser Gln Asp Val Asp Lys Glu Asp Glu Phe Gly Tyr Ser Trp
            1250                1255                1260

Lys Asn Ile Arg Glu Arg Tyr Gly Thr Leu Thr Gly Glu Leu His Met
1265                1270                1275                1280

Ile Glu Leu Glu Lys Gly His Ser Gly Leu Gly Leu Ser Leu Ala Gly
            1285                1290                1295

Asn Lys Asp Arg Ser Arg Met Ser Val Phe Ile Val Gly Ile Asp Pro
            1300                1305                1310

Asn Gly Ala Ala Gly Lys Asp Gly Arg Leu Gln Ile Ala Asp Glu Leu
            1315                1320                1325

Leu Glu Ile Asn Gly Gln Ile Leu Tyr Gly Arg Ser His Gln Asn Ala
            1330                1335                1340

Ser Ser Ile Ile Lys Cys Ala Pro Ser Lys Val Lys Ile Ile Phe Ile
1345                1350                1355                1360

Arg Asn Lys Asp Ala Val Asn Gln Met Ala Val Cys Pro Gly Asn Ala
            1365                1370                1375

Val Glu Pro Leu Pro Ser Asn Ser Glu Asn Leu Gln Asn Lys Glu Thr
            1380                1385                1390

Glu Pro Thr Val Thr Thr Ser Asp Ala Ala Val Asp Leu Ser Ser Phe
```

-continued

```
              1395                1400               1405
Lys Asn Val Gln His Leu Glu Leu Pro Lys Asp Gln Gly Gly Leu Gly
    1410                1415                1420

Ile Ala Ile Ser Glu Glu Asp Thr Leu Ser Gly Val Ile Ile Lys Ser
1425                1430                1435                1440

Leu Thr Glu His Gly Val Ala Ala Thr Asp Gly Arg Leu Lys Val Gly
                1445                1450                1455

Asp Gln Ile Leu Ala Val Asp Asp Glu Ile Val Val Gly Tyr Pro Ile
                1460                1465                1470

Glu Lys Phe Ile Ser Leu Leu Lys Thr Ala Lys Met Thr Val Lys Leu
    1475                1480                1485

Thr Ile His Ala Glu Asn Pro Asp Ser Gln Ala Val Pro Ser Ala Ala
    1490                1495                1500

Gly Ala Ala Ser Gly Glu Lys Lys Asn Ser Ser Gln Ser Leu Met Val
1505                1510                1515                1520

Pro Gln Ser Gly Ser Pro Glu Pro Glu Ser Ile Arg Asn Thr Ser Arg
                1525                1530                1535

Ser Ser Thr Pro Ala Ile Phe Ala Ser Asp Pro Ala Thr Cys Pro Ile
    1540                1545                1550

Ile Pro Gly Cys Glu Thr Thr Ile Glu Ile Ser Lys Gly Arg Thr Gly
    1555                1560                1565

Leu Gly Leu Ser Ile Val Gly Gly Ser Asp Thr Leu Leu Gly Ala Phe
    1570                1575                1580

Ile Ile His Glu Val Tyr Glu Glu Gly Ala Ala Cys Lys Asp Gly Arg
1585                1590                1595                1600

Leu Trp Ala Gly Asp Gln Ile Leu Glu Val Asn Gly Ile Asp Leu Arg
                1605                1610                1615

Lys Ala Thr His Asp Glu Ala Ile Asn Val Leu Arg Gln Thr Pro Gln
                1620                1625                1630

Arg Val Arg Leu Thr Leu Tyr Arg Asp Glu Ala Pro Tyr Lys Glu Glu
    1635                1640                1645

Glu Val Cys Asp Thr Leu Thr Ile Glu Leu Gln Lys Lys Pro Gly Lys
    1650                1655                1660

Gly Leu Gly Leu Ser Ile Val Gly Lys Arg Asn Asp Thr Gly Val Phe
1665                1670                1675                1680

Val Ser Asp Ile Val Lys Gly Gly Ile Ala Asp Pro Asp Gly Arg Leu
                1685                1690                1695

Ile Gln Gly Asp Gln Ile Leu Leu Val Asn Gly Glu Asp Val Arg Asn
                1700                1705                1710

Ala Ser Gln Glu Ala Val Ala Ala Leu Leu Lys Cys Ser Leu Gly Thr
                1715                1720                1725

Val Thr Leu Glu Val Gly Arg Ile Lys Ala Gly Pro Phe His Ser Glu
    1730                1735                1740

Arg Arg Pro Ser Gln Thr Ser Gln Val Ser Glu Gly Ser Leu Ser Ser
1745                1750                1755                1760

Phe Thr Phe Pro Leu Ser Gly Ser Ser Thr Ser Glu Ser Leu Glu Ser
                1765                1770                1775

Ser Ser Lys Lys Asn Ala Leu Ala Ser Glu Ile Gln Gly Leu Arg Thr
                1780                1785                1790

Val Glu Met Lys Lys Gly Pro Thr Asp Ser Leu Gly Ile Ser Ile Ala
    1795                1800                1805

Gly Gly Val Gly Ser Pro Leu Gly Asp Val Pro Ile Phe Ile Ala Met
    1810                1815                1820
```

-continued

```
Met His Pro Thr Gly Val Ala Ala Gln Thr Gln Lys Leu Arg Val Gly
1825                1830                1835                1840

Asp Arg Ile Val Thr Ile Cys Gly Thr Ser Thr Glu Gly Met Thr His
                1845                1850                1855

Thr Gln Ala Val Asn Leu Leu Lys Asn Ala Ser Gly Ser Ile Glu Met
            1860                1865                1870

Gln Val Val Ala Gly Gly Asp Val Ser Val Thr Gly His His Gln
        1875                1880                1885

Glu Pro Ala Ser Ser Ser Leu Ser Phe Thr Gly Leu Thr Ser Thr Ser
    1890                1895                1900

Ile Phe Gln Asp Asp Leu Gly Pro Pro Gln Cys Lys Ser Ile Thr Leu
1905                1910                1915                1920

Glu Arg Gly Pro Asp Gly Leu Gly Phe Ser Ile Val Gly Gly Tyr Gly
                1925                1930                1935

Ser Pro His Gly Asp Leu Pro Ile Tyr Val Lys Thr Val Phe Ala Lys
                1940                1945                1950

Gly Ala Ala Ser Glu Asp Gly Arg Leu Lys Arg Gly Asp Gln Ile Ile
            1955                1960                1965

Ala Val Asn Gly Gln Ser Leu Glu Gly Val Thr His Glu Glu Ala Val
    1970                1975                1980

Ala Ile Leu Lys Arg Thr Lys Gly Thr Val Thr Leu Met Val Leu Ser
1985                1990                1995                2000

<210> SEQ ID NO 83
<211> LENGTH: 2070
<212> TYPE: PRT
<213> ORGANISM: Homo sapiens

<400> SEQUENCE: 83

Met Leu Glu Ala Ile Asp Lys Asn Arg Ala Leu His Ala Ala Glu Arg
  1               5                  10                  15

Leu Gln Thr Lys Leu Arg Glu Arg Gly Asp Val Ala Asn Glu Asp Lys
                20                  25                  30

Leu Ser Leu Leu Lys Ser Val Leu Gln Ser Pro Leu Phe Ser Gln Ile
            35                  40                  45

Leu Ser Leu Gln Thr Ser Val Gln Gln Leu Lys Asp Gln Val Asn Ile
        50                  55                  60

Ala Thr Ser Ala Thr Ser Asn Ile Glu Tyr Ala His Val Pro His Leu
 65                  70                  75                  80

Ser Pro Ala Val Ile Pro Thr Leu Gln Asn Glu Ser Phe Leu Leu Ser
                85                  90                  95

Pro Asn Asn Gly Asn Leu Glu Ala Leu Thr Gly Pro Gly Ile Pro His
            100                 105                 110

Ile Asn Gly Lys Pro Ala Cys Asp Glu Phe Asp Gln Leu Ile Lys Asn
        115                 120                 125

Met Ala Gln Gly Arg His Val Glu Val Phe Glu Leu Leu Lys Pro Pro
    130                 135                 140

Ser Gly Gly Leu Gly Phe Ser Val Val Gly Leu Arg Ser Glu Asn Arg
145                 150                 155                 160

Gly Glu Leu Gly Ile Phe Val Gln Glu Ile Gln Glu Gly Ser Val Ala
                165                 170                 175

His Arg Asp Gly Arg Leu Lys Glu Thr Asp Gln Ile Leu Ala Ile Asn
            180                 185                 190

Gly Gln Ala Leu Asp Gln Thr Ile Thr His Gln Gln Ala Ile Ser Ile
```

```
                195                 200                 205
Leu Gln Lys Ala Lys Asp Thr Val Gln Leu Val Ile Ala Arg Gly Ser
    210                 215                 220

Leu Pro Gln Leu Val Ser Pro Ile Val Ser Arg Ser Pro Ser Ala Ala
225                 230                 235                 240

Ser Thr Ile Ser Ala His Ser Asn Pro Val His Trp Gln His Met Glu
                245                 250                 255

Thr Ile Glu Leu Val Asn Asp Gly Ser Gly Leu Gly Phe Gly Ile Ile
            260                 265                 270

Gly Gly Lys Ala Thr Gly Val Ile Val Lys Thr Ile Leu Pro Gly Gly
        275                 280                 285

Val Ala Asp Gln His Gly Arg Leu Cys Ser Gly Asp His Ile Leu Lys
    290                 295                 300

Ile Gly Asp Thr Asp Leu Ala Gly Met Ser Ser Glu Gln Val Ala Gln
305                 310                 315                 320

Val Leu Arg Gln Cys Gly Asn Arg Val Lys Leu Met Ile Ala Arg Ser
                325                 330                 335

Ala Ile Glu Glu Arg Thr Ala Pro Thr Ala Leu Gly Ile Thr Leu Ser
            340                 345                 350

Ser Ser Pro Thr Ser Thr Pro Glu Leu Arg Val Asp Ala Ser Thr Gln
        355                 360                 365

Lys Gly Glu Glu Ser Glu Thr Phe Asp Val Glu Leu Thr Lys Asn Val
    370                 375                 380

Gln Gly Leu Gly Ile Thr Ile Ala Gly Tyr Ile Gly Asp Lys Lys Leu
385                 390                 395                 400

Glu Pro Ser Gly Ile Phe Val Lys Ser Ile Thr Lys Ser Ser Ala Val
                405                 410                 415

Glu His Asp Gly Arg Ile Gln Ile Gly Asp Gln Ile Ile Ala Val Asp
            420                 425                 430

Gly Thr Asn Leu Gln Gly Phe Thr Asn Gln Gln Ala Val Glu Val Leu
        435                 440                 445

Arg His Thr Gly Gln Thr Val Leu Leu Thr Leu Met Arg Arg Gly Met
    450                 455                 460

Lys Gln Glu Ala Glu Leu Met Ser Arg Glu Asp Val Thr Lys Asp Ala
465                 470                 475                 480

Asp Leu Ser Pro Val Asn Ala Ser Ile Ile Lys Glu Asn Tyr Glu Lys
                485                 490                 495

Asp Glu Asp Phe Leu Ser Ser Thr Arg Asn Thr Asn Ile Leu Pro Thr
            500                 505                 510

Glu Glu Glu Gly Tyr Pro Leu Leu Ser Ala Glu Ile Glu Glu Ile Glu
        515                 520                 525

Asp Ala Gln Lys Gln Glu Ala Ala Leu Leu Thr Lys Trp Gln Arg Ile
    530                 535                 540

Met Gly Ile Asn Tyr Glu Ile Val Val Ala His Val Ser Lys Phe Ser
545                 550                 555                 560

Glu Asn Ser Gly Leu Gly Ile Ser Leu Glu Ala Thr Val Gly His His
                565                 570                 575

Phe Ile Arg Ser Val Leu Pro Glu Gly Pro Val Gly His Ser Gly Lys
            580                 585                 590

Leu Phe Ser Gly Asp Glu Leu Leu Glu Val Asn Gly Ile Thr Leu Leu
        595                 600                 605

Gly Glu Asn His Gln Asp Val Val Asn Ile Leu Lys Glu Leu Pro Ile
    610                 615                 620
```

-continued

```
Glu Val Thr Met Val Cys Cys Arg Arg Thr Val Pro Thr Thr Gln
625                 630                 635                 640

Ser Glu Leu Asp Ser Leu Asp Leu Cys Asp Ile Glu Leu Thr Glu Lys
                645                 650                 655

Pro His Val Asp Leu Gly Glu Phe Ile Gly Ser Ser Glu Pro Glu Asp
                660                 665                 670

Pro Val Leu Ala Met Thr Asp Ala Gly Gln Ser Thr Glu Glu Val Gln
                675                 680                 685

Ala Pro Leu Ala Met Trp Glu Ala Gly Ile Gln His Ile Met Leu Glu
690                 695                 700

Lys Gly Ser Lys Gly Leu Gly Phe Ser Ile Leu Asp Tyr Gln Asp Pro
705                 710                 715                 720

Ile Asp Pro Ala Ser Thr Val Ile Ile Ile Arg Ser Leu Val Pro Gly
                725                 730                 735

Gly Ile Ala Glu Lys Asp Gly Arg Leu Leu Pro Gly Asp Arg Leu Met
                740                 745                 750

Phe Val Asn Asp Val Asn Leu Glu Asn Ser Ser Leu Glu Glu Ala Val
                755                 760                 765

Glu Ala Leu Lys Gly Ala Pro Ser Gly Thr Val Arg Ile Gly Val Ala
770                 775                 780

Lys Pro Leu Pro Leu Ser Pro Glu Glu Gly Tyr Val Ser Ala Lys Glu
785                 790                 795                 800

Asp Ser Phe Leu Tyr Pro Pro His Ser Cys Glu Glu Ala Gly Leu Ala
                805                 810                 815

Asp Lys Pro Leu Phe Arg Ala Asp Leu Ala Leu Val Gly Thr Asn Asp
                820                 825                 830

Ala Asp Leu Val Asp Glu Ser Thr Phe Glu Ser Pro Tyr Ser Pro Glu
                835                 840                 845

Asn Asp Ser Ile Tyr Ser Thr Gln Ala Ser Ile Leu Ser Leu His Gly
850                 855                 860

Ser Ser Cys Gly Asp Gly Leu Asn Tyr Gly Ser Ser Leu Pro Ser Ser
865                 870                 875                 880

Pro Pro Lys Asp Val Ile Glu Asn Ser Cys Asp Pro Val Leu Asp Leu
                885                 890                 895

His Met Ser Leu Glu Glu Leu Tyr Thr Gln Asn Leu Leu Glu Arg Gln
                900                 905                 910

Asp Glu Asn Thr Pro Ser Val Asp Ile Ser Met Gly Pro Ala Ser Gly
                915                 920                 925

Phe Thr Ile Asn Asp Tyr Thr Pro Ala Asn Ala Ile Glu Gln Gln Tyr
                930                 935                 940

Glu Cys Glu Asn Thr Ile Val Trp Thr Glu Ser His Leu Pro Ser Glu
945                 950                 955                 960

Val Ile Ser Ser Ala Glu Leu Pro Ser Val Leu Pro Asp Ser Ala Gly
                965                 970                 975

Lys Gly Ser Glu Tyr Leu Leu Glu Gln Ser Ser Leu Ala Cys Asn Ala
                980                 985                 990

Glu Cys Val Met Leu Gln Asn Val Ser Lys Glu Ser Phe Glu Arg Thr
                995                 1000                1005

Ile Asn Ile Ala Lys Gly Asn Ser Ser Leu Gly Met Thr Val Ser Ala
                1010                1015                1020

Asn Lys Asp Gly Leu Gly Met Ile Val Arg Ser Ile Ile His Gly Gly
1025                1030                1035                1040
```

-continued

```
Ala Ile Ser Arg Asp Gly Arg Ile Ala Ile Gly Asp Cys Ile Leu Ser
            1045                1050                1055

Ile Asn Glu Glu Ser Thr Ile Ser Val Thr Asn Ala Gln Ala Arg Ala
            1060                1065                1070

Met Leu Arg Arg His Ser Leu Ile Gly Pro Asp Ile Lys Ile Thr Tyr
            1075                1080                1085

Val Pro Ala Glu His Leu Glu Glu Phe Lys Ile Ser Leu Gly Gln Gln
            1090                1095                1100

Ser Gly Arg Val Met Ala Leu Asp Ile Phe Ser Ser Tyr Thr Gly Arg
1105                1110                1115                1120

Asp Ile Pro Glu Leu Pro Glu Arg Glu Gly Glu Gly Glu Glu Ser
            1125                1130                1135

Glu Leu Gln Asn Thr Ala Tyr Ser Asn Trp Asn Gln Pro Arg Arg Val
            1140                1145                1150

Glu Leu Trp Arg Glu Pro Ser Lys Ser Leu Gly Ile Ser Ile Val Gly
            1155                1160                1165

Gly Arg Gly Met Gly Ser Arg Leu Ser Asn Gly Glu Val Met Arg Gly
            1170                1175                1180

Ile Phe Ile Lys His Val Leu Glu Asp Arg Pro Ala Gly Lys Asn Gly
1185                1190                1195                1200

Thr Leu Lys Pro Gly Asp Arg Ile Val Glu Val Asp Gly Met Asp Leu
            1205                1210                1215

Arg Asp Ala Ser His Glu Gln Ala Val Glu Ala Ile Arg Lys Ala Gly
            1220                1225                1230

Asn Pro Val Val Phe Met Val Gln Ser Ile Ile Asn Arg Pro Arg Lys
            1235                1240                1245

Ser Pro Leu Pro Ser Leu Leu His Asn Leu Tyr Pro Lys Tyr Asn Phe
            1250                1255                1260

Ser Ser Thr Asn Pro Phe Ala Asp Ser Leu Gln Ile Asn Ala Asp Lys
1265                1270                1275                1280

Ala Pro Ser Gln Ser Glu Ser Glu Pro Glu Lys Ala Pro Leu Cys Ser
            1285                1290                1295

Val Pro Pro Pro Pro Ser Ala Phe Ala Glu Met Gly Ser Asp His
            1300                1305                1310

Thr Gln Ser Ser Ala Ser Lys Ile Ser Gln Asp Val Asp Lys Glu Asp
            1315                1320                1325

Glu Phe Gly Tyr Ser Trp Lys Asn Ile Arg Glu Arg Tyr Gly Thr Leu
            1330                1335                1340

Thr Gly Glu Leu His Met Ile Glu Leu Glu Lys Gly His Ser Gly Leu
1345                1350                1355                1360

Gly Leu Ser Leu Ala Gly Asn Lys Asp Arg Ser Arg Met Ser Val Phe
            1365                1370                1375

Ile Val Gly Ile Asp Pro Asn Gly Ala Ala Gly Lys Asp Gly Arg Leu
            1380                1385                1390

Gln Ile Ala Asp Glu Leu Leu Glu Ile Asn Gly Gln Ile Leu Tyr Gly
            1395                1400                1405

Arg Ser His Gln Asn Ala Ser Ser Ile Ile Lys Cys Ala Pro Ser Lys
            1410                1415                1420

Val Lys Ile Ile Phe Ile Arg Asn Lys Asp Ala Val Asn Gln Met Ala
1425                1430                1435                1440

Val Cys Pro Gly Asn Ala Val Glu Pro Leu Pro Ser Asn Ser Glu Asn
            1445                1450                1455

Leu Gln Asn Lys Glu Thr Glu Pro Thr Val Thr Thr Ser Asp Ala Ala
```

-continued

```
                1460                1465                1470
Val Asp Leu Ser Ser Phe Lys Asn Val Gln His Leu Glu Leu Pro Lys
        1475                1480                1485
Asp Gln Gly Gly Leu Gly Ile Ala Ile Ser Glu Glu Asp Thr Leu Ser
        1490                1495                1500
Gly Val Ile Ile Lys Ser Leu Thr Glu His Gly Val Ala Ala Thr Asp
1505                1510                1515                1520
Gly Arg Leu Lys Val Gly Asp Gln Ile Leu Ala Val Asp Asp Glu Ile
            1525                1530                1535
Val Val Gly Tyr Pro Ile Glu Lys Phe Ile Ser Leu Leu Lys Thr Ala
        1540                1545                1550
Lys Met Thr Val Lys Leu Thr Ile His Ala Glu Asn Pro Asp Ser Gln
        1555                1560                1565
Ala Val Pro Ser Ala Ala Gly Ala Ser Gly Glu Lys Lys Asn Ser
        1570                1575                1580
Ser Gln Ser Leu Met Val Pro Gln Ser Gly Ser Pro Glu Pro Glu Ser
1585                1590                1595                1600
Ile Arg Asn Thr Ser Arg Ser Ser Thr Pro Ala Ile Phe Ala Ser Asp
            1605                1610                1615
Pro Ala Thr Cys Pro Ile Ile Pro Gly Cys Glu Thr Thr Ile Glu Ile
            1620                1625                1630
Ser Lys Gly Arg Thr Gly Leu Gly Leu Ser Ile Val Gly Gly Ser Asp
        1635                1640                1645
Thr Leu Leu Gly Ala Phe Ile Ile His Glu Val Tyr Glu Glu Gly Ala
        1650                1655                1660
Ala Cys Lys Asp Gly Arg Leu Trp Ala Gly Asp Gln Ile Leu Glu Val
1665                1670                1675                1680
Asn Gly Ile Asp Leu Arg Lys Ala Thr His Asp Glu Ala Ile Asn Val
            1685                1690                1695
Leu Arg Gln Thr Pro Gln Arg Val Arg Leu Thr Leu Tyr Arg Asp Glu
            1700                1705                1710
Ala Pro Tyr Lys Glu Glu Val Cys Asp Thr Leu Thr Ile Glu Leu
        1715                1720                1725
Gln Lys Lys Pro Gly Lys Gly Leu Gly Leu Ser Ile Val Gly Lys Arg
        1730                1735                1740
Asn Asp Thr Gly Val Phe Val Ser Asp Ile Val Lys Gly Gly Ile Ala
1745                1750                1755                1760
Asp Pro Asp Gly Arg Leu Ile Gln Gly Asp Gln Ile Leu Leu Val Asn
            1765                1770                1775
Gly Glu Asp Val Arg Asn Ala Ser Gln Glu Ala Val Ala Ala Leu Leu
            1780                1785                1790
Lys Cys Ser Leu Gly Thr Val Thr Leu Glu Val Gly Arg Ile Lys Ala
        1795                1800                1805
Gly Pro Phe His Ser Glu Arg Arg Pro Ser Gln Thr Ser Gln Val Ser
        1810                1815                1820
Glu Gly Ser Leu Ser Ser Phe Thr Phe Pro Leu Ser Gly Ser Ser Thr
1825                1830                1835                1840
Ser Glu Ser Leu Glu Ser Ser Lys Lys Asn Ala Leu Ala Ser Glu
            1845                1850                1855
Ile Gln Gly Leu Arg Thr Val Glu Met Lys Lys Gly Pro Thr Asp Ser
            1860                1865                1870
Leu Gly Ile Ser Ile Ala Gly Gly Val Gly Ser Pro Leu Gly Asp Val
        1875                1880                1885
```

-continued

```
Pro Ile Phe Ile Ala Met Met His Pro Thr Gly Val Ala Ala Gln Thr
            1890                1895                1900

Gln Lys Leu Arg Val Gly Asp Arg Ile Val Thr Ile Cys Gly Thr Ser
1905                1910                1915                1920

Thr Glu Gly Met Thr His Thr Gln Ala Val Asn Leu Leu Lys Asn Ala
                1925                1930                1935

Ser Gly Ser Ile Glu Met Gln Val Val Ala Gly Gly Asp Val Ser Val
                1940                1945                1950

Val Thr Gly His His Gln Glu Pro Ala Ser Ser Leu Ser Phe Thr
            1955                1960                1965

Gly Leu Thr Ser Thr Ser Ile Phe Gln Asp Asp Leu Gly Pro Pro Gln
            1970                1975                1980

Cys Lys Ser Ile Thr Leu Glu Arg Gly Pro Asp Gly Leu Gly Phe Ser
1985                1990                1995                2000

Ile Val Gly Gly Tyr Gly Ser Pro His Gly Asp Leu Pro Ile Tyr Val
                2005                2010                2015

Lys Thr Val Phe Ala Lys Gly Ala Ala Ser Glu Asp Gly Arg Leu Lys
                2020                2025                2030

Arg Gly Asp Gln Ile Ile Ala Val Asn Gly Gln Ser Leu Glu Gly Val
            2035                2040                2045

Thr His Glu Glu Ala Val Ala Ile Leu Lys Arg Thr Lys Gly Thr Val
            2050                2055                2060

Thr Leu Met Val Leu Ser
2065                2070

<210> SEQ ID NO 84
<211> LENGTH: 1239
<212> TYPE: PRT
<213> ORGANISM: Homo sapiens

<400> SEQUENCE: 84

Met Leu Glu Ala Ile Asp Lys Asn Arg Ala Leu His Ala Ala Glu Arg
  1               5                  10                  15

Leu Gln Thr Lys Leu Arg Glu Arg Gly Asp Val Ala Asn Glu Asp Lys
             20                  25                  30

Leu Ser Leu Leu Lys Ser Val Leu Gln Ser Pro Leu Phe Ser Gln Ile
         35                  40                  45

Leu Ser Leu Gln Thr Ser Val Gln Gln Leu Lys Asp Gln Val Asn Ile
     50                  55                  60

Ala Thr Ser Ala Thr Ser Asn Ile Glu Tyr Ala His Val Pro His Leu
 65                  70                  75                  80

Ser Pro Ala Val Ile Pro Thr Leu Gln Asn Glu Ser Phe Leu Leu Ser
                 85                  90                  95

Pro Asn Asn Gly Asn Leu Glu Ala Leu Thr Gly Pro Gly Ile Pro His
            100                 105                 110

Ile Asn Gly Lys Pro Ala Cys Asp Glu Phe Asp Gln Leu Ile Lys Asn
        115                 120                 125

Met Ala Gln Gly Arg His Val Glu Val Phe Glu Leu Leu Lys Pro Pro
    130                 135                 140

Ser Gly Gly Leu Gly Phe Ser Val Val Gly Leu Arg Ser Glu Asn Arg
145                 150                 155                 160

Gly Glu Leu Gly Ile Phe Val Gln Glu Ile Gln Glu Gly Ser Val Ala
                165                 170                 175

His Arg Asp Gly Arg Leu Lys Glu Thr Asp Gln Ile Leu Ala Ile Asn
```

-continued

```
            180                 185                 190
Gly Gln Ala Leu Asp Gln Thr Ile Thr His Gln Ala Ile Ser Ile
        195                 200                 205
Leu Gln Lys Ala Lys Asp Thr Val Gln Leu Val Ile Ala Arg Gly Ser
210                 215                 220
Leu Pro Gln Leu Val Ser Pro Ile Val Ser Arg Ser Pro Ser Ala Ala
225                 230                 235                 240
Ser Thr Ile Ser Ala His Ser Asn Pro Val His Trp Gln His Met Glu
                245                 250                 255
Thr Ile Glu Leu Val Asn Asp Gly Ser Gly Leu Gly Phe Gly Ile Ile
            260                 265                 270
Gly Gly Lys Ala Thr Gly Val Ile Val Lys Thr Ile Leu Pro Gly Gly
        275                 280                 285
Val Ala Asp Gln His Gly Arg Leu Cys Ser Gly Asp His Ile Leu Lys
290                 295                 300
Ile Gly Asp Thr Asp Leu Ala Gly Met Ser Ser Glu Gln Val Ala Gln
305                 310                 315                 320
Val Leu Arg Gln Cys Gly Asn Arg Val Lys Leu Met Ile Ala Arg Ser
                325                 330                 335
Ala Ile Glu Glu Arg Thr Ala Pro Thr Ala Leu Gly Ile Thr Leu Ser
            340                 345                 350
Ser Ser Pro Thr Ser Thr Pro Glu Leu Arg Val Asp Ala Ser Thr Gln
        355                 360                 365
Lys Gly Glu Glu Ser Glu Thr Phe Asp Val Glu Leu Thr Lys Asn Val
370                 375                 380
Gln Gly Leu Gly Ile Thr Ile Ala Gly Tyr Ile Gly Asp Lys Lys Leu
385                 390                 395                 400
Glu Pro Ser Gly Ile Phe Val Lys Ser Ile Thr Lys Ser Ser Ala Val
                405                 410                 415
Glu His Asp Gly Arg Ile Gln Ile Gly Asp Gln Ile Ile Ala Val Asp
            420                 425                 430
Gly Thr Asn Leu Gln Gly Phe Thr Asn Gln Gln Ala Val Glu Val Leu
        435                 440                 445
Arg His Thr Gly Gln Thr Val Leu Leu Thr Leu Met Arg Arg Gly Met
450                 455                 460
Lys Gln Glu Ala Glu Leu Met Ser Arg Glu Asp Val Thr Lys Asp Ala
465                 470                 475                 480
Asp Leu Ser Pro Val Asn Ala Ser Ile Ile Lys Glu Asn Tyr Glu Lys
                485                 490                 495
Asp Glu Asp Phe Leu Ser Ser Thr Arg Asn Thr Asn Ile Leu Pro Thr
            500                 505                 510
Glu Glu Glu Gly Tyr Pro Leu Leu Ser Ala Glu Ile Glu Glu Ile Glu
        515                 520                 525
Asp Ala Gln Lys Gln Glu Ala Ala Leu Leu Thr Lys Trp Gln Arg Ile
530                 535                 540
Met Gly Ile Asn Tyr Glu Ile Val Val Ala His Val Ser Lys Phe Ser
545                 550                 555                 560
Glu Asn Ser Gly Leu Gly Ile Ser Leu Glu Ala Thr Val Gly His His
                565                 570                 575
Phe Ile Arg Ser Val Leu Pro Glu Gly Pro Val Gly His Ser Gly Lys
            580                 585                 590
Leu Phe Ser Gly Asp Glu Leu Leu Glu Val Asn Gly Ile Thr Leu Leu
        595                 600                 605
```

-continued

```
Gly Glu Asn His Gln Asp Val Val Asn Ile Leu Lys Glu Leu Pro Ile
    610                 615                 620

Glu Val Thr Met Val Cys Cys Arg Arg Thr Val Pro Pro Thr Thr Gln
625                 630                 635                 640

Ser Glu Leu Asp Ser Leu Asp Leu Cys Asp Ile Glu Leu Thr Glu Lys
                645                 650                 655

Pro His Val Asp Leu Gly Glu Phe Ile Gly Ser Ser Glu Pro Glu Asp
            660                 665                 670

Pro Val Leu Ala Met Thr Asp Ala Gly Gln Ser Thr Glu Glu Val Gln
        675                 680                 685

Ala Pro Leu Ala Met Trp Glu Ala Gly Ile Gln His Ile Met Leu Glu
    690                 695                 700

Lys Gly Ser Lys Gly Leu Gly Phe Ser Ile Leu Asp Tyr Gln Asp Pro
705                 710                 715                 720

Ile Asp Pro Ala Ser Thr Val Ile Ile Ile Arg Ser Leu Val Pro Gly
                725                 730                 735

Gly Ile Ala Glu Lys Asp Gly Arg Leu Leu Pro Gly Asp Arg Leu Met
            740                 745                 750

Phe Val Asn Asp Val Asn Leu Glu Asn Ser Ser Leu Glu Glu Ala Val
        755                 760                 765

Glu Ala Leu Lys Gly Ala Pro Ser Gly Thr Val Arg Ile Gly Val Ala
    770                 775                 780

Lys Pro Leu Pro Leu Ser Pro Glu Glu Gly Tyr Val Ser Ala Lys Glu
785                 790                 795                 800

Asp Ser Phe Leu Tyr Pro Pro His Ser Cys Glu Glu Ala Gly Leu Ala
                805                 810                 815

Asp Lys Pro Leu Phe Arg Ala Asp Leu Ala Leu Val Gly Thr Asn Asp
            820                 825                 830

Ala Asp Leu Val Asp Glu Ser Thr Phe Glu Ser Pro Tyr Ser Pro Glu
        835                 840                 845

Asn Asp Ser Ile Tyr Ser Thr Gln Ala Ser Ile Leu Ser Leu His Gly
    850                 855                 860

Ser Ser Cys Gly Asp Gly Leu Asn Tyr Gly Ser Ser Leu Pro Ser Ser
865                 870                 875                 880

Pro Pro Lys Asp Val Ile Glu Asn Ser Cys Asp Pro Val Leu Asp Leu
                885                 890                 895

His Met Ser Leu Glu Glu Leu Tyr Thr Gln Asn Leu Leu Glu Arg Gln
            900                 905                 910

Asp Glu Asn Thr Pro Ser Val Asp Ile Ser Met Gly Pro Ala Ser Gly
        915                 920                 925

Phe Thr Ile Asn Asp Tyr Thr Pro Ala Asn Ala Ile Glu Gln Gln Tyr
    930                 935                 940

Glu Cys Glu Asn Thr Ile Val Trp Thr Glu Ser His Leu Pro Ser Glu
945                 950                 955                 960

Val Ile Ser Ser Ala Glu Leu Pro Ser Val Leu Pro Asp Ser Ala Gly
                965                 970                 975

Lys Gly Ser Glu His Leu Leu Glu Gln Ser Ser Leu Ala Cys Asn Ala
            980                 985                 990

Glu Cys Val Met Leu Gln Asn Val Ser Lys Glu Ser Phe Glu Arg Thr
        995                 1000                1005

Ile Asn Ile Ala Lys Gly Asn Ser Ser Leu Gly Met Thr Val Ser Ala
    1010                1015                1020
```

```
Asn Lys Asp Gly Leu Gly Met Ile Val Arg Ser Ile His Gly Gly
1025                1030                1035                1040

Ala Ile Ser Arg Asp Gly Arg Ile Ala Ile Gly Asp Cys Ile Leu Ser
            1045                1050                1055

Ile Asn Glu Glu Ser Thr Ile Ser Val Thr Asn Ala Gln Ala Arg Ala
        1060                1065                1070

Met Leu Arg Arg His Ser Leu Ile Gly Pro Asp Ile Lys Ile Thr Tyr
    1075                1080                1085

Val Pro Ala Glu His Leu Glu Glu Phe Lys Ile Ser Leu Gly Gln Gln
1090                1095                1100

Ser Gly Arg Val Met Ala Leu Asp Ile Phe Ser Ser Tyr Thr Gly Arg
1105                1110                1115                1120

Asp Ile Pro Glu Leu Pro Glu Arg Glu Glu Gly Glu Gly Glu Glu Ser
                1125                1130                1135

Glu Leu Gln Asn Thr Ala Tyr Ser Asn Trp Asn Gln Pro Arg Arg Val
            1140                1145                1150

Glu Leu Trp Arg Glu Pro Ser Lys Ser Leu Gly Ile Ser Ile Val Gly
        1155                1160                1165

Gly Arg Gly Met Gly Ser Arg Leu Ser Asn Gly Glu Val Met Arg Gly
    1170                1175                1180

Ile Phe Ile Lys His Val Leu Glu Asp Ser Pro Ala Gly Lys Asn Gly
1185                1190                1195                1200

Thr Leu Lys Pro Gly Asp Arg Ile Val Glu Val Asp Gly Met Asp Leu
                1205                1210                1215

Arg Asp Ala Ser His Glu Gln Ala Val Glu Ala Ile Arg Lys Ala Gly
            1220                1225                1230

Asn Pro Val Val Phe Met Val
        1235

<210> SEQ ID NO 85
<211> LENGTH: 6540
<212> TYPE: DNA
<213> ORGANISM: Homo sapiens
<220> FEATURE:
<221> NAME/KEY: CDS
<222> LOCATION: (71)...(6070)

<400> SEQUENCE: 85
ttctcagtca cgcagttcca tttttaattgc tgttaatcat ttcagagaag aacactgaac      60
tttgaaaaaa atg ttg gaa gcc att gac aaa aat cgg gcc ctg cat gca         109
           Met Leu Glu Ala Ile Asp Lys Asn Arg Ala Leu His Ala
             1               5                  10 gca gag cgc ttg caa acc aag ctg cga gaa cgt ggg gat gta gca aat        157
Ala Glu Arg Leu Gln Thr Lys Leu Arg Glu Arg Gly Asp Val Ala Asn
 15                  20                  25 gaa gac aaa ctg agc ctt ctg aag tca gtc ctg cag agc cct ctc ttc        205
Glu Asp Lys Leu Ser Leu Leu Lys Ser Val Leu Gln Ser Pro Leu Phe
 30                  35                  40                  45 agt cag att ctg agc ctt cag act tct gta cag cag ctg aaa gac cag        253
Ser Gln Ile Leu Ser Leu Gln Thr Ser Val Gln Gln Leu Lys Asp Gln
             50                  55                  60 gta aat att gca act tca gca act tca aat att gaa tat gcc cac gtt        301
Val Asn Ile Ala Thr Ser Ala Thr Ser Asn Ile Glu Tyr Ala His Val
         65                  70                  75 cct cat ctc agc cca gct gtg att cct act ctg caa aat gaa tcg ttt        349
Pro His Leu Ser Pro Ala Val Ile Pro Thr Leu Gln Asn Glu Ser Phe
     80                  85                  90
```

-continued

| | | |
|---|---|---|
| tta tta tcc cca aac aat ggg aat ctg gaa gca ctt aca gga cct ggt<br>Leu Leu Ser Pro Asn Asn Gly Asn Leu Glu Ala Leu Thr Gly Pro Gly<br>     95                        100                      105 | 397 |
| att cca cac att aat ggg aaa cct gct tgt gat gaa ttt gat cag ctt<br>Ile Pro His Ile Asn Gly Lys Pro Ala Cys Asp Glu Phe Asp Gln Leu<br>110                    115                      120                      125 | 445 |
| atc aaa aat atg gcc cag ggt cgc cat gta gaa gtt ttt gag ctc ctc<br>Ile Lys Asn Met Ala Gln Gly Arg His Val Glu Val Phe Glu Leu Leu<br>                          130                      135                      140 | 493 |
| aaa cct cca tct gga ggc ctt ggg ttt agt gtt gtg gga cta aga agt<br>Lys Pro Pro Ser Gly Gly Leu Gly Phe Ser Val Val Gly Leu Arg Ser<br>                        145                      150                      155 | 541 |
| gaa aac aga gga gag ctg gga ata ttt gtt caa gag ata caa gag ggc<br>Glu Asn Arg Gly Glu Leu Gly Ile Phe Val Gln Glu Ile Gln Glu Gly<br>                  160                      165                      170 | 589 |
| agt gtg gcc cat aga gat gga aga ttg aaa gaa act gat caa att ctt<br>Ser Val Ala His Arg Asp Gly Arg Leu Lys Glu Thr Asp Gln Ile Leu<br>175                    180                      185 | 637 |
| gct atc aat gga cag gct ctt gat cag aca att aca cat cag cag gct<br>Ala Ile Asn Gly Gln Ala Leu Asp Gln Thr Ile Thr His Gln Gln Ala<br>190                    195                      200                      205 | 685 |
| atc agc atc ctg cag aaa gcc aaa gat act gtc cag cta gtt att gcc<br>Ile Ser Ile Leu Gln Lys Ala Lys Asp Thr Val Gln Leu Val Ile Ala<br>                  210                      215                      220 | 733 |
| aga ggc tca ttg cct cag ctt gtc agc ccc ata gtt tcc cgt tct cca<br>Arg Gly Ser Leu Pro Gln Leu Val Ser Pro Ile Val Ser Arg Ser Pro<br>                          225                      230                      235 | 781 |
| tct gca gcc agc aca att tca gct cac tct aat ccg gtt cac tgg caa<br>Ser Ala Ala Ser Thr Ile Ser Ala His Ser Asn Pro Val His Trp Gln<br>                  240                      245                      250 | 829 |
| cac atg gaa acg att gaa ttg gtg aat gat gga tct ggt ttg gga ttt<br>His Met Glu Thr Ile Glu Leu Val Asn Asp Gly Ser Gly Leu Gly Phe<br>                  255                      260                      265 | 877 |
| ggc atc ata gga gga aaa gca act ggt gtg ata gta aaa acc att ctg<br>Gly Ile Ile Gly Gly Lys Ala Thr Gly Val Ile Val Lys Thr Ile Leu<br>270                    275                      280                      285 | 925 |
| cct gga gga gta gct gat cag cat ggg cgt tta tgc agt gga gac cac<br>Pro Gly Gly Val Ala Asp Gln His Gly Arg Leu Cys Ser Gly Asp His<br>                        290                      295                      300 | 973 |
| att cta aag att ggt gac aca gat cta gca gga atg agc agt gag caa<br>Ile Leu Lys Ile Gly Asp Thr Asp Leu Ala Gly Met Ser Ser Glu Gln<br>                  305                      310                      315 | 1021 |
| gta gca caa gtc ctt agg caa tgt gga aat aga gtt aag ttg atg att<br>Val Ala Gln Val Leu Arg Gln Cys Gly Asn Arg Val Lys Leu Met Ile<br>                  320                      325                      330 | 1069 |
| gca aga agt gcc ata gaa gaa cgt aca gca ccc act gct ttg ggc atc<br>Ala Arg Ser Ala Ile Glu Glu Arg Thr Ala Pro Thr Ala Leu Gly Ile<br>335                    340                      345 | 1117 |
| acc ctc tcc tca tcc cca act tca acg cca gag ttg cgg gtt gat gct<br>Thr Leu Ser Ser Ser Pro Thr Ser Thr Pro Glu Leu Arg Val Asp Ala<br>350                    355                      360                      365 | 1165 |
| tct act cag aaa ggt gaa gaa agt gag aca ttt gat gta gaa ctc act<br>Ser Thr Gln Lys Gly Glu Glu Ser Glu Thr Phe Asp Val Glu Leu Thr<br>                    370                      375                      380 | 1213 |
| aaa aat gtc caa gga tta gga att acc att gct ggc tac att gga gat<br>Lys Asn Val Gln Gly Leu Gly Ile Thr Ile Ala Gly Tyr Ile Gly Asp<br>                  385                      390                      395 | 1261 |
| aaa aaa ttg gaa cct tca gga atc ttt gta aag agc att aca aaa agc<br>Lys Lys Leu Glu Pro Ser Gly Ile Phe Val Lys Ser Ile Thr Lys Ser<br>                  400                      405                      410 | 1309 |

-continued

| | |
|---|---|
| agt gcc gtt gag cat gat gga aga atc caa att gga gac caa att ata<br>Ser Ala Val Glu His Asp Gly Arg Ile Gln Ile Gly Asp Gln Ile Ile<br>415                    420                      425 | 1357 |
| gca gta gat ggc aca aac ctt cag ggt ttt act aat cag caa gca gta<br>Ala Val Asp Gly Thr Asn Leu Gln Gly Phe Thr Asn Gln Gln Ala Val<br>430                    435                    440                    445 | 1405 |
| gag gta ttg cga cat aca gga caa act gtg ctc ctg aca cta atg agg<br>Glu Val Leu Arg His Thr Gly Gln Thr Val Leu Leu Thr Leu Met Arg<br>                    450                    455                    460 | 1453 |
| aga gga atg aag cag gaa gcc gag ctc atg tca agg gaa gac gtc aca<br>Arg Gly Met Lys Gln Glu Ala Glu Leu Met Ser Arg Glu Asp Val Thr<br>            465                    470                    475 | 1501 |
| aaa gat gca gat ttg tct cct gtt aat gcc agc ata atc aaa gaa aat<br>Lys Asp Ala Asp Leu Ser Pro Val Asn Ala Ser Ile Ile Lys Glu Asn<br>480                    485                    490 | 1549 |
| tat gaa aaa gat gaa gat ttt tta tct tcg acg aga aac acc aac ata<br>Tyr Glu Lys Asp Glu Asp Phe Leu Ser Ser Thr Arg Asn Thr Asn Ile<br>495                    500                    505 | 1597 |
| tta cca act gaa gaa gaa ggg tat cca tta ctg tca gct gag ata gaa<br>Leu Pro Thr Glu Glu Glu Gly Tyr Pro Leu Leu Ser Ala Glu Ile Glu<br>510                    515                    520                    525 | 1645 |
| gaa ata gaa gat gca caa aaa caa gaa gct gct ctg ctg aca aaa tgg<br>Glu Ile Glu Asp Ala Gln Lys Gln Glu Ala Ala Leu Leu Thr Lys Trp<br>                    530                    535                    540 | 1693 |
| caa agg att atg gga att aac tat gaa ata gtg gtg gcc cat gtg agc<br>Gln Arg Ile Met Gly Ile Asn Tyr Glu Ile Val Val Ala His Val Ser<br>            545                    550                    555 | 1741 |
| aag ttt agt gag aac agt gga ttg ggg ata agc ctg gaa gcg aca gtg<br>Lys Phe Ser Glu Asn Ser Gly Leu Gly Ile Ser Leu Glu Ala Thr Val<br>560                    565                    570 | 1789 |
| gga cat cat ttt atc cga tct gtt cta cca gag ggt cct gtt gga cac<br>Gly His His Phe Ile Arg Ser Val Leu Pro Glu Gly Pro Val Gly His<br>575                    580                    585 | 1837 |
| agc ggg aag ctc ttc agt gga gac gag cta ttg gaa gta aat ggc ata<br>Ser Gly Lys Leu Phe Ser Gly Asp Glu Leu Leu Glu Val Asn Gly Ile<br>590                    595                    600                    605 | 1885 |
| act tta ctt ggg gaa aat cac caa gat gtg gtg aat atc tta aaa gaa<br>Thr Leu Leu Gly Glu Asn His Gln Asp Val Val Asn Ile Leu Lys Glu<br>                    610                    615                    620 | 1933 |
| ctg cct ata gaa gtg aca atg gtg tgc tgt cgt cga act gtg cca ccc<br>Leu Pro Ile Glu Val Thr Met Val Cys Cys Arg Arg Thr Val Pro Pro<br>            625                    630                    635 | 1981 |
| acc acc caa tca gaa ttg gat agc ctg gac tta tgt gat att gag cta<br>Thr Thr Gln Ser Glu Leu Asp Ser Leu Asp Leu Cys Asp Ile Glu Leu<br>640                    645                    650 | 2029 |
| aca gaa aag cct cac gta gat cta ggt gag ttc atc ggg tca tca gag<br>Thr Glu Lys Pro His Val Asp Leu Gly Glu Phe Ile Gly Ser Ser Glu<br>655                    660                    665 | 2077 |
| cca gag gat cca gtg ctg gcg atg act gat gcg ggt cag agt aca gaa<br>Pro Glu Asp Pro Val Leu Ala Met Thr Asp Ala Gly Gln Ser Thr Glu<br>670                    675                    680                    685 | 2125 |
| gag gtt caa gca cct ttg gcc atg tgg gag gct ggc att cag cac ata<br>Glu Val Gln Ala Pro Leu Ala Met Trp Glu Ala Gly Ile Gln His Ile<br>                    690                    695                    700 | 2173 |
| atg ctg gag aaa ggg agc aaa gga ctt ggt ttt agc att tta gat tat<br>Met Leu Glu Lys Gly Ser Lys Gly Leu Gly Phe Ser Ile Leu Asp Tyr<br>            705                    710                    715 | 2221 |
| cag gat cca att gat cca gca agc act gtg att ata att cgt tct ttg<br>Gln Asp Pro Ile Asp Pro Ala Ser Thr Val Ile Ile Ile Arg Ser Leu | 2269 |

```
                      720              725              730
gtg cct ggc ggc att gct gaa aag gat gga cga ctt ctt cct ggt gac    2317
Val Pro Gly Gly Ile Ala Glu Lys Asp Gly Arg Leu Leu Pro Gly Asp
        735              740              745 cga ctc atg ttt gta aac gat gtt aac ttg gaa aac agc agt ctt gag    2365
Arg Leu Met Phe Val Asn Asp Val Asn Leu Glu Asn Ser Ser Leu Glu
750              755              760              765 gaa gct gta gaa gca ctg aag gga gca ccg tca ggg act gtg aga ata    2413
Glu Ala Val Glu Ala Leu Lys Gly Ala Pro Ser Gly Thr Val Arg Ile
                770              775              780 gga gtt gct aag cct tta ccc ctt tca cca gaa gaa ggt tat gtt tct    2461
Gly Val Ala Lys Pro Leu Pro Leu Ser Pro Glu Glu Gly Tyr Val Ser
            785              790              795 gct aag gag gat tcc ttt ctc tac cca cca cac tcc tgt gag gaa gca    2509
Ala Lys Glu Asp Ser Phe Leu Tyr Pro Pro His Ser Cys Glu Glu Ala
        800              805              810 ggg ctg gct gac aaa ccc ctc ttc agg gct gac ttg gct ctg gtg ggc    2557
Gly Leu Ala Asp Lys Pro Leu Phe Arg Ala Asp Leu Ala Leu Val Gly
815              820              825 aca aat gat gct gac tta gta gat gaa tcc aca ttt gag tct cca tac    2605
Thr Asn Asp Ala Asp Leu Val Asp Glu Ser Thr Phe Glu Ser Pro Tyr
830              835              840              845 tct cct gaa aat gac agc atc tac tct act caa gcc tct att tta tct    2653
Ser Pro Glu Asn Asp Ser Ile Tyr Ser Thr Gln Ala Ser Ile Leu Ser
                850              855              860 ctt cat ggc agt tct tgt ggt gat ggc ctg aac tat ggt tct tcc ctt    2701
Leu His Gly Ser Ser Cys Gly Asp Gly Leu Asn Tyr Gly Ser Ser Leu
            865              870              875 cca tca tct cct cct aag gat gtt att gaa aat tct tgt gat cca gta    2749
Pro Ser Ser Pro Pro Lys Asp Val Ile Glu Asn Ser Cys Asp Pro Val
        880              885              890 ctt gat ctg cat atg tct ctg gag gaa cta tat acc cag aat ctc ctg    2797
Leu Asp Leu His Met Ser Leu Glu Glu Leu Tyr Thr Gln Asn Leu Leu
895              900              905 gaa aga cag gat gag aat aca cct tcg gtg gac ata agt atg ggg cct    2845
Glu Arg Gln Asp Glu Asn Thr Pro Ser Val Asp Ile Ser Met Gly Pro
910              915              920              925 gct tct ggc ttt act ata aat gac tac aca cct gca aat gct att gaa    2893
Ala Ser Gly Phe Thr Ile Asn Asp Tyr Thr Pro Ala Asn Ala Ile Glu
                930              935              940 caa caa tat gaa tgt gaa aac aca ata gtg tgg act gaa tct cat tta    2941
Gln Gln Tyr Glu Cys Glu Asn Thr Ile Val Trp Thr Glu Ser His Leu
            945              950              955 cca agt gaa gtt ata tca agt gca gaa ctt cct tct gtg cta ccc gat    2989
Pro Ser Glu Val Ile Ser Ser Ala Glu Leu Pro Ser Val Leu Pro Asp
        960              965              970 tca gct gga aag ggc tct gag cac ctg ctt gaa cag agc tcc ctg gcc    3037
Ser Ala Gly Lys Gly Ser Glu His Leu Leu Glu Gln Ser Ser Leu Ala
975              980              985 tgt aat gct gag tgt gtc atg ctt caa aat gta tct aaa gaa tct ttt    3085
Cys Asn Ala Glu Cys Val Met Leu Gln Asn Val Ser Lys Glu Ser Phe
990              995              1000             1005 gaa agg act att aat ata gca aaa ggc aat tct agc cta gga atg aca    3133
Glu Arg Thr Ile Asn Ile Ala Lys Gly Asn Ser Ser Leu Gly Met Thr
                1010             1015             1020 gtt agt gct aat aaa gat ggc ttg ggg atg atc gtt cga agc att att    3181
Val Ser Ala Asn Lys Asp Gly Leu Gly Met Ile Val Arg Ser Ile Ile
            1025             1030             1035 cat gga ggt gcc att agt cga gat ggc cgg att gcc att ggg gac tgc    3229
```

-continued

```
                His Gly Gly Ala Ile Ser Arg Asp Gly Arg Ile Ala Ile Gly Asp Cys
                        1040                1045                1050 atc ttg tcc att aat gaa gag tct acc atc agt gta acc aat gcc cag           3277
Ile Leu Ser Ile Asn Glu Glu Ser Thr Ile Ser Val Thr Asn Ala Gln
        1055                1060                1065 gca cga gct atg ttg aga aga cat tct ctc att ggc cct gac ata aaa           3325
Ala Arg Ala Met Leu Arg Arg His Ser Leu Ile Gly Pro Asp Ile Lys
1070                1075                1080                1085 att act tat gtg cct gca gaa cat ttg gaa gag ttc aaa ata agc ttg           3373
Ile Thr Tyr Val Pro Ala Glu His Leu Glu Glu Phe Lys Ile Ser Leu
                1090                1095                1100 gga caa caa tct gga aga gta atg gca ctg gat att ttt tct tca tac           3421
Gly Gln Gln Ser Gly Arg Val Met Ala Leu Asp Ile Phe Ser Ser Tyr
            1105                1110                1115 act ggc aga gac att cca gaa tta cca gag cga gaa gag gga gag ggt           3469
Thr Gly Arg Asp Ile Pro Glu Leu Pro Glu Arg Glu Glu Gly Glu Gly
        1120                1125                1130 gaa gaa agc gaa ctt caa aac aca gca tat agc aat tgg aat cag ccc           3517
Glu Glu Ser Glu Leu Gln Asn Thr Ala Tyr Ser Asn Trp Asn Gln Pro
    1135                1140                1145 agg cgg gtg gaa ctc tgg aga gaa cca agc aaa tcc tta ggc atc agc           3565
Arg Arg Val Glu Leu Trp Arg Glu Pro Ser Lys Ser Leu Gly Ile Ser
1150                1155                1160                1165 att gtt ggt gga cga ggg atg ggg agt cgg cta agc aat gga gaa gtg           3613
Ile Val Gly Gly Arg Gly Met Gly Ser Arg Leu Ser Asn Gly Glu Val
                1170                1175                1180 atg agg ggc att ttc atc aaa cat gtt ctg gaa gat agt cca gct ggc           3661
Met Arg Gly Ile Phe Ile Lys His Val Leu Glu Asp Ser Pro Ala Gly
            1185                1190                1195 aaa aat gga acc ttg aaa cct gga gat aga atc gta gag gca ccc agt           3709
Lys Asn Gly Thr Leu Lys Pro Gly Asp Arg Ile Val Glu Ala Pro Ser
        1200                1205                1210 cag tca gag tca gag cca gag aag gct cca ttg tgc agt gtg ccc cca           3757
Gln Ser Glu Ser Glu Pro Glu Lys Ala Pro Leu Cys Ser Val Pro Pro
    1215                1220                1225 ccc cct cct tca gcc ttt gcc gaa atg ggt agt gat cac aca cag tca           3805
Pro Pro Pro Ser Ala Phe Ala Glu Met Gly Ser Asp His Thr Gln Ser
1230                1235                1240                1245 tct gca agc aaa atc tca caa gat gtg gac aaa gag gat gag ttt ggt           3853
Ser Ala Ser Lys Ile Ser Gln Asp Val Asp Lys Glu Asp Glu Phe Gly
                1250                1255                1260 tac agc tgg aaa aat atc aga gag cgt tat gga acc cta aca ggc gag           3901
Tyr Ser Trp Lys Asn Ile Arg Glu Arg Tyr Gly Thr Leu Thr Gly Glu
            1265                1270                1275 ctg cat atg att gaa ctg gag aaa ggt cat agt ggt ttg ggc cta agt           3949
Leu His Met Ile Glu Leu Glu Lys Gly His Ser Gly Leu Gly Leu Ser
        1280                1285                1290 ctt gct ggg aac aaa gac cga tcc agg atg agt gtc ttc ata gtg ggg           3997
Leu Ala Gly Asn Lys Asp Arg Ser Arg Met Ser Val Phe Ile Val Gly
    1295                1300                1305 att gat cca aat gga gct gca gga aaa gat ggt cga ttg caa att gca           4045
Ile Asp Pro Asn Gly Ala Ala Gly Lys Asp Gly Arg Leu Gln Ile Ala
1310                1315                1320                1325 gat gag ctt cta gag atc aat ggt cag att tta tat gga aga agt cat           4093
Asp Glu Leu Leu Glu Ile Asn Gly Gln Ile Leu Tyr Gly Arg Ser His
                1330                1335                1340 cag aat gcc tca tca atc att aaa tgt gcc cct tct aaa gtg aaa ata           4141
Gln Asn Ala Ser Ser Ile Ile Lys Cys Ala Pro Ser Lys Val Lys Ile
            1345                1350                1355
```

```
att ttt atc aga aat aaa gat gca gtg aat cag atg gcc gta tgt cct      4189
Ile Phe Ile Arg Asn Lys Asp Ala Val Asn Gln Met Ala Val Cys Pro
        1360                1365                1370 gga aat gca gta gaa cct ttg cct tct aac tca gaa aat ctt caa aat      4237
Gly Asn Ala Val Glu Pro Leu Pro Ser Asn Ser Glu Asn Leu Gln Asn
1375                1380                1385 aag gag aca gag cca act gtt act act tct gat gca gct gtg gac ctc      4285
Lys Glu Thr Glu Pro Thr Val Thr Thr Ser Asp Ala Ala Val Asp Leu
1390                1395                1400                1405 agt tca ttt aaa aat gtg caa cat ctg gag ctt ccc aag gat cag ggg      4333
Ser Ser Phe Lys Asn Val Gln His Leu Glu Leu Pro Lys Asp Gln Gly
            1410                1415                1420 ggt ttg ggt att gct atc agc gaa gaa gat aca ctc agt gga gtc atc      4381
Gly Leu Gly Ile Ala Ile Ser Glu Glu Asp Thr Leu Ser Gly Val Ile
        1425                1430                1435 ata aag agc tta aca gag cat ggg gta gca gcc acg gat gga cga ctc      4429
Ile Lys Ser Leu Thr Glu His Gly Val Ala Ala Thr Asp Gly Arg Leu
    1440                1445                1450 aaa gtc gga gat cag ata ctg gct gta gat gat gaa att gtt gtt ggt      4477
Lys Val Gly Asp Gln Ile Leu Ala Val Asp Asp Glu Ile Val Val Gly
1455                1460                1465 tac cct att gaa aag ttt att agc ctt ctg aag aca gca aag atg aca      4525
Tyr Pro Ile Glu Lys Phe Ile Ser Leu Leu Lys Thr Ala Lys Met Thr
1470                1475                1480                1485 gta aaa ctt acc atc cat gct gag aat cca gat tcc cag gct gtt cct      4573
Val Lys Leu Thr Ile His Ala Glu Asn Pro Asp Ser Gln Ala Val Pro
            1490                1495                1500 tca gca gct ggt gca gcc agt gga gaa aaa aag aac agc tcc cag tct      4621
Ser Ala Ala Gly Ala Ala Ser Gly Glu Lys Lys Asn Ser Ser Gln Ser
        1505                1510                1515 ctg atg gtc cca cag tct ggc tcc cca gaa ccg gag tcc atc cga aat      4669
Leu Met Val Pro Gln Ser Gly Ser Pro Glu Pro Glu Ser Ile Arg Asn
    1520                1525                1530 aca agc aga tca tca aca cca gca att ttt gct tct gat cct gca acc      4717
Thr Ser Arg Ser Ser Thr Pro Ala Ile Phe Ala Ser Asp Pro Ala Thr
1535                1540                1545 tgc ccc att atc cct ggc tgc gaa aca acc atc gag att tcc aaa ggg      4765
Cys Pro Ile Ile Pro Gly Cys Glu Thr Thr Ile Glu Ile Ser Lys Gly
1550                1555                1560                1565 cga aca ggg ctg ggc ctg agc atc gtt ggg ggt tca gac acg ctg ctg      4813
Arg Thr Gly Leu Gly Leu Ser Ile Val Gly Gly Ser Asp Thr Leu Leu
            1570                1575                1580 ggt gcc ttt att atc cat gaa gtt tat gaa gaa gga gca gca tgt aaa      4861
Gly Ala Phe Ile Ile His Glu Val Tyr Glu Glu Gly Ala Ala Cys Lys
        1585                1590                1595 gat gga aga ctc tgg gct gga gat cag atc tta gag gtg aat gga att      4909
Asp Gly Arg Leu Trp Ala Gly Asp Gln Ile Leu Glu Val Asn Gly Ile
    1600                1605                1610 gac ttg agg aag gcc aca cat gat gaa gca atc aat gtc ctg aga cag      4957
Asp Leu Arg Lys Ala Thr His Asp Glu Ala Ile Asn Val Leu Arg Gln
1615                1620                1625 acg cca cag aga gtg cgc ctg aca ctc tac aga gat gag gcc cca tac      5005
Thr Pro Gln Arg Val Arg Leu Thr Leu Tyr Arg Asp Glu Ala Pro Tyr
1630                1635                1640                1645 aaa gag gag gaa gtg tgt gac acc ctc act att gag ctg cag aag aag      5053
Lys Glu Glu Glu Val Cys Asp Thr Leu Thr Ile Glu Leu Gln Lys Lys
            1650                1655                1660 ccg gga aaa ggc cta gga tta agt att gtt ggt aaa aga aac gat act      5101
Pro Gly Lys Gly Leu Gly Leu Ser Ile Val Gly Lys Arg Asn Asp Thr
        1665                1670                1675
```

```
gga gta ttt gtg tca gac att gtc aaa gga gga att gca gat ccc gat    5149
Gly Val Phe Val Ser Asp Ile Val Lys Gly Gly Ile Ala Asp Pro Asp
        1680                1685                1690 gga aga ctg atc cag gga gac cag ata tta ttg gtg aat ggg gaa gac    5197
Gly Arg Leu Ile Gln Gly Asp Gln Ile Leu Leu Val Asn Gly Glu Asp
        1695                1700                1705 gtt cgt aat gcc tcc caa gaa gcg gtt gcc gct ttg cta aag tgt tcc    5245
Val Arg Asn Ala Ser Gln Glu Ala Val Ala Ala Leu Leu Lys Cys Ser
1710                1715                1720                1725 cta ggc aca gta acc ttg gaa gtt gga aga atc aaa gct ggt cca ttc    5293
Leu Gly Thr Val Thr Leu Glu Val Gly Arg Ile Lys Ala Gly Pro Phe
                1730                1735                1740 cat tca gag agg agg cca tct caa acc agc cag gtg agt gaa ggc agc    5341
His Ser Glu Arg Arg Pro Ser Gln Thr Ser Gln Val Ser Glu Gly Ser
        1745                1750                1755 ctg tct tct ttc act ttt cca ctc tct gga tcc agt aca tct gag tca    5389
Leu Ser Ser Phe Thr Phe Pro Leu Ser Gly Ser Ser Thr Ser Glu Ser
        1760                1765                1770 ctg gaa agt agc tca aag aag aat gca ttg gca tct gaa ata cag gga    5437
Leu Glu Ser Ser Ser Lys Lys Asn Ala Leu Ala Ser Glu Ile Gln Gly
        1775                1780                1785 tta aga aca gtc gaa atg aaa aag ggc cct act gac tca ctg gga atc    5485
Leu Arg Thr Val Glu Met Lys Lys Gly Pro Thr Asp Ser Leu Gly Ile
1790                1795                1800                1805 agc atc gct gga gga gta ggc agc cca ctt ggt gat gtg cct ata ttt    5533
Ser Ile Ala Gly Gly Val Gly Ser Pro Leu Gly Asp Val Pro Ile Phe
                1810                1815                1820 att gca atg atg cac cca act gga gtt gca gca cag acc caa aaa ctc    5581
Ile Ala Met Met His Pro Thr Gly Val Ala Ala Gln Thr Gln Lys Leu
        1825                1830                1835 aga gtt ggg gat agg att gtc acc atc tgt ggc aca tcc act gag ggc    5629
Arg Val Gly Asp Arg Ile Val Thr Ile Cys Gly Thr Ser Thr Glu Gly
        1840                1845                1850 atg act cac acc caa gca gtt aac cta ctg aaa aat gca tct ggc tcc    5677
Met Thr His Thr Gln Ala Val Asn Leu Leu Lys Asn Ala Ser Gly Ser
        1855                1860                1865 att gaa atg cag gtg gtt gct gga gga gac gtg agt gtg gtc aca ggt    5725
Ile Glu Met Gln Val Val Ala Gly Gly Asp Val Ser Val Val Thr Gly
1870                1875                1880                1885 cat cat cag gag cct gca agt tcc agt ctt tct ttc act ggg ctg acg    5773
His His Gln Glu Pro Ala Ser Ser Ser Leu Ser Phe Thr Gly Leu Thr
                1890                1895                1900 tca acc agt ata ttt cag gat gat tta gga cct cct caa tgt aag tct    5821
Ser Thr Ser Ile Phe Gln Asp Asp Leu Gly Pro Pro Gln Cys Lys Ser
        1905                1910                1915 att aca cta gag cga gga cca gat ggc tta ggc ttc agt ata gtt gga    5869
Ile Thr Leu Glu Arg Gly Pro Asp Gly Leu Gly Phe Ser Ile Val Gly
        1920                1925                1930 gga tat ggc agc cct cat gga gac tta ccc att tat gtt aaa aca gtg    5917
Gly Tyr Gly Ser Pro His Gly Asp Leu Pro Ile Tyr Val Lys Thr Val
        1935                1940                1945 ttt gca aag gga gca gcc tct gaa gac gga cgt ctg aaa agg ggc gat    5965
Phe Ala Lys Gly Ala Ala Ser Glu Asp Gly Arg Leu Lys Arg Gly Asp
1950                1955                1960                1965 cag atc att gct gtc aat ggg cag agt cta gaa gga gtc acc cat gaa    6013
Gln Ile Ile Ala Val Asn Gly Gln Ser Leu Glu Gly Val Thr His Glu
                1970                1975                1980 gaa gct gtt gcc atc ctt aaa cgg aca aaa ggc act gtc act ttg atg    6061
Glu Ala Val Ala Ile Leu Lys Arg Thr Lys Gly Thr Val Thr Leu Met
```

-continued

```
                    1985              1990              1995
gtt ctc tct tgaattggct gccagaattg aaccaaccca acccctagct           6110
Val Leu Ser
        2000 cacctcctac tgtaaagaga atgcactggt cctgacaatt tttatgctgt gttcagccgg  6170 gtcttcaaaa ctgtagggggg gaaataacac ttaagtttct ttttctcatc tagaaatgct  6230 ttccttactg acaacctaac atcatttttc ttttcttctt gcattttgtg aacttaaaga  6290 gaaggaatat ttgtgtaggt gaatctcgtt tttatttgtg gagatatcta atgttttgta  6350 gtcacatggg caagaattat tacatgctaa gctggttagt ataaagaaag ataattctaa  6410 agctaaccaa agaaaatggc ttcagtaagt taggatgaaa aatgaaaata taaaataaag  6470 aagaaaatct cggggagttt aaaaaaaatg cctcaatttg gcaatctacc tcctctcccc  6530 accccaaact                                                          6540
```

<210> SEQ ID NO 86
<211> LENGTH: 6750
<212> TYPE: DNA
<213> ORGANISM: Homo sapiens
<220> FEATURE:
<221> NAME/KEY: CDS
<222> LOCATION: (71)...(6280)

<400> SEQUENCE: 86

```
ttctcagtca cgcagttcca ttttaattgc tgttaatcat ttcagagaag aacactgaac     60
tttgaaaaaa atg ttg gaa gcc att gac aaa aat cgg gcc ctg cat gca       109
            Met Leu Glu Ala Ile Asp Lys Asn Arg Ala Leu His Ala
              1               5                  10 gca gag cgc ttg caa acc aag ctg cga gaa cgt ggg gat gta gca aat       157
Ala Glu Arg Leu Gln Thr Lys Leu Arg Glu Arg Gly Asp Val Ala Asn
         15                  20                  25 gaa gac aaa ctg agc ctt ctg aag tca gtc ctg cag agc cct ctc ttc       205
Glu Asp Lys Leu Ser Leu Leu Lys Ser Val Leu Gln Ser Pro Leu Phe
 30                  35                  40                  45 agt cag att ctg agc ctt cag act tct gta cag cag ctg aaa gac cag       253
Ser Gln Ile Leu Ser Leu Gln Thr Ser Val Gln Gln Leu Lys Asp Gln
             50                  55                  60 gta aat att gca act tca gca act tca aat att gaa tat gcc cac gtt       301
Val Asn Ile Ala Thr Ser Ala Thr Ser Asn Ile Glu Tyr Ala His Val
         65                  70                  75 cct cat ctc agc cca gct gtg att cct act ctg caa aat gaa tcg ttt       349
Pro His Leu Ser Pro Ala Val Ile Pro Thr Leu Gln Asn Glu Ser Phe
     80                  85                  90 tta tta tcc cca aac aat ggg aat ctg gaa gca ctt aca gga cct ggt       397
Leu Leu Ser Pro Asn Asn Gly Asn Leu Glu Ala Leu Thr Gly Pro Gly
 95                 100                 105 att cca cac att aat ggg aaa cct gct tgt gat gaa ttt gat cag ctt       445
Ile Pro His Ile Asn Gly Lys Pro Ala Cys Asp Glu Phe Asp Gln Leu
110                 115                 120                 125 atc aaa aat atg gcc cag ggt cgc cat gta gaa gtt ttt gag ctc ctc       493
Ile Lys Asn Met Ala Gln Gly Arg His Val Glu Val Phe Glu Leu Leu
             130                 135                 140 aaa cct cca tct gga ggc ctt ggg ttt agt gtt gtg gga cta aga agt       541
Lys Pro Pro Ser Gly Gly Leu Gly Phe Ser Val Val Gly Leu Arg Ser
         145                 150                 155 gaa aac aga gga gag ctg gga ata ttt gtt caa gag ata caa gag ggc       589
Glu Asn Arg Gly Glu Leu Gly Ile Phe Val Gln Glu Ile Gln Glu Gly
     160                 165                 170
```

-continued

| | | |
|---|---|---|
| agt gtg gcc cat aga gat gga aga ttg aaa gaa act gat caa att ctt<br>Ser Val Ala His Arg Asp Gly Arg Leu Lys Glu Thr Asp Gln Ile Leu<br>175                       180                     185 | 637 |
| gct atc aat gga cag gct ctt gat cag aca att aca cat cag cag gct<br>Ala Ile Asn Gly Gln Ala Leu Asp Gln Thr Ile Thr His Gln Gln Ala<br>190                       195                     200                     205 | 685 |
| atc agc atc ctg cag aaa gcc aaa gat act gtc cag cta gtt att gcc<br>Ile Ser Ile Leu Gln Lys Ala Lys Asp Thr Val Gln Leu Val Ile Ala<br>                   210                     215                     220 | 733 |
| aga ggc tca ttg cct cag ctt gtc agc ccc ata gtt tcc cgt tct cca<br>Arg Gly Ser Leu Pro Gln Leu Val Ser Pro Ile Val Ser Arg Ser Pro<br>             225                     230                     235 | 781 |
| tct gca gcc agc aca att tca gct cac tct aat ccg gtt cac tgg caa<br>Ser Ala Ala Ser Thr Ile Ser Ala His Ser Asn Pro Val His Trp Gln<br>240                       245                     250 | 829 |
| cac atg gaa acg att gaa ttg gtg aat gat gga tct ggt ttg gga ttt<br>His Met Glu Thr Ile Glu Leu Val Asn Asp Gly Ser Gly Leu Gly Phe<br>     255                     260                     265 | 877 |
| ggc atc ata gga gga aaa gca act ggt gtg ata gta aaa acc att ctg<br>Gly Ile Ile Gly Gly Lys Ala Thr Gly Val Ile Val Lys Thr Ile Leu<br>270                       275                     280                     285 | 925 |
| cct gga gga gta gct gat cag cat ggg cgt tta tgc agt gga gac cac<br>Pro Gly Gly Val Ala Asp Gln His Gly Arg Leu Cys Ser Gly Asp His<br>                   290                     295                     300 | 973 |
| att cta aag att ggt gac aca gat cta gca gga atg agc agt gag caa<br>Ile Leu Lys Ile Gly Asp Thr Asp Leu Ala Gly Met Ser Ser Glu Gln<br>             305                     310                     315 | 1021 |
| gta gca caa gtc ctt agg caa tgt gga aat aga gtt aag ttg atg att<br>Val Ala Gln Val Leu Arg Gln Cys Gly Asn Arg Val Lys Leu Met Ile<br>320                       325                     330 | 1069 |
| gca aga agt gcc ata gaa gaa cgt aca gca ccc act gct ttg ggc atc<br>Ala Arg Ser Ala Ile Glu Glu Arg Thr Ala Pro Thr Ala Leu Gly Ile<br>     335                     340                     345 | 1117 |
| acc ctc tcc tca tcc cca act tca acg cca gag ttg cgg gtt gat gct<br>Thr Leu Ser Ser Ser Pro Thr Ser Thr Pro Glu Leu Arg Val Asp Ala<br>350                       355                     360                     365 | 1165 |
| tct act cag aaa ggt gaa gaa agt gag aca ttt gat gta gaa ctc act<br>Ser Thr Gln Lys Gly Glu Glu Ser Glu Thr Phe Asp Val Glu Leu Thr<br>                   370                     375                     380 | 1213 |
| aaa aat gtc caa gga tta gga att acc att gct ggc tac att gga gat<br>Lys Asn Val Gln Gly Leu Gly Ile Thr Ile Ala Gly Tyr Ile Gly Asp<br>               385                     390                     395 | 1261 |
| aaa aaa ttg gaa cct tca gga atc ttt gta aag agc att aca aaa agc<br>Lys Lys Leu Glu Pro Ser Gly Ile Phe Val Lys Ser Ile Thr Lys Ser<br>400                       405                     410 | 1309 |
| agt gcc gtt gag cat gat gga aga atc caa att gga gac caa att ata<br>Ser Ala Val Glu His Asp Gly Arg Ile Gln Ile Gly Asp Gln Ile Ile<br>     415                     420                     425 | 1357 |
| gca gta gat ggc aca aac ctt cag ggt ttt act aat cag caa gca gta<br>Ala Val Asp Gly Thr Asn Leu Gln Gly Phe Thr Asn Gln Gln Ala Val<br>430                       435                     440                     445 | 1405 |
| gag gta ttg cga cat aca gga caa act gtg ctc ctg aca cta atg agg<br>Glu Val Leu Arg His Thr Gly Gln Thr Val Leu Leu Thr Leu Met Arg<br>                   450                     455                     460 | 1453 |
| aga gga atg aag cag gaa gcc gag ctc atg tca agg gaa gac gtc aca<br>Arg Gly Met Lys Gln Glu Ala Glu Leu Met Ser Arg Glu Asp Val Thr<br>             465                     470                     475 | 1501 |
| aaa gat gca gat ttg tct cct gtt aat gcc agc ata atc aaa gaa aat<br>Lys Asp Ala Asp Leu Ser Pro Val Asn Ala Ser Ile Ile Lys Glu Asn<br>480                       485                     490 | 1549 |

```
                                                          -continued tat gaa aaa gat gaa gat ttt tta tct tcg acg aga aac acc aac ata        1597
Tyr Glu Lys Asp Glu Asp Phe Leu Ser Ser Thr Arg Asn Thr Asn Ile
495                 500                 505 tta cca act gaa gaa gaa ggg tat cca tta ctg tca gct gag ata gaa        1645
Leu Pro Thr Glu Glu Glu Gly Tyr Pro Leu Leu Ser Ala Glu Ile Glu
510                 515                 520                 525 gaa ata gaa gat gca caa aaa caa gaa gct gct ctg ctg aca aaa tgg        1693
Glu Ile Glu Asp Ala Gln Lys Gln Glu Ala Ala Leu Leu Thr Lys Trp
                530                 535                 540 caa agg att atg gga att aac tat gaa ata gtg gtg gcc cat gtg agc        1741
Gln Arg Ile Met Gly Ile Asn Tyr Glu Ile Val Val Ala His Val Ser
            545                 550                 555 aag ttt agt gag aac agt gga ttg ggg ata agc ctg gaa gcg aca gtg        1789
Lys Phe Ser Glu Asn Ser Gly Leu Gly Ile Ser Leu Glu Ala Thr Val
        560                 565                 570 gga cat cat ttt atc cga tct gtt cta cca gag ggt cct gtt gga cac        1837
Gly His His Phe Ile Arg Ser Val Leu Pro Glu Gly Pro Val Gly His
575                 580                 585 agc ggg aag ctc ttc agt gga gac gag cta ttg gaa gta aat ggc ata        1885
Ser Gly Lys Leu Phe Ser Gly Asp Glu Leu Leu Glu Val Asn Gly Ile
590                 595                 600                 605 act tta ctt ggg gaa aat cac caa gat gtg gtg aat atc tta aaa gaa        1933
Thr Leu Leu Gly Glu Asn His Gln Asp Val Val Asn Ile Leu Lys Glu
                610                 615                 620 ctg cct ata gaa gtg aca atg gtg tgc tgt cgt cga act gtg cca ccc        1981
Leu Pro Ile Glu Val Thr Met Val Cys Cys Arg Arg Thr Val Pro Pro
            625                 630                 635 acc acc caa tca gaa ttg gat agc ctg gac tta tgt gat att gag cta        2029
Thr Thr Gln Ser Glu Leu Asp Ser Leu Asp Leu Cys Asp Ile Glu Leu
        640                 645                 650 aca gaa aag cct cac gta gat cta ggt gag ttc atc ggg tca tca gag        2077
Thr Glu Lys Pro His Val Asp Leu Gly Glu Phe Ile Gly Ser Ser Glu
655                 660                 665 cca gag gat cca gtg ctg gcg atg act gat gcg ggt cag agt aca gaa        2125
Pro Glu Asp Pro Val Leu Ala Met Thr Asp Ala Gly Gln Ser Thr Glu
670                 675                 680                 685 gag gtt caa gca cct ttg gcc atg tgg gag gct ggc att cag cac ata        2173
Glu Val Gln Ala Pro Leu Ala Met Trp Glu Ala Gly Ile Gln His Ile
                690                 695                 700 atg ctg gag aaa ggg agc aaa gga ctt ggt ttt agc att tta gat tat        2221
Met Leu Glu Lys Gly Ser Lys Gly Leu Gly Phe Ser Ile Leu Asp Tyr
            705                 710                 715 cag gat cca att gat cca gca agc act gtg att ata att cgt tct ttg        2269
Gln Asp Pro Ile Asp Pro Ala Ser Thr Val Ile Ile Ile Arg Ser Leu
        720                 725                 730 gtg cct ggc ggc att gct gaa aag gat gga cga ctt ctt cct ggt gac        2317
Val Pro Gly Gly Ile Ala Glu Lys Asp Gly Arg Leu Leu Pro Gly Asp
735                 740                 745 cga ctc atg ttt gta aac gat gtt aac ttg gaa aac agc agt ctt gag        2365
Arg Leu Met Phe Val Asn Asp Val Asn Leu Glu Asn Ser Ser Leu Glu
750                 755                 760                 765 gaa gct gta gaa gca ctg aag gga gca ccg tca ggg act gtg aga ata        2413
Glu Ala Val Glu Ala Leu Lys Gly Ala Pro Ser Gly Thr Val Arg Ile
                770                 775                 780 gga gtt gct aag cct tta ccc ctt tca cca gaa gaa ggt tat gtt tct        2461
Gly Val Ala Lys Pro Leu Pro Leu Ser Pro Glu Glu Gly Tyr Val Ser
            785                 790                 795 gct aag gag gat tcc ttt ctc tac cca cca cac tcc tgt gag gaa gca        2509
Ala Lys Glu Asp Ser Phe Leu Tyr Pro Pro His Ser Cys Glu Glu Ala
```

```
                800              805              810
ggg ctg gct gac aaa ccc ctc ttc agg gct gac ttg gct ctg gtg ggc      2557
Gly Leu Ala Asp Lys Pro Leu Phe Arg Ala Asp Leu Ala Leu Val Gly
        815              820              825 aca aat gat gct gac tta gta gat gaa tcc aca ttt gag tct cca tac      2605
Thr Asn Asp Ala Asp Leu Val Asp Glu Ser Thr Phe Glu Ser Pro Tyr
830              835              840              845 tct cct gaa aat gac agc atc tac tct act caa gcc tct att tta tct      2653
Ser Pro Glu Asn Asp Ser Ile Tyr Ser Thr Gln Ala Ser Ile Leu Ser
                 850              855              860 ctt cat ggc agt tct tgt ggt gat ggc ctg aac tat ggt tct tcc ctt      2701
Leu His Gly Ser Ser Cys Gly Asp Gly Leu Asn Tyr Gly Ser Ser Leu
        865              870              875 cca tca tct cct cct aag gat gtt att gaa aat tct tgt gat cca gta      2749
Pro Ser Ser Pro Pro Lys Asp Val Ile Glu Asn Ser Cys Asp Pro Val
880              885              890 ctt gat ctg cat atg tct ctg gag gaa cta tat acc cag aat ctc ctg      2797
Leu Asp Leu His Met Ser Leu Glu Glu Leu Tyr Thr Gln Asn Leu Leu
        895              900              905 gaa aga cag gat gag aat aca cct tcg gtg gac ata agt atg ggg cct      2845
Glu Arg Gln Asp Glu Asn Thr Pro Ser Val Asp Ile Ser Met Gly Pro
910              915              920              925 gct tct ggc ttt act ata aat gac tac aca cct gca aat gct att gaa      2893
Ala Ser Gly Phe Thr Ile Asn Asp Tyr Thr Pro Ala Asn Ala Ile Glu
                 930              935              940 caa caa tat gaa tgt gaa aac aca ata gtg tgg act gaa tct cat tta      2941
Gln Gln Tyr Glu Cys Glu Asn Thr Ile Val Trp Thr Glu Ser His Leu
        945              950              955 cca agt gaa gtt ata tca agt gca gaa ctt cct tct gtg cta ccc gat      2989
Pro Ser Glu Val Ile Ser Ser Ala Glu Leu Pro Ser Val Leu Pro Asp
960              965              970 tca gct gga aag ggc tct gag tac ctg ctt gaa cag agc tcc ctg gcc      3037
Ser Ala Gly Lys Gly Ser Glu Tyr Leu Leu Glu Gln Ser Ser Leu Ala
        975              980              985 tgt aat gct gag tgt gtc atg ctt caa aat gta tct aaa gaa tct ttt      3085
Cys Asn Ala Glu Cys Val Met Leu Gln Asn Val Ser Lys Glu Ser Phe
990              995              1000             1005 gaa agg act att aat ata gca aaa ggc aat tct agc cta gga atg aca      3133
Glu Arg Thr Ile Asn Ile Ala Lys Gly Asn Ser Ser Leu Gly Met Thr
        1010             1015             1020 gtt agt gct aat aaa gat ggc ttg ggg atg atc gtt cga agc att att      3181
Val Ser Ala Asn Lys Asp Gly Leu Gly Met Ile Val Arg Ser Ile Ile
         1025             1030             1035 cat gga ggt gcc att agt cga gat ggc cgg att gcc att ggg gac tgc      3229
His Gly Gly Ala Ile Ser Arg Asp Gly Arg Ile Ala Ile Gly Asp Cys
        1040             1045             1050 atc ttg tcc att aat gaa gag tct acc atc agt gta acc aat gcc cag      3277
Ile Leu Ser Ile Asn Glu Glu Ser Thr Ile Ser Val Thr Asn Ala Gln
        1055             1060             1065 gca cga gct atg ttg aga aga cat tct ctc att ggc cct gac ata aaa      3325
Ala Arg Ala Met Leu Arg Arg His Ser Leu Ile Gly Pro Asp Ile Lys
1070             1075             1080             1085 att act tat gtg cct gca gaa cat ttg gaa gag ttc aaa ata agc ttg      3373
Ile Thr Tyr Val Pro Ala Glu His Leu Glu Glu Phe Lys Ile Ser Leu
                 1090             1095             1100 gga caa caa tct gga aga gta atg gca ctg gat att ttt tct tca tac      3421
Gly Gln Gln Ser Gly Arg Val Met Ala Leu Asp Ile Phe Ser Ser Tyr
        1105             1110             1115 act ggc aga gac att cca gaa tta cca gag cga gaa gag gga gag ggt      3469
```

```
                Thr Gly Arg Asp Ile Pro Glu Leu Pro Glu Arg Glu Gly Glu Gly
                    1120                1125                1130 gaa gaa agc gaa ctt caa aac aca gca tat agc aat tgg aat cag ccc        3517
Glu Glu Ser Glu Leu Gln Asn Thr Ala Tyr Ser Asn Trp Asn Gln Pro
        1135                1140                1145 agg cgg gtg gaa ctt tgg aga gaa cca agc aaa tcc tta ggc atc agc        3565
Arg Arg Val Glu Leu Trp Arg Glu Pro Ser Lys Ser Leu Gly Ile Ser
1150                1155                1160                1165 att gtt ggt gga cga ggg atg ggg agt cgg cta agc aat gga gaa gtg        3613
Ile Val Gly Gly Arg Gly Met Gly Ser Arg Leu Ser Asn Gly Glu Val
                1170                1175                1180 atg agg ggc att ttc atc aaa cat gtt ctg gaa gat agg cca gct ggc        3661
Met Arg Gly Ile Phe Ile Lys His Val Leu Glu Asp Arg Pro Ala Gly
        1185                1190                1195 aaa aat gga acc ttg aag cct gga gat aga atc gta gag gtg gat gga        3709
Lys Asn Gly Thr Leu Lys Pro Gly Asp Arg Ile Val Glu Val Asp Gly
        1200                1205                1210 atg gac ctc aga gat gca agc cat gaa caa gct gtg gaa gcc att cgg        3757
Met Asp Leu Arg Asp Ala Ser His Glu Gln Ala Val Glu Ala Ile Arg
        1215                1220                1225 aaa gca ggc aac cct gta gtc ttt atg gta cag agc att ata aac aga        3805
Lys Ala Gly Asn Pro Val Val Phe Met Val Gln Ser Ile Ile Asn Arg
1230                1235                1240                1245 cca agg aaa tcc cct ttg cct tcc ttg ctg cac aac ctt tac cct aag        3853
Pro Arg Lys Ser Pro Leu Pro Ser Leu Leu His Asn Leu Tyr Pro Lys
                1250                1255                1260 tac aac ttc agc agc act aac cca ttt gct gac tct cta caa atc aac        3901
Tyr Asn Phe Ser Ser Thr Asn Pro Phe Ala Asp Ser Leu Gln Ile Asn
        1265                1270                1275 gcc gac aag gca ccc agt cag tca gag tca gag cca gag aag gct cca        3949
Ala Asp Lys Ala Pro Ser Gln Ser Glu Ser Glu Pro Glu Lys Ala Pro
        1280                1285                1290 ttg tgc agt gtg ccc cca ccc cct cct tca gcc ttt gcc gaa atg ggt        3997
Leu Cys Ser Val Pro Pro Pro Pro Pro Ser Ala Phe Ala Glu Met Gly
        1295                1300                1305 agt gat cac aca cag tca tct gca agc aaa atc tca caa gat gtg gac        4045
Ser Asp His Thr Gln Ser Ser Ala Ser Lys Ile Ser Gln Asp Val Asp
1310                1315                1320                1325 aaa gag gat gag ttt ggt tac agc tgg aaa aat atc aga gag cgt tat        4093
Lys Glu Asp Glu Phe Gly Tyr Ser Trp Lys Asn Ile Arg Glu Arg Tyr
                1330                1335                1340 gga acc cta aca ggc gag ctg cat atg att gaa ctg gag aaa ggt cat        4141
Gly Thr Leu Thr Gly Glu Leu His Met Ile Glu Leu Glu Lys Gly His
        1345                1350                1355 agt ggt ttg ggc cta agt ctt gct ggg aac aaa gac cga tcc agg atg        4189
Ser Gly Leu Gly Leu Ser Leu Ala Gly Asn Lys Asp Arg Ser Arg Met
        1360                1365                1370 agt gtc ttc ata gtg ggg att gat cca aat gga gct gca gga aaa gat        4237
Ser Val Phe Ile Val Gly Ile Asp Pro Asn Gly Ala Ala Gly Lys Asp
1375                1380                1385 ggt cga ttg caa att gca gat gag ctt cta gag atc aat ggt cag att        4285
Gly Arg Leu Gln Ile Ala Asp Glu Leu Leu Glu Ile Asn Gly Gln Ile
1390                1395                1400                1405 tta tat gga aga agt cat cag aat gcc tca tca atc att aaa tgt gcc        4333
Leu Tyr Gly Arg Ser His Gln Asn Ala Ser Ser Ile Ile Lys Cys Ala
                1410                1415                1420 cct tct aaa gtg aaa ata att ttt atc aga aat aaa gat gca gtg aat        4381
Pro Ser Lys Val Lys Ile Ile Phe Ile Arg Asn Lys Asp Ala Val Asn
        1425                1430                1435
```

-continued

| | |
|---|---|
| cag atg gcc gta tgt cct gga aat gca gta gaa cct ttg cct tct aac<br>Gln Met Ala Val Cys Pro Gly Asn Ala Val Glu Pro Leu Pro Ser Asn<br>  1440         1445        1450 | 4429 |
| tca gaa aat ctt caa aat aag gag aca gag cca act gtt act act tct<br>Ser Glu Asn Leu Gln Asn Lys Glu Thr Glu Pro Thr Val Thr Thr Ser<br>1455         1460        1465 | 4477 |
| gat gca gct gtg gac ctc agt tca ttt aaa aat gtg caa cat ctg gag<br>Asp Ala Ala Val Asp Leu Ser Ser Phe Lys Asn Val Gln His Leu Glu<br>1470       1475        1480        1485 | 4525 |
| ctt ccc aag gat cag ggg ggt ttg ggt att gct atc agc gaa gaa gat<br>Leu Pro Lys Asp Gln Gly Gly Leu Gly Ile Ala Ile Ser Glu Glu Asp<br>      1490        1495        1500 | 4573 |
| aca ctc agt gga gtc atc ata aag agc tta aca gag cat ggg gta gca<br>Thr Leu Ser Gly Val Ile Ile Lys Ser Leu Thr Glu His Gly Val Ala<br>      1505        1510        1515 | 4621 |
| gcc acg gat gga cga ctc aaa gtc gga gat cag ata ctg gct gta gat<br>Ala Thr Asp Gly Arg Leu Lys Val Gly Asp Gln Ile Leu Ala Val Asp<br>1520         1525        1530 | 4669 |
| gat gaa att gtt gtt ggt tac cct att gaa aag ttt att agc ctt ctg<br>Asp Glu Ile Val Val Gly Tyr Pro Ile Glu Lys Phe Ile Ser Leu Leu<br>1535        1540        1545 | 4717 |
| aag aca gca aag atg aca gta aaa ctt acc atc cat gct gag aat cca<br>Lys Thr Ala Lys Met Thr Val Lys Leu Thr Ile His Ala Glu Asn Pro<br>1550         1555        1560        1565 | 4765 |
| gat tcc cag gct gtt cct tca gca gct ggt gca gcc agt gga gaa aaa<br>Asp Ser Gln Ala Val Pro Ser Ala Ala Gly Ala Ala Ser Gly Glu Lys<br>      1570        1575        1580 | 4813 |
| aag aac agc tcc cag tct ctg atg gtc cca cag tct ggc tcc cca gaa<br>Lys Asn Ser Ser Gln Ser Leu Met Val Pro Gln Ser Gly Ser Pro Glu<br>      1585        1590        1595 | 4861 |
| ccg gag tcc atc cga aat aca agc aga tca tca aca cca gca att ttt<br>Pro Glu Ser Ile Arg Asn Thr Ser Arg Ser Ser Thr Pro Ala Ile Phe<br>1600         1605        1610 | 4909 |
| gct tct gat cct gca acc tgc ccc att atc cct ggc tgc gaa aca acc<br>Ala Ser Asp Pro Ala Thr Cys Pro Ile Ile Pro Gly Cys Glu Thr Thr<br>1615        1620        1625 | 4957 |
| atc gag att tcc aaa ggg cga aca ggg ctg ggc ctg agc atc gtt ggg<br>Ile Glu Ile Ser Lys Gly Arg Thr Gly Leu Gly Leu Ser Ile Val Gly<br>1630        1635        1640        1645 | 5005 |
| ggt tca gac acg ctg ctg ggt gcc ttt att atc cat gaa gtt tat gaa<br>Gly Ser Asp Thr Leu Leu Gly Ala Phe Ile Ile His Glu Val Tyr Glu<br>      1650        1655        1660 | 5053 |
| gaa gga gca gca tgt aaa gat gga aga ctc tgg gct gga gat cag atc<br>Glu Gly Ala Ala Cys Lys Asp Gly Arg Leu Trp Ala Gly Asp Gln Ile<br>      1665        1670        1675 | 5101 |
| tta gag gtg aat gga att gac ttg agg aag gcc aca cat gat gaa gca<br>Leu Glu Val Asn Gly Ile Asp Leu Arg Lys Ala Thr His Asp Glu Ala<br>      1680        1685        1690 | 5149 |
| atc aat gtc ctg aga cag acg cca cag aga gtg cgc ctg aca ctc tac<br>Ile Asn Val Leu Arg Gln Thr Pro Gln Arg Val Arg Leu Thr Leu Tyr<br>1695        1700        1705 | 5197 |
| aga gat gag gcc cca tac aaa gag gag gaa gtg tgt gac acc ctc act<br>Arg Asp Glu Ala Pro Tyr Lys Glu Glu Glu Val Cys Asp Thr Leu Thr<br>1710        1715        1720        1725 | 5245 |
| att gag ctg cag aag aag ccg gga aaa ggc cta gga tta agt att gtt<br>Ile Glu Leu Gln Lys Lys Pro Gly Lys Gly Leu Gly Leu Ser Ile Val<br>      1730        1735        1740 | 5293 |
| ggt aaa aga aac gat act gga gta ttt gtg tca gac att gtc aaa gga<br>Gly Lys Arg Asn Asp Thr Gly Val Phe Val Ser Asp Ile Val Lys Gly<br>      1745        1750        1755 | 5341 |

```
gga att gca gat ccc gat gga aga ctg atc cag gga gac cag ata tta      5389
Gly Ile Ala Asp Pro Asp Gly Arg Leu Ile Gln Gly Asp Gln Ile Leu
            1760                1765                1770 ttg gtg aat ggg gaa gac gtt cgt aat gcc tcc caa gaa gcg gtt gcc      5437
Leu Val Asn Gly Glu Asp Val Arg Asn Ala Ser Gln Glu Ala Val Ala
        1775                1780                1785 gct ttg cta aag tgt tcc cta ggc aca gta acc ttg gaa gtt gga aga      5485
Ala Leu Leu Lys Cys Ser Leu Gly Thr Val Thr Leu Glu Val Gly Arg
1790                1795                1800                1805 atc aaa gct ggt cca ttc cat tca gag agg agg cca tct caa acc agc      5533
Ile Lys Ala Gly Pro Phe His Ser Glu Arg Arg Pro Ser Gln Thr Ser
                1810                1815                1820 cag gtg agt gaa ggc agc ctg tct tct ttc act ttt cca ctc tct gga      5581
Gln Val Ser Glu Gly Ser Leu Ser Ser Phe Thr Phe Pro Leu Ser Gly
            1825                1830                1835 tcc agt aca tct gag tca ctg gaa agt agc tca aag aag aat gca ttg      5629
Ser Ser Thr Ser Glu Ser Leu Glu Ser Ser Ser Lys Lys Asn Ala Leu
        1840                1845                1850 gca tct gaa ata cag gga tta aga aca gtc gaa atg aaa aag ggc cct      5677
Ala Ser Glu Ile Gln Gly Leu Arg Thr Val Glu Met Lys Lys Gly Pro
1855                1860                1865 act gac tca ctg gga atc agc atc gct gga gga gta ggc agc cca ctt      5725
Thr Asp Ser Leu Gly Ile Ser Ile Ala Gly Gly Val Gly Ser Pro Leu
                1875                1880                1885
1870 ggt gat gtg cct ata ttt att gca atg atg cac cca act gga gtt gca      5773
Gly Asp Val Pro Ile Phe Ile Ala Met Met His Pro Thr Gly Val Ala
                1890                1895                1900 gca cag acc caa aaa ctc aga gtt ggg gat agg att gtc acc atc tgt      5821
Ala Gln Thr Gln Lys Leu Arg Val Gly Asp Arg Ile Val Thr Ile Cys
            1905                1910                1915 ggc aca tcc act gag ggc atg act cac acc caa gca gtt aac cta ctg      5869
Gly Thr Ser Thr Glu Gly Met Thr His Thr Gln Ala Val Asn Leu Leu
        1920                1925                1930 aaa aat gca tct ggc tcc att gaa atg cag gtg gtt gct gga gga gac      5917
Lys Asn Ala Ser Gly Ser Ile Glu Met Gln Val Val Ala Gly Gly Asp
1935                1940                1945 gtg agt gtg gtc aca ggt cat cat cag gag cct gca agt tcc agt ctt      5965
Val Ser Val Val Thr Gly His His Gln Glu Pro Ala Ser Ser Ser Leu
1950                1955                1960                1965 tct ttc act ggg ctg acg tca acc agt ata ttt cag gat gat tta gga      6013
Ser Phe Thr Gly Leu Thr Ser Thr Ser Ile Phe Gln Asp Asp Leu Gly
            1970                1975                1980 cct cct caa tgt aag tct att aca cta gag cga gga cca gat ggc tta      6061
Pro Pro Gln Cys Lys Ser Ile Thr Leu Glu Arg Gly Pro Asp Gly Leu
        1985                1990                1995 ggc ttc agt ata gtt gga gga tat ggc agc cct cat gga gac tta ccc      6109
Gly Phe Ser Ile Val Gly Gly Tyr Gly Ser Pro His Gly Asp Leu Pro
2000                2005                2010 att tat gtt aaa aca gtg ttt gca aag gga gca gcc tct gaa gac gga      6157
Ile Tyr Val Lys Thr Val Phe Ala Lys Gly Ala Ala Ser Glu Asp Gly
                2015                2020                2025 cgt ctg aaa agg ggc gat cag atc att gct gtc aat ggg cag agt cta      6205
Arg Leu Lys Arg Gly Asp Gln Ile Ile Ala Val Asn Gly Gln Ser Leu
            2030                2035                2040                2045 gaa gga gtc acc cat gaa gaa gct gtt gcc atc ctt aaa cgg aca aaa      6253
Glu Gly Val Thr His Glu Glu Ala Val Ala Ile Leu Lys Arg Thr Lys
        2050                2055                2060 ggc act gtc act ttg atg gtt ctc tct tgaattggct gccagaattg            6300
Gly Thr Val Thr Leu Met Val Leu Ser
```

-continued

```
                    2065                2070
aaccaaccca acccctagct cacctcctac tgtaaagaga atgcactggt cctgacaatt       6360
tttatgctgt gttcagccgg gtcttcaaaa ctgtagggg gaaataacac ttaagtttct        6420
ttttctcatc tagaaatgct ttccttactg acaacctaac atcattttc ttttcttctt       6480 gcattttgtg aacttaaaga gaaggaatat ttgtgtaggt gaatctcgtt tttatttgtg        6540
gagatatcta atgttttgta gtcacatggg caagaattat tacatgctaa gctgttagt        6600 ataaagaaag ataattctaa agctaaccaa agaaaatggc ttcagtaagt taggatgaaa        6660
aatgaaaata taaataaag aagaaaatct cggggagttt aaaaaaaatg cctcaatttg        6720
gcaatctacc tcctctcccc accccaaact                                        6750
```

```
<210> SEQ ID NO 87
<211> LENGTH: 6666
<212> TYPE: DNA
<213> ORGANISM: Homo sapiens
<220> FEATURE:
<221> NAME/KEY: CDS
<222> LOCATION: (71)...(3787)

<400> SEQUENCE: 87
```

```
ttctcagtca cgcagttcca tttaattgc tgttaatcat ttcagagaag aacactgaac        60
tttgaaaaaa atg ttg gaa gcc att gac aaa aat cgg gcc ctg cat gca         109
             Met Leu Glu Ala Ile Asp Lys Asn Arg Ala Leu His Ala
               1               5                  10 gca gag cgc ttg caa acc aag ctg cga gaa cgt ggg gat gta gca aat         157
Ala Glu Arg Leu Gln Thr Lys Leu Arg Glu Arg Gly Asp Val Ala Asn
 15                  20                  25 gaa gac aaa ctg agc ctt ctg aag tca gtc ctg cag agc cct ctc ttc         205
Glu Asp Lys Leu Ser Leu Leu Lys Ser Val Leu Gln Ser Pro Leu Phe
 30                  35                  40                  45 agt cag att ctg agc ctt cag act tct gta cag cag ctg aaa gac cag         253
Ser Gln Ile Leu Ser Leu Gln Thr Ser Val Gln Gln Leu Lys Asp Gln
                 50                  55                  60 gta aat att gca act tca gca act tca aat att gaa tat gcc cac gtt         301
Val Asn Ile Ala Thr Ser Ala Thr Ser Asn Ile Glu Tyr Ala His Val
             65                  70                  75 cct cat ctc agc cca gct gtg att cct act ctg caa aat gaa tcg ttt         349
Pro His Leu Ser Pro Ala Val Ile Pro Thr Leu Gln Asn Glu Ser Phe
         80                  85                  90 tta tta tcc cca aac aat ggg aat ctg gaa gca ctt aca gga cct ggt         397
Leu Leu Ser Pro Asn Asn Gly Asn Leu Glu Ala Leu Thr Gly Pro Gly
     95                 100                 105 att cca cac att aat ggg aaa cct gct tgt gat gaa ttt gat cag ctt         445
Ile Pro His Ile Asn Gly Lys Pro Ala Cys Asp Glu Phe Asp Gln Leu
110                 115                 120                 125 atc aaa aat atg gcc cag ggt cgc cat gta gaa gtt ttt gag ctc ctc         493
Ile Lys Asn Met Ala Gln Gly Arg His Val Glu Val Phe Glu Leu Leu
                130                 135                 140 aaa cct cca tct gga ggc ctt ggg ttt agt gtt gtg gga cta aga agt         541
Lys Pro Pro Ser Gly Gly Leu Gly Phe Ser Val Val Gly Leu Arg Ser
            145                 150                 155 gaa aac aga gga gag ctg gga ata ttt gtt caa gag ata caa gag ggc         589
Glu Asn Arg Gly Glu Leu Gly Ile Phe Val Gln Glu Ile Gln Glu Gly
        160                 165                 170 agt gtg gcc cat aga gat gga aga ttg aaa gaa act gat caa att ctt         637
Ser Val Ala His Arg Asp Gly Arg Leu Lys Glu Thr Asp Gln Ile Leu
    175                 180                 185
```

```
gct atc aat gga cag gct ctt gat cag aca att aca cat cag cag gct        685
Ala Ile Asn Gly Gln Ala Leu Asp Gln Thr Ile Thr His Gln Gln Ala
190                 195                 200                 205 atc agc atc ctg cag aaa gcc aaa gat act gtc cag cta gtt att gcc        733
Ile Ser Ile Leu Gln Lys Ala Lys Asp Thr Val Gln Leu Val Ile Ala
            210                 215                 220 aga ggc tca ttg cct cag ctt gtc agc ccc ata gtt tcc cgt tct cca        781
Arg Gly Ser Leu Pro Gln Leu Val Ser Pro Ile Val Ser Arg Ser Pro
                225                 230                 235 tct gca gcc agc aca att tca gct cac tct aat ccg gtt cac tgg caa        829
Ser Ala Ala Ser Thr Ile Ser Ala His Ser Asn Pro Val His Trp Gln
    240                 245                 250 cac atg gaa acg att gaa ttg gtg aat gat gga tct ggt ttg gga ttt        877
His Met Glu Thr Ile Glu Leu Val Asn Asp Gly Ser Gly Leu Gly Phe
255                 260                 265 ggc atc ata gga gga aaa gca act ggt gtg ata gta aaa acc att ctg        925
Gly Ile Ile Gly Gly Lys Ala Thr Gly Val Ile Val Lys Thr Ile Leu
270                 275                 280                 285 cct gga gga gta gct gat cag cat ggg cgt tta tgc agt gga gac cac        973
Pro Gly Gly Val Ala Asp Gln His Gly Arg Leu Cys Ser Gly Asp His
                290                 295                 300 att cta aag att ggt gac aca gat cta gca gga atg agc agt gag caa       1021
Ile Leu Lys Ile Gly Asp Thr Asp Leu Ala Gly Met Ser Ser Glu Gln
    305                 310                 315 gta gca caa gtc ctt agg caa tgt gga aat aga gtt aag ttg atg att       1069
Val Ala Gln Val Leu Arg Gln Cys Gly Asn Arg Val Lys Leu Met Ile
320                 325                 330 gca aga agt gcc ata gaa gaa cgt aca gca ccc act gct ttg ggc atc       1117
Ala Arg Ser Ala Ile Glu Glu Arg Thr Ala Pro Thr Ala Leu Gly Ile
335                 340                 345 acc ctc tcc tca tcc cca act tca acg cca gag ttg cgg gtt gat gct       1165
Thr Leu Ser Ser Ser Pro Thr Ser Thr Pro Glu Leu Arg Val Asp Ala
350                 355                 360                 365 tct act cag aaa ggt gaa gaa agt gag aca ttt gat gta gaa ctc act       1213
Ser Thr Gln Lys Gly Glu Glu Ser Glu Thr Phe Asp Val Glu Leu Thr
                370                 375                 380 aaa aat gtc caa gga tta gga att acc att gct ggc tac att gga gat       1261
Lys Asn Val Gln Gly Leu Gly Ile Thr Ile Ala Gly Tyr Ile Gly Asp
    385                 390                 395 aaa aaa ttg gaa cct tca gga atc ttt gta aag agc att aca aaa agc       1309
Lys Lys Leu Glu Pro Ser Gly Ile Phe Val Lys Ser Ile Thr Lys Ser
400                 405                 410 agt gcc gtt gag cat gat gga aga atc caa att gga gac caa att ata       1357
Ser Ala Val Glu His Asp Gly Arg Ile Gln Ile Gly Asp Gln Ile Ile
415                 420                 425 gca gta gat ggc aca aac ctt cag ggt ttt act aat cag caa gca gta       1405
Ala Val Asp Gly Thr Asn Leu Gln Gly Phe Thr Asn Gln Gln Ala Val
430                 435                 440                 445 gag gta ttg cga cat aca gga caa act gtg ctc ctg aca cta atg agg       1453
Glu Val Leu Arg His Thr Gly Gln Thr Val Leu Leu Thr Leu Met Arg
                450                 455                 460 aga gga atg aag cag gaa gcc gag ctc atg tca agg gaa gac gtc aca       1501
Arg Gly Met Lys Gln Glu Ala Glu Leu Met Ser Arg Glu Asp Val Thr
    465                 470                 475 aaa gat gca gat ttg tct cct gtt aat gcc agc ata atc aaa gaa aat       1549
Lys Asp Ala Asp Leu Ser Pro Val Asn Ala Ser Ile Ile Lys Glu Asn
480                 485                 490 tat gaa aaa gat gaa gat ttt tta tct tcg acg aga aac acc aac ata       1597
Tyr Glu Lys Asp Glu Asp Phe Leu Ser Ser Thr Arg Asn Thr Asn Ile
495                 500                 505
```

-continued

| | | |
|---|---|---|
| tta cca act gaa gaa gaa ggg tat cca tta ctg tca gct gag ata gaa<br>Leu Pro Thr Glu Glu Glu Gly Tyr Pro Leu Leu Ser Ala Glu Ile Glu<br>510                        515                    520                 525 | 1645 |
| gaa ata gaa gat gca caa aaa caa gaa gct gct ctg ctg aca aaa tgg<br>Glu Ile Glu Asp Ala Gln Lys Gln Glu Ala Ala Leu Leu Thr Lys Trp<br>                       530                    535                   540 | 1693 |
| caa agg att atg gga att aac tat gaa ata gtg gtg gcc cat gtg agc<br>Gln Arg Ile Met Gly Ile Asn Tyr Glu Ile Val Val Ala His Val Ser<br>      545                    550                    555 | 1741 |
| aag ttt agt gag aac agt gga ttg ggg ata agc ctg gaa gcg aca gtg<br>Lys Phe Ser Glu Asn Ser Gly Leu Gly Ile Ser Leu Glu Ala Thr Val<br>           560                    565                    570 | 1789 |
| gga cat cat ttt atc cga tct gtt cta cca gag ggt cct gtt gga cac<br>Gly His His Phe Ile Arg Ser Val Leu Pro Glu Gly Pro Val Gly His<br>575                       580                    585 | 1837 |
| agc ggg aag ctc ttc agt gga gac gag cta ttg gaa gta aat ggc ata<br>Ser Gly Lys Leu Phe Ser Gly Asp Glu Leu Leu Glu Val Asn Gly Ile<br>590                     595                    600                 605 | 1885 |
| act tta ctt ggg gaa aat cac caa gat gtg gtg aat atc tta aaa gaa<br>Thr Leu Leu Gly Glu Asn His Gln Asp Val Val Asn Ile Leu Lys Glu<br>                    610                    615                 620 | 1933 |
| ctg cct ata gaa gtg aca atg gtg tgc tgt cgt cga act gtg cca ccc<br>Leu Pro Ile Glu Val Thr Met Val Cys Cys Arg Arg Thr Val Pro Pro<br>625                       630                    635 | 1981 |
| acc acc caa tca gaa ttg gat agc ctg gac tta tgt gat att gag cta<br>Thr Thr Gln Ser Glu Leu Asp Ser Leu Asp Leu Cys Asp Ile Glu Leu<br>                    640                    645                 650 | 2029 |
| aca gaa aag cct cac gta gat cta ggt gag ttc atc ggg tca tca gag<br>Thr Glu Lys Pro His Val Asp Leu Gly Glu Phe Ile Gly Ser Ser Glu<br>655                       660                    665 | 2077 |
| cca gag gat cca gtg ctg gcg atg act gat gcg ggt cag agt aca gaa<br>Pro Glu Asp Pro Val Leu Ala Met Thr Asp Ala Gly Gln Ser Thr Glu<br>670                     675                   680                 685 | 2125 |
| gag gtt caa gca cct ttg gcc atg tgg gag gct ggc att cag cac ata<br>Glu Val Gln Ala Pro Leu Ala Met Trp Glu Ala Gly Ile Gln His Ile<br>                    690                    695                 700 | 2173 |
| atg ctg gag aaa ggg agc aaa gga ctt ggt ttt agc att tta gat tat<br>Met Leu Glu Lys Gly Ser Lys Gly Leu Gly Phe Ser Ile Leu Asp Tyr<br>705                       710                    715 | 2221 |
| cag gat cca att gat cca gca agc act gtg att ata att cgt tct ttg<br>Gln Asp Pro Ile Asp Pro Ala Ser Thr Val Ile Ile Ile Arg Ser Leu<br>                    720                    725                 730 | 2269 |
| gtg cct ggc ggc att gct gaa aag gat gga cga ctt ctt cct ggt gac<br>Val Pro Gly Gly Ile Ala Glu Lys Asp Gly Arg Leu Leu Pro Gly Asp<br>735                       740                    745 | 2317 |
| cga ctc atg ttt gta aac gat gtt aac ttg gaa aac agc agt ctt gag<br>Arg Leu Met Phe Val Asn Asp Val Asn Leu Glu Asn Ser Ser Leu Glu<br>750                     755                    760                 765 | 2365 |
| gaa gct gta gaa gca ctg aag gga gca ccg tca ggg act gtg aga ata<br>Glu Ala Val Glu Ala Leu Lys Gly Ala Pro Ser Gly Thr Val Arg Ile<br>                    770                    775                 780 | 2413 |
| gga gtt gct aag cct tta ccc ctt tca cca gaa gaa ggt tat gtt tct<br>Gly Val Ala Lys Pro Leu Pro Leu Ser Pro Glu Glu Gly Tyr Val Ser<br>                       785                    790                 795 | 2461 |
| gct aag gag gat tcc ttt ctc tac cca cca cac tcc tgt gag gaa gca<br>Ala Lys Glu Asp Ser Phe Leu Tyr Pro Pro His Ser Cys Glu Glu Ala<br>800                       805                    810 | 2509 |
| ggg ctg gct gac aaa ccc ctc ttc agg gct gac ttg gct ctg gtg ggc<br>Gly Leu Ala Asp Lys Pro Leu Phe Arg Ala Asp Leu Ala Leu Val Gly | 2557 |

```
                    815                 820                 825
aca aat gat gct gac tta gta gat gaa tcc aca ttt gag tct cca tac        2605
Thr Asn Asp Ala Asp Leu Val Asp Glu Ser Thr Phe Glu Ser Pro Tyr
830                 835                 840                 845 tct cct gaa aat gac agc atc tac tct act caa gcc tct att tta tct        2653
Ser Pro Glu Asn Asp Ser Ile Tyr Ser Thr Gln Ala Ser Ile Leu Ser
                850                 855                 860 ctt cat ggc agt tct tgt ggt gat ggc ctg aac tat ggt tct tcc ctt        2701
Leu His Gly Ser Ser Cys Gly Asp Gly Leu Asn Tyr Gly Ser Ser Leu
                    865                 870                 875 cca tca tct cct cct aag gat gtt att gaa aat tct tgt gat cca gta        2749
Pro Ser Ser Pro Pro Lys Asp Val Ile Glu Asn Ser Cys Asp Pro Val
880                 885                 890 ctt gat ctg cat atg tct ctg gag gaa cta tat acc cag aat ctc ctg        2797
Leu Asp Leu His Met Ser Leu Glu Glu Leu Tyr Thr Gln Asn Leu Leu
        895                 900                 905 gaa aga cag gat gag aat aca cct tcg gtg gac ata agt atg ggg cct        2845
Glu Arg Gln Asp Glu Asn Thr Pro Ser Val Asp Ile Ser Met Gly Pro
910                 915                 920                 925 gct tct ggc ttt act ata aat gac tac aca cct gca aat gct att gaa        2893
Ala Ser Gly Phe Thr Ile Asn Asp Tyr Thr Pro Ala Asn Ala Ile Glu
                930                 935                 940 caa caa tat gaa tgt gaa aac aca ata gtg tgg act gaa tct cat tta        2941
Gln Gln Tyr Glu Cys Glu Asn Thr Ile Val Trp Thr Glu Ser His Leu
            945                 950                 955 cca agt gaa gtt ata tca agt gca gaa ctt cct tct gtg cta ccc gat        2989
Pro Ser Glu Val Ile Ser Ser Ala Glu Leu Pro Ser Val Leu Pro Asp
        960                 965                 970 tca gct gga aag ggc tct gag cac ctg ctt gaa cag agc tcc ctg gcc        3037
Ser Ala Gly Lys Gly Ser Glu His Leu Leu Glu Gln Ser Ser Leu Ala
    975                 980                 985 tgt aat gct gag tgt gtc atg ctt caa aat gta tct aaa gaa tct ttt        3085
Cys Asn Ala Glu Cys Val Met Leu Gln Asn Val Ser Lys Glu Ser Phe
990                 995                 1000                1005 gaa agg act att aat ata gca aaa ggc aat tct agc cta gga atg aca        3133
Glu Arg Thr Ile Asn Ile Ala Lys Gly Asn Ser Ser Leu Gly Met Thr
                1010                1015                1020 gtt agt gct aat aaa gat ggc ttg ggg atg atc gtt cga agc att att        3181
Val Ser Ala Asn Lys Asp Gly Leu Gly Met Ile Val Arg Ser Ile Ile
            1025                1030                1035 cat gga ggt gcc att agt cga gat ggc cgg att gcc att ggg gac tgc        3229
His Gly Gly Ala Ile Ser Arg Asp Gly Arg Ile Ala Ile Gly Asp Cys
        1040                1045                1050 atc ttg tcc att aat gaa gag tct acc atc agt gta acc aat gcc cag        3277
Ile Leu Ser Ile Asn Glu Glu Ser Thr Ile Ser Val Thr Asn Ala Gln
    1055                1060                1065 gca cga gct atg ttg aga aga cat tct ctc att ggc cct gac ata aaa        3325
Ala Arg Ala Met Leu Arg Arg His Ser Leu Ile Gly Pro Asp Ile Lys
1070                1075                1080                1085 att act tat gtg cct gca gaa cat ttg gaa gag ttc aaa ata agc ttg        3373
Ile Thr Tyr Val Pro Ala Glu His Leu Glu Glu Phe Lys Ile Ser Leu
                1090                1095                1100 gga caa caa tct gga aga gta atg gca ctg gat att ttt tct tca tac        3421
Gly Gln Gln Ser Gly Arg Val Met Ala Leu Asp Ile Phe Ser Ser Tyr
            1105                1110                1115 act ggc aga gac att cca gaa tta cca gag cga gaa gag gga gag ggt        3469
Thr Gly Arg Asp Ile Pro Glu Leu Pro Glu Arg Glu Glu Gly Glu Gly
        1120                1125                1130 gaa gaa agc gaa ctt caa aac aca gca tat agc aat tgg aat cag ccc        3517
```

-continued

| | | | | | | | | | | | | | | |
|---|---|---|---|---|---|---|---|---|---|---|---|---|---|---|
|Glu|Glu|Ser|Glu|Leu|Gln|Asn|Thr|Ala|Tyr|Ser|Asn|Trp|Asn|Gln|Pro|
| |1135| | | |1140| | | |1145| | | | | |

```
agg cgg gtg gaa ctc tgg aga gaa cca agc aaa tcc tta ggc atc agc      3565
Arg Arg Val Glu Leu Trp Arg Glu Pro Ser Lys Ser Leu Gly Ile Ser
1150                1155                1160                1165 att gtt ggt gga cga ggg atg ggg agt cgg cta agc aat gga gaa gtg      3613
Ile Val Gly Gly Arg Gly Met Gly Ser Arg Leu Ser Asn Gly Glu Val
            1170                1175                1180 atg agg ggc att ttc atc aaa cat gtt ctg gaa gat agt cca gct ggc      3661
Met Arg Gly Ile Phe Ile Lys His Val Leu Glu Asp Ser Pro Ala Gly
        1185                1190                1195 aaa aat gga acc ttg aaa cct gga gat aga atc gta gag gtg gat gga      3709
Lys Asn Gly Thr Leu Lys Pro Gly Asp Arg Ile Val Glu Val Asp Gly
    1200                1205                1210 atg gac ctc aga gat gca agc cat gaa caa gct gtg gaa gcc att cgg      3757
Met Asp Leu Arg Asp Ala Ser His Glu Gln Ala Val Glu Ala Ile Arg
1215                1220                1225 aaa gca ggc aac cct gta gtc ttt atg gta tagagcttta ttacagacca        3807
Lys Ala Gly Asn Pro Val Val Phe Met Val
1230                1235 agggcaccca gtcagtcagt cagagtcaga gtcagagtca gagccagaga aggctccatt   3867
gtgcagtgtg cccccacccc ctccttcagc ctttgccgaa atgggtagtg atcacacaca   3927
gtcatctgca agcaaaatct cacaagatgt ggacaaagag gatgagtttg ttacagctg    3987
gaaaaatatc agagagcgtt atggaaccct aacaggcgag ctgcatatga ttgaactgga   4047
gaaaggtcat agtggtttgg gcctaagtct tgctgggaac aaagaccgat ccaggatgag   4107
tgtcttcata gtggggattg atccaaatgg agctgcagga aaagatggtc gattgcaaat   4167
tgcagatgag cttctagaga tcaatggtca gattttatat ggaagaagtc atcagaatgc   4227
ctcatcaatc attaaatgtg ccccttctaa agtgaaaata atttttatca gaataaaga    4287
tgcagtgaat cagatggccg tatgtcctgg aaatgcagta gaaccctttgc cttctaactc  4347
agaaaatctt caaaataagg agacagagcc aactgttact acttctgatg cagctgtgga   4407
cctcagttca tttaaaaatg tgcaacatct ggagcttccc aaggatcagg ggggtttggg   4467
tattgctatc agcgaagaag atacactcag tggagtcatc ataaagagct aacagagca    4527
tggggtagca gccacggatg gacgactcaa agtcggagat cagatactgg ctgtagatga   4587
tgaaattgtt gttggttacc ctattgaaaa gtttattagc cttctgaaga cagcaaagat   4647
gacagtaaaa cttaccatcc atgctgagaa tccagattcc caggctgttc cttcagcagc   4707
tggtgcagcc agtggagaaa aaagaacag ctcccagtct ctgatggtcc cacagtctgg    4767
ctccccagaa ccggagtcca tccgaaatac aagcagatca tcaacaccag caatttttgc   4827
ttctgatcct gcaacctgcc ccattatccc tggctgcgaa acaaccatcg agatttccaa   4887
agggcgaaca gggctgggcc tgagcatcgt tgggggttca gacacgctgc tgggtgcctt   4947
tattatccat gaagtttatg aagaaggagc agcatgtaaa gatggaagac tctgggctgg   5007
agatcagatc ttagaggtga atggaattga cttgaggaag gccacacatg atgaagcaat   5067
caatgtcctg agacagacgc cacagagagt gcgcctgaca ctctacagag atgaggcccc   5127
atacaaagag gaggaagtgt gtgacaccct cactattgag ctgcagaaga agccgggaaa   5187
aggcctagga ttaagtattg ttggtaaaag aaacgatact ggagtatttg tgtcagacat   5247
tgtcaaagga ggaattgcag atcccgatgg aagactgatc cagggagacc agatattatt   5307
ggtgaatggg gaagacgttc gtaatgcctc ccaagaagcg gttgccgctt tgctaaagtg   5367
```

-continued

```
ttccctaggc acagtaacct tggaagttgg aagaatcaaa gctggtccat tccattcaga    5427
gaggaggcca tctcaaacca gccaggtgag tgaaggcagc ctgtcttctt tcactttccc    5487
actctctgga tccagtacat ctgagtcact ggaaagtagc tcaaagaaga atgcattggc    5547
atctgaaata cagggattaa aacagtcga atgaaaaag ggccctactg actcactggg     5607
aatcagcatc gctggaggag taggcagccc acttggtgat gtgcctatat ttattgcaat    5667
gatgcaccca actggagttg cagcacagac ccaaaaactc agagttgggg ataggattgt    5727
caccatctgt ggcacatcca ctgagggcat gactcacacc caagcagtta acctactgaa    5787
aaatgcatct ggctccattg aaatgcaggt ggttgctgga ggagacgtga gtgtggtcac    5847
aggtcatcat caggagcctg caagttccag tctttctttc actgggctga cgtcaaccag    5907
tatatttcag gatgatttag gacctcctca atgtaagtct attacactag agcgaggacc    5967
agatggctta ggcttcagta tagttggagg atatggcagc cctcatggag acttacccat    6027
ttatgttaaa acagtgtttg caagggagc agcctctgaa gacggacgtc tgaaaagggg    6087
cgatcagatc attgctgtca atgggcagag tctagaagga gtcacccatg aagaagctgt    6147
tgccatcctt aaacggacaa aaggcactgt cactttgatg gttctctctt gaattggctg    6207
ccagaattga accaacccaa cccctagctc acctcctact gtaaagagaa tgcactggtc    6267
ctgacaattt ttatgctgtg ttcagccggg tcttcaaaac tgtagggggg aaataacact    6327
taagtttctt tttctcatct agaaatgctt tccttactga caacctaaca tcatttttct    6387
tttcttcttg cattttgtga acttaaagag aaggaatatt tgtgtaggtg aatctcgttt    6447
ttatttgtgg agatatctaa tgttttgtag tcacatgggc aagaattatt acatgctaag    6507
ctggttagta taaagaaaga taattctaaa gctaaccaaa gaaatggct tcagtaagtt     6567 aggatgaaaa atgaaaatat aaaataaaga agaaaatctc ggggagttta aaaaaaatgc    6627
ctcaatttgg caatctacct cctctcccca ccccaaact                            6666
```

<210> SEQ ID NO 88
<211> LENGTH: 763
<212> TYPE: PRT
<213> ORGANISM: Homo sapiens

<400> SEQUENCE: 88

```
Met Gly Ser Asn His Thr Gln Ser Ser Ala Ser Lys Ile Ser Gln Asp
  1               5                  10                  15

Val Asp Lys Glu Asp Glu Phe Gly Tyr Ser Trp Lys Asn Ile Arg Glu
             20                  25                  30

Arg Tyr Gly Thr Leu Thr Gly Glu Leu His Met Ile Glu Leu Glu Lys
         35                  40                  45

Gly His Ser Gly Leu Gly Leu Ser Leu Ala Gly Asn Lys Asp Arg Ser
     50                  55                  60

Arg Met Ser Val Phe Ile Val Gly Ile Asp Pro Asn Gly Ala Ala Gly
 65                  70                  75                  80

Lys Asp Gly Arg Leu Gln Ile Ala Asp Glu Leu Leu Glu Ile Asn Gly
                 85                  90                  95

Gln Ile Leu Tyr Gly Arg Ser His Gln Asn Ala Ser Ser Ile Ile Lys
            100                 105                 110

Cys Ala Pro Ser Lys Val Lys Ile Ile Phe Ile Arg Asn Lys Asp Ala
        115                 120                 125

Val Asn Gln Met Ala Val Cys Pro Gly Asn Ala Val Glu Pro Leu Pro
    130                 135                 140
```

```
Ser Asn Ser Glu Asn Leu Gln Asn Lys Glu Pro Glu Pro Thr Val Thr
145                 150                 155                 160

Thr Ser Asp Ala Ala Val Asp Leu Ser Ser Phe Lys Asn Val Gln His
            165                 170                 175

Leu Glu Leu Pro Lys Asp Gln Gly Gly Leu Gly Ile Ala Ile Ser Glu
            180                 185                 190

Glu Asp Thr Leu Ser Gly Val Ile Ile Lys Ser Leu Thr Glu His Gly
        195                 200                 205

Val Ala Ala Thr Asp Gly Arg Leu Lys Val Gly Asp Gln Ile Leu Ala
        210                 215                 220

Val Asp Asp Glu Ile Val Val Gly Tyr Pro Ile Glu Lys Phe Ile Ser
225                 230                 235                 240

Leu Leu Lys Thr Ala Lys Met Thr Val Lys Leu Thr Ile His Ala Glu
            245                 250                 255

Asn Pro Asp Ser Gln Ala Val Pro Ser Ala Gly Ala Ala Ser Gly
            260                 265                 270

Glu Lys Lys Asn Ser Ser Gln Ser Leu Met Val Pro Gln Ser Gly Ser
        275                 280                 285

Pro Glu Pro Glu Ser Ile Arg Asn Thr Ser Arg Ser Ser Thr Pro Ala
        290                 295                 300

Ile Phe Ala Ser Asp Pro Ala Thr Cys Pro Ile Ile Pro Gly Cys Glu
305                 310                 315                 320

Thr Thr Ile Glu Ile Ser Lys Gly Arg Thr Gly Leu Gly Leu Ser Ile
            325                 330                 335

Val Gly Gly Ser Asp Thr Leu Leu Gly Ala Phe Ile Ile His Glu Val
            340                 345                 350

Tyr Glu Glu Gly Ala Ala Cys Lys Asp Gly Arg Leu Trp Ala Gly Asp
        355                 360                 365

Gln Ile Leu Glu Val Asn Gly Ile Asp Leu Arg Lys Ala Thr His Asp
        370                 375                 380

Glu Ala Ile Asn Val Leu Arg Gln Thr Pro Gln Arg Val Arg Leu Thr
385                 390                 395                 400

Leu Tyr Arg Asp Glu Ala Pro Tyr Lys Glu Glu Val Cys Asp Thr
            405                 410                 415

Leu Thr Ile Glu Leu Gln Lys Lys Pro Gly Lys Gly Leu Gly Leu Ser
            420                 425                 430

Ile Val Gly Lys Arg Asn Asp Thr Gly Val Phe Val Ser Asp Ile Val
        435                 440                 445

Lys Gly Gly Ile Ala Asp Pro Asp Gly Arg Leu Ile Gln Gly Asp Gln
450                 455                 460

Ile Leu Leu Val Asn Gly Glu Asp Val Arg Asn Ala Ser Gln Glu Ala
465                 470                 475                 480

Val Ala Ala Leu Leu Lys Cys Ser Leu Gly Thr Val Thr Leu Glu Val
            485                 490                 495

Gly Arg Ile Lys Ala Gly Pro Phe His Ser Glu Arg Arg Pro Ser Gln
            500                 505                 510

Thr Ser Gln Val Ser Glu Gly Ser Leu Ser Ser Phe Thr Phe Pro Leu
        515                 520                 525

Ser Gly Ser Ser Thr Ser Glu Ser Leu Glu Ser Ser Lys Lys Asn
        530                 535                 540

Ala Leu Ala Ser Glu Ile Gln Gly Leu Arg Thr Val Glu Met Lys Lys
545                 550                 555                 560

Gly Pro Thr Asp Ser Leu Gly Ile Ser Ile Ala Gly Gly Val Gly Ser
```

-continued

```
                565                 570                 575
Pro Leu Gly Asp Val Pro Ile Phe Ile Ala Met Met His Pro Thr Gly
            580                 585                 590

Val Ala Ala Gln Thr Gln Lys Leu Arg Val Gly Asp Arg Ile Val Thr
            595                 600                 605

Ile Cys Gly Thr Ser Thr Glu Gly Met Thr His Thr Gln Ala Val Asn
            610                 615                 620

Leu Leu Lys Asn Ala Ser Gly Ser Ile Glu Met Gln Val Val Ala Gly
625                 630                 635                 640

Gly Asp Val Ser Val Val Thr Gly His His Gln Glu Pro Ala Ser Ser
            645                 650                 655

Ser Leu Ser Phe Thr Gly Leu Thr Ser Thr Ser Ile Phe Gln Asp Asp
            660                 665                 670

Leu Gly Pro Pro Gln Cys Lys Ser Ile Thr Leu Glu Arg Gly Pro Asp
            675                 680                 685

Gly Leu Gly Phe Ser Ile Val Gly Gly Tyr Gly Ser Pro His Gly Asp
            690                 695                 700

Leu Pro Ile Tyr Val Lys Thr Val Phe Ala Lys Gly Ala Ala Ser Glu
705                 710                 715                 720

Asp Gly Arg Leu Lys Arg Gly Asp Gln Ile Ile Ala Val Asn Gly Gln
            725                 730                 735

Ser Leu Glu Gly Val Thr His Glu Glu Ala Val Ala Ile Leu Lys Arg
            740                 745                 750

Thr Lys Gly Thr Val Thr Leu Met Val Leu Ser
            755                 760

<210> SEQ ID NO 89
<211> LENGTH: 590
<212> TYPE: PRT
<213> ORGANISM: Homo sapiens

<400> SEQUENCE: 89

Ile Thr His Gln Gln Ala Ile Ser Ile Leu Gln Lys Ala Lys Asp Thr
1               5                   10                  15

Val Gln Leu Val Ile Ala Arg Gly Ser Leu Pro Gln Leu Val Ser Pro
            20                  25                  30

Ile Val Ser Arg Ser Pro Ser Ala Ala Ser Thr Ile Ser Ala His Ser
            35                  40                  45

Asn Pro Val His Trp Gln His Met Glu Thr Ile Glu Leu Val Asn Asp
        50                  55                  60

Gly Ser Gly Leu Gly Phe Gly Ile Ile Gly Gly Lys Ala Thr Gly Val
65                  70                  75                  80

Ile Val Lys Thr Ile Leu Pro Gly Gly Val Ala Asp Gln His Gly Arg
                85                  90                  95

Leu Cys Ser Gly Asp His Ile Leu Lys Ile Gly Asp Thr Asp Leu Ala
                100                 105                 110

Gly Met Ser Ser Glu Gln Val Ala Gln Val Leu Arg Gln Cys Gly Asn
            115                 120                 125

Arg Val Lys Leu Met Ile Ala Arg Ser Ala Ile Glu Glu Arg Thr Ala
        130                 135                 140

Pro Thr Ala Leu Gly Ile Thr Leu Ser Ser Ser Pro Thr Ser Thr Pro
145                 150                 155                 160

Glu Leu Arg Val Asp Ala Ser Thr Gln Lys Gly Glu Glu Ser Glu Thr
                165                 170                 175
```

-continued

```
Phe Asp Val Glu Leu Thr Lys Asn Val Gln Gly Leu Gly Ile Thr Ile
            180                 185                 190
Ala Gly Tyr Ile Gly Asp Lys Lys Leu Glu Pro Ser Gly Ile Phe Val
        195                 200                 205
Lys Ser Ile Thr Lys Ser Ser Ala Val Glu His Asp Gly Arg Ile Gln
    210                 215                 220
Ile Gly Asp Gln Ile Ile Ala Val Asp Gly Thr Asn Leu Gln Gly Phe
225                 230                 235                 240
Thr Asn Gln Gln Ala Val Glu Val Leu Arg His Thr Gly Gln Thr Val
                245                 250                 255
Leu Leu Thr Leu Met Arg Arg Gly Met Lys Gln Glu Ala Glu Leu Met
            260                 265                 270
Ser Arg Glu Asp Val Thr Lys Asp Ala Asp Leu Ser Pro Val Asn Ala
        275                 280                 285
Ser Ile Ile Lys Glu Asn Tyr Glu Lys Asp Glu Asp Phe Leu Ser Ser
    290                 295                 300
Thr Arg Asn Thr Asn Ile Leu Pro Thr Glu Glu Gly Tyr Pro Leu
305                 310                 315                 320
Leu Ser Ala Glu Ile Glu Glu Ile Glu Asp Ala Gln Lys Gln Glu Ala
                325                 330                 335
Ala Leu Leu Thr Lys Trp Gln Arg Ile Met Gly Ile Asn Tyr Glu Ile
            340                 345                 350
Val Val Ala His Val Ser Lys Phe Ser Glu Asn Ser Gly Leu Gly Ile
        355                 360                 365
Ser Leu Glu Ala Thr Val Gly His His Phe Ile Arg Ser Val Leu Pro
    370                 375                 380
Glu Gly Pro Val Gly His Ser Gly Lys Leu Phe Ser Gly Asp Glu Leu
385                 390                 395                 400
Leu Glu Val Asn Gly Ile Thr Leu Leu Gly Glu Asn His Gln Asp Val
                405                 410                 415
Val Asn Ile Leu Lys Glu Leu Pro Ile Glu Val Thr Met Val Cys Cys
            420                 425                 430
Arg Arg Thr Val Pro Pro Thr Thr Gln Ser Glu Leu Asp Ser Leu Asp
            435                 440                 445
Leu Cys Asp Ile Glu Leu Thr Glu Lys Pro His Val Asp Leu Gly Glu
    450                 455                 460
Phe Ile Gly Ser Ser Glu Pro Glu Asp Pro Val Leu Ala Met Thr Asp
465                 470                 475                 480
Ala Gly Gln Ser Thr Glu Val Gln Ala Pro Leu Ala Met Trp Glu
                485                 490                 495
Ala Gly Ile Gln His Ile Met Leu Glu Lys Gly Ser Lys Gly Leu Gly
            500                 505                 510
Phe Ser Ile Leu Asp Tyr Gln Asp Pro Ile Asp Pro Ala Ser Thr Val
        515                 520                 525
Ile Ile Ile Arg Ser Leu Val Pro Gly Gly Ile Ala Glu Lys Asp Gly
    530                 535                 540
Arg Leu Leu Pro Gly Asp Arg Leu Met Phe Val Asn Asp Val Asn Leu
545                 550                 555                 560
Glu Asn Ser Ser Leu Glu Glu Ala Val Glu Ala Leu Lys Gly Ala Pro
                565                 570                 575
Ser Gly Thr Val Arg Ile Gly Val Ala Lys Pro Leu Pro Leu
            580                 585                 590
```

-continued

<210> SEQ ID NO 90
<211> LENGTH: 235
<212> TYPE: PRT
<213> ORGANISM: Homo sapiens

<400> SEQUENCE: 90

```
Met Leu Glu Ala Ile Asp Lys Asn Arg Ala Leu His Ala Ala Glu Arg
  1               5                  10                  15

Leu Gln Thr Lys Leu Arg Glu Arg Gly Asp Val Ala Asn Glu Asp Lys
             20                  25                  30

Leu Ser Leu Leu Lys Ser Val Leu Gln Ser Pro Leu Phe Ser Gln Ile
         35                  40                  45

Leu Ser Leu Gln Thr Ser Val Gln Gln Leu Lys Asp Gln Val Asn Ile
     50                  55                  60

Ala Thr Ser Ala Thr Ser Asn Ile Glu Tyr Ala His Val Pro His Leu
 65                  70                  75                  80

Ser Pro Ala Val Ile Pro Thr Leu Gln Asn Glu Ser Phe Leu Leu Ser
                 85                  90                  95

Pro Asn Gly Asn Leu Glu Ala Leu Thr Gly Pro Gly Ile Pro His
            100                 105                 110

Ile Asn Gly Lys Pro Ala Cys Asp Glu Phe Asp Gln Leu Ile Lys Asn
        115                 120                 125

Met Ala Gln Gly Arg His Val Glu Val Phe Glu Leu Leu Lys Pro Pro
    130                 135                 140

Ser Gly Gly Leu Gly Phe Ser Val Val Gly Leu Arg Ser Glu Asn Arg
145                 150                 155                 160

Gly Glu Leu Gly Ile Phe Val Gln Glu Ile Gln Glu Gly Ser Val Ala
                165                 170                 175

His Arg Asp Gly Arg Leu Lys Glu Thr Asp Gln Ile Leu Ala Ile Asn
            180                 185                 190

Gly Gln Ala Leu Asp Gln Thr Ile Thr His Gln Gln Ala Ile Ser Ile
        195                 200                 205

Leu Gln Lys Ala Lys Asp Thr Val Gln Leu Val Ile Ala Arg Gly Ser
    210                 215                 220

Leu Pro Gln Leu Val Ser Pro Ile Val Ser Arg
225                 230                 235
```

<210> SEQ ID NO 91
<211> LENGTH: 251
<212> TYPE: PRT
<213> ORGANISM: Homo sapiens

<400> SEQUENCE: 91

```
Pro Ser Val Leu Pro Asp Ser Ala Gly Lys Gly Ser Glu Tyr Leu Leu
  1               5                  10                  15

Glu Gln Ser Ser Leu Ala Cys Asn Ala Glu Cys Val Met Leu Gln Asn
             20                  25                  30

Val Ser Lys Glu Ser Phe Glu Arg Thr Ile Asn Ile Ala Lys Gly Asn
         35                  40                  45

Ser Ser Leu Gly Met Thr Val Ser Ala Asn Lys Asp Gly Leu Gly Met
     50                  55                  60

Ile Val Arg Ser Ile Ile His Gly Gly Ala Ile Ser Arg Asp Gly Arg
 65                  70                  75                  80

Ile Ala Ile Gly Asp Cys Ile Leu Ser Ile Asn Glu Glu Ser Thr Ile
                 85                  90                  95

Ser Val Thr Asn Ala Gln Ala Arg Ala Met Leu Arg Arg His Ser Leu
```

```
            100                 105                 110
Ile Gly Pro Asp Ile Lys Ile Thr Tyr Val Pro Ala Glu His Leu Glu
        115                 120                 125

Glu Phe Lys Ile Ser Leu Gly Gln Gln Ser Gly Arg Val Met Ala Leu
    130                 135                 140

Asp Ile Phe Ser Ser Tyr Thr Gly Arg Asp Ile Pro Glu Leu Pro Glu
145                 150                 155                 160

Arg Glu Glu Gly Glu Gly Glu Ser Glu Leu Gln Asn Thr Ala Tyr
                165                 170                 175

Ser Asn Trp Asn Gln Pro Arg Arg Val Glu Leu Trp Arg Glu Pro Ser
            180                 185                 190

Lys Ser Leu Gly Ile Ser Ile Val Gly Gly Arg Gly Met Gly Ser Arg
        195                 200                 205

Leu Ser Asn Gly Glu Val Met Arg Gly Ile Phe Ile Lys His Val Leu
    210                 215                 220

Glu Asp Ser Pro Ala Gly Lys Asn Gly Thr Leu Lys Pro Gly Asp Arg
225                 230                 235                 240

Ile Val Glu Ala Pro Ser Gln Ser Glu Ser Glu
                245                 250

<210> SEQ ID NO 92
<211> LENGTH: 272
<212> TYPE: PRT
<213> ORGANISM: Homo sapiens

<400> SEQUENCE: 92

Pro Ser Val Leu Pro Asp Ser Ala Gly Lys Gly Ser Glu Tyr Leu Leu
  1               5                  10                  15

Glu Gln Ser Ser Leu Ala Cys Asn Ala Glu Cys Val Met Leu Gln Asn
            20                  25                  30

Val Ser Lys Glu Ser Phe Glu Arg Thr Ile Asn Ile Ala Lys Gly Asn
        35                  40                  45

Ser Ser Leu Gly Met Thr Val Ser Ala Asn Lys Asp Gly Leu Gly Met
    50                  55                  60

Ile Val Arg Ser Ile Ile His Gly Gly Ala Ile Ser Arg Asp Gly Arg
65                  70                  75                  80

Ile Ala Ile Gly Asp Cys Ile Leu Ser Ile Asn Glu Glu Ser Thr Ile
                85                  90                  95

Ser Val Thr Asn Ala Gln Ala Arg Ala Met Leu Arg Arg His Ser Leu
            100                 105                 110

Ile Gly Pro Asp Ile Lys Ile Thr Tyr Val Pro Ala Glu His Leu Glu
        115                 120                 125

Glu Phe Lys Ile Ser Leu Gly Gln Gln Ser Gly Arg Val Met Ala Leu
    130                 135                 140

Asp Ile Phe Ser Ser Tyr Thr Gly Arg Asp Ile Pro Glu Leu Pro Glu
145                 150                 155                 160

Arg Glu Glu Gly Glu Gly Glu Ser Glu Leu Gln Asn Thr Ala Tyr
                165                 170                 175

Ser Asn Trp Asn Gln Pro Arg Arg Val Glu Leu Trp Arg Glu Pro Ser
            180                 185                 190

Lys Ser Leu Gly Ile Ser Ile Val Gly Gly Arg Gly Met Gly Ser Arg
        195                 200                 205

Leu Ser Asn Gly Glu Val Met Arg Gly Ile Phe Ile Lys His Val Leu
    210                 215                 220
```

```
Glu Asp Ser Pro Ala Gly Lys Asn Gly Thr Leu Lys Pro Gly Asp Arg
225                 230                 235                 240

Ile Val Glu Val Asp Gly Met Asp Leu Arg Asp Ala Ser His Glu Gln
                245                 250                 255

Ala Val Glu Ala Ile Arg Lys Ala Gly Asn Pro Val Val Phe Met Val
            260                 265                 270

<210> SEQ ID NO 93
<211> LENGTH: 321
<212> TYPE: PRT
<213> ORGANISM: Homo sapiens

<400> SEQUENCE: 93

Pro Ser Val Leu Pro Asp Ser Ala Gly Lys Gly Ser Glu Tyr Leu Leu
1               5                   10                  15

Glu Gln Ser Ser Leu Ala Cys Asn Ala Glu Cys Val Met Leu Gln Asn
                20                  25                  30

Val Ser Lys Glu Ser Phe Glu Arg Thr Ile Asn Ile Ala Lys Gly Asn
            35                  40                  45

Ser Ser Leu Gly Met Thr Val Ser Ala Asn Lys Asp Gly Leu Gly Met
50                  55                  60

Ile Val Arg Ser Ile Ile His Gly Gly Ala Ile Ser Arg Asp Gly Arg
65                  70                  75                  80

Ile Ala Ile Gly Asp Cys Ile Leu Ser Ile Asn Glu Glu Ser Thr Ile
                85                  90                  95

Ser Val Thr Asn Ala Gln Ala Arg Ala Met Leu Arg Arg His Ser Leu
                100                 105                 110

Ile Gly Pro Asp Ile Lys Ile Thr Tyr Val Pro Ala Glu His Leu Glu
            115                 120                 125

Glu Phe Lys Ile Ser Leu Gly Gln Gln Ser Gly Arg Val Met Ala Leu
130                 135                 140

Asp Ile Phe Ser Ser Tyr Thr Gly Arg Asp Ile Pro Glu Leu Pro Glu
145                 150                 155                 160

Arg Glu Glu Gly Glu Gly Glu Ser Glu Leu Gln Asn Thr Ala Tyr
                165                 170                 175

Ser Asn Trp Asn Gln Pro Arg Arg Val Glu Leu Trp Arg Glu Pro Ser
            180                 185                 190

Lys Ser Leu Gly Ile Ser Ile Val Gly Gly Arg Gly Met Gly Ser Arg
            195                 200                 205

Leu Ser Asn Gly Glu Val Met Arg Gly Ile Phe Ile Lys His Val Leu
210                 215                 220

Glu Asp Ser Pro Ala Gly Lys Asn Gly Thr Leu Lys Pro Gly Asp Arg
225                 230                 235                 240

Ile Val Glu Val Asp Gly Met Asp Leu Arg Asp Ala Ser His Glu Gln
                245                 250                 255

Ala Val Glu Ala Ile Arg Lys Ala Gly Asn Pro Val Val Phe Met Val
            260                 265                 270

Gln Ser Ile Ile Asn Arg Pro Arg Lys Ser Pro Leu Pro Ser Leu Leu
            275                 280                 285

His Asn Leu Tyr Pro Lys Tyr Asn Phe Ser Ser Thr Asn Pro Phe Ala
        290                 295                 300

Asp Ser Leu Gln Ile Asn Ala Asp Lys Ala Pro Ser Gln Ser Glu Ser
305                 310                 315                 320

Glu
```

PROTEIN HAVING PDZ DOMAIN SEQUENCE

This is a continuation-in-part of PCT/JP98/03603 filed Aug. 12, 1998, and claims priority from Japanese Patent Application Nos. 9/230356, filed Aug. 12, 1997, and Ser. No. 10/189,944, filed Jun. 18, 1998.

TECHNICAL FIELD

The present invention relates to novel proteins having the PDZ domain sequence and also to gene encoding the proteins.

BACKGROUND ART

Proteins such as PSD-95, hDlg, ZO-1, p55, Dsh, LIN-7, InaD, and PTPL1/FAP1 are known to possess the PDZ domain and are called the PDZ family. A structure having approximately 80 to 90 amino acid residues, repeated three times and each containing a conserved "Gly-Leu-Gly-Phe (GLGF)" 4 amino acid motif (Neuron 9:929–942 (1992)), was initially identified in the 95 KDa post-synaptic density protein, PSD-95. The same domain structure was later found in the *Drosophila* lethal (1) discs large-1 tumor suppressor protein, DlgA (Cell 66:451–464 (1991)), and in the tight junction protein, ZO-1 (J. Cell Biol. 121:491–502 (1993)). The repeat sequence was therefore named the "PDZ domain" by combining the initials of PSD-95, DlgA, and ZO-1. (It is also called the "GLGF repeat" or "DHR (DlgA homology region) domain.") A protein having the PDZ domain is known to bind to other proteins by means of the sequence of this PDZ domain. For example, the PSD-95 protein is known to bind to the NMDA receptor 2B (Kornau, H. C., et al., Science 269:1737–1740 (1995)) and the Shaker-type $K^+$ channel (Kim, E., et al., Nature 378:85–88 (1995)). The hDlg protein has been reported to bind directly to the protein encoded by the adenomatous polyposis coli tumor suppressor gene/APC (Matsumine et al., Science 272:1020–1023 (1996)), and the Dsh protein has been reported to bind directly to the Notch protein (Axelrod, J. D., et al., Science 271:1826–1832 (1996)). Furthermore, the InaD protein has been reported to bind to a $Ca^{2+}$ channel protein, TRP, that functions in the *Drosophila* visual signal transduction cascade (Shieh, B. H. and Zhu, M. Y., Neuron 16:991–998 (1996)). The structure of proteins having the PDZ domain varies because some of the proteins contain only one domain (p55 and Dsh), while others contain two (SIP-1: Yanagisawa, J., et al., J. Biol. Chem. 272:7167–7172 (1997)), three (PSD-95 and hDlg), five (InaD and PTPL1/FAP1), seven (GRIP: Dong, H., et al., Nature 386:279–284 (1997)), or thirteen (Ullmer, C., et al., FEBS Letters 424: 63–68 (1998)). Also a recently reported mouse gene lacks a region encoding an N-terminal peptide of the protein, but which encodes a peptide having four PDZ domains within this incomplete genetic region (Recorded to GenBank on May 18, 1997; accession number AF000168). Although there are a few exceptions, proteins having the PDZ domain are known to bind to other proteins that have a hydrophobic amino acid region consisting of three amino acids represented by "Thr/Ser-Xaa-Val" (Xaa being an arbitrary amino acid residue) at their C-terminus. Most of these proteins are transmembrane proteins and are presumed to function in signal transduction within the cell (TIBS 21:455–458 (1996), Yanagisawa, J., et al., J. Biol. Chem. 272:7167–7172 (1997)).

Since the above proteins having the PDZ domain and proteins that interact with these proteins are involved in neural transmission, apoptosis, and malignant conversion, they have recently drawn attention as targets for developing pharmaceuticals.

DISCLOSURE OF THE INVENTION

An objective of the present invention is to provide a novel protein having the PDZ domain sequence and a DNA encoding the protein. Another objective of the present invention is to provide a vector containing the DNA, a transformant harboring the DNA in which the DNA can be expressed, and a method of producing the recombinant protein utilizing the transformant. A further objective of the present invention is to provide an antisense DNA against the DNA and antibody that binds to the protein. Still another objective of the present invention is to provide a screening method for proteins that bind to the PDZ-domain protein.

While analyzing the changes of gene expression in human umbilical vascular endothelial cells by TNFα, the present inventors isolated a gene whose expression was increased by TNFα stimulation. Screening was performed using the gene as a probe, and, as a result, a gene encoding novel proteins was isolated. The present inventors analyzed the structure of the proteins encoded by the isolated gene and found that the proteins contain within the molecule the PDZ domain sequence that plays an important role in the interactions with other proteins involved in neural transmission, apoptosis, and malignant conversion. The present inventors also found that the single gene produces at least five different transcriptional products through the differences in transcription initiation sites and in splicing.

The present inventors succeeded in preparing the proteins encoded by the gene as recombinant proteins by incorporating the isolated gene into an expression vector, and by transfecting it into *E. coli* cells and culturing the cells. In addition, by immunizing rabbits with the proteins thus prepared, the present inventors succeeded in preparing antibodies that bind to the proteins.

The present invention relates to a group of novel proteins having the PDZ domain sequence within the molecule and to their gene, and more specifically, to (1) a protein comprising the amino acid sequence described in SEQ ID NOs: 1, 2, 82, 83, or 84;

(2) a protein comprising the amino acid sequence described in SEQ ID NOs: 1, 2, 82, 83, or 84, in which one or more amino acids have been substituted, deleted, and/or added, and having affinities to other proteins characteristic to the PDZ domain;

(3) a fusion protein comprising the protein described in (1) or (2) and a protein or a peptide containing at least one antibody recognition site;

(4) a DNA encoding the protein of any one of (1) through (3);

(5) an antisense DNA against the DNA or a part thereof whose nucleotide sequence is described in SEQ ID NO: 2;

(6) a vector containing the DNA of (4);

(7) a transformant harboring the DNA of (4), in which the DNA can be expressed;

(8) a method of producing the protein of any one of (1) through (3), comprising the process of culturing the transformants described in (7);

(9) a screening method for proteins that bind to the protein of (1) or (2), comprising the process of selecting the proteins that bind to the proteins by contacting sample proteins with the proteins of any one of (1) through (3);

(10) a screening method for genes encoding the proteins that bind to the proteins of (1) or (2), comprising the process of selecting the genes corresponding to the gene products that bind to the proteins of (1) or (2) by contacting the gene products of the sample genes with the protein of (1) or (2);

(11) a protein that binds to the protein of (1) or (2);

(12) the protein of (11) that can be isolated by the method of (9);

(13) a gene encoding a protein that bind to the protein of (1) or (2);

(14) the gene of (13) that can be isolated by the method of (10); and

(15) an antibody that bind to the protein of (1) or (2).

In the present invention, the "PDZ domain sequence" refers to a sequence having 80 to 90 amino acids, containing the four amino acid motif that consists of "Gly-Leu-Gly-Phe" or similar amino acids (cf. TIBS 20:102–103 (1995)).

The present invention relates to novel proteins having the PDZ domain sequence. Although there are a few exceptions, proteins having the PDZ domain are known to interact with other proteins that have a hydrophobic amino acid region at their C-terminal ends. The other proteins are transmembrane proteins and are presumed to function in signal transduction within the cell (TIBS 21: 455–458 (1996), Yanagisawa, J., et al., J. Biol. Chem. 272:7167–7172 (1997)).

The present inventors have discovered five different transcription products among those that encode proteins having the PDZ domain. These products are thought to arise from a single gene through differences in transcription initiation sites and in splicing. The amino acid sequences of the proteins encoded by these transcription products are shown in SEQ ID NOs: 1, 2, 82, 83, and 84.

The protein having the amino acid sequence described in SEQ ID NO: 1, which is included in the proteins of the present invention, possesses nine PDZ domains that correspond to amino acid positions 69 to 158 (SEQ ID NO: 4), positions 371 to 461 (SEQ ID NO: 5), positions 520 to 615 (SEQ ID NO: 6), positions 649 to 734 (SEQ ID NO: 7), positions 782 to 865 (SEQ ID NO: 8), positions 928 to 1013 (SEQ ID NO: 9), positions 1024 to 1108 (SEQ ID NO: 10), positions 1161 to 1249 (SEQ ID NO: 11), and positions 1286 to 1373 (SEQ ID NO: 12)(see FIG. 8).

Similarly, the protein having the amino acid sequence described in SEQ ID NO: 2, which is also included in the proteins of the present invention, corresponds to amino acids 369 to 1373 of the sequence described in SEQ ID NO: 1. The difference between the structures of these proteins is considered to arise from the difference in the mRNA transcription initiation sites.

The protein described in SEQ ID NO: 2 possesses a total of eight PDZ domain sequences, corresponding to amino acids 3 to 93, 152 to 247, 281 to 366, 414 to 497, 560 to 645, 656 to 740, 793 to 881, and 918 to 1005. However, it does not possess the first PDZ domain found in the protein described in SEQ ID NO: 1. Although its biological significance is not clear, considering the specific expression of the mRNA corresponding to the protein described in SEQ ID NO: 2 in the liver (Example 5) and the fact that the PDZ domain plays an important role in protein—protein interactions, the protein described in SEQ ID NO: 2, by lacking this domain, may be involved in controlling the signal in the liver differently from the other tissues.

The protein having the amino acid sequence described in SEQ ID NO: 82 (the 32-8-1a protein), which is also included in the proteins of the present invention, consists of 2,000 amino acids. These amino acids are predicted by combining sequences of two cDNAs. One cDNA was discovered in the search for a cDNA derived from the human brain and contains a 5' upstream region of a cDNA encoding a protein having the amino acid sequence described in SEQ ID NO: 1. The other cDNA (SEQ ID NO: 3) encodes the protein having the amino acid sequence described in SEQ ID NO: 1. The 32-8-1a protein possesses a total of 13 PDZ domain sequences, corresponding to amino acids 133 to 222, 253 to 335, 373 to 461, 549 to 632, 696 to 784, 1004 to 1087, 1147 to 1240, 1276 to 1361, 1409 to 1492, 1555 to 1640, 1651 to 1735, 1788 to 1870, and 1913 to 2000 (FIG. 25).

Similarly, the amino acid sequences of the proteins encoded by the two splicing variants that are thought to result from the different splicing from the transcription product encoding the 32-8-1a protein and are also included in the proteins of the present invention, are shown in SEQ ID NO: 83 (the 32-8-1b protein) and in SEQ ID NO: 84 (the 32-8-1c protein). The 32-8-1b protein, similar to the 32-8-1a protein, consists of 2,070 amino acids, possessing 13 PDZ domains. The PDZ domains of the 32-8-1b protein exist at positions 133 to 222, 253 to 335, 373 to 461, 549 to 632, 696 to 784, 1004 to 1087, 1147 to 1241, 1346 to 1431, 1479 to 1562, 1625 to 1710, 1721 to 1805, 1858 to 1946, and 1983 to 2070 of its amino acid sequence.

In contrast, the 32-8-1c protein has a shorter chain length than 32-8-1a or 32-8-1b because of the termination codon created by the splicing, and consists of 1,239 amino acids, possessing seven PDZ domains. The PDZ domains of the 32-8-1c protein exist at positions 133 to 222, 253 to 335, 373 to 461, 549 to 632, 696 to 784, 1004 to 1087, and 1147 to 1239 of its amino acid sequence.

It is clinically very significant that these proteins of the present invention are all of human origin, as opposed to being derived from other animals. In particular, proteins derived from other organisms (e.g., mice or rats) cause serious side effects such as reduction or loss of therapeutic effects by generating antibodies or by inducing serum sickness and anaphylactic shock, due to the immunogenicity when they are used to treat humans. Therefore, it is desirable to use proteins of human origin as therapeutic materials for humans.

The proteins of the present invention can be prepared from natural proteins, but they can also be prepared as recombinant proteins using recombinant genetics technology. The natural proteins can be isolated from such sources as the human umbilical vascular endothelial cells (HUVEC) by means of methods well-known to persons skilled in the art. For example, they can be isolated as described below, with an affinity column in which an antibody against the protein of the present invention has been bound to an appropriate support. The affinity column can be constructed, for example, according to the method described by Wilchek et al. (Wilchek et al., Methods Enzymol. 104:3–55 (1984)). Furthermore, the recombinant protein can be prepared by culturing the cells transformed with the DNA encoding the protein of the present invention, as will be described later.

The proteins of the present invention also include functional derivatives of the proteins having the amino acid sequences described in SEQ ID NOs: 1, 2, 82, 83, and 84. A "functional derivative" means a protein that differs from the amino acid sequences described in SEQ ID NOs: 1, 2, 82, 83, and 84 by one or more amino acid residues through substitution, deletion, or addition, but that still maintains the affinity to the other proteins characteristic of the PDZ domain. This affinity normally arises from the affinity to a hydrophobic amino acid region that exists in the C-terminal ends of the other proteins. The hydrophobic amino acid region contains a hydrophobic amino acid motif represented by "Thr/Ser-Xaa-Val" (Xaa being an arbitrary amino acid residue) (cf. Science 269:1737 (1995), Nature 378:85 (1995), Science 277:1511 (1997), Neuron 20:693 (1998), Oncogene 16:643 (1998), J. Biol. Chem. 273:1591 (1998), Science 272:1020 (1996), Proc. Natl. Acad. Sci. USA 94:6670 (1997), Proc. Natl. Acad. Sci. USA 94:11612 (1997), J. Neurosci. 18:128 (1998), J. Neurosci. 16:7407 (1996), Nature Biotech. 15:336 (1997), FEBS Letters 409: 53 (1997), Nature 386:284 (1997), Nature 386:279 (1997), Nature Structure Biol. 5:19 (1998), J. Neurosci. 16:24 (1996), J. Biol. Chem. 272:24191 (1997), Science 271:1826 (1996), TIBS 21:455 (1996), Cell 85:195 (1996), Neuron 18:95 (1997), Proc. Natl. Acad. Sci. USA 94:12682 (1997), J. Biol. Chem. 272:8539 (1997), J. Biol. Chem. 272:24333 (1997), J. Biol. Chem. 272:7167 (1997), Proc. Natl. Acad. Sci. USA 94:13683 (1997), Nature 392:6676 (1998), J. Biol. Chem. 272:32019 (1997), Mol. Biol. Cell 9:671 (1998)).

Functional derivatives occur naturally or can be produced artificially; both of these are included in the present invention. Methods to alter amino acids, which are well known to persons skilled in the art, include the methods developed by Kunkel et al. (Methods Enzymol. 85:2763–2766 (1988)) and those that utilize polymerase chain reaction (PCR). In the Kunkel method, uracil is incorporated by using dut⁻ or ung⁻ E. coli as a host when preparing the single-stranded DNA to be used as the template. Primers containing the desired mutations are annealed to this template containing uracil, and ordinary DNA synthesis is performed in vitro. When the double-stranded DNA thus produced with the uracil-containing DNA is introduced into ordinary E. coli cells, the uracil-containing DNA strand becomes degraded, and DNA synthesis proceeds with the mutated DNA strand as the template. As a result, DNA into which mutations have been introduced can be obtained with a very high efficiency. An example of the methods of introducing mutations using PCR follows. Two sets of primers are prepared. One of the primers in each set encompasses the region into which the mutation will be introduced, and the other contains a restriction enzyme recognition site or a sequence just outside of it. A region containing appropriate restriction enzyme sites is thus targeted. PCR reactions are then performed with the two sets of primers. After the products of the two PCR reactions are mixed, the DNA is amplified using primers having sequences corresponding to the recognition sites of the two restriction enzymes or the sequences just outside of them. The product is next digested with appropriate restriction enzymes so that the resultant fragment contains the region into which the mutation has been introduced. The fragment thus obtained is substituted for the said region in the original DNA (Saiki et al., Science 239:487–491 (1988), Current Protocols in Molecular Biology, Greene Publishing Associates and Wiley-Interscience Publishing, Unit 8.5.1–8.5.10 (1997), Supplement to Jikken Igaku (Experimental Medicine) "Shin Idenshi Kogaku Handbook (New Genetic Engineering Handbook)," Yohdosha, pp251–261). The desired number of amino acids to be substituted in a functional derivative is generally 10 or less, more preferably 6 or less, and still more preferably 3 or less.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The present invention also relates to the DNA encoding the proteins of the present invention described above. The DNA encoding the proteins of the present invention can be cDNA, genomic DNA, or synthetic DNA. The DNA of the present invention can be used, for example, to produce the proteins of the present invention as recombinant proteins. More specifically, the proteins of the present invention can be prepared as recombinant proteins by inserting the DNA encoding the proteins of the present invention into appropriate expression vectors, culturing the transformants obtained by introducing the said vectors into appropriate cells, and purifying the expressed proteins.

By hybridization under "stringent conditions" is meant hybridization at 37° C., 1× SSC, followed by washing at 42° C., 0.5× SSC.

The "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12. BLAST protein searches are performed with the XBLAST program, score=50, wordlength=3. Where gaps exist between two sequences, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See http://www.ncbi.nlm.nih.gov.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

The cells to be used for producing the recombinant proteins include, but are not limited to, animal cells such as Chinese hamster ovary (CHO) cells, COS cells (a cell line obtained by transforming monkey CV-1 fibroblasts by the SV40 virus lacking the replication origin), mouse NIH3T3 cells, human HeLa cells, and human lymphoid Namalva cells (Current Protocols in Molecular Biology, Greene Publishing Associates and Wiley-Interscience Publishing, Unit 16.12–16.14 (1991)). As the vectors, pSV2neo, pcDNAI, pCD8, pRcRSV, pREP4, pCEP4 (Invitrogen), PMAM, pMAMneo (Clontech), pCI-neo mammalian expression vector, pSI-neo mammalian expression vector, PTARGET™ mammalian expression vector (Promega), and the like can be used. Both plasmid vectors and recombinant viruses can be constructed for producing the recombinant protein. Recombinant adenoviruses using the pAdex vector (Supplement to Jikken Igaku (Experimental Medicine) "Shin Idenshi Kogaku Handbook (New Genetic Engineering Handbook)," Yohdosha, pp 238–244), the LN and LXSN vector series, the pBabe vector series (a modified version of the preceding series), recombinant retroviruses using such vectors as the MFG vectors (Supplement to Jikken Igaku (Experimental Medicine) "Shin Idenshi Kogaku Handbook (New Genetic Engineering Handbook)," Yohdosha, pp 245–250, Current Protocols in Molecular Biology, Greene Publishing Associates and Wiley-Interscience Publishing, Unit 9.10.1–9.14.3 (1992)), Sindbis viruses, and vaccinia viruses (Current Protocols in Molecular Biology, Greene Publishing Associates and Wiley-Interscience Publishing, Unit 16.15.1–16.19.9 (1992)) can also be used to produce the recombinant proteins. It is also possible to produce the recombinant proteins by utilizing baculoviruses, and silkworm larvae. Alternatively, cultured cell lines such as SF21, SF9, and High Five™ cells can be used as the host (Supplement to Jikken Igaku (Experimental Medicine) "Bio Manual Series 7: Bunshi Seibutsu Kenkyu No Tame No Tanpakushitsu Jikken Hou (Protein Experimentation Methods for Molecular Biology Research)," Yohdosha, pp167–171 (1994), OReilly, D. R. et al., "Baculovirus Expression Vectors, A Laboratory Manual," Oxford University Press (1992)). As the baculovirus expression vectors, pBacPAK8, 9, pBacPAK-His 1/2/3, pAcUW31 (Clontech), pBlueBac (Invitrogen), PBAC, pBACgus (Novagen), etc., can be used.

The promoters utilized to express the proteins efficiently in animal cells include, for example, the SV40 early promoter (Rigby In Williamson (ed.), Genetic Engineering, Vol. 3, Academic Press, London, pp 83–141 (1982)), the EF-1α promoter (Kim et al., Gene 91:217–223 (1990)), the CAG promoter (Niwa et al., Gene 108:193–200 (1991)), the RSV LTR promoter (Cullen, Methods in Enzymology 152:684–704 (1987)), the SRa promoter (Takabe et al., Mol. Cell. Biol. 8:466 (1988)), the CMV early promoter (Seed and Aruffo, Proc. Natl. Acad. Sci. USA 84:3365–3369 (1987)), the SV40 late promoter (Gheysen and Fiers, J. Mol. Appl. Genet. 1:385–394 (1982)), the Adenovirus late promoter (Kaufman et al., Mol. Cell. Biol. 9:946 (1989)), the HSV TK promoter, and inducible expression promoters. The MMTV promoter induced by glucocorticoids, the MT (metallothionein) II promoter induced by phorbol esters or heavy metals, the Tet-On/Off system that can be turned on and off by tetracycline (Clontech), the expression system that can be induced by ecdysone (Invitrogen), and the Lac Switch expression system induced by IPTG are preferred examples of the inducible expression promoters.

It is also possible to use yeast cells to produce the proteins. Protease-deficient cell lines such as BJ2168, BJ926, and CB023, and cell lines for secretion vectors, such as 20B-12, can be used as hosts (Supplement to Jikken Igaku (Experimental Medicine) "Bio Manual Series 4: Idenshi Donyu To Hatsugen Kaisekihou (Gene Introduction and Expression Analysis Methods)," Yohdosha, pp166–176 (1994)). The expression vectors include pYEUra3 (Clontech), pYEX™-BX, and pYEX™-S1. It is also possible to express the protein in fission yeast SP-Q01, using fission yeast expression vector pESP-1 (Stratagene). The PGK promoter and the ADH1 promoter, which are constitutive; the CUP1 promoter, which is inducible by copper ions; the Gal1–Gal10 promoter, which is induced by galactose and repressed by glucose; and the PHO5 promoter, which is induced by a reduction in phosphate concentrations and repressed by high phosphate concentrations are preferable as promoters that efficiently express the protein in the yeast cells. In fission yeast, promoters such as the nmt1 promoter are preferable.

Four broad categories of expression promoters can be used to produce recombinant proteins using *E. coli* cells. The λPL promoter is regulated by the clts857 repressor and is induced by heat shock. N4830-1 and M5219 can be used as the host, and vectors such as pPL-lambda, pKC30, and pRIT2T can be used for expression. The tac promoter is regulated by the lacI$^q$ repressor and is induced by adding isopropyl β-D-thiogalactoside (IPTG). JM105 and XL1-Blue can be used as the host, and vectors such as pDR540, pKK233-3, pGEX-3×, and pMAL-c2 can be used for expression. The trp promoter is regulated by the trp repressor and is induced by adding β indole acrylic acid (IAA). HB101 and the like can be used as the host; vectors such as pBTrp2 can be used for expression. The T7 phage promoter is recognized for expression by only the T7RNA polymerase. Therefore, the BL21(DE3) strain can be used as the host. This strain can be prepared by lysogenizing the *E. coli* BL21 strain with X phage DE3, into which the lacI gene and a DNA fragment containing the T7RNA polymerase gene under the control of the lacUV5 promoter are inserted within its int gene. The inducible expression directed by the T7 promoter becomes possible by adding IPTG, which induces the T7RNA polymerase. The vectors include pET-3c and pET-8c. BL21(DE3)pLysS contains, in addition to the above plasmid, a plasmid producing the T7 lysozyme. This lysozyme is a natural inhibitor that binds to the T7RNA polymerase and inhibits its transcription, in order to suppress the basal level T7RNA polymerase activity. Therefore, BL21(DE3)pLysS can also be used as the host. pET-11c, pET-11d, and the like, which possess the T7lac promoter with the lac operator sequence inserted downstream of the T7 promoter transcription initiation site, can also be used as the expression vector (Studier, F., et al., J. Mol. Biol. 189:113–130 (1996), Studier, F., et al., Methods Enzymol. 185:60–8 (1990)).

Methods of introducing the vector into the host include the electroporation method (Chu, G., et al., Nucl. Acids Res. 15:1311–1326 (1987)), the calcium phosphate method (Chen, C. and Okayama, H., Mol. Cell. Biol. 7:2745–2752 (1987)), the DEAE dextran method (Lopata, M. A., et al., Nucl. Acids Res. 12:5707–5717 (1984); Sussman, D. J. and Milman, G., Mol. Cell. Biol. 4:1642–1643 (1985)), and the lipofectin method (Derijard, B., Cell 7:1025–1037 (1994); Lamb, B. T., et al., Nature Genetics 5:22–30 (1993); Rabindran, S. K., et al., Science 259:230–234 (1993)), but any method can be used.

The recombinant protein can be purified from the transformant thus obtained by means of the gel filtration method, ion exchange chromatography, affinity chromatography, reverse phase chromatography, hydroxyapatite chromatography, hydrogen bonding chromatography, and chelating columns (Deutscher, M. P., ed., Methods Enzymol. 182, Guide to Protein Purification, 1990; Principles and Methods Series: Gel Filtration, Ion Exchange chromatography, and Affinity chromatography. Pharmacia). Antibodies against the protein of the present invention are prepared as described below, and the protein can be highly purified by means of affinity chromatography using the antibodies.

Persons skilled in the art can, by using the prepared protein of the present invention, easily prepare the antibodies that bind to it. The antibodies of the present invention can be obtained by expressing the gene of the present invention using an appropriate $E.$ $coli$ expression vector; purifying the product; and immunizing rabbits, mice, rats, goats, or chickens with it. It is also possible to synthesize peptides that correspond to appropriate regions of the protein encoded by the gene of the present invention, and to immunize the animals described above, thereby obtaining the antibodies to the gene product. Methods to establish mouse or rat hybridomas can be used to produce monoclonal antibodies (Kohler and Milstein, Nature 256:495–497 (1975)). Specifically, mice, rats, or Armenian hamsters are first immunized with the prepared protein of the present invention. The antibody-producing cells are then collected from the spleen or the lymph nodes and fused in vitro with myeloma cells, and clones are selected through screening using the antigen (Harlow, E. and Lane, D., Antibodies: A Laboratory Manual. Cold Spring Harbor Laboratory, Cold Spring Harbor, N.Y. (1988)). The mouse myeloma cells include p3-x63-Ag8-U1 (P3-U1), P3-NSI/1-Ag4-1 (NS-1), and SP2/0-Ag14 (AP2/0), and the rat myeloma cells include YB2/3HL.P2G11.16Ag20 (YB2/0). The cells can be fused using polyethylene glycol or electric pulses. Monoclonal antibodies, such as that contained in the cultured supernatant of the hybridomas and that contained in the ascites of the mouse treated with an immunosuppressant and with the mass-cultured hybridoma injected into its abdominal cavity, can be purified by, for example, protein A-Sepharose (Pharmacia). Furthermore, monoclonal antibodies can also be purified using an affinity column having the protein of the present invention immobilized onto the support (Harlow, E. and Lane, D., Antibodies: A Laboratory Manual. Cold Spring Harbor Laboratory, Cold Spring Harbor, N.Y. (1988)).

When the antibodies thus obtained are administered to humans, it is beneficial to use a human or humanized antibody in order to reduce the immunogenicity. The methods to humanize antibodies include the CDR graft method, in which the antibody gene is cloned from the monoclonal antibody producing cells and the antigen determining region is transplanted to a known human antibody (Immunology Methods Manual 1: pp 98–107, Academic Press). Human antibodies can also be produced by immunizing a mouse that has its immune system replaced with the human immune system, following a procedure similar to the one used with regular monoclonal antibodies. The human B cell hybridoma method (Kozbor, et al., Immunology Today 4:72 (1983)), and the Epstein-Barr virus (EBV)-Hybridoma method (Cole, et al. in Monoclonal Antibodies and Cancer Therapy, Ala R. Liss, Inc. pp 77–96 (1985)) can also be used to produce monoclonal antibodies.

The antibodies thus obtained can be used not only to detect the proteins of the present invention and as antibody therapies, but also to screen the proteins described below that interact with the proteins of the present invention.

The present invention also relates to the methods used to screen for the proteins that bind to the proteins of the present invention. The group of proteins having the PDZ domain, such as those of the present invention, share a common property of interacting with other proteins having the region of hydrophobic amino acids on the C-terminus. These and other binding proteins can be isolated by the screening methods of the present invention. These screening methods include the process to select the proteins that bind to the proteins of the present invention. In such a process, the sample proteins are brought into contact with the proteins of the present invention in the form of lysates from the cells or tissues that are expected to contain the target proteins.

An example of the specific methods is the immunoprecipitation method. The immunoprecipitation method is the most common method used to detect protein—protein binding. In immunoprecipitation, biological samples, such as lysates from cells or tissues, for example, cell lysates prepared by dissolving cells such as human umbilical vascular endothelial cells with Triton X-100 or sodium deoxycholate, are usually brought into contact with the proteins of the present invention. The antibodies are then applied to the complex thus formed between the proteins of the present invention with their binding proteins. The immune complexes thus formed are then precipitated (Supplement to Jikken Igaku (Experimental Medicine) "Shin Idenshi Kogaku Handbook (New Genetic Engineering Handbook)," Yohdosha, pp 304–308 (1996)).

The immune complex can be precipitated by, for example, using protein A-Sepharose or protein G-Sepharose when the antibody is a mouse IgG antibody. General methods can be found, for example, in "Antibodies" (Harlow, E. and Lane, D., Antibodies. pp 511–552, Cold Spring Harbor Laboratory Publications, New York (1988)). Moreover, methods based on those described above can generally be used even in the case of antibodies from other animal species.

The proteins of the present invention, which are used in the immunoprecipitation, can have a recognition site (epitope) for the monoclonal antibody, whose specificity has been well characterized, that is introduced into the N-terminus or the C-terminus of the proteins. The proteins have thus been made into fusion proteins with the epitope, and the immune complexes can be formed by reacting the antibody to the epitope.

A variety of epitope-antibody systems are commercially available, and these can also be used (Jikken Igaku (Experimental Medicine) 13:85–90 (1995)). Some commercially available vectors can express relatively large fusion proteins, such as those with β-galactosidase, maltose-binding protein, glutathione S-transferase, and Green fluorescent protein, by incorporating the DNA encoding the desired protein through multi-cloning sites. In order to minimize the changes in the properties of the desired protein due to fusing, methods have been reported in which only a small epitope portion having several to a dozen or so amino acids is inserted. For example, the epitopes in poly-histidine (His-tag), influenza hemagglutinin HA, human c-myc, FLAG, vesicular stomatitis virus glycoprotein (VSV-GP), T7 gene 10 protein (T7-tag), human herpes simplex virus glycoprotein (HSV-tag), E-tag (an epitope on a monoclonal phage), etc., and their corresponding antibodies that recognize the epitopes can be used (Jikken Igaku 13: 85–90 (1995)). Any other epitope-antibody system can be used, as long as it can detect the fusion protein. It should be noted that the fusion proteins that bind to the proteins of the present invention can be isolated by means of affinity chromatography, without using antibodies. For example, the glutathione-Sepharose 4B column can be used for a GST-fusion protein.

SDS-PAGE is generally used to analyze the immunoprecipitated proteins. In this method, gel of an appropriate concentration is used according to the molecular weights of the proteins so that the bound proteins can be analyzed. It is generally difficult to detect the bound proteins with ordinary staining methods for proteins (e.g., the Coomassie Brilliant Blue (CBB) staining method or the silver staining method). However, the cells can be cultured in a medium to which $^{35}$S-methionine or $^{35}$S-cysteine has been added to label the proteins, in order to increase the detection sensitivity. Once the molecular weight of a protein becomes known, it is possible to purify the protein directly from the SDS-polyacrylamide gel and to determine its sequence. In addition to the immunoprecipitation method described above, it is also possible to prepare the proteins by running the culture supernatant or the cellular extracts of the cells expected to express the proteins that bind to the proteins of the present invention through an affinity column having the proteins of the present invention immobilized onto it, then purifying the proteins that specifically bound to the column.

It is also possible to directly screen for the genes encoding the proteins that bind by using the proteins of the present invention. In this screening method, the gene products of the sample genes are brought into contact with the proteins of the present invention, thereby selecting the genes corresponding to the gene products that bind to the proteins of the present invention. There are no restrictions on the sample genes, but cDNA libraries prepared from the cells expected to express the proteins that bind to the proteins of the present invention are preferable. A specific example of the method utilizes the yeast 2 hybrid system (Fields, S. and Song, O., Nature 340:245–247 (1989)). Namely, one can express the proteins of the present invention within the yeast cells by fusing them with the SRF binding region, GAL4 binding region, or LexA binding region. One can then introduce the cDNA libraries prepared from the cells expected to express the proteins that bind to the proteins of the present invention into the above yeast cells so that the proteins are expressed in a form fused with the VP16, GAL4 transcription activation domain, or the *E. Coli* B42 peptide. Finally, one can isolate the library-derived cDNA from the positive clones. (When a protein that binds to the protein of the present invention is expressed within the yeast cell, the binding between these proteins activates the reporter gene, enabling the detection of the positive clone.)

The vectors and expression libraries to be used in this system can be purchased from several sources (Clontech, MATCHMAKER Two-Hybrid System; Stratagene, HybriZAP II Two-Hybrid System). For the specific method, one can follow the manufacturer's manual. The genes encoding the proteins that bind to the proteins of the present invention can be obtained directly by this method. In fact, the bindings between APC and hDLG (Matsumine, A., et al., Science 272:1020–1023 (1996)), between GRIP and the AMPA receptor (Dong, H., et al., Nature 386:279–284 (1997)), between Homer and the glutamate receptor (Brakeman, P. R., et al., Nature 386:284–288 (1997)), and between SRY and SIP-1 (Poulat, F., et al. J. Biol. Chem. 272: 7167–7172 (1997)) were confirmed and the target proteins of the proteins having the PDZ domain were identified using this yeast 2 hybrid system.

It is also possible to screen the proteins by the "west-western blotting method" (Skolnik, E. Y., Margolis, B., Mohammadi, M., Lowenstein, E., Fischer, R., Drepps, A., Ullrich, A., and Schlessinger, J., Cloning of PI3 kinase-associated p85 utilizing a novel method for expression/cloning of target proteins for receptor tyrosine kinases. Cell 65:83–90 (1991)). In this method, a cDNA library is prepared using a phage vector (such as λgt11 and ZAP) from the cells expected to express the proteins that bind to the proteins of the present invention (e.g., human umbilical vascular endothelial cells). The protein is then expressed on an LB-agarose, and the expressed proteins are fixed onto a filter with which the protein of the present invention that has been biotin-labeled or purified as a fusion protein with the GST protein is reacted. The plaques expressing the binding proteins are detected with streptavidin or an anti-GST antibody. It is then also possible to introduce the isolated genes from the above procedure into *E. coli* or other cells to express them and to prepare the proteins encoded by the genes.

It should be possible to determine the signal transduction pathways mediated by the protein—protein interaction by using the proteins of the present invention to isolate and analyze their binding proteins and the genes encoding them. Furthermore, as the relationship between the signal transduction and diseases becomes clearer, it will be possible to develop pharmaceuticals targeted at the proteins of the present invention and the proteins that interact with them.

It is also expected that treatments using antisense DNA against the DNA encoding these proteins will become possible. In the present invention, "antisense DNA" refers to the DNA encoding the RNA that is complementary to the transcription product of the target gene, thereby employing the activity to suppress the expression of the target gene. Antisense DNA does not have to be perfectly complementary to the transcription product of the target gene, as long as it can effectively block the expression of the target gene. It preferably possesses 90% or more, and more preferably 95% or more, complementarity. The chain length of the antisense DNA is 15 nucleotides or more, preferably 100 nucleotides or more, and more preferably 500 nucleotides or more. Various modified antisense oligonucleotides are being utilized as antisense DNA. For example, phosphorothioates (S-oligos) are preferable in terms of stability and solubility. The methods for introducing antisense DNA include direct administration, lipofection, the HVJ method, and the HVJ-liposome method. It is also possible to perform the treatment with antisense RNA using vectors. In this case, the gene therapy is achieved by inserting the DNA of the present invention backwards into the vector used in the recombinant protein production in animal cells described above. The DNA is then expressed within the body by introducing it through direct administration, lipofection, the HVJ method, the HVJ-liposome method, etc. It is also possible to employ the methods of gene introduction using virus vectors such as adeno-associated virus, Adenovirus, human herpes simplex virus, vaccinia virus, and Fowlpox virus, in order to express the antisense RNA within the body. Treatments using ribozymes, instead of antisense DNA, are also possible.

BRIEF DESCRIPTION OF THE DRAWINGS

FIG. 1. Sequence comparisons between "32-8-1" (top) and "AF00168" (bottom) are shown.

FIG. 2. Sequence comparisons between "32-8-1" (top) and "AJ001319" (bottom) are shown.

FIG. 3 Sequence comparisons between "32-8-1" (top) and "AJ001320" (bottom) are shown.

FIG. 4. Continuation of FIG. 3, sequence comparisons between "32-8-1" (top) and "AJ001320" (bottom) are shown.

The lanes are 1. Heart, 2. Brain, 3. Placenta, 4. Lung, 5. Liver, 6. Skeletal muscle, 7. Kidney, and 8. Pancreas. "H4" indicates the results with the Human Multiple Tissue Northern (MTN) Blot IV (Clontech #7766-1), and the lanes are 1. Spleen, 2. Thymus, 3. Prostate, 4. Testis, 5. Uterus, 6. Small intestine, 7. Colon, and 8. Peripheral Blood Leukocyte. "F2" indicates the results with the Human Fetal Multiple Tissue Northern (MTN) Blot II (Clontech #7756-1), and the lanes are 1. Fetal brain, 2. Fetal lung, 3. Fetal liver, and 4. Fetal kidney.

Figure 6:
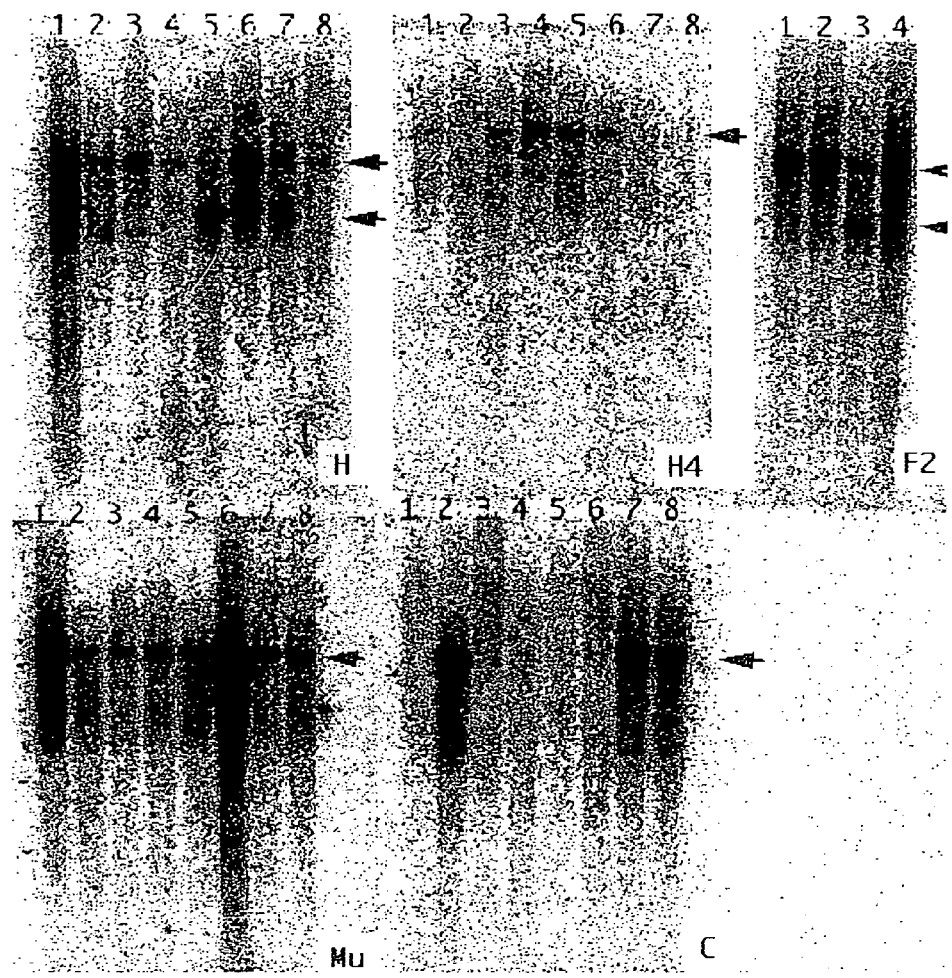

FIG. 6. Photograph of the electrophoresis showing the results of northern blot analysis of the "32-8-1 gene" is shown. The NdeI 1.2 kb-#l probe was used. "H" in the figure indicates the results with the Human Multiple Tissue Northern (MTN) Blot (Clontech #7760-1), and the lanes are 1. Heart, 2. Brain, 3. Placenta, 4. Lung, 5. Liver, 6. Skeletal muscle, 7. Kidney, and 8. Pancreas. "H4" indicates the results with the Human Multiple Tissue Northern (MTN) Blot IV (Clontech #7766-1), and the lanes are 1. Spleen, 2. Thymus, 3. Prostate, 4. Testis, 5. Uterus, 6. Small intestine, 7. Colon, and 8. Peripheral Blood Leukocyte. "F2" indicates the results with the Human Fetal Multiple Tissue Northern (MTN) Blot II (Clontech #7756-1), and the lanes are 1. Fetal brain, 2. Fetal lung, 3. Fetal liver, and 4. Fetal kidney. "Mu" indicates the results with the Human Muscle Multiple Tissue Northern (MTN) Blot (Clontech #7765-1), and the lanes are 1. Skeletal muscle, 2. Uterus, 3. Colon, 4. Small intestine, 5. Bladder, 6. Heart, 7. Stomach, and 8. Prostate. "C" indicates the results with the Human Cancer Cell Line Multiple Tissue Northern (MTN) Blot (Clontech #7757-1), and the lanes are 1. Promyelocytic leukemia HL-60 cells, 2. HeLa S3 cells, 3. Chronic myelogenous leukemia K-562 cells, 4. Lymphoblastic leukemia MOLT-4 cells, 5. Burkitt's lymphoma Raji cells, 6. Colorectal adenocarcinoma SW480 cells, 7. Lung carcinoma A549 cells, and 8. Melanoma G361 cells.

Figure 7:
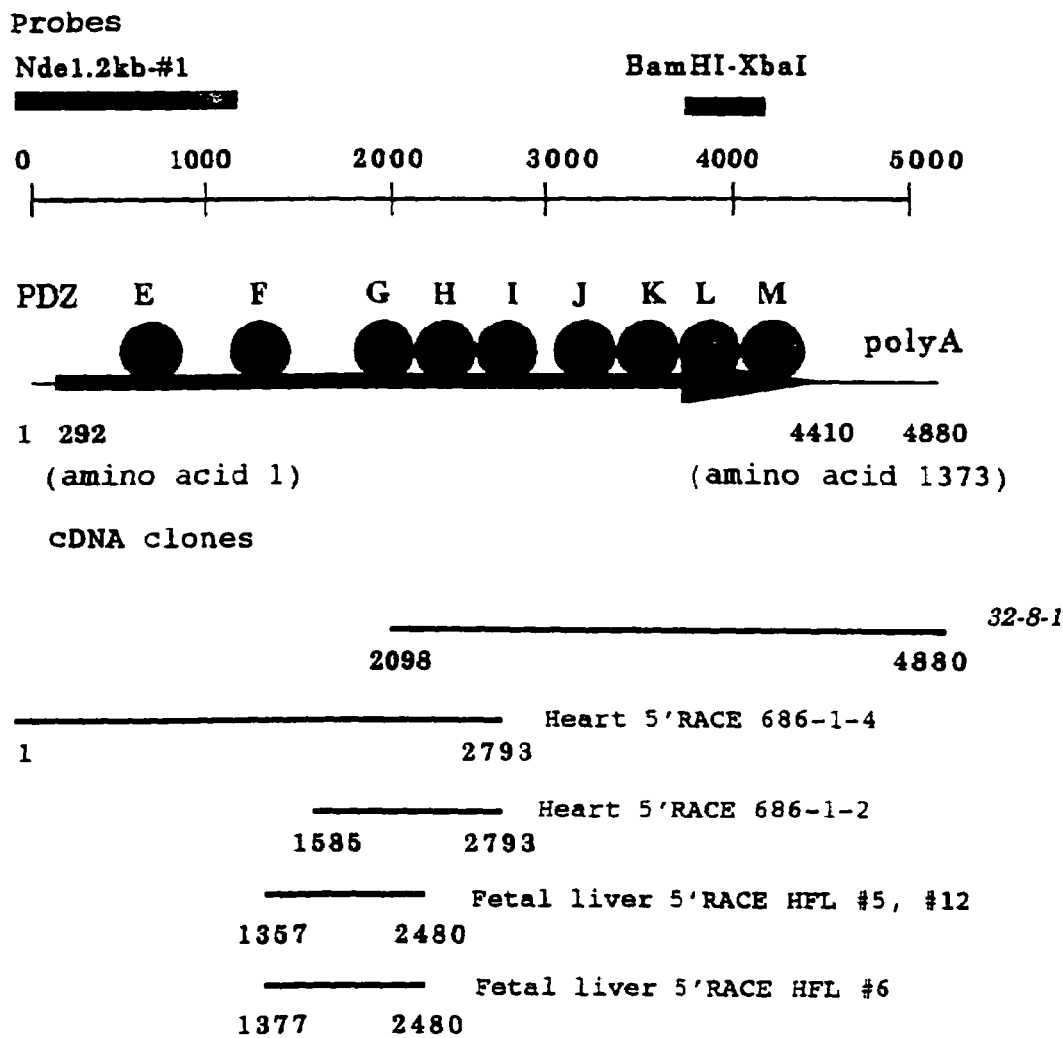

FIG. 7. Positional relationships among various clones isolated by the present inventors are presented. These are the "32-8-1" cDNA clone; the heart cDNA derived "686-1-2" and "686-1-4" clones. The fetal liver cDNA derived "FL #5," "#12," and "#6" clones are also shown. The PDZ domains encoded by the 32-8-1 gene are indicated by circles. The translation initiation site at nucleotide 292 and the translation termination site at nucleotide 4410 are also indicated in the figure. The positions of the probes, NdeI 1.2 kb-#1 and BamHI-XbaI, are also shown.

FIG. 8. PDZ domain sequences of the protein (SEQ ID NO: 1) encoded by the 32-8-1 gene are shown. The PDZ domain sequences that exist within the protein encoded by the 32-8-1 gene are aligned.

Figure 9:
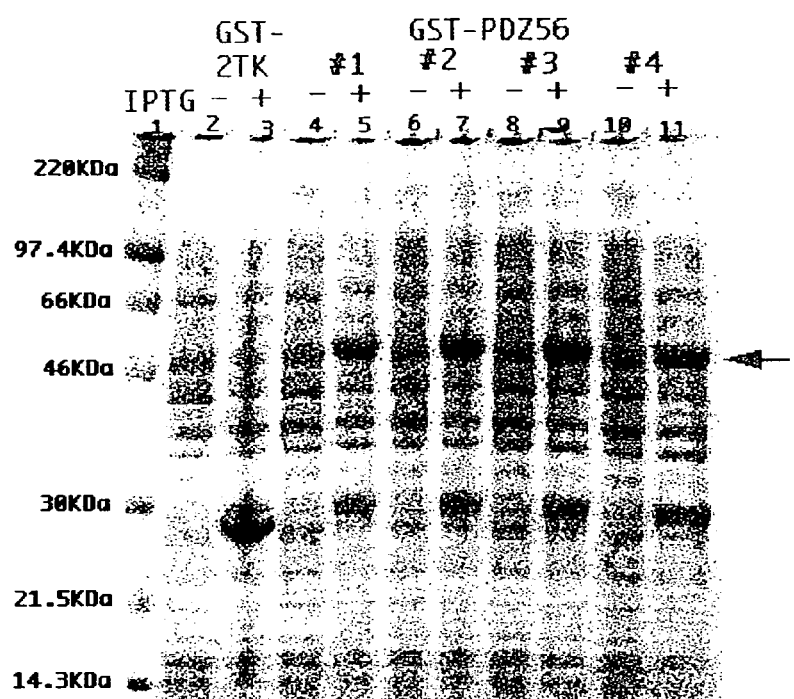

FIG. 9. Four colonies of E. coli transformants expressing GST-PDZ56 were picked, and the expression was compared depending on the presence or absence of the isopropyl thiogalactoside (IPTG) induction. Transformants with pGST-2TK were used as a control. The samples from each clone were analyzed on a 10% to 20% SDS-polyacrylamide gel, with even-numbered lanes before the IPTG induction and odd-numbered lanes three hours after the IPTG induction. Lanes 2 and 3 correspond to the pGST-2TK transformants, and lanes 4 through 11 correspond to clone 1 through 4 of the E. coli transformants expressing GST-PDZ56. Lane 1 shows molecular weight markers. The bands corresponding to the induced expression of GST-PDZ56 are indicated with an arrow.

Figure 10:
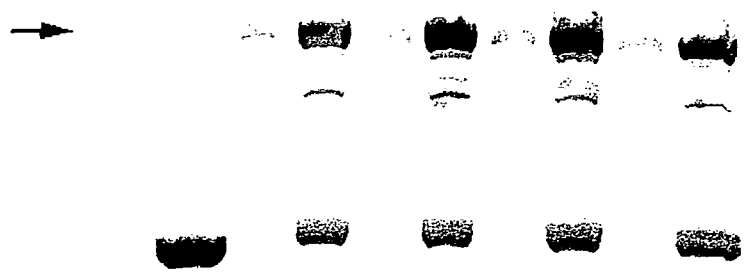

FIG. 10. The same samples used in the experiment shown in FIG. 9 were analyzed by western blot. Bands (indicated with an arrow) corresponding to the induced expression of the 55 kDa protein were detected with the anti-GST antibody. The bands near 30 kDa seen in the samples three hours after the IPTG induction are interpreted to represent the degradation of the GST-PDZ56 protein.

Figure 11:
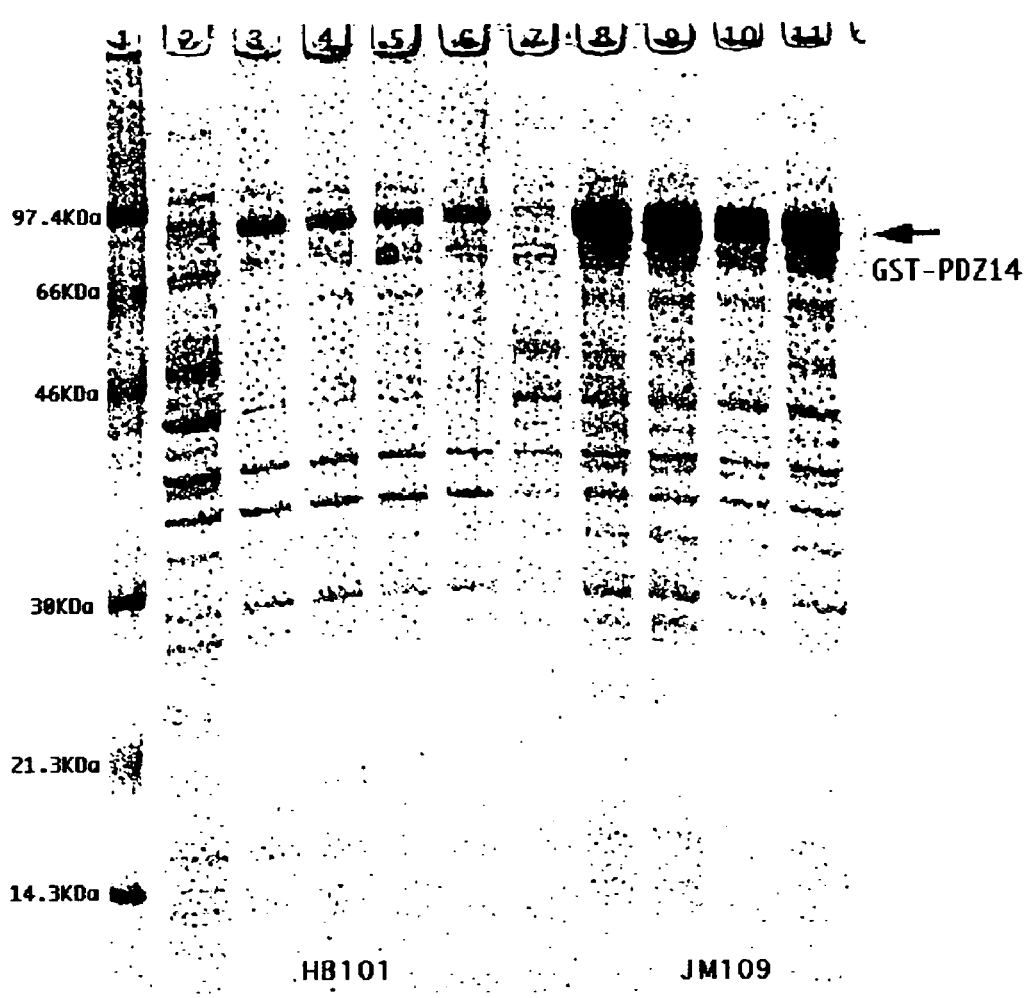

FIG. 11. The expression of GST-PDZ14 from the E. coli transformants three hours after the IPTG induction was analyzed by Coomassie blue staining. Lanes 2 and 6 correspond to the samples prior to the IPTG induction; lanes 3 through 6 correspond to clones 1, 2, 3, and 4 of the E. coli HB101 transformants; and lanes 8 through 11 correspond to clones 1, 2, 3, and 4 of the E. coli JM109 transformants, showing the results of GST-PDZ14 expression after the IPTG induction (arrow). Lane 1 shows molecular weight markers.

Figure 12:
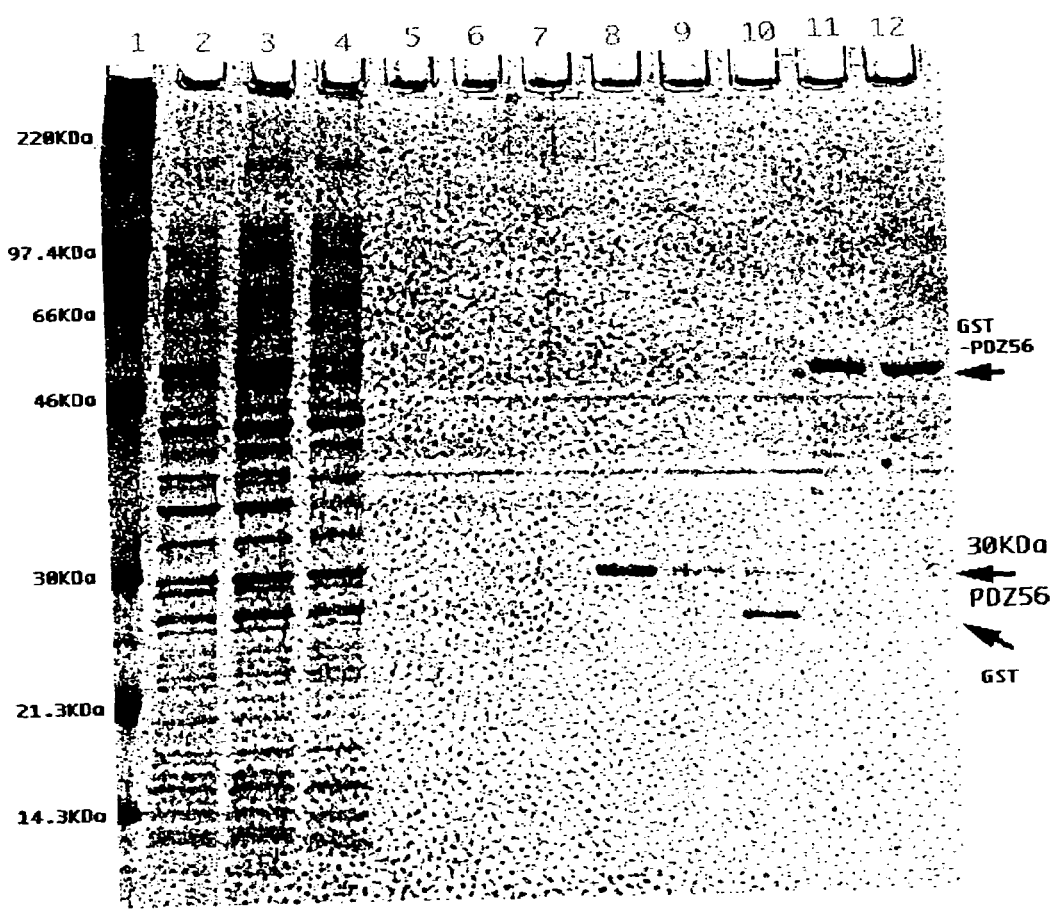

FIG. 12. The purification process of PDZ56 is shown. Coomassie blue staining was used. Lane 1 shows molecular weight markers. Lane 2 corresponds to the culture media; lane 3, to the sonicated sample; lane 4, to the fraction unbound to the glutathione-Sepharose column; lanes 5 through 7, to the washes; and lanes 8 and 9, to the PDZ56 protein not containing the GST protein portion, which has come off the glutathione-Sepharose column after digestion by thrombin. Bands at approximately 30 kDa can be clearly seen (arrow indicates PDZ56). Lane 10 corresponds to the GST protein portion bound to the glutathione-Sepharose column, which was eluted after digestion by thrombin (arrow indicates GST). Lanes 11 and 12 show the GST-PDZ56 fusion protein that was eluted without thrombin digestion in a regular elution buffer containing glutathione (arrow indicates GST-PDZ56).

Figure 13:
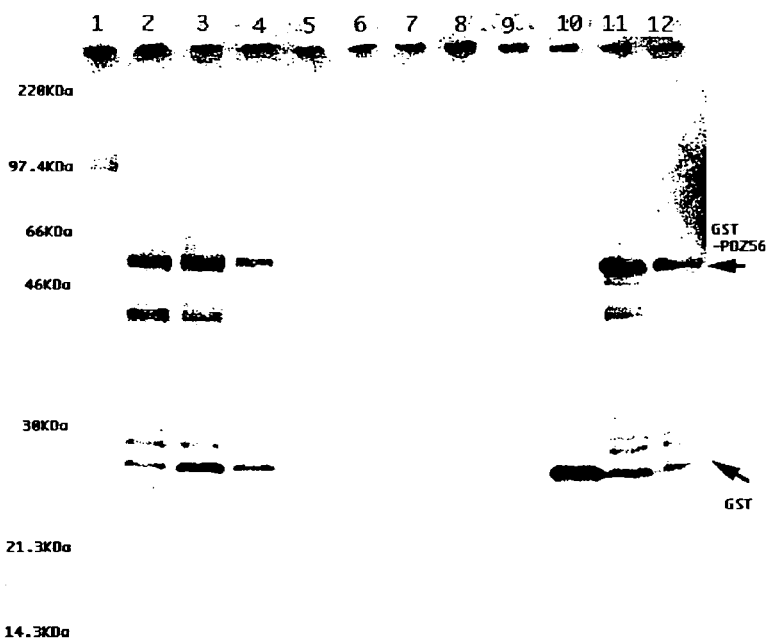

FIG. 13. The results of western blotting performed with anti-GST antibody using a filter onto which the same samples used in the experiment shown in FIG. 12 were blotted are shown. Comparing lanes 8 and 9 with lane 10 (arrow: GST) clearly shows that the 55 kDa GST-PDZ56 fusion protein (arrow indicates GST-PDZ56) shown in lanes 11 and 12 has been cleaved by thrombin to yield only PDZ56 that does not contain the GST portion. Bands in lanes 8 and 9 of FIG. 12 cannot be detected by the GST antibody used in FIG. 13 because they do not contain GST.

Figure 14:
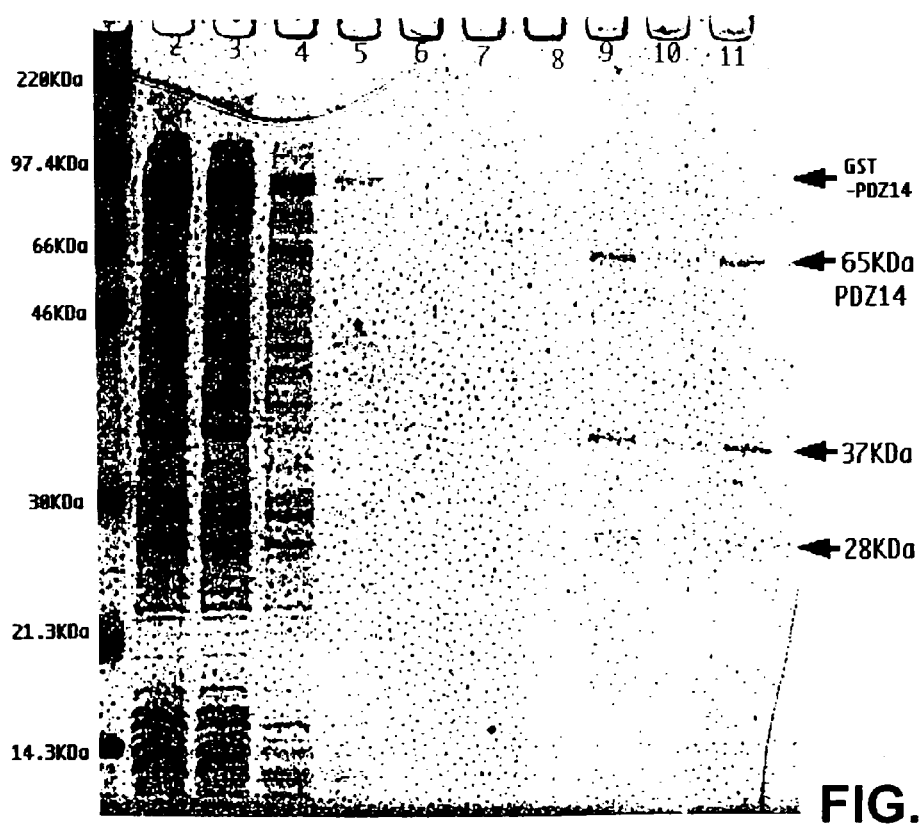

FIG. 14. The purification process of PDZ14, similar to that in FIG. 9, is shown. Lane 1 shows molecular weight markers. Lane 2 corresponds to the culture media; lane 3, to the sonicated sample; lane 4, to the fraction unbound from the glutathione-Sepharose column; lanes 5 through 8, to the washes; and lanes 9, 10, and 11, to the PDZ14 protein not containing the GST protein portion, which came off the glutathione-Sepharose column after digestion by thrombin. Bands at 65 kDa can be clearly seen (arrow indicates PDZ14). However, degradation products of the PDZ14 protein were also detected at 28 kDa and 37 kDa (arrows indicate 37 kDa and 28 kDa).

Figure 15:
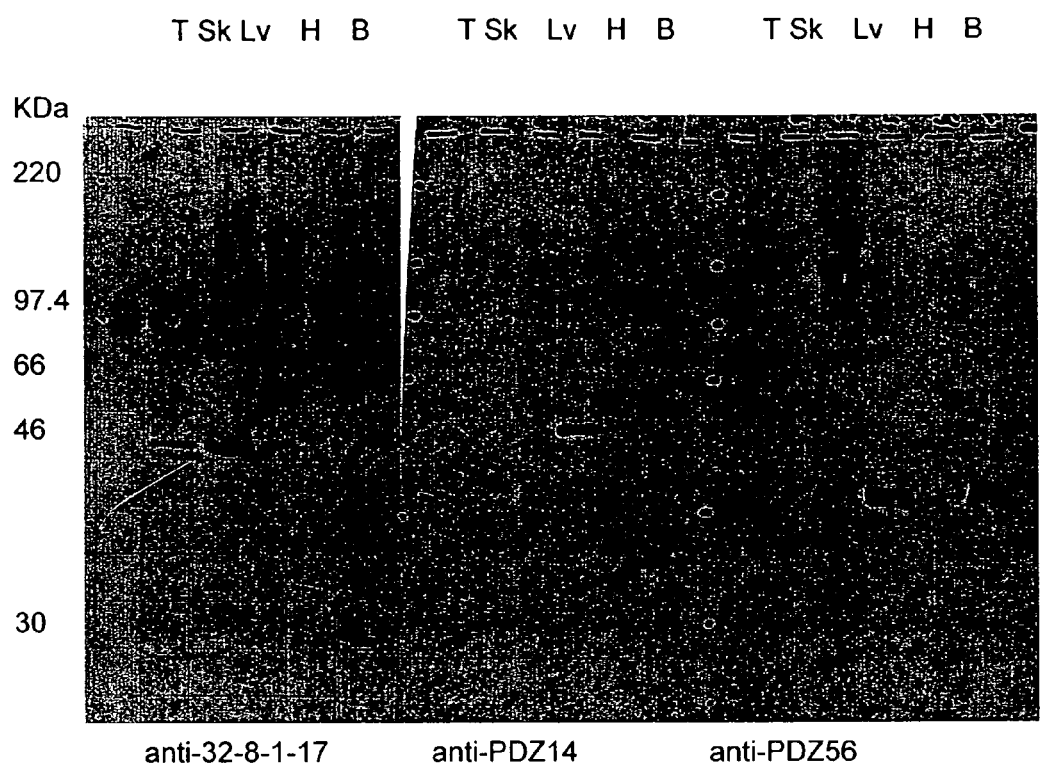

FIG. 15. Out of the Protein Medley (Clontech), the filters blotted with 100 mg each of the cell lysates from human testis (T), skeletal muscle (Sk), liver (Lv), heart (H), and brain (B) were reacted with the antisera from the rabbits immunized with peptide 32-8-1-17, PDZ14, or PDZ56 for western blotting. The filters were reacted sequentially with the 5,000-fold diluted rabbit antiserum, the 1,000-fold diluted biotin-labeled anti-rabbit Ig antibody, and the 2,500-fold diluted horseradish peroxidase (HRP)-labeled streptavidin-biotin complex (Amersham). The results of detection by chemiluminescence of the proteins that react with the rabbit antisera are shown. In the liver tissue, the present inventors were able to detect a band at around 130 kDa. This band is expected to have been derived from the 32-8-1 protein (arrow).

Figure 16:
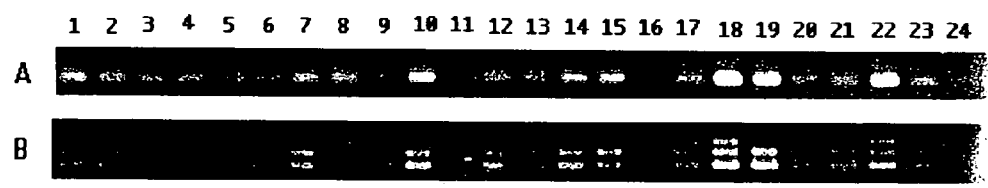

FIG. 16. The results of an analysis of the tissue specificity of the 32-8-1 gene expression by RT-PCR are shown. The 24-types of first strand cDNAs used were 1. brain, 2. heart, 3. kidney, 4. liver, 5. lung, 6. pancreas, 7. placenta, 8. skeletal muscle, 9. colon, 10. ovary, 11. peripheral leukocyte, 12. prostate, 13. small intestine, 14. spleen, 15. testis, 16. thymus, 17. fetal brain, 18. fetal heart, 19. fetal kidney, 20. fetal liver, 21. fetal lung, 22. fetal skeletal muscle, 23. fetal spleen, and 24. fetal thymus. Single bands at 650 bp were detected in panel A, and three bands (750 bp, 850 bp, and 950 bp) were detected in panel B.

FIG. 17. The comparisons among the sequences of FH750, FH850, and FH950 are shown.

FIG. 18. The continuation of FIG. 17 showing the comparisons among the sequences of FH750, FH850, and FH950 is shown.

Figure 19:
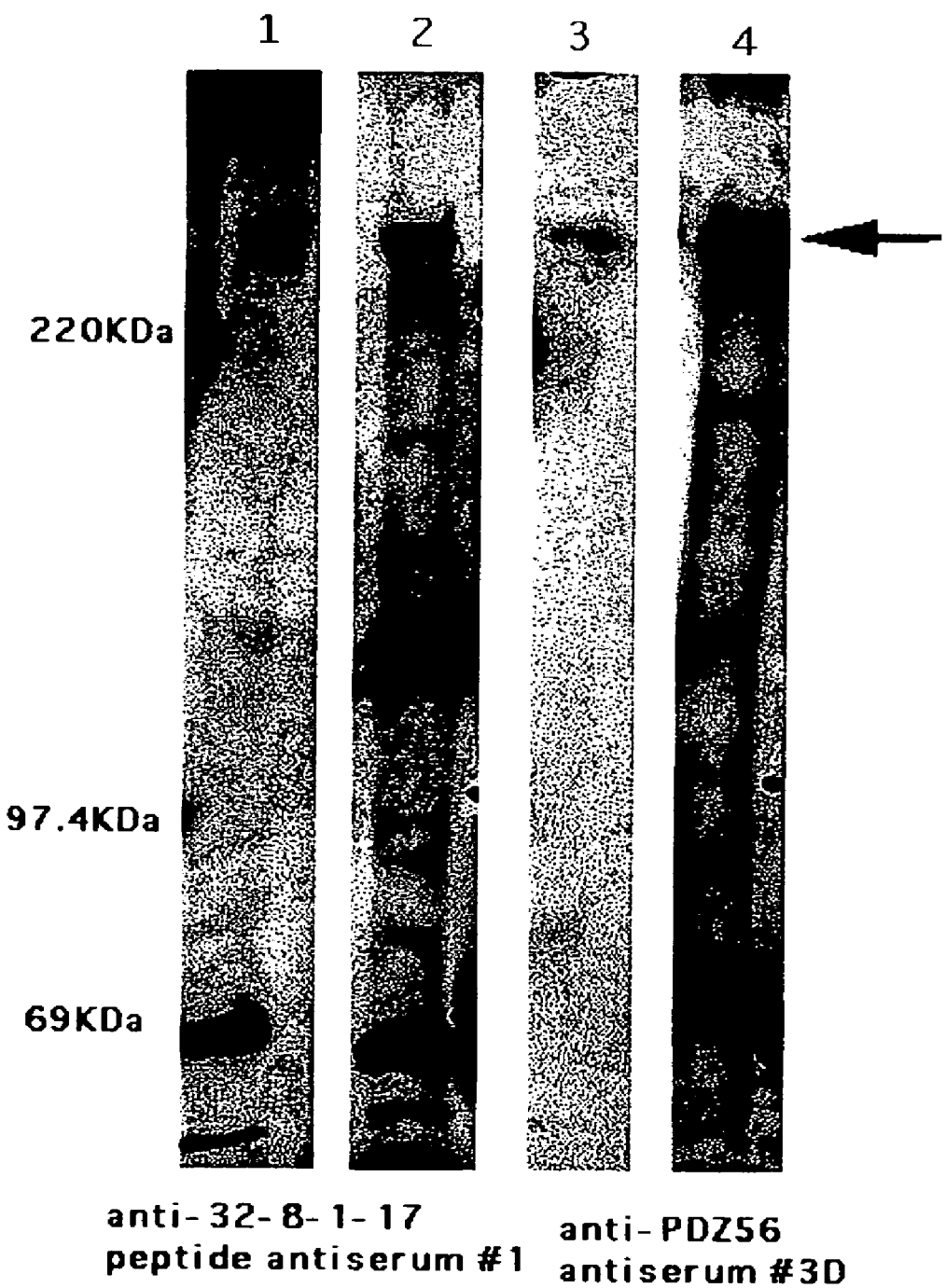

FIG. 19. A photograph of an electrophoresis presenting the results of detection of the 32-8-1b protein by western blotting is shown. Lanes 1 and 2 were detected with the antisera against the 32-8-1-17 peptide, and lanes 3 and 4 were detected with the antisera against PDZ56. Cell lysates from neuroblastoma cells SH-SY5Y (lanes 1 and 3) and the NT-N cells (lanes 2 and 4), which are neurons differentiated from NT-2 by the retinoic acid stimulation, were separated on an SDS-polyacrylamide gel. Bands that are expected to correspond to the 32-8-1b protein were detected with a size of 250 kDa or more.

Figure 20:
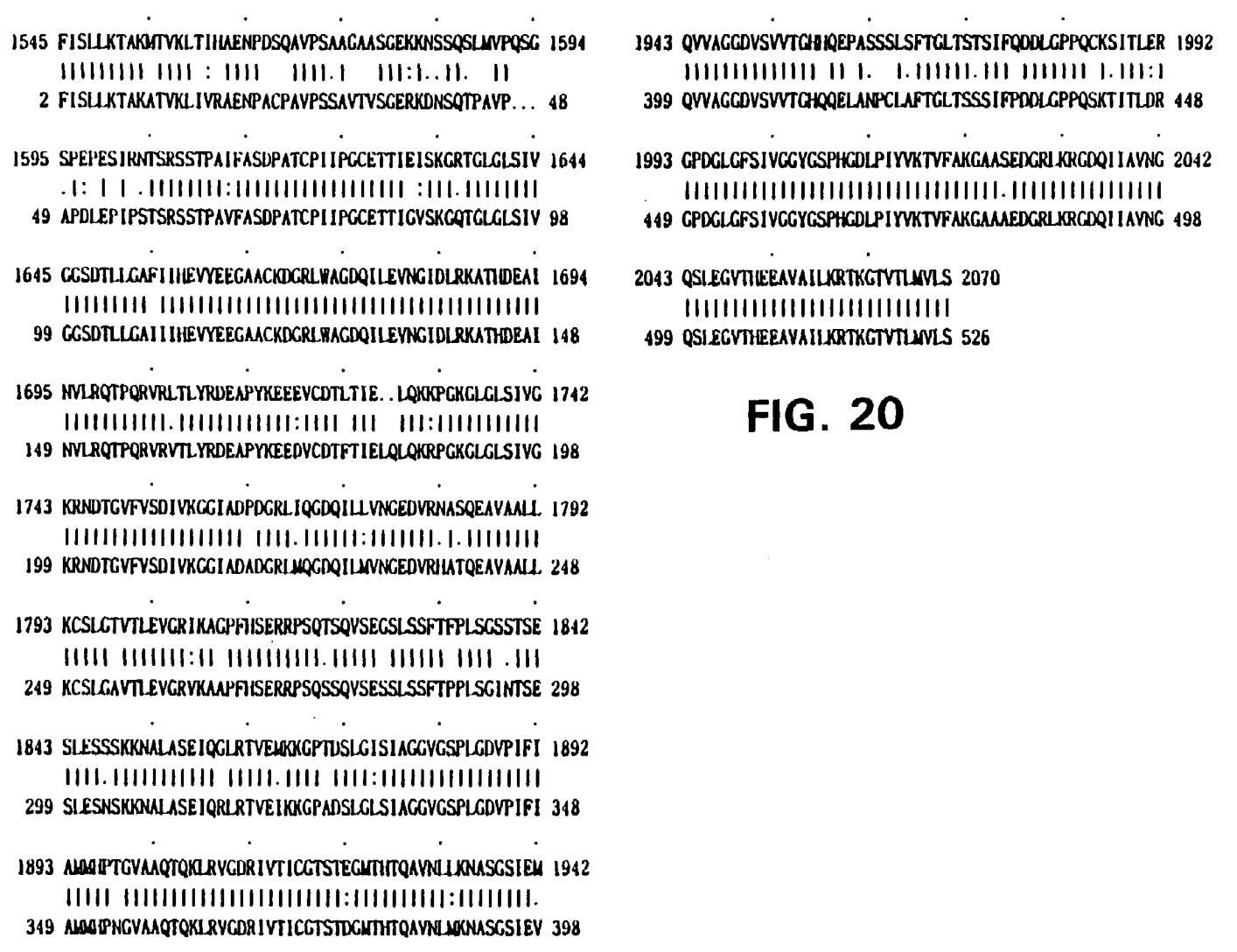

FIG. 20. Sequence comparisons between "32-8-1b" (top) and "AF00168" (bottom) are shown.

Figure 21:
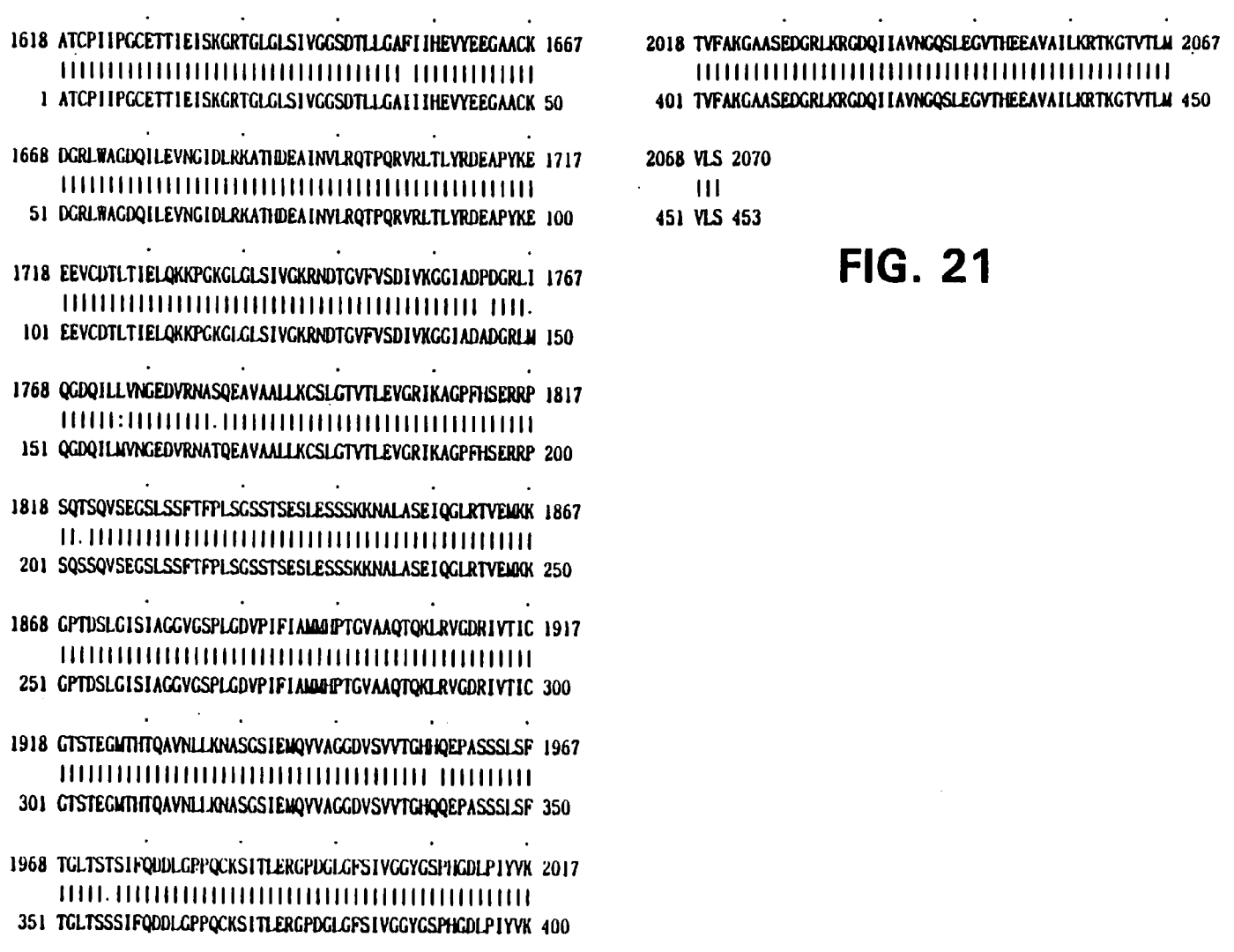

FIG. 21. Sequence comparisons between "32-8-1b" (top) and "AJ001319" (bottom) are shown.

FIG. 22. Sequence comparisons between "32-8-1b" (top) and "AJ001320" (bottom) are shown.

Figure 23:
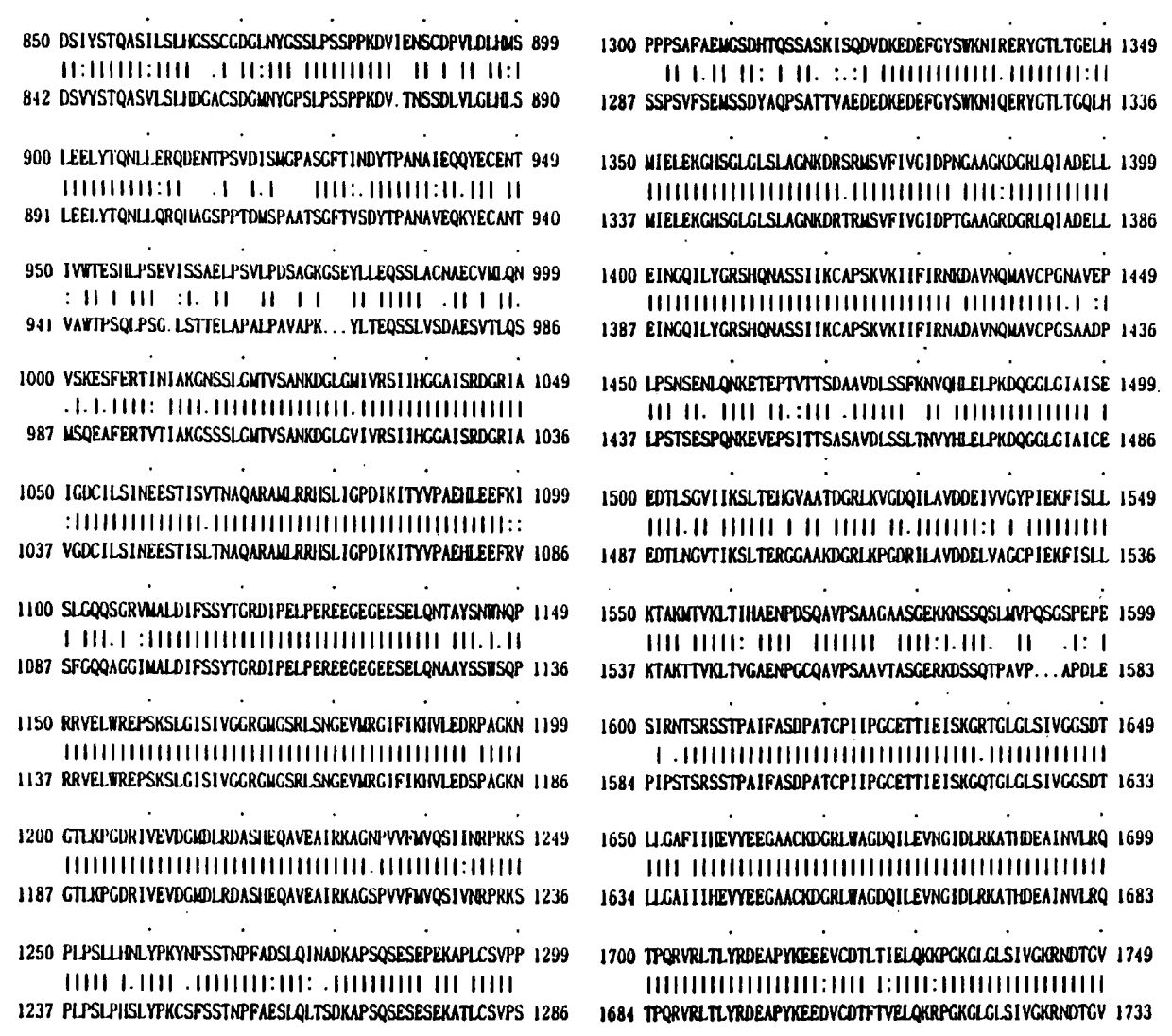

FIG. 23. The continuation of FIG. 22, which presents sequence comparisons between "32-8-1b" and "AJ001320," is shown.

FIG. 24. The continuation of FIG. 23, which presents sequence comparisons between "32-8-1b" and "AJ001320," is shown.

FIG. 25. The sequences of the PDZ domains in the protein (SEQ ID NO: 83) encoded by the 32-8-1b gene are shown. The sequences of the PDZ domains that exist within the protein encoded by the 32-8-1b gene are aligned.

Figure 26:
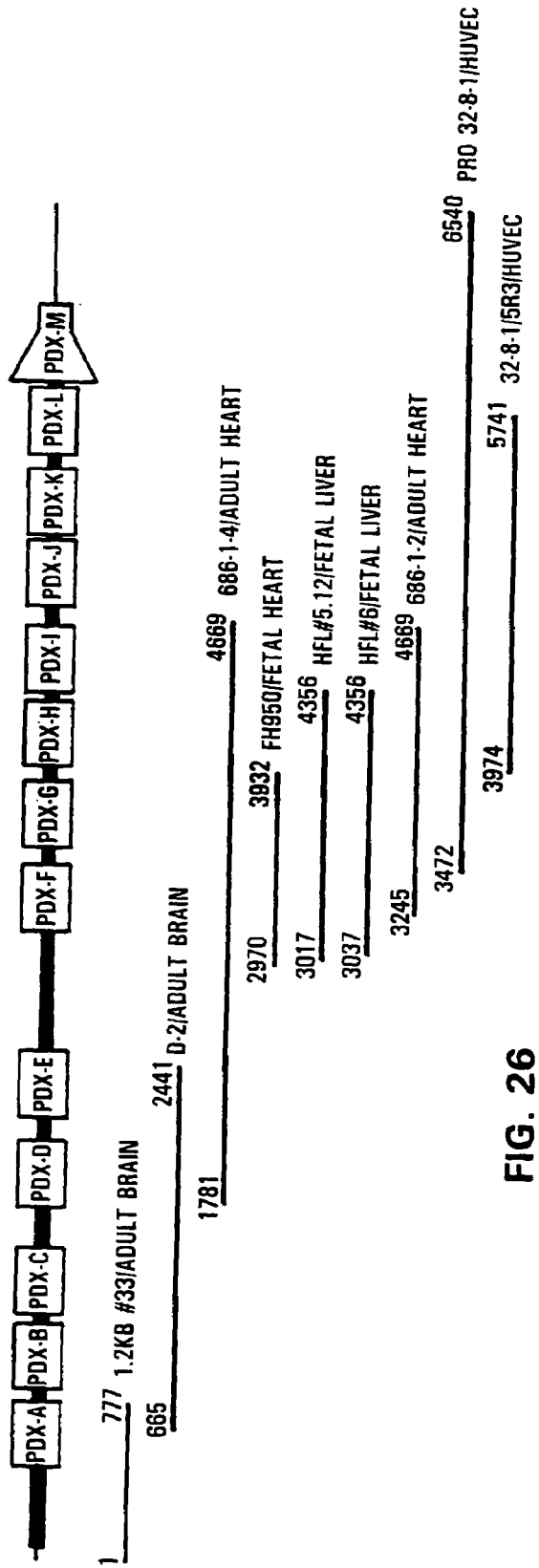

FIG. 26. The positional relationships among the various clones isolated by the present inventors are shown. These are the "32-8-1" cDNA clone; the heart cDNA derived "686-1-2" clone, "686-1-4" clone, and "FH950" clone; the fetal liver cDNA derived "FL#5," "#12," and "#6" clones; and the brain derived "1.2 kb #33" clone and "D-2" clone are shown. The PDZ domains encoded by the "32-8-1b" gene are indicated by rectangles.

BEST MODE FOR IMPLEMENTING THE INVENTION

Embodiments of the present invention are exemplified below. However, the present invention shall in no way be limited by these examples.

EXAMPLE 1

Cloning of Genes (1) Differential Display

The human umbilical vascular endothelial cells (HUVEC) were obtained from Morinaga Biochemistry Research Institute and cultured by using the Normal Human Vascular Endothelial Cell Culturing kit (Catalog #680051). When the cells became subconfluent, 10 ng/ml Recombinant Human Tumor Necrosis Factor-α (TNFα, Catalog #300-01A, PEPROTECH Inc.) was added, and the cells were cultured for another 24 hours. The expressed genes were compared with those from the cells without the addition of TNFa. Cells were detached from the plate with trypsin-EDTA, precipitated by centrifugation at 1,000 rpm for 5 minutes, and washed once with PBS. The total RNA was then recovered by using an RNAeasy Total RNA kit (QIAGEN). Using 0.2 μg of the recovered total RNA, the present inventors synthesized cDNA by means of the H-T11G anchor primer. The conditions were based on those given in the manual for the RNAimage kit (GenHunter). Genes were randomly amplified using the TAKARA Taq polymerase through 40 cycles of polymerase chain reaction (PCR). Each cycle consisted of 94° C. for 30 seconds, 40° C. for 2 minutes, and 72° C. for 30 seconds, for each of the eight kinds of arbitrary primers H-AP1 through H-AP8. The reaction mixture contained α-$^{32}$P DATP. The products were separated on sequencing gels, and those genes whose bands were intensified by the TNFα stimulation, that is, the genes whose mRNA expression was increased as compared to the case with no stimulation, were amplified again with the same conditions. The primer DNA was then removed from the reaction mixture using a Qiaquick Spin PCR Purification kit. The nucleotide sequence information of "DDEST32" shown in SEQ ID NO: 13 was obtained by analyzing the products with a Dye Terminator Cycle Sequencing FS Ready Reaction kit (Perkin Elmer, Catalog #402122) using the same primers used for amplification.

(2) Construction of cDNA Library

A cDNA library was constructed using a ZAP-cDNA synthesis kit (Stratagene). A 10×1$^{st}$ strand buffer (5 μl), 3 μl of 1$^{st}$ strand methyl nucleotides mix, 2 μl of linker-primer (1.4 μg/μl), 1 ml of RNase Block ribonuclease inhibitor (40 U/μl), 10 μl of TNFα-stimulated HUVEC poly A+ mRNA (0.5 μg/μl), and 24 μl of diethyl pyrocarbonate (DEPC)-treated water were gently mixed and allowed to stand at room temperature for 10 minutes. SuperScript II reverse transcriptase (5 μl, 200 U/μl, GIBCO-BRL) was mixed with the cDNA library. The mixture was incubated at 37° C. for 40 minutes then at 45° C. for 70 minutes. The reaction mixture was put on ice, and 20 μl of 10×2$^{nd}$ strand buffer, 6 μl of 2$^{nd}$ strand nucleotide mix, 115.9 μl of sterilized distilled water, RNase H (1.5 U/μl), and 11.1 μl of DNA polymerase I (9 U/μl) were mixed into 45 p of the reacted mixture by vortexing, and the mixture was incubated at 16° C. for 150 minutes. After the reaction, 23 μl of blunting dNTP mix and 2 μl of cloned Pfu DNA polymerase (2.5 U/μl) were added, and the mixture was incubated at 72° C. for 30 minutes. The mixture was then sequentially extracted with 200 μl of phenol/chloroform, and with chloroform, and further precipitated by adding 20 μl of 3M sodium acetate and 400 μl of 100% ethanol. After overnight incubation at −20° C., the mixture was centrifuged at 15,000 rpm for 60 minutes (4° C.), and the precipitate was washed with 500 μl of 70% ethanol and dried. The precipitate was dissolved in 9 μl of 0.4 μg/μl EcoRI adapter and incubated at 4° C. for 45 minutes. 10× ligase buffer (1 μl), 1 μl of 10 mM ATP, and 1 μl of T4 DNA ligase (4 U/μl) were then added to the above, and the ligation reaction was performed overnight at 8° C. The mixture was incubated at 70° C. for 30 minutes to inactivate the enzyme, spun down to collect the solution on the bottom of the tube, and let sit for 5 minutes at room temperature. To the mixture were added 1 μl of 10× ligase buffer, 2 μl of ATP, 6 μl of sterilized water, and 1 μl of T4 polynucleotide kinase (10 U/μl). The mixture was incubated at 37° C. for 30 minutes then incubated again at 70° C. for 30 minutes to inactivate the enzyme. XhoI buffer supplement (28 μl) and 3 μl of XhoI (40 U/μl) were added to the above, and the mixture was reacted at 37° C. for 90 minutes. The mixture was cooled to room temperature, then 5 μl of 10× STE buffer was added. The mixture was then applied to a Sephacryl S-500 column and eluted twice with 60 μl of 1× STE buffer. Ethanol (120 ml) was then added to the mixture, and the mixture was allowed to stand at −20° C. overnight. It was then centrifuged at 15,000 rpm for 60 minutes (4° C.) to obtain the precipitate. The precipitate was washed with 200 μl of 80% ethanol and dried. It was then dissolved with 6 μl of sterilized water, and 2.5 μl of it was used for the ligation reaction with the vector. To 2.5 μl of the cDNA, 1 μl of Uni-ZAP XR vector (1 μg), 0.5 μl of 10× ligase buffer, 0.5 μl of 10 mM ATP, and 0.5 μl of T4 DNA ligase (4 U/μl) were added and reacted at 12° C. overnight. The ligation mixture (1 μl) was added to the GigapackIII Gold Packaging extract, mixed well, and incubated for two hours at room temperature. SM buffer (500 μl; 5.8 g NaCl, 2.0 g $MgSO_4.7H_2O$, 50 ml 1 M Tris-HCl (pH 7.5), and 5 ml 2% (w/v) gelatin, brought up to 1 L with deionized water) was added to the above, and after 20 μl of chloroform was added, it was gently mixed. The mixture was then centrifuged, and the supernatant was transferred to another tube and stored at 4° C. The phage titer was measured using 0.1 μl and 1 μl of the packaging reaction. Since approximately 300 plaques were obtained from 0.1 μl, the titer was estimated to be 3,000 PFU (plaque-forming units) per microliter. XL1 Blue MRF' was used as the host E. coli. It was cultured in 20 ml LB/10 mM $MgSO_4$/0.2% maltose at 37° C. for 6 hours, placed on ice for 5 minutes before the $OD_{600}$ became 1.0, and centrifuged at 500×g for 10 minutes. To resuspend the precipitated cells, 10 ml of 10 mM $MgSO_4$ was added, and cells were diluted with 10 mM $MgSO_4$ so that the $OD_{600}$ became 0.5. The packaging reaction (17 μl) was added to 600 μl of the freshly prepared XL-1 Blue MRF', and incubated at 37° C. for 15 minutes. NZY top agar (6.5 ml; made by adding 0.7% (w/v) agarose to the NZY medium and autoclaving it), which had been incubated at 45° C., was added to the above and plated onto NZY agar plates. The plates were prepared as follows. NaCl (5 g), $MgSO_4.7H_2O$ (2.0 g), yeast extracts (5 g), NZ amines (10 g), and agar (15 g) were dissolved in deionized water to make the total volume 1 L. The solution 4 pH was adjusted with NaOH to 7.5, after which the solution was autoclaved and poured into sterilized culture plates. After culturing at 37° C. for six hours, the plaques were transferred onto a Hybond N+ filter (Amersham, $RPN_2O_3B$) by placing the filter on the plate, denatured with 1.5 M NaCl-0.5 M NaOH for 7 minutes, neutralized by treating with 1.5 M NaCl-0.5 M Tris-HCl (pH 7.2)/1 mM EDTA for 5 minutes, and finally rinsed with 2× SSC. After the filter was dried, the plaques were fixed onto the filter by StrataLinker (Stratagene).

(3) Screening of the cDNA Library

The "DDEST32" DNA fragment was isolated on a 2% agarose gel, and recovered from an agarose gel slice with a QIAEX II gel extraction kit (QIAGEN). The fragment was labeled by random labeling so it could be used as the probe. Using a Megaprime kit (Amersham, $RPN_{16}O_7$), 5 μl of primer solution was added to 25 ng of the probe DNA, and incubated at 95° C. for 5 minutes. After the solution was incubated at room temperature, 10 μl of labeling buffer, 18 μl of water, 5 μl of $\alpha^{32}p$ dCTP (~3000 ci/mmol; Amersham), and 2 μl of Klenow fragment were added to it, and the mixed solution was incubated at 37° C. for 30 minutes. The reaction was stopped by adding 2 μl of 0.5 M EDTA, and the free $\alpha$-$^{32}$P dCTP was removed with a Pharmacia ProbeQuant G-50 column. After prehybridization at 60° C. in the Rapid hybri buffer (Amersham, RPN1636), the labeled probe was heat-denatured at 95° C., rapidly chilled on ice, and added to the hybridization buffer. Hybridization was then performed by shaking at 60° C. for two hours. The probe was used at a concentration of $2×10^6$ cpm/ml. The filter was washed three times in 2× SSC/0.05% SDS at room temperature for ten minutes each, and twice more in 0.1× SSC/0.1% SDS at 60° C. for 20 minutes each. The phage collected from positive plaques was diluted in SM buffer and plated onto 10-cm plates so that approximately 100 plaques were formed per plate. The secondary and tertiary screenings were performed similarly. As a result, clone "#32-8-1" was obtained as the positive clone. The gene that had been cloned in the Uni-ZAP vector was recovered as ordinary plasmid DNA by the in vivo excision method.

Example 2

Sequence Determination of the "32-8-1" Gene (1) Preparation of the cDNA Library for RACE The cDNA for RACE was synthesized using a Marathon cDNA amplification kit (Clontech). The total RNA (1 μg) obtained from the TNFα-stimulated HUVEC cells was used for the experiment. Oligo dT primer (1 μl, 10 μM) was added to the above, the total volume was brought to 5 μl, and the mixture was incubated at 70° C. for 2 minutes and then placed on ice for 2 minutes. Two microliters of 5×$1^{st}$ strand buffer, 1 μl of 10 mM dNTP mix, and 1 μl of 100 U/μl MMLV reverse transcriptase were added to the above, and the total volume was made 10 μl. The mixture was then incubated at 42° C. for 1 hour to synthesize the first strand cDNA. Sixteen microliters of 5×$2^{nd}$ strand buffer, 1.6 μl of 10 mM dNTP mix, and 4 μl of 20×$2^{nd}$ strand enzyme cocktail were next added to the mixture, the total volume was adjusted to 80 μl with water, and the mixture was incubated at 16° C. for 90 minutes. T4 DNA polymerase (2 μl, 5 U/μl) was then added, and the reaction was performed at 16° C. for 45 minutes. After 4 μl of 20× EDTA/glycogen was added to the mixture, it was deproteinized with equal volumes of phenol/chloroform, and isoamyl alcohol/chloroform.

Ethanol precipitation was done with 35 μl of 4 M ammonium acetate and 263 μl of 95% ethanol, and the precipitate was washed with 80% ethanol and spontaneously dried for 10 minutes. The dried precipitate was dissolved in 10 μl of deionized water, and 7.5 μl was used for the adapter ligation reaction. Marathon cDNA adapter (3 μl, 10 μM), 3 μl of 5×DNA ligation buffer, and 1.5 μl of T4 DNA ligase (1 U/μl) were added to the above and reacted overnight at 16° C. The enzyme was inactivated by incubation at 70° C. for 5 minutes, and the total volume was adjusted to 150 μl by using 135 μl of Tricine-EDTA buffer contained in the kit.

(2) cDNA Cloning by RACE and Sequence Determination

Clone #32-8-1 was subcloned by utilizing the restriction enzyme recognition sites within the gene (PstI, XbaI, BamHI, and EcoRI), and the nucleotide sequence was determined by the cycle sequence method using a Dye Terminator Cycle Sequencing FS Ready Reaction kit (Perkin Elmer, Catalog #402122).

The sequences of the primers used are shown in Table 1. "C" indicates a primer for the complementary DNA strand.

TABLE 1

| Primer # | | DNA sequence | SEQ ID NO: |
|---|---|---|---|
| 106 | C | CTCCCCATCCCTCGTCCACC | 14 |
| XE | C | CTCTGACTCTGACTGACTGG | 15 |
| EX | | ATGAGTTTGGTTACAGCTGG | 16 |
| 402 | | TCAGAGAGCGTTATGGAACC | 17 |
| XER | | AGTCTTGCTGGGAACAAAGA | 18 |
| 801 | | ACTGTTACTACTTCTGATGC | 19 |
| 1192-1161 | | TCTGATGGTCCCACAGTCTG | 20 |
| 1282 | C | GTTGTTTCGCAGCCAGGGAT | 21 |
| 1524 | | CTGAGCATCGTTGGGGGTTC | 22 |
| 1449 | C | CCTCATCTCTGTAGAGTGTC | 23 |
| 1683 | | TGTTAGCCCCCTCACTAAGG | 24 |
| 1803 | | GCTATGTGCTAGGAAATACG | 25 |
| 2116 | | TAGGGAGAAGGATCAGAGCG | 26 |
| 607-93 | | ACAGATTTCTGACTCACTGG | 27 |
| 128 | | TGGAAATAGGCATTCTTCAG | 28 |
| 607-462 | | ATACAAAGACGGTCTAATCC | 29 |
| 2920 | C | CCGCTTTCCCATCTTTAGAAAC | 30 |
| 3121 | | TATCTCGTGTGGAAGATGTG | 31 |
| 2266-107 | C | ACATAAATGTTGCTATCACC | 32 |
| 3361 | | TGCCACTTAGTAGCCGAGTG | 33 |
| 3615 | | GCATTGCATTACAGTTGAGC | 34 |
| 1301 | C | TCCTCCTTTGACAATGTCTG | 35 |
| BXR | C | CATTTCGACTGTTCTTAATC | 36 |
| XB | C | TCAGTGGATGTGCCACAGAT | 37 |
| 4221 | C | CAGTAGGTTAACTGCTTCGG | 38 |
| BX | | AGTTCCAGTCTTTCTTTCGG | 39 |
| 4335 | | TTTCTTTCACTGGGCTGAAGTC | 40 |
| XBR | | CCTCTGAAGACGGACGTCTG | 41 |

Accordingly, a nucleotide sequence of 5,146 bp was determined. When the first G of the EcoRI recognition site was counted as nucleotide 1, the PDZ domain started at nucleotide 468. A stop codon immediately followed three repeated stretches of approximately 80 amino acids. The sequence in the 3' region of the gene also contained three PDZ domains at a distance of approximately 2 kb from the stop codon described above. (An experiment conducted later revealed that clone #32-8-1 contains a sequence of approximately 2 kb. This sequence has been derived from an intron, transcribed and inserted, thereby introducing the stop codon immediately after the first three PDZ domains.)

Therefore, the present inventors performed 5' Rapid Amplification of cDNA Ends (RACE) starting from the position of the three PDZ domains found in the latter half. Using 5 µl of the cDNA described above, 5' RACE was performed according to the manual contained in the kit. The reaction mixture consisted of 5 µl of cDNA, 5 µl of 10× Advantage™ KlenTaq buffer (which came with the kit), 4 µl of 2.5 mM dNTP, 1 µl of 10 µM AP1 primer (CCATC-CTAATACGACTCACTATAGGGC (SEQ ID NO: 42)), 1 µl of 10 µM 32-8-1 5' RACE primer #22(TTGGGGTGGG-GAGAGGAGGTAGATTGC (SEQ ID NO: 43)), 1 µl of Advantage™ KlenTaq polymerase mix (Toyobo, CLK8417-1), and 33 µl of deionized water to make the total 50 µl. PCR reaction was performed using a Perkin Elmer Thermal Cycler 2400. A reaction consisting of 94° C. for 1 minute, five cycles of 94° C. for 5 seconds and 72° C. for 2 minutes, five cycles of 94° C. for 5 seconds and 70° C. for 2 minutes, followed by 25 cycles of 94° C. for 5 seconds and 68° C. for 2 minutes did not produce clearly detectable bands. By performing nested PCR under the same conditions, the present inventors were able to obtain a band of approximately 1.8 kb. Here the AP2 primer (ACTCACTAT-AGGGCTCGAGCGGC (SEQ ID NO: 44)) and 32-8-1 5' RACE primer #1034 (GCACATCACCAAGTGGGCTGC-CTACTC (SEQ ID NO: 45)) were used as primers, and 5 µl of the 50-fold dilution of the initial PCR product was used. Also, the original 25 cycles of 94° C. for 5 seconds and 68° C. for 2 minutes was reduced to 15 cycles. As a result, cDNA clone "32-8-1/5R3," which does not contain the 2 kb gap, was obtained.

Next, the present inventors determined the sequence of clone 32-8-1/5R3. The sequences of the primers used for the sequence determination of 32-8-1/5R3 are shown in Table 2. "C" indicates a primer for the complementary DNA strand.

TABLE 2

| Primer # | | DNA sequence | SEQ ID NO: |
|---|---|---|---|
| EX | | ATGAGTTTGGTTACAGCTGG | 46 |
| 456 | C | AATCTAATGCAGCTCGCCTG | 47 |
| XER | | AGTCTTGCTGGGAACAAAGA | 48 |
| 678 | C | TCACTTTAGAAGGGGCACAT | 49 |
| 801 | | ACTGTTACTACTTCTGATGC | 50 |
| 1192-1161 | | TCTGATGGTCCCACAGTCTG | 51 |
| 1282 | C | GTTGTTTCGCAGCCAGGGAT | 52 |
| 1524 | | CTGAGCATCGTTGGGGGTTC | 53 |
| 1449 | C | CCTCATCTCTGTAGAGTGTC | 54 |
| 2116 | | TAGGGAGAAGGATCAGAGCG | 55 |
| 1301 | C | TCCTCCTTTGACAATGTCTG | 56 |
| 839 | | TTTCATCATCTACAGCCAGT | 57 |
| 1389 | | TGACACCCTCACTATTGAGC | 58 |

The nucleotide sequence of 2,819 bp, which was determined by combining the sequences of clones #32-8-1 and 32-8-1/5R3, is shown in SEQ ID NO: 59.

EXAMPLE 3

Cloning of a cDNA Clone Corresponding to the 5' Upstream Region of the 32-8-1/5R3 cDNA Clone by RACE The present inventors attempted to isolate the upstream cDNA located 5' to the 32-8-1/5R3 clone by the 5' Rapid Amplification of cDNA Ends (RACE) method. A human heart cDNA library and a human fetal liver cDNA library were used as cDNA sources. Two clones, 2.8 kb and 1.2 kb in size, were obtained from the human heart cDNA library. One 1.1 kb clone was obtained from the human fetal liver cDNA library. The cloning procedure is described below.

The present inventors used cDNA Library Human Heart (Takara Shuzo, Catalog #9604) for the human heart cDNA library. The XL1 Blue-MRF' E. coli cells transformed with the plasmid DNA containing the cDNA inserted into the pAP3neo vector (Genbank Accession No.AB003468) were cultured by the usual method, the plasmid DNA was recovered by the alkaline method, and the cDNA clone containing the 5' upstream region was obtained by PCR using 10 ng of the plasmid DNA as the template. The reaction mixture consisted of 10 ng of the cDNA, 5 µl of 10× Advantage™ KlenTaq buffer (which came with the kit), 4 µl of 2.5 mM dNTP, 1 µl of 10 µM AP3neo5' primer (which came with the kit; 5'-GCCCTTAGGACGCGTAATACGACTC-3' (SEQ ID NO: 60)), 1 µl of 10 µM 32-8-1 5' RACE primer #686 (5'-AGCCAGTATCTGATCTCCGACTTTG-3' (SEQ ID NO: 61)), and 1 µl of Advantage™ KlenTaq polymerase mix (Toyobo, CLK8417-1). These were mixed with deionized water to make the total 50 µl. PCR reaction was performed using a Perkin Elmer Thermal Cycler 2400. A reaction consisting of 94° C. for 1 minute, 5 cycles of 94° C. for 5 seconds and 72° C. for 4 minutes, and 5 cycles of 94° C. for 5 seconds and 70° C. for 4 minutes, followed by 25 cycles of 94° C. for 5 seconds and 68° C. for 4 minutes, yielded the bands of 2.8 kb and 1.2 kb. The products were separated on a 0.8% agarose gel. The corresponding bands were excised and purified with the QIAquick gel extraction kit (QIAGEN, 28706) and were subjected to TA cloning according to the manual for the pGEM-T Vector System I (Promega, A3600). The present inventors designated the two clones as 686-1-4 (2.8 kb) and 686-1-2 (1.2 kb). The sequence of clone 686-1-2 is contained in that of 686-1-4 (sequence 686-1-4), and ranges from nucleotide 1585 to nucleotide 2793 of SEQ ID NO: 3 (FIG. 7).

The present inventors performed 5' RACE using Marathon Ready human fetal liver cDNA (Clontech) as the human fetal liver cDNA library. The reaction mixture consisted of 5 μl of the cDNA, 5 μl of 10× Advantage™ KlenTaq buffer (which came with the kit), 4 μl of 2.5 mM dNTP, 1 μl of 10 μM AP1 primer (which came with the kit: 5'-CCATCCTAATACGACTCACTATAGGGC-3' (SEQ ID NO: 42)), 1 μl of 10 μM 32-8-1 5' RACE primer #686 (5'-AGCCAGTATCTGATCTCCGACTTTG-3' (SEQ ID NO: 61)), and 1 ml of Advantagem KlenTaq polymerase mix (Toyobo, CLK8417-1). These were mixed with 33 μl of deionized water to make the total 50 μl. PCR reaction was performed using a Perkin Elmer Thermal Cycler 2400. A reaction consisting of 94° C. for 1 minute, 5 cycles of 94° C. for 5 seconds and 72° C. for 6 minutes, 5 cycles of 94° C. for 5 seconds and 70° C. for 6 minutes, and 25 cycles of 94° C. for 5 seconds and 68° C. for 6 minutes did not produce clearly detectable bands. The reaction mixture was then diluted 50 fold, 5 μml of which was mixed with 5 μml of 10× Advantage™ KlenTaq buffer (which came with the kit), 4 μl of 2.5 mM dNTP, 1 μl of 10 μM AP2 primer (which came with the kit; 5'-ACTCACTATAGGGCTC-GAGCGGC-3 (SEQ ID NO: 44)), 1 μl of 10 μM 32-8-1 5' RACE nested primer #FLN (5'-ATTTTCACTTTA-GAAGGGGCACAT-3'(SEQ ID NO: 62)), 1 μl of Advantage™ KlenTaq polymerase mix (Toyobo, CLK8417-1), and 33 μl of deionized water to make the total 50 μl. Nested PCR was performed at 94° C. for 1 minute, 5 cycles of 94° C. for 5 seconds and 72° C. for 6 minutes, 5 cycles of 94° C. for 5 seconds and 70° C. for 6 minutes, and 15 cycles of 94° C. for 5 seconds and 68° C. for 6 minutes, which produced a band of approximately 1.1 kb. The products were separated on a 0.8% agarose gel. The corresponding bands were then excised and purified with a QIAquick gel extraction kit (QIAGEN, 28706) and were subjected to TA cloning according to the manual for the pGEM-T Vector System I (Promega, A3600). Three different clones were thus obtained and designated HFL#5, HFL#12, and HFL#6. HFL#5 and HFL#12 started from nucleotide 1357 of SEQ ID NO: 3, while HFL#6 started from nucleotide 1377 of SEQ ID NO: 3. Of course, all three contained the sequence up to that of primer #FLN, which was used in the RACE (FIG. 7).

The nucleotide sequences were determined as described above, by means of the cycle sequence method using a Dye Terminator Cycle Sequencing FS Ready Reaction kit (Perkin Elmer, Catalog #402122). The combined sequence of the previously determined one and the newly determined one is shown in SEQ ID NO: 3. FIG. 8 shows the sequences of nine PDZ domains aligned. The primers used for the cycle sequencing method are listed in Table 3.

TABLE 3

| Primer # | DNA sequence | SEQ ID NO: |
|----------|--------------|------------|
| 686A | GGCATAACTTTACTTACTTG | 63 |
| 686B | ATCTACTAAGTCAGCATCAT | 64 |
| 686C | ATTTGCAGGTGTGTAGTCAT | 65 |
| 686D | TTCCTTCTGTGCTACCCGAT | 66 |
| 686E | GGACTATCTTCCAGAACATG | 67 |

Example 4

Search for Proteins having Homology to the Protein Encoded by the "38-2-1" Gene

The BLASTN search and the BLASTP search detected "*Mus musculus* 90RF binding protein 1 (9BP-1) mRNA, partial cds." (LOCUS: MMAF000168, ACCESSION: AF000168) that consists of 2703 bp as a gene having homology to the "32-8-1" gene. This gene was recorded toGenBank on 18 MAY 1997. The amino acid sequence of the protein encoded by the "32-8-1" gene (the sequence after amino acid 847 of SEQ ID NO: 1) and that of AF000168 are aligned and shown in FIG. 1. In the figure, the amino acid 847 of SEQ ID NO: 1 was regarded as the "first" amino acid, and comparisons are shown with the amino acid sequence thereafter.

In addition, "*Rattus norvegius* mRNA for multi PDZ domain protein" (LOCUS: RNMUPP1, ACCESSION: AJ001320) consisting of 7516 bp, and "*Homo sapiens* mRNA for multi PDZ domain protein" (LOCUS: HSMUPP1, ACCESSION: AJ001319) consisting of 1768 bp were detected as genes having homology. These genes were registered on 26 MAR 1998. The amino acid sequence of the protein encoded by the "32-8-1" gene (the sequence after amino acid 921 of SEQ ID NO: 1) and that of AJ001319 are aligned and shown in FIG. 2. The amino acid sequence of the protein encoded by the "32-8-1" gene (the sequence of SEQ ID NO: 1) and that of AJ001320 are aligned and shown in FIGS. 3 and 4.

EXAMPLE 5

Analysis of Tissue Specificity of Expression by Northern Blotting

Figure 5:
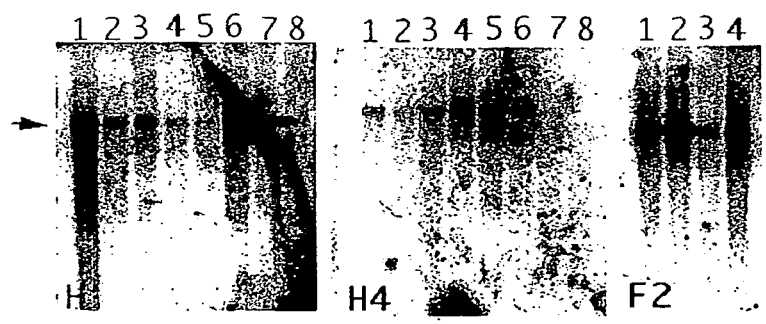
FIG. 5. Photograph of the electrophoresis showing the results of northern blot analysis of the "32-8-1 gene" is shown. The BamHI-XbaI fragment was used as the probe. "H" in the figure indicates the results with the Human Multiple Tissue Northern (MTN) Blot (Clontech #7760-1).

Clontech Human Multiple Tissue Northern (MTN) Blot (Catalog #7760-1), Human MTN Blot IV (Catalog #7766-1), Human Fetal MTN Blot II (#7756-1), Human Muscle MTN Blot (#7765-1) and Human Cancer Cell Line MTN Blot (#7757-1) were used to analyze the tissue specificity of gene expression. Northern blot was performed according to the standard method, using the BamHI-XbaI fragment (from position 3709 to position 4337 of SEQ ID NO: 3) and the NdeI 1.2 kb-#l probe (from position 3709 to position 4337 of SEQ ID NO:3) as the probe (see FIG. 7 for the position of the probe), and 25 ng of the DNA fragment was labeled with α-$^{32}$P dCTP using a Megaprime DNA labeling kit (Amersham, Catalog RPN$_{16}$O$_7$). These MTN Blots were prehybridized in 5 ml of the ExpressHyb hybridization solution (Clontech, Catalog #8015-2) at 68° C. for 30 minutes, and then hybridized with 1×10$^7$ cpm of the labeled probe also in 5 ml of the ExpressHyb hybridization solution (2×10$^6$ cpm/ml) at 68° C. for 2 hours. The filters were washed three times in 2× SSC (0.3 M NaCl, 0.03 M sodium citrate (pH 7.0))/0.05% SDS at room temperature for 10 minutes each, washed twice more in 0.1× SSC/0.1% SDS at 50° C. for 15 minutes each, exposed on FUJI imaging plates overnight, and analyzed by a FUJI BAS2000. As shown in FIGS. 5 and 6 strong expression of the approximately 8 kb transcription product was detected in the heart, placenta, skeletal muscle, fetal brain, fetal lung, fetal kidney, small intestine, bladder, stomach, prostate, HeLa S3 cells, lung cancer A549 cells, and melanoma G361 cells. However, the expression was either absent or weak in the lung, lymphoid tissues (spleen and thymus), and cell lines (lanes 1, 3, 4, 5, and 6 of blot C). In the heart, liver, kidney, and fetal liver, a 5.5 kb transcription product was expressed.

Similarly, northern blot analysis was performed using the NdeI 1.2 kb-#1 probe (from position 1 to position 1091 of SEQ ID NO: 3) (see FIG. 7 for the position of the probe). However, the band corresponding to the 5.5 kb transcription product was not detected (FIG. 6). Considering this and the fact that the cDNAs cloned by 5' RACE from the fetal liver only contained the 5' sequences 1,357 and 1,377 nucleotides downstream from the 5' end of the transcription product expressed in the heart (FIG. 7), it can be deduced that the difference of the transcription initiation sites in the heart and liver caused the difference in the lengths of the transcription products. Therefore, the peptide encoded by the 32-8-1 gene that is expressed in the liver is expected to start with the first methionine encoded by the ATG codon beginning with the $1396^{th}$ nucleotide. This results in the transcription product from the liver consisting of 1,005 amino acids, compared with that from the heart consisting of 1,373 amino acids. Consequently, it does not contain PDZ domain E and is shorter by 368 amino acids. Although the biological significance of not having PDZ domain E is unclear at present, it is highly possible that this protein, by lacking this portion, is involved in a different signal regulation in the liver cells than in the other tissues since PDZ domains are important for protein—protein interactions.

Example 6

Expression of the 32-8-1 Protein in E. coli (1) Construction of the Expression Vector In order to express the 32-8-1 protein in E. coli as a fusion protein with the glutathione-S-transferase (GST) protein, part of the 32-8-1 gene was ligated to the carboxyl terminus of the GST gene in Pharmacia's pGEX-2TK (Genbank Accession U13851). The vector was constructed based on the method of W. Dietmaier et al. for the di-/tri-nucleotide sticky end cloning described in the PCR Application Manual (Boehringer Mannheim). pGEX-2TK (1 μg) was reacted in a mixture of 2 ml of 10× High buffer and 20 units each of restriction enzymes EcoRI and BamHI in a total volume of 20 μl at 37° C. for 3 hours. Proteins were removed by using a QIAquick column (QIAGEN) according to the manual, and the purified DNA was eluted with 30 μl of distilled water. 10× Klenow buffer (3 μl; 100 mM Tris-HCl (pH 7.5), 70 mM $MgCl_2$, 1 mM DTT), which comes with Takara's Klenow enzyme, and 1.5 μl of 2 mM dGTP were mixed with 27 μl of the above. Four units of Klenow enzyme were then added, and the reaction was allowed to proceed at room temperature for 15 minutes. After the enzyme was inactivated by heating at 75° C. for 15 minutes, the DNA was purified by deproteinizing with a QIAquick column (QIAGEN) according to the manual.

The region of the 32-8-1 gene to be expressed, which encodes amino acids 1112 to 1373, was amplified by PCR using 50 ng of #32-8-1 DNA as the template. The amplification reaction was done by adding 5 μl of 10× Reaction buffer #1 for KOD DNA polymerase (Toyobo), 5 μl each of 10 μM primer 502–508 (5'-ATCGGGTCCATTCCATTCA-GAGAGG-3' (SEQ ID NO: 68)) and 10 μM primer 758–763E (5'-AATTGTCAAGAGAGAACCAT-CAAAGTGG-3'(SEQ ID NO: 69)), 4 μl of 2.5 mM dNTP, 2 μl of 25 mM $MgCl_2$, and 27 μl of sterilized water. 2.5 μl of KOD DNA polymerase was then mixed into the solution, which was then incubated at 94° C. for 2 minutes and subjected to 25 cycles of 98° C. for 15 seconds, 65° C. for 2 seconds, and 74° C. for 30 seconds. Using the QIAquick PCR purification kit, the 798 bp PCR product was purified according to the manual. The purified PCR fragment (2 μl) was mixed with 7 μl of the Boehringer's 5× T4 DNA polymerase buffer (330 mM Tris-acetate, pH 8.0; 660 mM potassium acetate; 100 mM magnesium acetate; and 5 mM DTT), 1.5 μl of 2 mM dCTP, and 21.5 μl of sterilized water. Three units of T4 DNA polymerase were then added, and the solution was reacted at 12° C. for 30 minutes. The present inventors inactivated the enzyme by incubation at 80° C. for 15 minutes and purified the mixture with the QIAquick PCR purification kit according to the manual. The pGEX-2TK plasmid, which had been digested with restriction enzymes EcoRI and BamHI and modified with Klenow, and the T4 polymerase-treated PCR product were ligated by one unit of T4 DNA ligase (Promega) using the attached buffer (30 mM Tris-HCl (pH 7.8), 10 mM $MgCl_2$, 10 mM DTT, and 1 mM ATP) at 15° C. overnight. The reaction mixture was then used to transform E. coli DH5 alpha. The recombinant protein expressed by the transformant was designated GST-PDZ56.

Similarly, a PCR product encoding the amino acids from position 611 to position 1142 of SEQ ID NO: 1 was prepared by the above described method with primer 1–7 (5'-ATC-GATGGGTAGTAATCACACACAG-3' (SEQ ID NO: 70)) and primer 527–532E (5'-AATTGCTATACTGGATCCA-GAGAGTGG-3' (SEQ ID NO: 71)), using clone 32-8-1/5R3 as the template. The preparation was treated with T4 polymerase under the same conditions as before, purified with the EcoRI and BamHI-digested and Klenow-treated pGEX-2TK, and ligated. The reaction mixture was used to transform E. coli DH5 alpha. The recombinant protein expressed by the transformant was designated GST-PDZ14.

The E. coli transformants that express GST-PDZ56 were selected by the following method. Four colonies of the E. coli transformants obtained from the above were shake-cultured at 37° C. overnight in 2 ml of the LB medium (5 g of Bacto-yeast extract (DIFCO), 10 g of Bacto-trypton (DIFCO), and 10 g of NaCl made to 1 L by dissolving them in distilled water) containing 100 μg/ml ampicillin. The solution was then diluted 100 fold in the medium of the same composition, and isopropyl thiogalactoside (IPTG) was added to a final concentration of 0.1 mM. The solution was then shake-cultured at 37° C. for 3 hours. A 100 μl sample was precipitated by centrifugation at 15,000 rpm for 10 seconds and analyzed on a 10% to 20% SDS-polyacrylamide gel. The subsequent Coomassie staining easily detected the IPTG-induced expression of the approximately 55 kDa GST fusion protein from every transformant (FIG. 9). Furthermore, western blotting with an anti-GST antibody also confirmed the induced expression of the 55 kDa protein band (FIG. 10). For detection, the proteins in the samples separated on the 10% to 20% SDS-polyacrylamide gel were transferred onto Immobilon-P (Millipore) using a Semidry blotter (Bio-Rad) according to the methods described in the manual. The filter was then blocked at 4° C. overnight with 5% skim milk (DIFCO), 2.5% bovine serum albumin (Sigma, A5940), and T-TBS (20 mM Tris-HCl (pH 7.5), 150 mM NaCl, and 0.05% Tween 20). It was next reacted at room temperature for 1 hour with the anti-sheep GST antibody (Pharmacia) diluted 1,000 fold in the antibody dilution buffer (1% skim milk, 0.5% bovine serum albumin, T-TBS), then reacted at room temperature for 1 hour with the alkaline phosphatase-labeled anti-sheep IgG antibody diluted 1,000 fold in the antibody dilution buffer. Finally, the protein was detected by a GST Detection Module (Pharmacia).

The GST-PDZ14 was similarly expressed. However, E. coli HB101 and JM109 were used as hosts because E. coli DH5 did not produce an efficient IPTG-induced expression. The results shown in FIG. 11 indicate that E. coli HB101 did not produce very large amounts of expression products, but that the GST-PDZ14-derived band near 90 kDa was highly induced in E. coli JM109. E. coli JM109 was subsequently used to express and purify the fusion protein.

(2) Expression and Purification of the GST 32-8-1 Fusion Protein

The present inventors followed the method for preparing fusion proteins described on page 217 of the Supplement to Jikken Igaku (Experimental Medicine) "Shin Idenshi Kogaku Handbook (New Genetic Engineering Handbook) edited by Masami Muramatsu, et. al." published by Yohdosha to express and purify the GST fusion proteins. GST-PDZ14 and GST-PDZ56 were each cultured at 37° C. for 1 hour in 2 L of LB medium to which IPTG was added to achieve a final concentration of 0.1 mM, then shake-cultured at 25° C. for 5 hours. The cells were collected at 7,000 rpm for 10 minutes, resuspended in a sonication buffer consisting of PBS and 1% Triton X-100, and sonicated 1 minute for five times while chilling. The supernatant was obtained by centrifugation at 10,000 rpm for 15 minutes. It was then applied onto a glutathione-Sepharose column, washed well with PBS, and purified with the GST Purification Module elution buffer (Pharmacia Biotech).

The 32-8-1 gene was inserted into the multi-cloning site of the pGEX-2TK expression vector (Pharmacia). This vector has a region encording the string of amino acids "Leu-Val-Pro-Arg-Gly-Ser" recognized by thrombin protease in frame after GST protein gene, so the GST protein portion can be separated from GST-32-8-1 fusion protein by applying the thrombin protease that recognizes this sequence and digesting the protein. This is useful for preparing antibodies against the protein encoded by the 32-8-1 gene (the 32-8-1 protein). Because the glutathione-Sepharose column binds to the GST protein, it was possible to purify the PDZ14 and PDZ56 portions only as the fractions not binding to the glutathione-Sepharose (FIGS. 12, 13, and 14) by applying the protein solution that had been digested with the thrombin protease onto the glutathione-Sepharose column. The 55 kDa GST-PDZ56 protein bands seen in FIG. 12 (lanes 11 and 12) were digested by thrombin into the 25 kDa GST protein and the 30 kDa PDZ56 protein (lane 10). Furthermore, the results of western blotting using the anti-GST antibody indicated that the anti-GST antibody reacted only with the 55 kDa and 25 kDa proteins, both of which contained the GST protein (FIG. 13). Together, these confirmed that the PDZ56 protein portion was cut off as the 30 kDa band (lanes 8 and 9). Similarly to GST-PDZ14, the 90 kDa GST-PDZ14 can be separated by thrombin digestion into the 25 kDa GST protein and the 65 kDa PDZ14 protein portion, as shown in FIG. 14. Therefore, the protein was purified according to the following procedure. The present inventors used the method described in the Supplement to Jikken Igaku (Experimental Medicine) "Shin Idenshi Kogaku Handbook (New Genetic Engineering Handbook) edited by Masami Muramatsu, et. al" published by Yohdosha to culture E. coli cells. They then used the supernatant of the sonicated cells to digest the proteins by thrombin. The detailed method followed the procedure described under Thrombin Cleavage on page 16 of the GST Gene Fusion System (Pharmacia). They next added 10 µl (10 cleavage units) of thrombin per 1 mg of the fusion protein and incubated the mixture at room temperature for 16 hours to separate the PDZ14 protein or the PDZ56 protein portion from the GST portion. By letting the cleaved GST protein portion bind to the glutathione-Sepharose column (Pharmacia), they recovered 0.56 mg of the PDZ14 or 3.5 mg of the PDZ56 protein portion as the flow-through from the column.

(3) Preparation of Polyclonal Antibodies Using the Antigens Expressed in E. coli The present inventors obtained polyclonal antibodies by immunizing two rabbits each with the purified PDZ14 or PDZ56 antigen. The initial immunization was done by subcutaneously injecting 0.5 mg of PDZ56 or 0.22 mg of PDZ14 bound with the carrier protein per animal as an antigen emulsion mixed with an equal amount of Freund's complete adjuvant (FCA) by the standard method. Booster injections of 0.25 mg of PDZ56 or PDZ14 were given subcutaneously as an antigen emulsion mixed with an equal amount of Freund's incomplete adjuvant (FICA) three times at two-week intervals. The proteins used as antigens were separated by SDS-PAGE and transferred onto a PVDF membrane (Immobilon-P, Millipore); the reactivity was confirmed by western blotting.

(4) Preparation of Polyclonal Antibodies Using a Peptide

Iwaki Glass synthesized Peptide 32-8-1-17 (SEQ ID NO: 72) consisting of 21 amino acids under contract. The Keyhole limpet hemocyanin (KLH) protein was coupled to the peptide as a carrier protein by the Sulfo-MBS method, and two rabbits were immunized with the product. The initial immunization was done by subcutaneously injecting 0.4 mg of the 32-8-1-17 peptide bound with the carrier protein per animal as an antigen emulsion mixed with an equal amount of Freund's complete adjuvant (FCA) by the standard method. The second through the fifth immunizations were given at two-week intervals by subcutaneously injecting 0.2 mg of the 32-8-1-17 peptide bound with the carrier protein as an antigen emulsion mixed with an equal amount of Freund's incomplete adjuvant (FICA). The antibody titers were measured using an ELISA plate coated with the 32-8-1-17 peptide; the antisera were obtained when the titer had risen sufficiently.

(5) Reactivity of the Polyclonal Antibodies

Antisera were obtained by immunizing the rabbits with peptide 32-8-1-17 or with PDZ14 or PDZ56 protein expressed as a GST-fusion protein and then digested with thrombin to retain only the 32-8-1 gene product. The reactivity of the antisera was detected by western blotting using Protein Medley manufactured by Clontech. More specifically, 100 µg each of the cell lysates of the tissues from the human Testis (T), Skeletal Muscle (Sk), Liver (Lv), Heart (H), and Brain (B) of the Protein Medley manufactured by Clontech was separated on a 10% to 20% SDS-polyacrylamide gel. The cell lysates were then transferred onto Immobilon-P (Millipore) using the Semidry blotter (Bio-Rad) according to the methods described in the manual. The filter was then blocked at 4° C. overnight with 5% skim milk (DIFCO), 2.5% bovine serum albumin (Sigma, A5940), and T-TBS (20 mM Tris-HCl (pH 7.5), 150 mM NaCl, and 0.05% Tween 20). The filter was next reacted at room temperature for 1 hour with the individual rabbit antisera diluted 5,000 fold in the antibody dilution buffer (1% skim milk, 0.5% bovine serum albumin, and T-TBS). It was then reacted at room temperature for 1 hour with the biotin-labeled anti-rabbit Ig diluted 1,000 fold in the antibody dilution buffer. Finally, the filter was further reacted at room temperature for 15 minutes with the horseradish peroxidase (HRP)-labeled streptavidin-biotin complex (Amersham) diluted 2,500 fold in the antibody dilution buffer and washed well with T-TBS. The reacting bands were detected by chemiluminescence using an ECL detection kit (Amersham) according to the manual. Consequently, as shown in FIG. 15, a band that reacted with every antibody and is presumed to be derived from the 32-8-1 protein was detected in the liver tissue sample near the 130 kDa.

EXAMPLE 7

Cloning of an Upstream cDNA of 686-1-4 by RACE

The present inventors attempted to obtain a cDNA clone 5' upstream of 686-1-4, which was cloned from the human heart, by the 5' Rapid Amplification of cDNA Ends (RACE) method. The details follow.

(1) Cloning of cDNA Clone D-2 by RACE

The present inventors performed 5' Rapid Amplification of cDNA Ends (RACE) by using the Marathon Ready human brain cDNA (Clontech, #7400-1) as the adult human brain cDNA library. The 5'RACE mixture consisted of 5 µl of the Marathon Ready adult human brain cDNA, 1 µl each of 10 µM primer #878 (5'-TTTGTGCCCACCAGAGC-CAAGTCAG-3' (SEQ ID NO: 73)) and 10 µM AP1 primer (which came with the kit: 5'-CCATCCTAATACGACT-CACTATAGGGC-3' (SEQ ID NO: 42)), 1 µl of Advantage™ KlenTaq polymerase mix (Toyobo, CLK8417-1), and 33 µl of deionized water to make the total 50 µl. A PCR reaction using the Thermal Cycler (95° C. for 1 minute, five cycles of 95° C. for 5 seconds and 72° C. for 4 minutes, five cycles of 95° C. for 5 seconds and 70° C. for 4 minutes, and 25 cycles of 95° C. for 5 seconds and 68° C. for 4 minutes) did not produce clearly detectable bands. Therefore, the reaction mixture was diluted 50 fold, and 5 µl of this was mixed with 5 µl of 10× Advantage™ KlenTaq buffer (which came with the kit), 4 µl of 2.5 mM dNTP, 1 µl of 10 µM AP2 primer (which came with the kit; 5' ACTCACTAT-AGGGCTCGAGCGGC-3 (SEQ ID NO: 44)), 1 µl of 10 µM 32-8-1 5' RACE nested primer #757 (5'-GTGAAAGGGG-TAAAGGCTTAGCAAC-3' (SEQ ID NO: 74)), 1 µl of Advantage™ KlenTaq polymerase mix (Toyobo, CLK8417-1), and 33 µl of deionized water to make the total 50 µl. Nested PCR was performed at 95° C. for 1 minute, five cycles of 95° C. for 5 seconds and 72° C. for four minutes, and five cycles of 95° C. for 5 seconds and 70° C. for 4 minutes. Subsequent treatment of 15 cycles at 95° C. for 5 seconds and 68° C. for 4 minutes produced a band of 1.8 kb. The products were separated on a 0.8% agarose gel. The corresponding band was excised and purified with the QIAquick gel extraction kit (QIAGEN, 28706) and subjected to TA cloning according to the manual for the PGEM-T Vector System I (Promega, A3600). The resulting clone was designated D-2.

The nucleotide sequence determination was done as previously described, and the nucleotide sequence of 1,776 base pairs was determined by means of the cycle sequence method using the Dye Terminator Cycle Sequencing FS Ready Reaction kit (Perkin Elmer, Catalog #402122). The nucleotide sequence thus determined was found to encode 590 amino acids (SEQ ID NO: 75).

(2) Cloning of cDNA Clone 1.2 kb#33 by RACE

The open reading frame that exists within the sequence of Clone D-2 is a sequence upstream of the $781^{st}$ nucleotide of SEQ ID NO: 3. This open reading frame is not closed, that is, it does not have a stop codon, so it was assumed that the open reading frame continues further upstream. Thus the present inventors prepared a new primer and performed 5' RACE. By using the Marathon Ready human brain cDNA (Clontech, #7400-1) as the template, the present inventors performed 5' Rapid Amplification of cDNA Ends (RACE). The 5'RACE mixture consisted of 5 µl of the Marathon Ready adult human brain cDNA, 1 µl each of 10 µM primer B5R-1 (5'-GCAGATGGAGAACGGGAAACTATGG-3' (SEQ ID NO: 76)) and 10 mM AP1 primer (which came with the kit; 5'-CCATCCTAATACGACTCACTATAGGGC-3' (SEQ ID NO: 42)), 5 µl of 10× Advantage™ KlenTaq buffer (which came with the kit), 4 µl of 2.5 mM dNTP, 1 µl of Advantage™ KlenTaq polymerase mix (Toyobo, CLK8417-1), and 33 µl of deionized water to make a total of 50 µl. A PCR reaction using the Thermal Cycler (95° C. for 1 minute, five cycles of 95° C. for 5 seconds and 72° C. for 3 minutes, and five cycles of 95° C. for 5 seconds and 70° C. for 3 minutes, followed by 25 cycles of 95° C. for 5 seconds and 68° C. for 3 minutes) did not produce detectable bands. Therefore, the reaction mixture was diluted 50 fold, and 5 µl of this was used as the template to perform nested PCR. The template was mixed with 5 µl of 10× Advantage™ KlenTaq buffer (which came with the kit), 4 µl of 2.5 mM dNTP, 1 µl of 10 µM AP2 primer (which came with the kit; 5'-ACTCACTATAGGGCTCGAGCGGC-3 (SEQ ID NO: 44)), 1 µl of 10 µM primer B5R-2 (5'-GAACGGGAAAC-TATGGGGCTGACAA-3' (SEQ ID NO: 77)), 1 µl of Advantage™ KlenTaq polymerase mix (Toyobo, CLK8417-1), and 33 µl of deionized water to make the total 50 µl. A reaction consisting of 95° C. for 1 minute, five cycles of 95° C. for 5 seconds and 72° C. for 3 minutes, five cycles of 95° C. for 5 seconds and 70° C. for 3 minutes, followed by 15 cycles of 95° C. for 5 seconds and 68° C. for 3 minutes produced a band of 0.8 kb. The products were separated on a 0.8% agarose gel, the corresponding band was excised and purified with the QIAquick gel extraction kit (QIAGEN, 28706). It was then subjected to TA cloning according to the manual for the pGEM-T Vector System I (Promega, A3600). The resulting clone was designated 1.2 kb#33. The results of the nucleotide sequence determination (conducted as described before) revealed that the ATG codon starting with the $71^{st}$ nucleotide corresponded to the first methionine, and that the clone encoded 235 amino acids. The last amino acid, arginine, corresponded to the arginine encoded by the nucleotides from position 108 to position 110 of clone D-2, and the nucleotides from position 1 to position 110 of the clone D-2 sequence overlapped with clone 1.2 kb#33. Therefore, the present inventors concluded that all the upstream sequences of the deduced open reading frame were cloned.

(3) Analysis of the Difference in Amounts of Expression in Tissues

Amounts of mRNA expression in 24 types of tissues, including those that were examined by the northern blot above, were compared by RT-PCR. Human MTC panel I (K1402-1), human MTC panel II (K1421-1), and human fetal MTC panel I (K1425-1), which are commercially available from Clontech, were used as the cDNA. Results of the PCR reaction with the following reaction conditions are shown in FIG. 16-A. PreMixTaq (10 µl; ExTaq™ Version) (Takara, PR003A), 2 µl of 2 µM 686D primer (SEQ ID NO: 66, corresponding to positions 2970 to 2989 of SEQ ID NO: 83, and to positions 1 to 20 of FIG. 17), 2 µl of 2 µM 686E primer (SEQ ID NO: 67, corresponding to positions 3635 to 3654 of SEQ ID NO: 83, and to positions 666 to 685 of FIG. 17), 1 µl of the first strand cDNA, and 5 µl of deionized water were mixed to make a total of 20 µl and reacted. Reaction of 94° C. for 5 minutes, and 30 cycles of a three-step PCR reaction consisting of 94° C. for 15 seconds, 50° C. for 30 seconds, and 72° C. for 30 seconds, followed by an extension reaction of 72° C. for 7 minutes were performed.

As a result, high degrees of expression were seen in the brain (1), placenta (7), skeletal muscle (8), ovary (10), spleen (14), testis (15), fetal heart (18), fetal kidney (19), and fetal skeletal muscle (22). In addition, 15 µl of PreMixTaq (ExTaq™ Version) (Takara, PRO003A), 3 µl of 2 µM 686D primer (SEQ ID NO: 66), 3 µl of 2 µM XE primer (SEQ ID NO: 15, which corresponds to positions 3915 to 3934 of SEQ ID NO: 83, and to positions 946 to 965 of FIG. 17), 1 µl of the first strand cDNA, and 8 µl of deionized water were mixed to make a total of 30 µl and reacted. Reaction of 94° C. for 5 minutes, and 30 cycles of a three-step PCR reaction consisting of 94° C. for 15 seconds, 50° C. for 30 seconds, and 72° C. for 1 minute, followed by an extension reaction of 72° C. for 7 minutes were performed. As shown in FIG. 16-B, bands of 750 bp, 850 bp, and 950 bp, which are presumed to be derived from three types of transcription products, were detected. Since the experiments in FIG. 16-A and 16-B both used the same 686D primer, three types of splicing should take place within the sequences that exist in between the 686E primer and the XE primer, producing the transcription products of different lengths. The three types of PCR products were cloned from those of the fetal heart that showed the highest expression. Cloning was done by excising the corresponding bands and purifying them using the QIAquick gel extraction kit (QIAGEN, 28706), and by following the manual for the pGEM-T Vector System I (Promega, A3600).

(4) Analysis of the Gene Sequences of Clones FH750, FH850, and FH950

The nucleotide sequences for the cloned PCR products were determined according to the method described above. The determined nucleotide sequences of FH750, FH850, and FH950 are shown in SEQ ID NO: 79, 80, and 81, respectively. The sequences of the three kinds of DNA are aligned and shown in FIGS. 17 and 18. Although the sequences of the three kinds of DNA are identical up to sequence position 731, FH850 diverges from FH950 beginning with the 819th nucleotide, which suggests that splicing takes place at some sequence immediately preceding this position. As a result of this splicing, FH850 generates a stop codon with the sequence from position 819 to position 821, and the translation is expected to terminate at this position.

In FH750, positions 732 to 941 of the FH950 sequence are spliced out, creating a 210 bp deletion of the gene. However, the protein encoded by the transcription product of the FH750 type splicing is predicted to lack 70 amino acids compared with FH950 type splicing since the sequences before and after the deleted region are expected to be translated in the same frame as in those of FH950.

The sequence obtained by combining 1.2 kb#33 (SEQ ID NO: 78), D-2 (SEQ ID NO: 75), and SEQ ID NO: 3 (FIG. 26) was bordered by primer 686D and primer XE derived from the 686-1-4 sequence and was identical to FH750. The clone corresponding to the transcription product expected to be generated by the FH750 type splicing was designated 32-8-1a. (The amino acid sequence of the protein is shown in SEQ ID NO: 82, and the nucleotide sequence of the cDNA is shown in SEQ ID NO: 85.) Clone 32-8-1a can code for 2,000 amino acids. The clone corresponding to the transcription product expected to be generated by the FH950 type splicing was designated 32-8-1b. (The amino acid sequence of the protein is shown in SEQ ID NO: 83, and the nucleotide sequence of the cDNA is shown in SEQ ID NO: 86.) Code 32-8-1b can code for 2,070 amino acids. These two genes possess 13 PDZ domains. Furthermore, the transcription product generated by the FH850 type splicing will contain a stop codon in this region, and it can only code for 1,239 amino acids. This means that it possesses only seven PDZ domains. The clone corresponding to this transcription product was designated 32-8-1c. (The amino acid sequence of the protein is shown in SEQ ID NO: 84, and the nucleotide sequence of the cDNA is shown in SEQ ID NO: 87.) Sequence comparisons between "32-8-1b" and "AF00168" (*Mus musculus* 90RF binding protein 1 (9BP-1) mRNA, partial cds.) are shown in FIG. 20; between "32-8-1b" and "AJ001319" (*Homo sapiens* mRNA for multi PDZ domain protein), in FIG. 21; and between "32-8-1b" and "AJ001320" (*Rattus* norvegius mRNA for multi PDZ domain protein), in FIGS. 22 through 24. The PDZ domain sequences of the protein encoded by the 32-8-1b gene (SEQ ID NO: 83) are also shown in FIG. 25.

(6) Identification of the 32-8-1b High Molecular Weight Protein by Western Blotting Human neuroblastoma SH-SY5Y cells and human teratocarcinoma NT-2 cells stimulated by retinoic acid to differentiate into neurons were directly dissolved into SDS-PAGE sample buffer and separated on a 7.5% SDS-polyacrylamide gel by electrophoresis. The proteins were transferred onto Immobilon-P (Millipore) using the Semidry blotter (Bio-Rad) according to the methods described in the manual. The filter was then blocked at 4° C. overnight with 5% skim milk (DIFCO), 2.5% bovine serum albumin (Sigma, A5940), and T-TBS (20 mM Tris-HCl (pH 7.5), 150 mM NaCl, and 0.05% Tween 20). It was next reacted at room temperature for 1 hour with the individual rabbit antisera diluted 5,000 fold in the antibody dilution buffer (1% skim milk, 0.5% bovine serum albumin, and T-TBS). It was then reacted at room temperature for 1 hour with the biotin-labeled anti-rabbit Ig diluted 1,000 fold in the antibody dilution buffer. Finally, it was reacted at room temperature for 15 minutes with the horseradish peroxidase (HRP)-labeled streptavidin-biotin complex (Amersham) diluted 2,500 fold in the antibody dilution buffer and washed well with T-TBS. The reacting bands were then detected by chemiluminescence using an ECL detection kit (Amersham) according to the manual. As shown in FIG. 19, a protein whose molecular weight exceeds 250 kDa was detected in both SH-SY5Y and NT-N with either rabbit antisera #1 raised against peptide 32-8-1-17 or rabbit antisera #3D raised against PDZ56 that had been expressed as a GST fusion protein and digested with thrombin to retain only the 32-8-1 gene product. The assumption that the full-length 32-8-1b protein consists of 2,070 amino acids agrees with the molecular weight observed.

INDUSTRIAL APPLICABILITY

By utilizing the proteins and the gene of the present invention, it has become possible to isolate the proteins and their genes that bind to the PDZ domains of the proteins of the present invention. It has been reported that proteins having the PDZ domain interact with the proteins that bind to them and function in the signal transduction related to cell proliferation, cell cycle, malignant conversion, apoptosis, cell adhesion, etc. Therefore, if the relationships between the proteins of the present invention and the proteins that interact with them, as well as the related signal transduction pathways, can be clarified, it should be possible to treat and diagnose disorders related to cell proliferation and others described above by targeting these proteins or their genes. These proteins and their genes are therefore useful for developing therapeutic medicines and diagnostic medicines.

---

What is claimed is:

1. A substantially pure polypeptide comprising the amino acid sequence of SEQ ID NO:1.

2. A method of screening for a compound that specifically binds to a polypeptide, the method comprising contacting a test compound with the polypeptide of claim 1, and comparing the extent to which the test compound binds to the polypeptide with extent to which a reference compound binds to the polypeptide, wherein a test compound binding to the polypeptide to a greater extent than the reference compound indicates that the test compound specifically binds to the polypeptide.

3. The method of claim 2, wherein the test compound is a test polypeptide.

4. The polypeptide of claim 1, wherein the polypeptide consists of the amino acid sequence of SEQ ID NO:1.

5. A substantially pure polypeptide comprising the amino acid sequence of SEQ ID NO:2.

6. The polypeptide of claim 1, wherein the polypeptide consists of the amino acid sequence of SEQ ID NO:1.

7. A method of screening for a compound that specifically binds to a polypeptide, the method comprising contacting a test compound with the polypeptide of claim 5, and comparing the extent to which the test compound binds to the polypeptide with the extent to which a reference compound binds to the polypeptide, wherein a test compound binding to the polypeptide to a greater extent than the reference compound indicates that the test compound specifically binds to the polypeptide.

8. The method of claim 7, wherein the test compound is a test polypeptide.

* * * * *

UNITED STATES PATENT AND TRADEMARK OFFICE
CERTIFICATE OF CORRECTION

PATENT NO. : 7,001,728 B1 Page 1 of 1
APPLICATION NO. : 09/502698
DATED : February 21, 2006
INVENTOR(S) : Shin-ichi Funahashi and Shoji Miyata It is certified that error appears in the above-identified patent and that said Letters Patent is hereby corrected as shown below:

On the title page item (57), ABSTRACT, Line 1: after "TNFα in" insert --human--

Column 173, Line 8, Claim 2: after "polypeptide with" insert --the--

Column 174, Line 1, Claim 6: after "claim" delete "1" and insert --5--

Column 174, Line 2, Claim 6: after "SEQ ID NO:" delete "1" and insert --2--

Signed and Sealed this

Second Day of January, 2007

JON W. DUDAS
*Director of the United States Patent and Trademark Office*